US012029778B2

(12) United States Patent
Ring

(10) Patent No.: US 12,029,778 B2
(45) Date of Patent: Jul. 9, 2024

(54) INTERLEUKIN-18 MIMICS AND METHODS OF USE

(71) Applicant: Yale University, New Haven, CT (US)

(72) Inventor: Aaron Ring, New Haven, CT (US)

(73) Assignee: Yale University, New Haven, CT (US)

(*) Notice: Subject to any disclaimer, the term of this patent is extended or adjusted under 35 U.S.C. 154(b) by 729 days.

(21) Appl. No.: 16/871,833

(22) Filed: May 11, 2020

(65) Prior Publication Data

US 2021/0015891 A1 Jan. 21, 2021

Related U.S. Application Data

(60) Provisional application No. 62/847,190, filed on May 13, 2019.

(51) Int. Cl.

| | |
|---|---|
| ***G01N 33/48*** | (2006.01) |
| ***A61K 38/16*** | (2006.01) |
| ***A61P 35/00*** | (2006.01) |
| ***C07K 14/54*** | (2006.01) |
| *G06G 7/48* | (2006.01) |
| *G06G 7/58* | (2006.01) |

(52) U.S. Cl.

CPC .............. *A61K 38/16* (2013.01); *A61P 35/00* (2018.01); *C07K 14/54* (2013.01); *G06G 7/48* (2013.01); *G06G 7/58* (2013.01)

(58) Field of Classification Search

None

See application file for complete search history.

(56) References Cited

U.S. PATENT DOCUMENTS

| | | | |
|---|---|---|---|
| 6,479,258 | B1 | 11/2002 | Short |
| 6,713,279 | B1 | 3/2004 | Short |
| 6,800,479 | B2 | 10/2004 | Im et al. |
| 7,037,685 | B2 | 5/2006 | Yamamoto et al. |
| 7,253,260 | B2 | 8/2007 | Janson et al. |
| 7,279,155 | B2 | 10/2007 | Dinarello et al. |
| 7,311,902 | B2 | 12/2007 | Bam et al. |
| 7,524,488 | B2 | 4/2009 | Dinarello et al. |
| 7,608,267 | B2 | 10/2009 | Paul |
| 7,736,639 | B2 | 6/2010 | Bam et al. |
| 7,875,709 | B2 | 1/2011 | Dinarello et al. |
| 7,928,197 | B2 | 4/2011 | Wonderling |
| 8,679,471 | B2 | 3/2014 | Carroll et al. |
| 2004/0023336 | A1 | 2/2004 | Heavner et al. |
| 2005/0008615 | A1 | 1/2005 | Bam et al. |
| 2005/0261213 | A1 | 11/2005 | Branigan et al. |
| 2009/0202475 | A1 | 8/2009 | Abbas et al. |
| 2011/0189131 | A1 | 8/2011 | Altarocca et al. |
| 2014/0112915 | A1 | 4/2014 | Bardroff et al. |

FOREIGN PATENT DOCUMENTS

| | | |
|---|---|---|
| EA | 005769 | 6/2005 |
| EP | 0861663 | 9/1998 |
| EP | 1669454 | 6/2006 |
| JP | 2004530432 | 10/2004 |
| JP | 2011105737 | 6/2011 |
| WO | 2002101049 | 12/2002 |
| WO | WO/2002101049 | 12/2002 |
| WO | 2004091517 A2 | 10/2004 |
| WO | 2005014642 A2 | 2/2005 |
| WO | 2005075648 | 8/2005 |
| WO | WO/2005075648 | 8/2005 |
| WO | 2017103088 | 6/2017 |
| WO | 2019051015 | 3/2019 |

OTHER PUBLICATIONS

Yadav, Brijesh S., et al. "Protein modeling, molecular network and molecular dynamics study of newly sequenced interleukin-18 (IL-18) gene in Mus musculus." Journal of cellular physiology 234.8 (2019): 14285-14295.*

Kato, Zenichiro, et al. "The structure and binding mode of interleukin-18." Nature Structural & Molecular Biology 10.11 (2003): 966-971.*

Krumm, Brian, et al. "Identification of small molecule inhibitors of Interleukin-18." Scientific reports 7.1 (2017): 1-8.*

Aagaard et al.("RNAi therapeutics: Principles, prospects and challenges." Advanced Drug Delivery Reviews 59 (2007) 75-86) (Year: 2007).

Argiris, A. et al., 2017, "Evidence-Based Treatment Options in Recurrent and/or Metastatic Squamous Cell Carcinoma of the Head and Neck.", Frontiers in Oncology 7:72, 14 pages.

Boland, P.M. et al., 2017, "Immunotherapy for Colorectal Cancer." Cancers 9(5): 50, 12 pages.

Bork ("Powers and Pitfalls in Sequence Analysis: the 70% Hurdle." Genome Research, 2000, 10:398-400) (Year: 2000).

Bowie et al. "Deciphering the Message in Protein Sequences: Tolerance to Amino Acid Substitutions." Science, 1990, 247:1306-1310.

Brown et al . . . ("Tolerance to Single, but not Multiple, Amino Acid Replacements in antibody VH CDR2." J Immunol. May 996;156(9):3285-91) (Year: 1996).

Burgess et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue." J of Cell Bio. 1990, 111:2129-2138.

Clark et al ("Discovery and Development of Janus Kinase (JAK) Inhibitors for Inflammatory Diseases." J. Med. Chem., 2014, 57 (12), pp. 5023-5038) (Year: 2014).

Dine, J. et al., 2017, "Immune Checkpoint Inhibitors: An Innovation in Immunotherapy for the Treatment and Management of Patients with Cancer." Asia-Pacific journal of oncology nursing 4(2): 127, 9 pages.

Fuereder, T., 2016, "Immunotherapy for head and neck squamous cell carcinoma." memo—Magazine of European Medical Oncology 9(2):66-69, 4 pages.

(Continued)

*Primary Examiner* — Anna Skibinsky

(74) *Attorney, Agent, or Firm* — Riverside Law LLP

(57) ABSTRACT

The present disclosure provides methods of making and methods of using IL-18 mimic polypeptides for use in therapeutic and non-therapeutic applications. The synthetic IL-18 mimics an increase IL-18R signaling activity even in the presence of an inhibitory molecule such as IL-18BP.

32 Claims, 39 Drawing Sheets

Specification includes a Sequence Listing.

(56) References Cited

OTHER PUBLICATIONS

Guido et al ("Virtual Screening and its Integration with Modern Drug Design Technologies." Curr Med Chem. 2008;15(1):37-46) (Year: 2008).

Guldbrandsen, K.F. et al., 2017, "Nuclear Molecular Imaging Strategies in Immune Checkpoint Inhibitor Therapy." Diagnostics, 7(2):23, 12 pages.

Johnson, D.B. et al., 2017, "Immune Checkpoint Inhibitors in Challenging Populations." Cancer, 123(11):1904-1911, 8 pages.

Kim, J.H. et al., 2017, "Prognostic value of KRAS mutation in advanced non-small-cell lung cancer treated with immune checkpoint inhibitors: A meta-analysis and review." Oncotarget 8(29):48248-48252, 5 pages.

Kim, Soo-Hyun M., et al., "Structural requirements of six naturally occurring isoforms of the IL-18 binding protein to Inhibit IL-18", Proc Natl Acad Sci, (2000), vol. 97(3):1190-5, ISSN 0004818513.

Lazar et al. "Transforming Growth Factor alpha: Mutation of Aspartic Acid 47 and Leucine 48 Results in Different Biological Activities." Molecular and Cellular Biology 8:1247-1252, 1988.

Ma Z et al: "Augmentation of immune checkpoint cancer immunotherapy with IL18", Clinical Cancer Research Jun. 15, 2016 American Association for Cancer Research Inc. USA, vol. 22, No. 12, Jun. 15, 2016 (Jun. 15, 2016), pp. 2969-2980, XP055392162, ISSN: 1078-0432.

Malhotra, J. et al., 2017, "Current state of immunotherapy for non-small cell lung cancer." Translational lung cancer research 6(2):196, 16 pages.

McKeague et al ("Challenges and Opportunities for Small Moleucle Aptamer Development." J Nucleic Acids. 2012;2012:748913. Epub Oct. 24, 2012) (Year: 2012).

NCBI reference for IL-18; downloaded from https://www.ncbi.nlnn.nih.gov/gene?ternn=(i118[gene])%20AND%20(Horno%20sapiens[orgn])%20AND%20alive[prop]%20NOT%20newentry[gene]&sort=weight on Feb. 2, 2020 (Year: 2020).

Office Action (Non-Final Rejection) dated May 25, 2022 for U.S. Appl. No. 16/123,063 (pp. 1-13).

Office Action dated Feb. 20, 2020 for U.S. Appl. No. 16/123,063 (pp. 1-24).

Office Action dated Jun. 24, 2021 for U.S. Appl. No. 16/123,063 (pp. 1-15).

Office Action dated Nov. 15, 2019 for U.S. Appl. No. 16/123,063 (p. 1-12).

Petrelli, F. et al., 2016, "Early analysis of surrogate endpoints for metastatic melanoma in immune checkpoint inhibitor trials." Medicine 95(26):e3997, 7 pages.

Singer et al., 2016, "A Distinct Gene Module for Dysfunction Uncoupled from Activation in Tumor-Infiltrating T Cells." Cell, 166:1500-1511, e1509.

Tinhofer, I. et al., 2016, "The rationale for including immune checkpoint inhibition into multimodal primary treatment concepts of head and neck cancer." Cancers of the Head & Neck 1:8, 11 pages.

Vajdos et al. ("Comprehensive Functional Maps of the Antigen-binding Site of an Anti-ErbB2 Antibody Obtained with Shotgun Scanning Mutagenesis." J Mol Biol. Jul. 5, 2002;320(2):415-28) (Year: 2002).

Warzocha et al ("Antisense Strategy: Biological Utility and Prospects in the Treatment of Hematological Malignancies." Leukemia and Lymphoma (1997) vol. 24. pp. 267-281) (Year: 1997).

Kim et al., 2001, "Site-specific mutations in the mature form of human IL-18 with enhanced biological activity and decreased neutralization by IL-18 binding protein." Proc. Natl. Acad. Sci., 98(6):3304-3309.

Singer et al., 2016, "A Distinct Gene Module for Dysfunction Uncoupled from Activation in Tumor-Infiltrating T Cells." Cell, 166(6):1500-1511.

Silva et al., 2019, "De novo design of potent and selective mimics of IL-2 and IL-15", Nature, vol. 565, 29 pages.

Tsutsumi et al., 2014, "The structural basis for receptor recognition of human interleukin-18", Nature Communications, pp. 1-13.

Tsutsumi et al., "The structural basis for receptor recognition of human interleukin-18", Supplementary Information, pp. 1-11.

* cited by examiner

Adapted from Singer et al., Cell, 2017

Human DR-IL-18 variants sequence summary

| | WT hIL-18 | 1 Y | 5 L | 8 K | 51 M | 53 K | 55 S | 59 G | 60 M | 77 E | 103 Q | 105 S | 110 D | 111 N | 153 V | 155 N |
|---|---|---|---|---|---|---|---|---|---|---|---|---|---|---|---|---|
| Selected Variants | hC4 | | | Q | T | | K | T | K | | | R | H | | | K |
| | hA8 | | | R | K | | K | A | Q | | | D | K | H | I | |
| | hD6 | | | R | D | | K | A | K | | | D | K | H | I | |
| | hH12 | | H | | T | R | | | K | | | D | N | | T | |
| | hB11 | | I | | K | | K | A | Q | | | K | Q | H | | K |
| | hC3 | | I | | T | | R | | K | | E | D | H | H | I | |
| | hC2 | | I | | T | | K | | K | | | D | K | H | T | H |
| | hG10 | | I | | T | | K | A | K | | | R | H | H | I | K |
| | hG1 | | I | R | T | | K | | K | | | D | | Y | I | K |
| | hF1 | | Y | R | T | R | | | K | | | D | E | H | | K |
| | hD2 | H | Y | | T | R | | | K | | | D | H | | | K |
| | hA1 | R | | | T | R | | A | K | | | D | Q | H | A | K |
| | hB3 | R | | R | D | R | | | R | | K | N | K | Y | | H |
| | hB4 | R | | R | N | R | | | Q | | K | R | N | H | | K |
| | hH3 | R | | R | T | | | | K | | | D | K | H | | |
| | hC5 | R | | R | T | R | | T | K | | | K | N | H | | K |
| | hH4 | R | | R | T | R | | A | K | | E | D | Q | H | I | K |
| | hE1 | R | | R | T | R | | T | K | | | N | H | D | | H |
| | hG2 | R | | R | T | | | A | K | | E | D | Q | H | I | K |
| | hB9 | R | H | | T | R | | | K | | E | N | K | Y | | |
| | hE12 | R | Y | | T | | | T | K | D | | D | K | H | | |
| Consensus Variants | **hCS1** | | | | T | | | | K | | | D | K | H | | |
| | **hCS2** | | | | T | | K | A | K | | | D | K | H | I | |
| | **hCS3** | R | | | T | | | | K | | | D | K | H | | |
| | **hCS4** | R | | | T | R | | | K | | | N | K | Y | | |

FIG. 4

FIG. 7A
| Residue | Codon | AA |
|---|---|---|
| 1Y | NWT | FYLHINVD |
| 51M | RNG | MTKRVAEG |
| 53K | VNS | LPHQRIMTNKSRVADEG |
| 56Q | VNA | LPQRITKRVAEG |
| 57P | VNA | LPQRITKRVAEG |
| 60M | MDG | MKRLQR |
| 103Q | VVR | QKERRGPTA |
| 105S | DMT | SYTNAD |
| 110D | RRW | DEKNSRGG |
| 111N | VRW | HQNKDERRSRGG |
| 113M | RNG | MTKRVAEG |
FIG. 7B
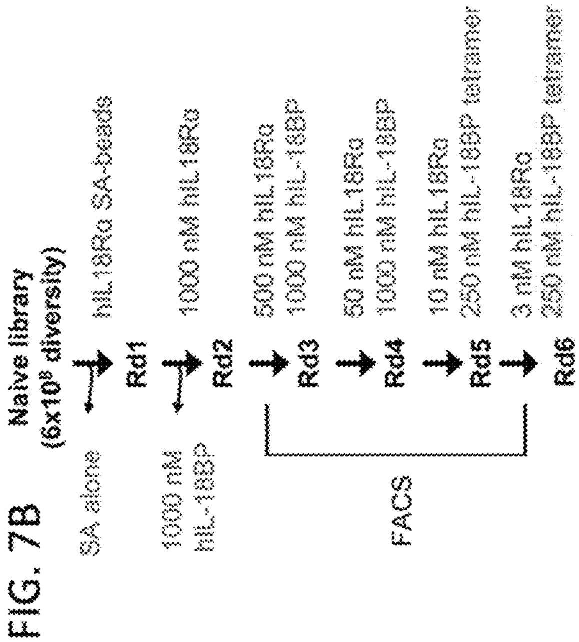
FIG. 7C
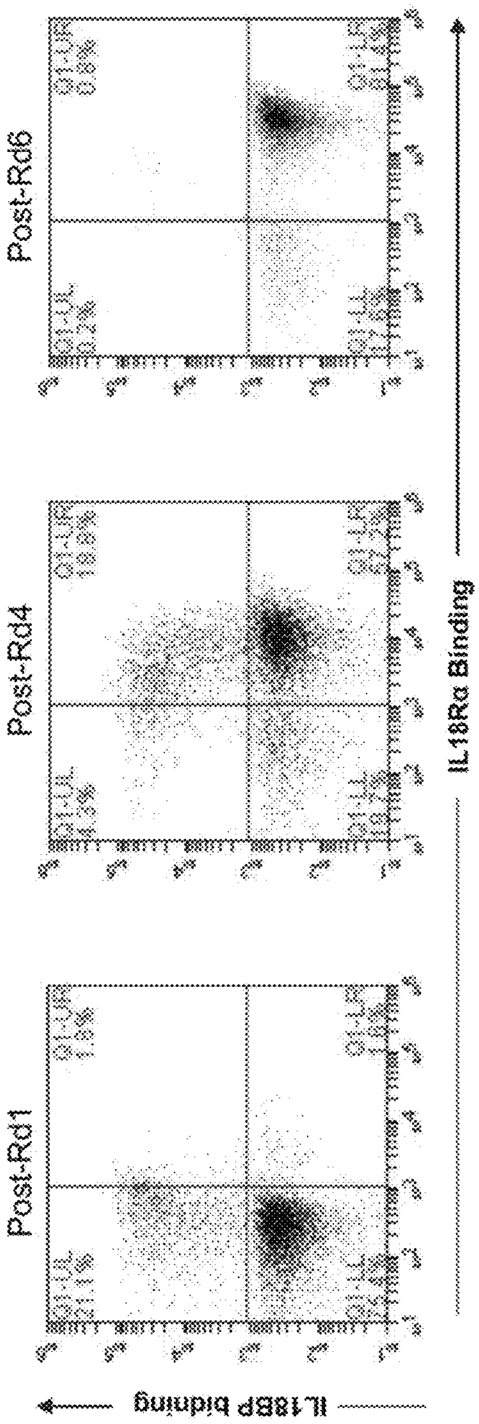

| | | 51 | 53 | 56 | 57 | 60 | 103 | 105 | 110 | 111 | 113 |
|---|---|---|---|---|---|---|---|---|---|---|---|
| | WT hIL-18 | M | K | Q | P | M | Q | S | D | N | M |
| Round 5 variants | 5-18 | E | | E | L | R | P | A | N | R | V |
| | 5-29 | K | | A | G | L | E | D | S | S | R |
| | 5-8 | K | G | A | A | L | | | K | R | |
| | 5-6 | K | G | R | G | L | E | D | N | S | R |
| | 5-26 | K | G | V | | L | A | A | S | R | T |
| | 5-20 | K | S | G | A | L | A | A | G | R | T |
| | 5-2 | K | S | K | A | | A | D | S | S | R |
| | 5-9 | K | S | L | A | L | | D | S | R | |
| | 5-42 | K | S | R | A | L | | N | G | R | |
| | 5-17 | K | S | R | A | L | A | | G | R | T |
| | 5-41 | K | S | R | A | L | A | D | S | G | R |
| | 5-1 | K | T | R | | L | E | D | S | S | K |
| | 5-33 | K | T | R | A | | E | D | N | D | R |
| | 5-21 | R | | G | K | L | R | | S | R | V |
| Round 6 variants | 6-31 | K | G | G | A | L | E | D | S | G | V |
| | 6-20 | K | G | R | | | | A | N | R | |
| | 6-12 | K | S | L | A | L | | D | S | R | |
| | 6-27 | K | S | R | A | L | A | | G | R | T |
| | 6-29 | K | S | R | A | L | | N | G | R | |

FIG. 8

FIG. 9A
IL-18Ra binding:
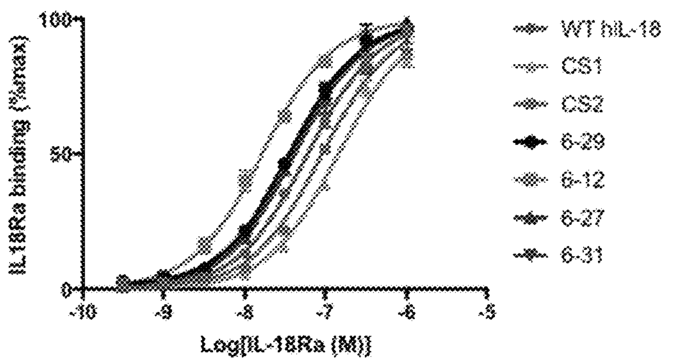
FIG. 9B
IL-18BP binding:
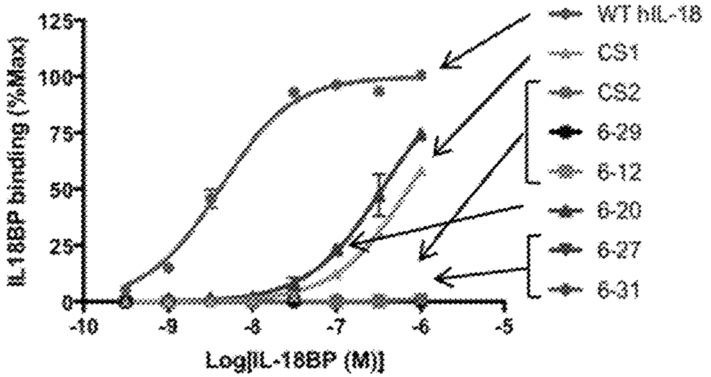
FIG. 9C
Thermal stability:
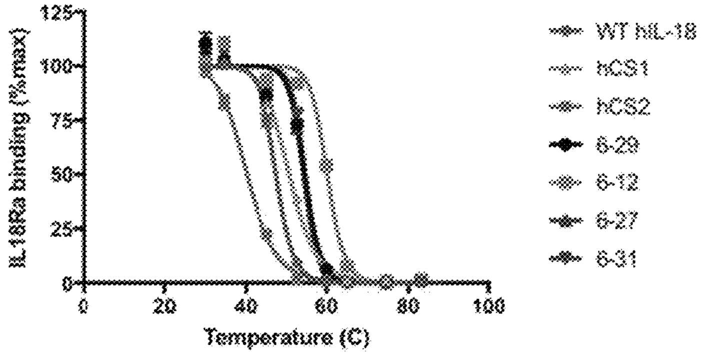
FIG. 9D
| Variant | IL18Rα (KD) | IL18BP (KD) | Rα:BP ratio (norm. to WT) | Tm (°C) |
|---|---|---|---|---|
| WT IL18 | 62 nM | 2.1 nM | 1.0 | 47.6 |
| hCS1 | 146 nM | 710 nM | 140 | 50.9 |
| hCS2 | 92 nM | NBD | >3,200 | 40.2 |
| 6-31 | 41 nM | NBD | >7,200 | 54.9 |
| 6-20 | N.D. | 340 nM | N.D | N.D. |
| 6-12 | 17 nM | NBD | >17,000 | 60.2 |
| 6-27 | 42 nM | NBD | >7,000 | 54.3 |
| 6-29 | 37 nM | NBD | >8,000 | 54.7 |

FIG. 10C

Murine DR-IL-18 variants sequence summary

| | | 1 | 50 | 51 | 52 | 54 | 55 | 56 | 57 | 58 | 59 | 104 | 109 | 151 |
|---|---|---|---|---|---|---|---|---|---|---|---|---|---|---|
| | **mIL-18** | N | M | Y | K | S | E | V | R | G | L | R | N | L |
| Selected Variants | mC1 | | A | | V | R | R | L | | | K | K | | |
| | mA12 | | S | | S | K | H | M | | | K | L | | |
| | mE8 | | V | | T | G | R | R | | | K | K | D | |
| | mC10 | H | A | | G | | H | M | | | K | Q | | V |
| | mB7 | H | A | | G | | N | A | G | | R | K | | |
| | mB1 | H | G | | A | | D | A | | A | K | S | | V |
| | mD1 | H | G | | S | R | G | S | K | | K | Q | | |
| | mH7 | Y | | | A | R | R | A | | | K | K | D | V |
| | mA7 | Y | A | | G | N | R | | | | K | | | |
| | mE1 | Y | G | | G | | | R | G | | R | | D | |
| | mH3 | Y | T | R | T | G | G | Q | K | | V | | D | |
| Consensus Variants | **mCS1** | | G | | A | | R | | | | K | | | |
| | **mCS2** | H | A | | G | | R | A | | | K | | | |

FIG. 20A
| Residue | Amino Acids | Codon |
|---|---|---|
| Y1 | YFLHVD | BWT |
| L5 | L,F,Y,H,R,C | YDT |
| D17 | D,A,G,R,H,P | SVT |
| E31 | E,A,G,T,K,R | RVA |
| T34 | T,A,E,K | RMA |
| D35 | D,A,S,Y | KMT |
| S36 | S,N,K,R | ARW |
| D37 | D,A,Y,S | SNT |
| D40 | D,A,Y,S | KMT |
| N41 | N,K,S,R | ARW |
| M51 | M,I,L,F | WTS |
| M60 | M,I,L,F | WTS |
| Q103 | Q,L,I,K | MWA |
| H109 | H,D,A,P | SMT |
| M113 | M,I,L,F | WTS |
| D132 | D,A,Y,S,V,F | KHY |
FIG. 20B
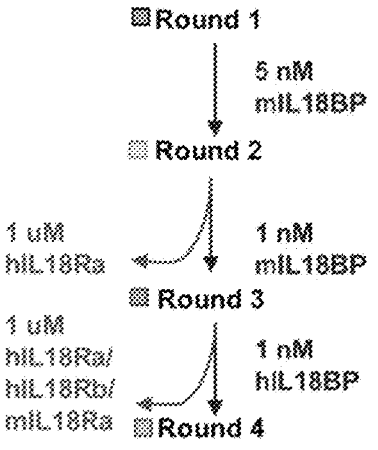
FIG. 20C
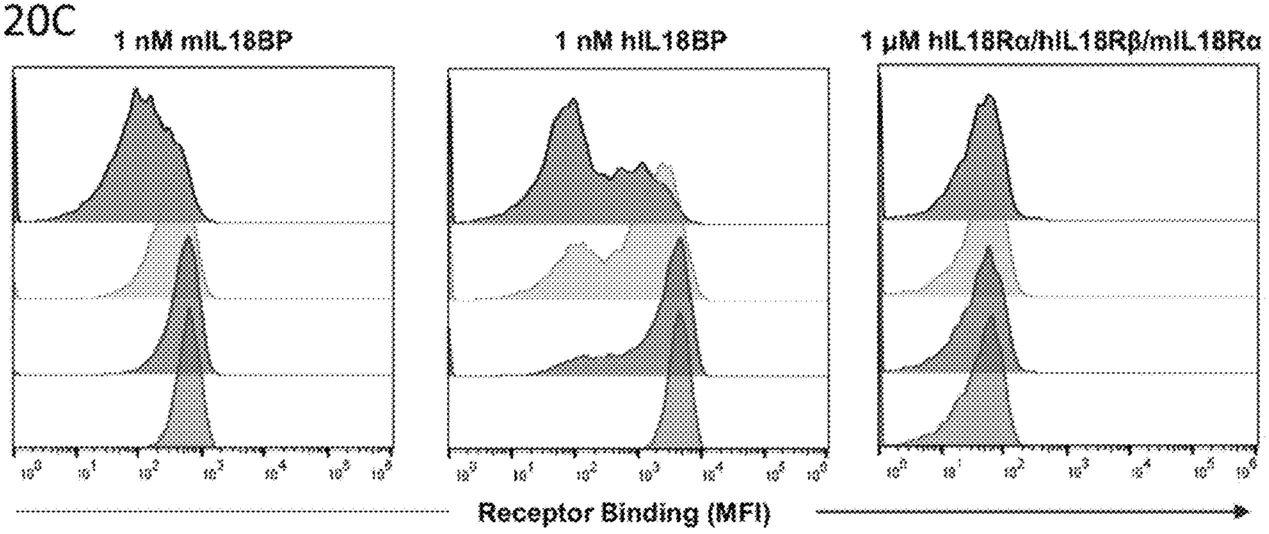

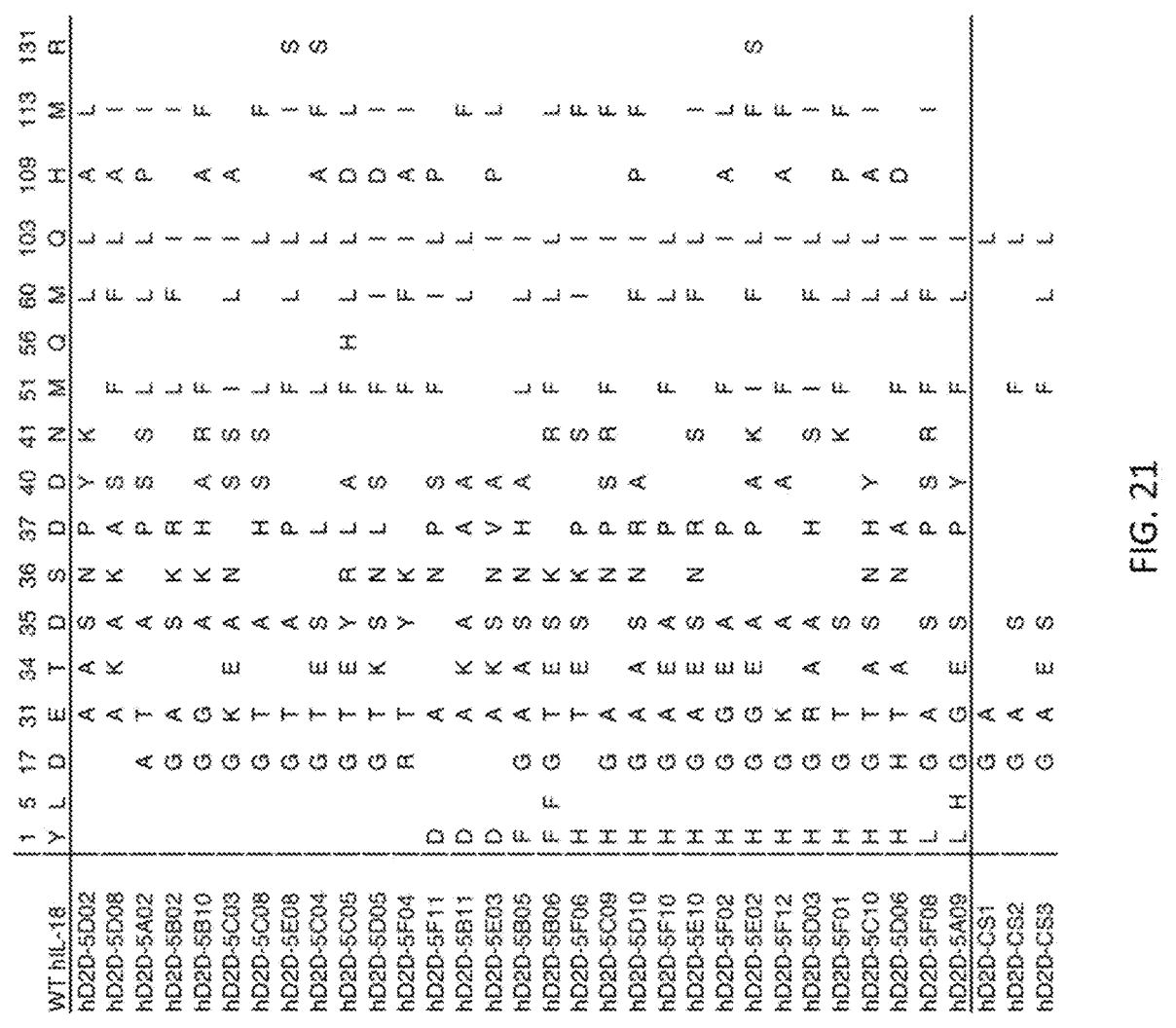

| | 1 | 5 | 17 | 31 | 34 | 35 | 36 | 37 | 40 | 41 | 51 | 56 | 60 | 103 | 109 | 113 | 131 |
|---|---|---|---|---|---|---|---|---|---|---|---|---|---|---|---|---|---|
| WT hIL-18 | Y | L | D | E | T | D | S | D | D | N | M | Q | M | Q | H | M | R |
| hD2D-5D02 | | | | A | A | S | N | P | Y | K | | | L | L | A | L | |
| hD2D-5D08 | | | | A | K | A | K | A | S | | F | | F | L | A | I | |
| hD2D-5A02 | | | A | T | | A | | P | S | S | L | | L | L | P | I | |
| hD2D-5B02 | | | G | A | | S | K | R | | | L | | F | I | | I | |
| hD2D-5B10 | | | G | G | | A | K | H | A | R | F | | | I | A | F | |
| hD2D-5C03 | | | G | K | E | A | N | | S | S | I | | L | I | A | | |
| hD2D-5C08 | | | G | T | | A | | H | S | S | L | | | L | | F | |
| hD2D-5E08 | | | G | T | | A | | P | | | F | | L | L | | I | S |
| hD2D-5C04 | | | G | T | E | S | | L | | | L | | | L | A | F | S |
| hD2D-5C05 | | | G | T | E | Y | R | L | A | | F | H | L | L | D | L | |
| hD2D-5D05 | | | G | T | K | S | N | L | S | | F | | I | I | D | I | |
| hD2D-5F04 | | | R | T | | Y | K | | | | F | | F | I | A | I | |
| hD2D-5F11 | D | | | A | | | N | P | S | | F | | I | L | P | | |
| hD2D-5B11 | D | | | A | K | A | | A | A | | | | L | L | | F | |
| hD2D-5E03 | D | | | A | K | S | N | V | A | | | | | I | P | L | |
| hD2D-5B05 | F | | G | A | A | S | N | H | A | | L | | L | I | | | |
| hD2D-5B06 | F | F | G | T | E | S | K | | | R | F | | L | L | | L | |
| hD2D-5F06 | H | | | T | E | S | K | P | | S | | | I | I | | F | |
| hD2D-5C09 | H | | G | A | | | N | P | S | R | F | | | I | | F | |
| hD2D-5D10 | H | | G | A | A | S | N | R | A | | | | F | I | P | F | |
| hD2D-5F10 | H | | G | A | E | A | | P | | | F | | L | L | | | |
| hD2D-5E10 | H | | G | A | E | S | N | R | | S | | | F | L | | I | |
| hD2D-5F02 | H | | G | G | E | A | | P | | | F | | | I | A | L | |
| hD2D-5E02 | H | | G | G | E | A | | P | A | K | I | | F | L | | F | S |
| hD2D-5F12 | H | | G | K | | A | | | A | | F | | | I | A | F | |
| hD2D-5D03 | H | | G | R | A | A | | H | | S | I | | F | L | | I | |
| hD2D-5F01 | H | | G | T | | S | | | | K | F | | L | L | P | F | |
| hD2D-5C10 | H | | G | T | A | S | N | H | Y | | | | L | L | A | I | |
| hD2D-5D06 | H | | H | T | A | | N | A | | | F | | L | I | D | | |
| hD2D-5F08 | L | | G | A | | S | | P | S | R | F | | F | I | | I | |
| hD2D-5A09 | L | H | G | G | E | S | | P | Y | | F | | L | I | | | |
| hD2D-CS1 | | | G | A | | | | | | | | | | L | | | |
| hD2D-CS2 | | | G | A | | S | | | | | F | | | L | | | |
| hD2D-CS3 | | | G | A | E | S | | | | | F | | L | L | | | |

FIG. 21

FIG. 22A
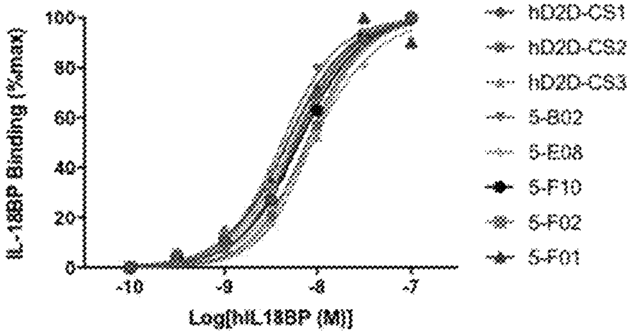
FIG. 22B
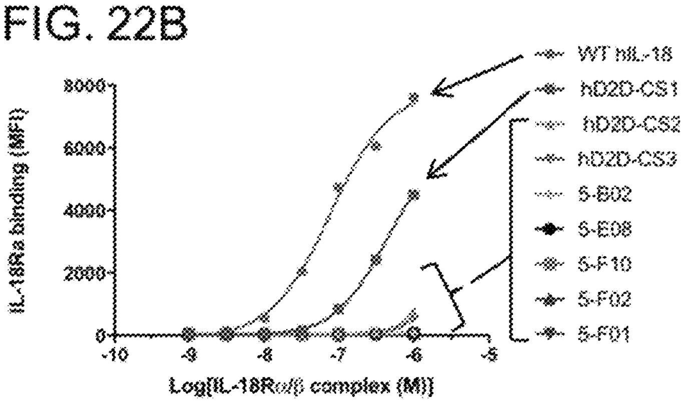
FIG. 22C
| Variant | IL18Rα (KD) | IL18BP (KD) | BP:Rα ratio (norm. to WT) |
|---|---|---|---|
| WT IL18 | 62 nM | 2.1 nM | 1 |
| hD2D-CS1 | 430 nM | 5.9 nM | 2.5 |
| hD2D-CS2 | 21 μM | 7.9 nM | 90 |
| hD2D-CS3 | 9.7 μM | 8.9 nM | 37 |
| 5-B02 | NBD | 4.2 nM | >170 |
| 5-E08 | NBD | 8.8 nM | >81 |
| 5-F10 | NBD | 6.4 nM | >110 |
| 5-F02 | NBD | 5.4 nM | >130 |
| 5-F01 | NBD | 4.8 nM | >150 |

| | 1 | 5 | 17 | 30 | 33 | 34 | 35 | 36 | 50 | 102 | 104 | 108 | 109 | 111 | 129 | 130 | SEQ ID NO: |
|---|---|---|---|---|---|---|---|---|---|---|---|---|---|---|---|---|---|
| WT mIL-18 | N | L | D | E | T | D | I | D | M | Q | R | H | N | M | D | D | 31 |
| mD2D-A5 | Y | Y | Q | A | G | Y | T | V | | L | E | | R | L | | E | 126 |
| mD2D-A6 | D | | | A | G | S | | A | F | L | A | D | | I | A | T | 127 |
| mD2D-A7 | Y | | G | R | A | | T | V | F | I | P | A | S | | A | G | 128 |
| mD2D-A8 | H | | | K | E | Y | T | V | | I | A | D | R | I | | N | 129 |
| mD2D-A9 | Y | | A | A | A | | K | G | | L | P | D | T | | F | G | 130 |
| mD2D-A11 | Y | | E | A | G | | R | H | | I | P | A | S | L | | | 131 |
| mD2D-A12 | H | | | R | G | A | | G | F | I | P | D | S | L | V | | 132 |
| mD2D-B4 | H | | S | T | G | S | | V | | I | G | D | | I | | R | 133 |
| mD2D-B7 | Y | | S | R | E | | T | P | F | I | | D | S | L | F | E | 134 |
| mD2D-B11 | H | | A | G | | A | T | V | F | I | P | D | S | L | | N | 135 |
| mD2D-B12 | | | N | K | E | Y | T | L | F | I | P | D | | L | Y | E | 136 |
| mD2D-C1 | Y | | G | A | E | A | T | R | F | I | G | A | | | | G | 137 |
| mD2D-C3 | | | G | A | R | A | | L | F | L | G | D | | L | | R | 138 |
| mD2D-C5 | Y | | A | A | E | A | T | A | F | I | G | A | S | | | G | 139 |
| mD2D-C6 | L | | G | A | G | A | T | L | | L | P | D | T | | A | S | 140 |
| mD2D-C9 | | | G | | A | Y | T | V | F | I | G | D | S | | Y | | 141 |
| mD2D-C10 | D | | | K | E | S | K | P | F | L | A | A | S | L | A | N | 142 |
| mD2D-C11 | L | | G | A | G | | K | V | | I | P | D | | L | | E | 143 |
| mD2D-D1 | Y | H | Q | R | A | A | T | R | | L | G | D | | | | | 144 |
| mD2D-D9 | | | Q | T | E | S | | G | F | L | A | A | | L | | S | 145 |
| mD2D-D12 | F | H | G | G | G | | R | V | | I | A | D | S | I | | G | 146 |
| mD2D-E3 | V | H | G | K | | Y | | | | L | A | D | T | | A | Q | 147 |
| mD2D-E4 | | | G | A | | A | T | R | | I | Q | A | | I | F | R | 148 |
| mD2D-E5 | D | | G | G | A | Y | | G | F | I | A | | S | I | S | G | 149 |
| mD2D-E7 | Y | | | R | G | S | | A | | I | P | A | T | L | | G | 150 |
| mD2D-E8 | Y | | E | T | E | A | | G | F | I | G | D | R | | | G | 151 |
| mD2D-E9 | F | | N | | E | Y | R | L | | L | P | A | S | L | S | | 152 |
| mD2D-E10 | | | N | A | E | | R | L | | L | G | D | | | | H | 153 |
| mD2D-E11 | Y | | A | R | G | Y | | L | L | L | P | D | T | I | | N | 154 |
| mD2D-E12 | Y | | | G | A | | T | A | F | I | P | D | S | | A | | 155 |
| mD2D-F3 | D | | G | | A | Y | | A | F | I | P | D | S | I | A | | 156 |
| mD2D-F4 | | | E | R | K | Y | | L | F | L | G | D | | | Y | G | 157 |
| mD2D-F5 | D | | E | T | A | Y | | L | F | I | A | D | S | L | | T | 158 |
| mD2D-F7 | D | | N | K | E | S | T | A | | L | G | A | S | L | A | G | 159 |
| mD2D-F8 | H | | E | A | E | A | | G | F | I | G | D | T | L | | G | 160 |
| mD2D-F9 | I | | E | K | R | Y | | V | F | I | E | A | S | L | | E | 161 |
| mD2D-G1 | Y | | A | T | G | Y | T | L | L | I | P | | | I | | R | 162 |
| mD2D-G7 | | | N | R | A | S | T | A | | I | G | | | I | | | 163 |
| mD2D-G9 | D | | G | | K | | R | A | F | L | A | | S | | | E | 164 |
| mD2D-H7 | | | E | A | | | | A | | L | P | D | I | | Y | G | 165 |
| mD2D-E1 | Y | | E | A | | | T | L | F | L | G | D | | | | T | 166 |
| mD2D-A10 | H | | G | K | K | Y | | V | | L | A | | S | I | | S | 169 |
| mD2D-F12 | Y | | G | | K | A | K | A | F | I | P | A | S | | | G | 171 |
| mD2D-E2 | L | | G | G | G | S | | P | F | I | H | A | T | | | N | 174 |
| mD2D-C4 | Y | | S | T | A | Y | T | V | F | I | A | D | S | L | | N | 176 |
| mD2D-C2 | Y | | G | T | G | A | R | V | F | L | P | D | | L | S | G | 178 |
| mD2D-A2 | D | | G | G | K | A | T | G | F | I | A | A | | L | A | G | 180 |
| mD2D-A1 | D | | S | R | G | S | | H | F | L | A | A | | L | | G | 182 |
| mD2D-D4 | Y | | E | K | K | | K | L | F | L | G | D | | L | F | G | 184 |
| mD2D-A3 | Y | | G | A | A | S | T | H | F | L | G | A | | I | | | 186 |
| mD2D-B9 | Y | | S | G | K | Y | | V | F | L | G | D | T | | S | G | 190 |

FIG. 23

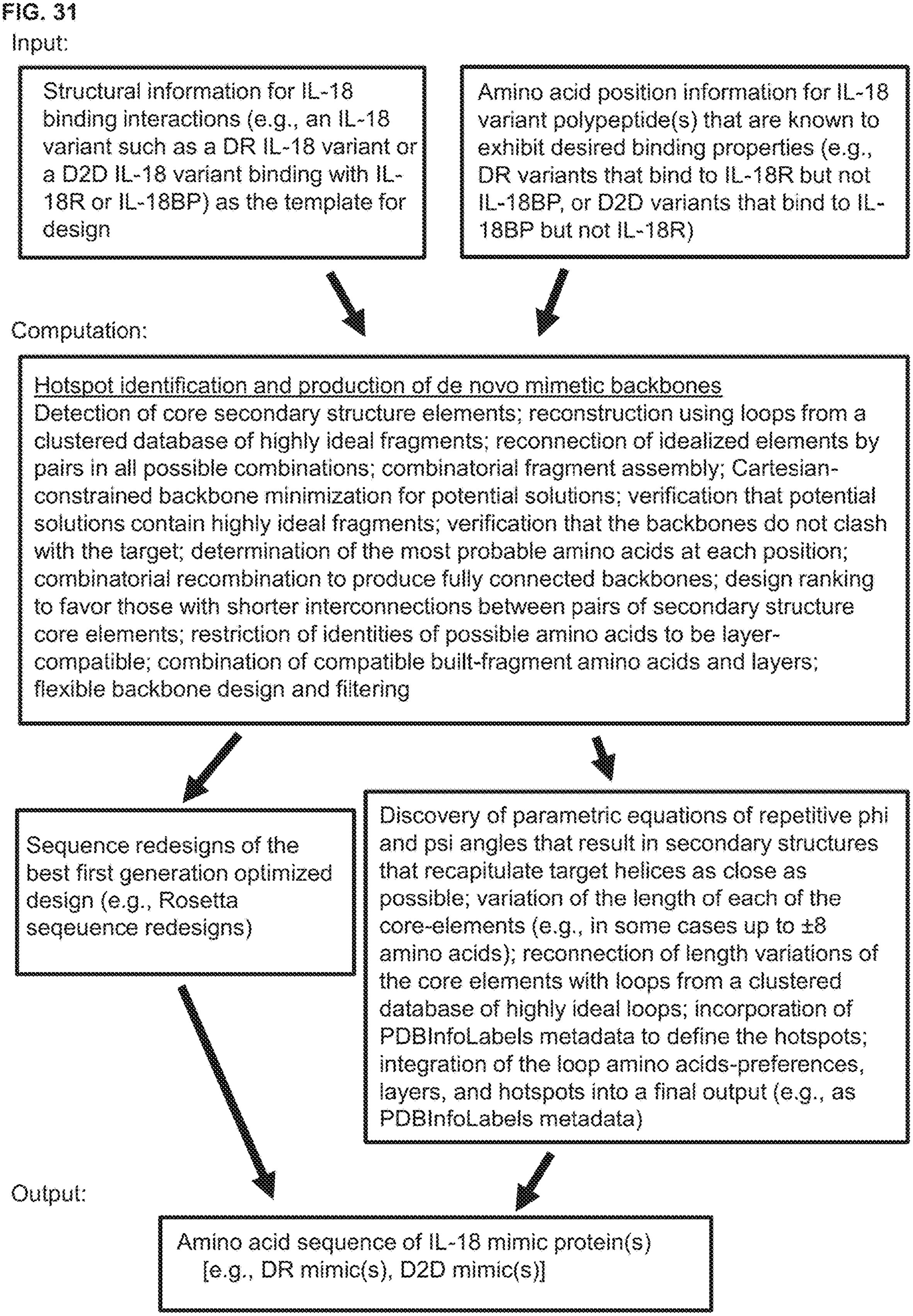

FIG. 31

Input:

| Structural information for IL-18 binding interactions (e.g., an IL-18 variant such as a DR IL-18 variant or a D2D IL-18 variant binding with IL-18R or IL-18BP) as the template for design | Amino acid position information for IL-18 variant polypeptide(s) that are known to exhibit desired binding properties (e.g., DR variants that bind to IL-18R but not IL-18BP, or D2D variants that bind to IL-18BP but not IL-18R) |

Computation:

<u>Hotspot identification and production of de novo mimetic backbones</u>
Detection of core secondary structure elements; reconstruction using loops from a clustered database of highly ideal fragments; reconnection of idealized elements by pairs in all possible combinations; combinatorial fragment assembly; Cartesian-constrained backbone minimization for potential solutions; verification that potential solutions contain highly ideal fragments; verification that the backbones do not clash with the target; determination of the most probable amino acids at each position; combinatorial recombination to produce fully connected backbones; design ranking to favor those with shorter interconnections between pairs of secondary structure core elements; restriction of identities of possible amino acids to be layer-compatible; combination of compatible built-fragment amino acids and layers; flexible backbone design and filtering

| Sequence redesigns of the best first generation optimized design (e.g., Rosetta seqeuence redesigns) | Discovery of parametric equations of repetitive phi and psi angles that result in secondary structures that recapitulate target helices as close as possible; variation of the length of each of the core-elements (e.g., in some cases up to ±8 amino acids); reconnection of length variations of the core elements with loops from a clustered database of highly ideal loops; incorporation of PDBInfoLabels metadata to define the hotspots; integration of the loop amino acids-preferences, layers, and hotspots into a final output (e.g., as PDBInfoLabels metadata) |

Output:

Amino acid sequence of IL-18 mimic protein(s) [e.g., DR mimic(s), D2D mimic(s)]

SEQUENCE LISTING

<160> NUMBER OF SEQ ID NOS: 193

<210> SEQ ID NO 1
<211> LENGTH: 58
<212> TYPE: DNA
<213> ORGANISM: artificial sequence
<220> FEATURE:
<223> OTHER INFORMATION: Synthetic sequence

<400> SEQUENCE: 1
cattttcatt aagatgcagt tacttcgctg tttttcaata ttttctgtta ttgctagc 58

<210> SEQ ID NO 2
<211> LENGTH: 80
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 2
aattacggat gaccgaaagt ykggattcaw ncttgccgaa anrtgctaaa acgctagcaa 60
taacagaaaa tattgaaaaa 80

<210> SEQ ID NO 3
<211> LENGTH: 51
<212> TYPE: DNA
<213> ORGANISM: artificial sequence
<220> FEATURE:
<223> OTHER INFORMATION: Synthetic sequence

<400> SEQUENCE: 3
actttcggtc atccgtaatt tgaacgacca agtccttttt attgaccagg g 51

<210> SEQ ID NO 4
<211> LENGTH: 55
<212> TYPE: DNA
<213> ORGANISM: artificial sequence
<220> FEATURE:
<223> OTHER INFORMATION: Synthetic sequence

<400> SEQUENCE: 4
actatccgtc atatcctcga ataagggacg attgccctgg tcaataaaaa ggact 55

<210> SEQ ID NO 5
<211> LENGTH: 44
<212> TYPE: DNA
<213> ORGANISM: artificial sequence
<220> FEATURE:
<223> OTHER INFORMATION: Synthetic sequence

<400> SEQUENCE: 5
cttattcgag gatatgacgg atagtgattg ccgtgacaac gccc 44

<210> SEQ ID NO 6
<211> LENGTH: 84
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t

<400> SEQUENCE: 6
actgagattg ttaccgcchb tnyacggggt tgwyyatcty tatasnyaga gatgatgaaa 60
attgtacgag gggcgttgtc acgg 84

<210> SEQ ID NO 7
<211> LENGTH: 52
<212> TYPE: DNA
<213> ORGANISM: artificial sequence
<220> FEATURE:
<223> OTHER INFORMATION: Synthetic sequence

<400> SEQUENCE: 7
ggcggtaaca atctcagtta agtgcgaaaa aatctcgaca ctttcttgtg aa 52

<210> SEQ ID NO 8
<211> LENGTH: 53
<212> TYPE: DNA
<213> ORGANISM: artificial sequence
<220> FEATURE:
<223> OTHER INFORMATION: Synthetic sequence

<400> SEQUENCE: 8
ggttcatttc cttgaacgaa atgatcttgt tttcacaaga aagtgtcgag att 53

<210> SEQ ID NO 9
<211> LENGTH: 62
<212> TYPE: DNA
<213> ORGANISM: artificial sequence
<220> FEATURE:
<223> OTHER INFORMATION: Synthetic sequence

<400> SEQUENCE: 9
catttcgttc aaggaaatga acccgccgga taatatcaag gatacaaaat cagatattat 60
tt 62

<210> SEQ ID NO 10

<211> LENGTH: 88
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (27)..(27)
<223> OTHER INFORMATION: n is a, c, g, or t

<400> SEQUENCE: 10
tgatgagctc tcgaattgca tcttatnwtb gtgtccaggc acwyyacgwt bgaagaaaat 60
aatatctgat tttgtatcct tgatatta 88

<210> SEQ ID NO 11
<211> LENGTH: 51
<212> TYPE: DNA
<213> ORGANISM: artificial sequence
<220> FEATURE:
<223> OTHER INFORMATION: Synthetic sequence

<400> SEQUENCE: 11
ataagatgca attcgagagc tcatcatacg aaggttactt tttagcctgc g 51

<210> SEQ ID NO 12
<211> LENGTH: 50
<212> TYPE: DNA
<213> ORGANISM: artificial sequence
<220> FEATURE:
<223> OTHER INFORMATION: Synthetic sequence

<400> SEQUENCE: 12
aattaactta aacaggtcgc gctccttctc gcaggctaaa aagtaacctt 50

<210> SEQ ID NO 13
<211> LENGTH: 49
<212> TYPE: DNA
<213> ORGANISM: artificial sequence
<220> FEATURE:
<223> OTHER INFORMATION: Synthetic sequence

<400> SEQUENCE: 13
gcgacctgtt taagttaatt cttaagaaag aagatgagtt gggggatcg 49

<210> SEQ ID NO 14
<211> LENGTH: 61
<212> TYPE: DNA
<213> ORGANISM: artificial sequence
<220> FEATURE:
<223> OTHER INFORMATION: Synthetic sequence

<400> SEQUENCE: 14
ccagaaccac cgtcctcwtb ctgadyggta aacatgatgc tacgatcccc caactcatct 60
t 61

<210> SEQ ID NO 15
<211> LENGTH: 52
<212> TYPE: DNA
<213> ORGANISM: artificial sequence
<220> FEATURE:
<223> OTHER INFORMATION: Synthetic sequence

<400> SEQUENCE: 15
gaggacggtg gttctggatc cgaacaaaag cttatctccg aagaagactt gg 52

<210> SEQ ID NO 16
<211> LENGTH: 41
<212> TYPE: DNA
<213> ORGANISM: artificial sequence
<220> FEATURE:
<223> OTHER INFORMATION: Synthetic sequence

<400> SEQUENCE: 16
ccaccagatc caccaccacc caagtcttct tcggagataa g 41

<210> SEQ ID NO 17
<211> LENGTH: 62
<212> TYPE: DNA
<213> ORGANISM: artificial sequence
<220> FEATURE:
<223> OTHER INFORMATION: Synthetic sequence

<400> SEQUENCE: 17
cattttcatt aagatgcagt tacttcgctg tttttcaata ttttctgtta ttgctagcgt 60
tt 62

<210> SEQ ID NO 18
<211> LENGTH: 55
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (25)..(25)
<223> OTHER INFORMATION: n is a, c, g, or t

<400> SEQUENCE: 18
ttgtacagtg aagtcggcca aaawntgcta aaacgctagc aataacagaa aatat 55

<210> SEQ ID NO 19
<211> LENGTH: 59
<212> TYPE: DNA
<213> ORGANISM: artificial sequence
<220> FEATURE:
<223> OTHER INFORMATION: Synthetic sequence

<400> SEQUENCE: 19
gccgacttca ctgtacaacc gcagtaatac ggaatataaa tgaccaagtt ctcttcgtt 59

<210> SEQ ID NO 20
<211> LENGTH: 67
<212> TYPE: DNA
<213> ORGANISM: artificial sequence
<220> FEATURE:
<223> OTHER INFORMATION: Synthetic sequence

<400> SEQUENCE: 20
ttgatcaata tcagtcatat cctcgaacac aggctgtctt ttgtcaacga agagaacttg 60
gtcattt 67

<210> SEQ ID NO 21
<211> LENGTH: 54
<212> TYPE: DNA
<213> ORGANISM: artificial sequence
<220> FEATURE:
<223> OTHER INFORMATION: Synthetic sequence

<400> SEQUENCE: 21
gtgttcgagg atatgactga tattgatcaa agtgccagtg aaccccagac caga 54

<210> SEQ ID NO 22
<211> LENGTH: 78
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t

<400> SEQUENCE: 22
tcacagagag ggtcacagcy hbtnywbybn bnybwyygtc snbnynsnyg tatattatca 60
gtctggtctg gggttcac 78

<210> SEQ ID NO 23
<211> LENGTH: 58
<212> TYPE: DNA
<213> ORGANISM: artificial sequence
<220> FEATURE:
<223> OTHER INFORMATION: Synthetic sequence

<400> SEQUENCE: 23
gctgtgaccc tctctgtgaa ggatagtaaa atgtctaccc tctcctgtaa gaacaaga 58

<210> SEQ ID NO 24
<211> LENGTH: 69
<212> TYPE: DNA
<213> ORGANISM: artificial sequence
<220> FEATURE:
<223> OTHER INFORMATION: Synthetic sequence

<400> SEQUENCE: 24
gtatatcatc aatattttca ggtggatcca tttcctcaaa ggaaatgatc ttgttcttac 60
aggagaggg 69

<210> SEQ ID NO 25
<211> LENGTH: 99
<212> TYPE: DNA
<213> ORGANISM: artificial sequence
<220> FEATURE:
<223> OTHER INFORMATION: Synthetic sequence
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t

<400> SEQUENCE: 25
aatggatcca cctgaaaata ttgatgatat acaaagtgat ctcatattct ttcagaaand 60
hgttccagga cacnataaga tggagtttga atcttcact 99

<210> SEQ ID NO 26
<211> LENGTH: 57
<212> TYPE: DNA
<213> ORGANISM: artificial sequence
<220> FEATURE:
<223> OTHER INFORMATION: Synthetic sequence

<400> SEQUENCE: 26
ccttttggca agcaagaaag tgtccttcat acagtgaaga ttcaaactcc atcttat 57

<210> SEQ ID NO 27
<211> LENGTH: 60
<212> TYPE: DNA
<213> ORGANISM: artificial sequence
<220> FEATURE:
<223> OTHER INFORMATION: Synthetic sequence

<400> SEQUENCE: 27
ctttcttgct tgccaaaagg aagatgatgc tttcaaactc attctgaaaa aaaaggatga 60

<210> SEQ ID NO 28
<211> LENGTH: 77
<212> TYPE: DNA
<213> ORGANISM: artificial sequence
<220> FEATURE:
<223> OTHER INFORMATION: Synthetic sequence

<400> SEQUENCE: 28
ccaccacttt gatgtaagtt agtrdbagtg aacattacag atttatcccc attttcatcc 60 tttttttca gaatgag 77

<210> SEQ ID NO 29
<211> LENGTH: 59
<212> TYPE: DNA
<213> ORGANISM: artificial sequence
<220> FEATURE:
<223> OTHER INFORMATION: Synthetic sequence

<400> SEQUENCE: 29
actaacttac atcaaagtgg tggttctgga tccgaacaaa agcttatctc cgaagaaga 59

<210> SEQ ID NO 30
<211> LENGTH: 157
<212> TYPE: PRT
<213> ORGANISM: homo sapiens

<400> SEQUENCE: 30

Tyr Phe Gly Lys Leu Glu Ser Lys Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

```
Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 31
<211> LENGTH: 157
<212> TYPE: PRT
<213> ORGANISM: mus musculus

<400> SEQUENCE: 31

Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 32
<211> LENGTH: 193
<212> TYPE: PRT
<213> ORGANISM: homo sapiens

<400> SEQUENCE: 32

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60
```

```
Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp
```

<210> SEQ ID NO 33
<211> LENGTH: 192
<212> TYPE: PRT
<213> ORGANISM: mus musculus

<400> SEQUENCE: 33

```
Met Ala Ala Met Ser Glu Asp Ser Cys Val Asn Phe Lys Glu Met Met
1               5                   10                  15

Phe Ile Asp Asn Thr Leu Tyr Phe Ile Pro Glu Glu Asn Gly Asp Leu
            20                  25                  30

Glu Ser Asp Asn Phe Gly Arg Leu His Cys Thr Thr Ala Val Ile Arg
        35                  40                  45

Asn Ile Asn Asp Gln Val Leu Phe Val Asp Lys Arg Gln Pro Val Phe
    50                  55                  60

Glu Asp Met Thr Asp Ile Asp Gln Ser Ala Ser Glu Pro Gln Thr Arg
65                  70                  75                  80

Leu Ile Ile Tyr Met Tyr Lys Asp Ser Glu Val Arg Gly Leu Ala Val
                85                  90                  95

Thr Leu Ser Val Lys Asp Ser Lys Met Ser Thr Leu Ser Cys Lys Asn
            100                 105                 110

Lys Ile Ile Ser Phe Glu Glu Met Asp Pro Pro Glu Asn Ile Asp Asp
        115                 120                 125

Ile Gln Ser Asp Leu Ile Phe Phe Gln Lys Arg Val Pro Gly His Asn
    130                 135                 140

Lys Met Glu Phe Glu Ser Ser Leu Tyr Glu Gly His Phe Leu Ala Cys
145                 150                 155                 160

Gln Lys Glu Asp Asp Ala Phe Lys Leu Ile Leu Lys Lys Lys Asp Glu
                165                 170                 175

Asn Gly Asp Lys Ser Val Met Phe Thr Leu Thr Asn Leu His Gln Ser
            180                 185                 190
```

<210> SEQ ID NO 34
<211> LENGTH: 157
<212> TYPE: PRT
<213> ORGANISM: artificial sequence
<220> FEATURE:
<223> OTHER INFORMATION: Synthetic sequence

<400> SEQUENCE: 34

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Lys Asp Ser Gln Pro Arg Gly Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asp Val Pro Gly His Lys His Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 35
<211> LENGTH: 157
<212> TYPE: PRT
<213> ORGANISM: artificial sequence
<220> FEATURE:
<223> OTHER INFORMATION: Synthetic sequence

<400> SEQUENCE: 35

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Lys Asp Lys Gln Pro Arg Ala Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asp Val Pro Gly His Lys His Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Ile Gln Asn Glu Asp
145                 150                 155
```

<210> SEQ ID NO 36
<211> LENGTH: 157
<212> TYPE: PRT
<213> ORGANISM: artificial sequence
<220> FEATURE:
<223> OTHER INFORMATION: Synthetic sequence

<400> SEQUENCE: 36

Arg Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Lys Asp Ser Gln Pro Arg Gly Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asp Val Pro Gly His Lys His Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 37
<211> LENGTH: 157
<212> TYPE: PRT
<213> ORGANISM: artificial sequence
<220> FEATURE:
<223> OTHER INFORMATION: Synthetic sequence

<400> SEQUENCE: 37

Arg Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Arg Asp Ser Gln Pro Arg Gly Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asn Val Pro Gly His Lys Tyr Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 38
<211> LENGTH: 157
<212> TYPE: PRT
<213> ORGANISM: artificial sequence
<220> FEATURE:

-continued

<223> OTHER INFORMATION: Synthetic sequence

<400> SEQUENCE: 38

Tyr Phe Gly Lys Leu Glu Ser Gln Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Thr Tyr Lys Asp Lys Gln Pro Arg Thr Lys Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Gln Arg Arg Val Pro Gly His His Asn Lys
100 105 110

Met Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Lys Glu Asp
145 150 155

<210> SEQ ID NO 39
<211> LENGTH: 157
<212> TYPE: PRT
<213> ORGANISM: artificial sequence
<220> FEATURE:
<223> OTHER INFORMATION: Synthetic sequence

<400> SEQUENCE: 39

Tyr Phe Gly Lys Leu Glu Ser Arg Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Lys Tyr Lys Asp Lys Gln Pro Arg Ala Gln Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Gln Arg Asp Val Pro Gly His Lys His Lys
100 105 110

Met Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Ile Gln Asn Glu Asp
145 150 155

<210> SEQ ID NO 40
<211> LENGTH: 157
<212> TYPE: PRT
<213> ORGANISM: artificial sequence -continued
<220> FEATURE:
<223> OTHER INFORMATION: Synthetic sequence
<220> FEATURE:
<221> NAME/KEY: misc_feature
<222> LOCATION: (60)..(60)
<223> OTHER INFORMATION: Xaa can be any naturally occurring amino acid

<400> SEQUENCE: 40

```
Tyr Phe Gly Lys Leu Glu Ser Arg Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Asp Tyr Lys Asp Lys Gln Pro Arg Ala Xaa Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asp Val Pro Gly His Lys His Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Ile Gln Asn Glu Asp
145                 150                 155
```

<210> SEQ ID NO 41
<211> LENGTH: 157
<212> TYPE: PRT
<213> ORGANISM: artificial sequence
<220> FEATURE:
<223> OTHER INFORMATION: Synthetic sequence

<400> SEQUENCE: 41

```
Tyr Phe Gly Lys His Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Arg Asp Ser Gln Pro Arg Gly Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asp Val Pro Gly His Asn Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Thr Gln Asn Glu Asp
145                 150                 155
```

<210> SEQ ID NO 42
<211> LENGTH: 157
<212> TYPE: PRT
<213> ORGANISM: artificial sequence
<220> FEATURE:
<223> OTHER INFORMATION: Synthetic sequence

<400> SEQUENCE: 42

```
Tyr Phe Gly Lys Ile Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Lys Asp Lys Gln Pro Arg Ala Gln Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Lys Val Pro Gly His Gln His Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Lys Glu Asp
145                 150                 155
```

<210> SEQ ID NO 43
<211> LENGTH: 157
<212> TYPE: PRT
<213> ORGANISM: artificial sequence
<220> FEATURE:
<223> OTHER INFORMATION: Synthetic sequence

<400> SEQUENCE: 43

```
Tyr Phe Gly Lys Ile Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Lys Asp Arg Gln Pro Arg Gly Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Glu Arg Asp Val Pro Gly His His His Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Ile Gln Asn Glu Asp
145                 150                 155
```

<210> SEQ ID NO 44
<211> LENGTH: 157
<212> TYPE: PRT
<213> ORGANISM: artificial sequence
<220> FEATURE:
<223> OTHER INFORMATION: Synthetic sequence

<400> SEQUENCE: 44

```
Tyr Phe Gly Lys Ile Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Lys Asp Lys Gln Pro Arg Gly Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asp Val Pro Gly His Lys His Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Thr Gln His Glu Asp
145                 150                 155
```

<210> SEQ ID NO 45
<211> LENGTH: 157
<212> TYPE: PRT
<213> ORGANISM: artificial sequence
<220> FEATURE:
<223> OTHER INFORMATION: Synthetic sequence

<400> SEQUENCE: 45

```
Tyr Phe Gly Lys Ile Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Lys Asp Lys Gln Pro Arg Ala Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Arg Val Pro Gly His His His Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140
```

Gly Asp Arg Ser Ile Met Phe Thr Ile Gln Lys Glu Asp
145 150 155

<210> SEQ ID NO 46
<211> LENGTH: 157
<212> TYPE: PRT
<213> ORGANISM: artificial sequence
<220> FEATURE:
<223> OTHER INFORMATION: Synthetic sequence

<400> SEQUENCE: 46

Tyr Phe Gly Lys Ile Glu Ser Arg Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Thr Tyr Lys Asp Lys Gln Pro Arg Gly Lys Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Gln Arg Asp Val Pro Gly His Asp Tyr Lys
100 105 110

Met Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Ile Gln Lys Glu Asp
145 150 155

<210> SEQ ID NO 47
<211> LENGTH: 157
<212> TYPE: PRT
<213> ORGANISM: artificial sequence
<220> FEATURE:
<223> OTHER INFORMATION: Synthetic sequence

<400> SEQUENCE: 47

Tyr Phe Gly Lys Tyr Glu Ser Arg Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Thr Tyr Arg Asp Ser Gln Pro Arg Gly Lys Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Gln Arg Asp Val Pro Gly His Glu His Lys
100 105 110

Met Gln Phe Glu Ser Ser Ser Tyr Glu Gly Tyr Phe Leu Ala Cys Glu
115 120 125

```
Lys Glu Arg Asp Leu Phe Lys Leu Ile Leu Lys Lys Glu Asp Glu Leu
    130                 135                 140

Gly Asp Arg Ser Ile Met Phe Thr Val Gln Lys Glu Asp
145                 150                 155
```

<210> SEQ ID NO 48
<211> LENGTH: 157
<212> TYPE: PRT
<213> ORGANISM: artificial sequence
<220> FEATURE:
<223> OTHER INFORMATION: Synthetic sequence

<400> SEQUENCE: 48

```
His Phe Gly Lys Tyr Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Arg Asp Ser Gln Pro Arg Gly Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asp Val Pro Gly His His Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Lys Glu Asp
145                 150                 155
```

<210> SEQ ID NO 49
<211> LENGTH: 157
<212> TYPE: PRT
<213> ORGANISM: artificial sequence
<220> FEATURE:
<223> OTHER INFORMATION: Synthetic sequence

<400> SEQUENCE: 49

```
Arg Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Arg Asp Ser Gln Pro Arg Ala Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asp Val Pro Gly His Gln His Lys
            100                 105                 110
```

```
Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Ala Gln Lys Glu Asp
145                 150                 155


<210> SEQ ID NO 50
<211> LENGTH: 157
<212> TYPE: PRT
<213> ORGANISM: artificial sequence
<220> FEATURE:
<223> OTHER INFORMATION: Synthetic sequence

<400> SEQUENCE: 50

Arg Phe Gly Lys Leu Glu Ser Arg Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Asp Tyr Arg Asp Ser Gln Pro Arg Gly Arg Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Lys Arg Asn Val Pro Gly His Lys Tyr Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln His Glu Asp
145                 150                 155


<210> SEQ ID NO 51
<211> LENGTH: 157
<212> TYPE: PRT
<213> ORGANISM: artificial sequence
<220> FEATURE:
<223> OTHER INFORMATION: Synthetic sequence

<400> SEQUENCE: 51

Arg Phe Gly Lys Leu Glu Ser Arg Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Asn Tyr Arg Asp Ser Gln Pro Arg Gly Gln Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95
```

```
Ser Asp Ile Ile Phe Phe Lys Arg Arg Val Pro Gly His Asn His Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Lys Glu Asp
145                 150                 155


<210> SEQ ID NO 52
<211> LENGTH: 157
<212> TYPE: PRT
<213> ORGANISM: artificial sequence
<220> FEATURE:
<223> OTHER INFORMATION: Synthetic sequence

<400> SEQUENCE: 52

Arg Phe Gly Lys Leu Glu Ser Arg Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Lys Asp Ser Gln Pro Arg Gly Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asp Val Pro Gly His Lys His Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 53
<211> LENGTH: 157
<212> TYPE: PRT
<213> ORGANISM: artificial sequence
<220> FEATURE:
<223> OTHER INFORMATION: Synthetic sequence

<400> SEQUENCE: 53

Arg Phe Gly Lys His Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Arg Asp Ser Gln Pro Arg Gly Lys Ala Val Thr Ile
    50                  55                  60

Ser Val Lys Cys Glu Lys Ile Ser Thr Leu Ser Cys Glu Asn Lys Ile
65                  70                  75                  80
```

Ile Ser Phe Lys Glu Met Asn Pro Pro Asp Asn Ile Lys Asp Thr Lys
85 90 95

Ser Asp Ile Ile Phe Phe Glu Arg Asn Val Pro Gly His Lys Tyr Lys
100 105 110

Met Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 54
<211> LENGTH: 157
<212> TYPE: PRT
<213> ORGANISM: artificial sequence
<220> FEATURE:
<223> OTHER INFORMATION: Synthetic sequence
<220> FEATURE:
<221> NAME/KEY: misc_feature
<222> LOCATION: (155)..(155)
<223> OTHER INFORMATION: Xaa can be any naturally occurring amino acid

<400> SEQUENCE: 54

Arg Phe Gly Lys Leu Glu Ser Arg Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Thr Tyr Arg Asp Ser Gln Pro Arg Ala Lys Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Glu Arg Asp Val Pro Gly His Gln His Lys
100 105 110

Met Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Ile Gln Xaa Glu Asp
145 150 155

<210> SEQ ID NO 55
<211> LENGTH: 157
<212> TYPE: PRT
<213> ORGANISM: artificial sequence
<220> FEATURE:
<223> OTHER INFORMATION: Synthetic sequence

<400> SEQUENCE: 55

Arg Phe Gly Lys Leu Glu Ser Arg Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

```
Ile Ser Thr Tyr Arg Asp Ser Gln Pro Arg Thr Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asn Val Pro Gly His His Asp Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln His Glu Asp
145                 150                 155


<210> SEQ ID NO 56
<211> LENGTH: 157
<212> TYPE: PRT
<213> ORGANISM: artificial sequence
<220> FEATURE:
<223> OTHER INFORMATION: Synthetic sequence

<400> SEQUENCE: 56

Arg Phe Gly Lys Leu Glu Ser Arg Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Lys Asp Ser Gln Pro Arg Ala Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Glu Arg Asp Val Pro Gly His Gln His Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Ile Gln Lys Glu Asp
145                 150                 155


<210> SEQ ID NO 57
<211> LENGTH: 157
<212> TYPE: PRT
<213> ORGANISM: artificial sequence
<220> FEATURE:
<223> OTHER INFORMATION: Synthetic sequence

<400> SEQUENCE: 57

Arg Phe Gly Lys His Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45
```

Ile Ser Thr Tyr Arg Asp Ser Gln Pro Arg Gly Lys Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Glu Arg Asn Val Pro Gly His Lys Tyr Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 58
<211> LENGTH: 157
<212> TYPE: PRT
<213> ORGANISM: artificial sequence
<220> FEATURE:
<223> OTHER INFORMATION: Synthetic sequence

<400> SEQUENCE: 58

Arg Phe Gly Lys Tyr Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Thr Tyr Lys Asp Ser Gln Pro Arg Thr Lys Ala Val Thr Ile
    50                  55                  60

Ser Val Lys Cys Glu Lys Ile Ser Thr Leu Ser Cys Asp Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asp Val Pro Gly His Lys His Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 59
<211> LENGTH: 157
<212> TYPE: PRT
<213> ORGANISM: artificial sequence
<220> FEATURE:
<223> OTHER INFORMATION: Synthetic sequence

<400> SEQUENCE: 59

Arg Phe Gly Lys Leu Glu Ser Arg Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
35 40 45

Ile Ser Thr Tyr Arg Asp Ser Gln Pro Arg Thr Lys Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Gln Arg Lys Val Pro Gly His Asn His Lys
100 105 110

Met Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Lys Glu Asp
145 150 155

<210> SEQ ID NO 60
<211> LENGTH: 157
<212> TYPE: PRT
<213> ORGANISM: artificial sequence
<220> FEATURE:
<223> OTHER INFORMATION: Synthetic sequence

<400> SEQUENCE: 60

Asn Phe Gly Arg Leu His Cys Thr Thr Ala Val Ile Arg Asn Ile Asn
1 5 10 15

Asp Gln Val Leu Phe Val Asp Lys Arg Gln Pro Val Phe Glu Asp Met
20 25 30

Thr Asp Ile Asp Gln Ser Ala Ser Glu Pro Gln Thr Arg Leu Ile Ile
35 40 45

Tyr Gly Tyr Ala Asp Ser Arg Val Arg Gly Lys Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Gln Lys Arg Val Pro Gly His Asn Lys Met Glu
100 105 110

Phe Glu Ser Ser Leu Tyr Glu Gly His Phe Leu Ala Cys Gln Lys Glu
115 120 125

Asp Asp Ala Phe Lys Leu Ile Leu Lys Lys Lys Asp Glu Asn Gly Asp
130 135 140

Lys Ser Val Met Phe Thr Leu Thr Asn Leu His Gln Ser
145 150 155

<210> SEQ ID NO 61
<211> LENGTH: 157
<212> TYPE: PRT
<213> ORGANISM: artificial sequence
<220> FEATURE:
<223> OTHER INFORMATION: Synthetic sequence

<400> SEQUENCE: 61

His Phe Gly Arg Leu His Cys Thr Thr Ala Val Ile Arg Asn Ile Asn
1 5 10 15

```
Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Ala Tyr Gly Asp Ser Arg Ala Arg Gly Lys Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 62
<211> LENGTH: 157
<212> TYPE: PRT
<213> ORGANISM: artificial sequence
<220> FEATURE:
<223> OTHER INFORMATION: Synthetic sequence

<400> SEQUENCE: 62

Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Ala Tyr Val Asp Arg Arg Leu Arg Gly Lys Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Lys Val Pro Gly His Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 63
<211> LENGTH: 157
<212> TYPE: PRT
<213> ORGANISM: artificial sequence
<220> FEATURE:
<223> OTHER INFORMATION: Synthetic sequence
```

<400> SEQUENCE: 63

```
Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Ser Tyr Ser Asp Lys His Met Arg Gly Lys Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Leu Val Pro Gly His Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 64
<211> LENGTH: 157
<212> TYPE: PRT
<213> ORGANISM: artificial sequence
<220> FEATURE:
<223> OTHER INFORMATION: Synthetic sequence

<400> SEQUENCE: 64

```
Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Val Tyr Thr Asp Gly Arg Arg Arg Gly Lys Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Lys Val Pro Gly His Asp Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 65
<211> LENGTH: 157
<212> TYPE: PRT
<213> ORGANISM: artificial sequence
<220> FEATURE:

<223> OTHER INFORMATION: Synthetic sequence

<400> SEQUENCE: 65

His Phe Gly Arg Leu His Cys Thr Thr Ala Val Ile Arg Asn Ile Asn
1 5 10 15

Asp Gln Val Leu Phe Val Asp Lys Arg Gln Pro Val Phe Glu Asp Met
20 25 30

Thr Asp Ile Asp Gln Ser Ala Ser Glu Pro Gln Thr Arg Leu Ile Ile
35 40 45

Tyr Ala Tyr Gly Asp Ser His Met Arg Gly Lys Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Gln Lys Gln Val Pro Gly His Asn Lys Met Glu
100 105 110

Phe Glu Ser Ser Leu Tyr Glu Gly His Phe Leu Ala Cys Gln Lys Glu
115 120 125

Asp Asp Ala Phe Lys Leu Ile Leu Lys Lys Lys Asp Glu Asn Gly Asp
130 135 140

Lys Ser Val Met Phe Thr Val Thr Asn Leu His Gln Ser
145 150 155

<210> SEQ ID NO 66
<211> LENGTH: 157
<212> TYPE: PRT
<213> ORGANISM: artificial sequence
<220> FEATURE:
<223> OTHER INFORMATION: Synthetic sequence

<400> SEQUENCE: 66

His Phe Gly Arg Leu His Cys Thr Thr Ala Val Ile Arg Asn Ile Asn
1 5 10 15

Asp Gln Val Leu Phe Val Asp Lys Arg Gln Pro Val Phe Glu Asp Met
20 25 30

Thr Asp Ile Asp Gln Ser Ala Ser Glu Pro Gln Thr Arg Leu Ile Ile
35 40 45

Tyr Ala Tyr Gly Asp Ser Asn Ala Gly Gly Arg Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Gln Lys Lys Val Pro Gly His Asn Lys Met Glu
100 105 110

Phe Glu Ser Ser Leu Tyr Glu Gly His Phe Leu Ala Cys Gln Lys Glu
115 120 125

Asp Asp Ala Phe Lys Leu Ile Leu Lys Lys Lys Asp Glu Asn Gly Asp
130 135 140

Lys Ser Val Met Phe Thr Leu Thr Asn Leu His Gln Ser
145 150 155

<210> SEQ ID NO 67
<211> LENGTH: 157
<212> TYPE: PRT
<213> ORGANISM: artificial sequence
<220> FEATURE:
<223> OTHER INFORMATION: Synthetic sequence

<400> SEQUENCE: 67

```
His Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Gly Tyr Ala Asp Ser Asp Ala Arg Ala Lys Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Ser Val Pro Gly His Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Val Thr Asn Leu His Gln Ser
145                 150                 155
```

<210> SEQ ID NO 68
<211> LENGTH: 157
<212> TYPE: PRT
<213> ORGANISM: artificial sequence
<220> FEATURE:
<223> OTHER INFORMATION: Synthetic sequence

<400> SEQUENCE: 68

```
His Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Gly Tyr Ser Asp Arg Gly Ser Lys Gly Lys Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Gln Val Pro Gly His Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 69
<211> LENGTH: 157
<212> TYPE: PRT

```
<213> ORGANISM: artificial sequence
<220> FEATURE:
<223> OTHER INFORMATION: Synthetic sequence

<400> SEQUENCE: 69

Tyr Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Met Tyr Ala Asp Arg Arg Ala Arg Gly Lys Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Lys Val Pro Gly His Asp Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Val Thr Asn Leu His Gln Ser
145                 150                 155


<210> SEQ ID NO 70
<211> LENGTH: 157
<212> TYPE: PRT
<213> ORGANISM: artificial sequence
<220> FEATURE:
<223> OTHER INFORMATION: Synthetic sequence

<400> SEQUENCE: 70

Tyr Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Ala Tyr Gly Asp Asn Arg Val Arg Gly Lys Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 71
<211> LENGTH: 157
```

<212> TYPE: PRT
<213> ORGANISM: artificial sequence
<220> FEATURE:
<223> OTHER INFORMATION: Synthetic sequence

<400> SEQUENCE: 71

```
Tyr Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Gly Tyr Gly Asp Ser Glu Arg Gly Gly Arg Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Arg Val Pro Gly His Asp Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 72
<211> LENGTH: 157
<212> TYPE: PRT
<213> ORGANISM: artificial sequence
<220> FEATURE:
<223> OTHER INFORMATION: Synthetic sequence

<400> SEQUENCE: 72

```
Tyr Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Thr Arg Thr Asp Gly Gly Gln Lys Gly Val Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Arg Val Pro Gly His Asp Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 73

```
<211> LENGTH: 157
<212> TYPE: PRT
<213> ORGANISM: artificial sequence
<220> FEATURE:
<223> OTHER INFORMATION: Synthetic sequence

<400> SEQUENCE: 73

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Glu Tyr Lys Asp Ser Glu Leu Arg Gly Arg Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Pro Arg Ala Val Pro Gly His Asn Arg Lys
            100                 105                 110

Val Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 74
<211> LENGTH: 157
<212> TYPE: PRT
<213> ORGANISM: artificial sequence
<220> FEATURE:
<223> OTHER INFORMATION: Synthetic sequence

<400> SEQUENCE: 74

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Lys Asp Ser Ala Gly Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Glu Arg Asp Val Pro Gly His Ser Asn Lys
            100                 105                 110

Val Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 75
<211> LENGTH: 157
<212> TYPE: PRT
<213> ORGANISM: artificial sequence
<220> FEATURE:
<223> OTHER INFORMATION: Synthetic sequence

<400> SEQUENCE: 75

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Gly Asp Ser Ala Ala Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Lys Arg Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 76
<211> LENGTH: 157
<212> TYPE: PRT
<213> ORGANISM: artificial sequence
<220> FEATURE:
<223> OTHER INFORMATION: Synthetic sequence

<400> SEQUENCE: 76

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Gly Asp Ser Arg Gly Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Glu Arg Asp Val Pro Gly His Asn Ser Lys
            100                 105                 110

Arg Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

```
<210> SEQ ID NO 77
<211> LENGTH: 157
<212> TYPE: PRT
<213> ORGANISM: artificial sequence
<220> FEATURE:
<223> OTHER INFORMATION: Synthetic sequence

<400> SEQUENCE: 77

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Gly Asp Ser Val Pro Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ala Arg Ala Val Pro Gly His Ser Arg Lys
            100                 105                 110

Thr Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 78
<211> LENGTH: 157
<212> TYPE: PRT
<213> ORGANISM: artificial sequence
<220> FEATURE:
<223> OTHER INFORMATION: Synthetic sequence

<400> SEQUENCE: 78

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Ser Asp Ser Gly Ala Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ala Arg Ala Val Pro Gly His Gly Arg Lys
            100                 105                 110

Thr Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 79
<211> LENGTH: 157
<212> TYPE: PRT
<213> ORGANISM: artificial sequence
<220> FEATURE:
<223> OTHER INFORMATION: Synthetic sequence

<400> SEQUENCE: 79

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Ser Asp Ser Lys Ala Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ala Arg Asp Val Pro Gly His Ser Ser Lys
            100                 105                 110

Arg Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 80
<211> LENGTH: 157
<212> TYPE: PRT
<213> ORGANISM: artificial sequence
<220> FEATURE:
<223> OTHER INFORMATION: Synthetic sequence

<400> SEQUENCE: 80

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Ser Asp Ser Leu Ala Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asp Val Pro Gly His Ser Arg Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140
```

```
Gly Asp Arg Ser Ile Met Phe Thr Val Gln Asn Glu Asp
145                 150                 155


<210> SEQ ID NO 81
<211> LENGTH: 157
<212> TYPE: PRT
<213> ORGANISM: artificial sequence
<220> FEATURE:
<223> OTHER INFORMATION: Synthetic sequence

<400> SEQUENCE: 81

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Ser Asp Ser Arg Ala Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asn Val Pro Gly His Gly Arg Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 82
<211> LENGTH: 157
<212> TYPE: PRT
<213> ORGANISM: artificial sequence
<220> FEATURE:
<223> OTHER INFORMATION: Synthetic sequence

<400> SEQUENCE: 82

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Ser Asp Ser Arg Ala Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ala Arg Ser Val Pro Gly His Gly Arg Lys
            100                 105                 110

Thr Gln Phe Glu Ser Ser Ser Tyr Glu Gly Tyr Phe Leu Ala Cys Glu
        115                 120                 125
```

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 83
<211> LENGTH: 157
<212> TYPE: PRT
<213> ORGANISM: artificial sequence
<220> FEATURE:
<223> OTHER INFORMATION: Synthetic sequence

<400> SEQUENCE: 83

Tyr Phe Gly Lys Leu Glu Ser Lys Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Lys Tyr Ser Asp Ser Arg Ala Arg Gly Leu Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Ala Arg Asp Val Pro Gly His Ser Gly Lys
100 105 110

Arg Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 84
<211> LENGTH: 157
<212> TYPE: PRT
<213> ORGANISM: artificial sequence
<220> FEATURE:
<223> OTHER INFORMATION: Synthetic sequence

<400> SEQUENCE: 84

Tyr Phe Gly Lys Leu Glu Ser Lys Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Lys Tyr Thr Asp Ser Arg Pro Arg Gly Leu Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Glu Arg Asp Val Pro Gly His Ser Ser Lys
100 105 110

Lys Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 85
<211> LENGTH: 157
<212> TYPE: PRT
<213> ORGANISM: artificial sequence
<220> FEATURE:
<223> OTHER INFORMATION: Synthetic sequence

<400> SEQUENCE: 85

Tyr Phe Gly Lys Leu Glu Ser Lys Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Lys Tyr Thr Asp Ser Arg Ala Arg Gly Met Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Glu Arg Asp Val Pro Gly His Asn Asp Lys
100 105 110

Arg Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 86
<211> LENGTH: 157
<212> TYPE: PRT
<213> ORGANISM: artificial sequence
<220> FEATURE:
<223> OTHER INFORMATION: Synthetic sequence

<400> SEQUENCE: 86

Tyr Phe Gly Lys Leu Glu Ser Lys Leu Ser Val Ile Arg Asn Leu Asn
1 5 10 15

Asp Gln Val Leu Phe Ile Asp Gln Gly Asn Arg Pro Leu Phe Glu Asp
20 25 30

Met Thr Asp Ser Asp Cys Arg Asp Asn Ala Pro Arg Thr Ile Phe Ile
35 40 45

Ile Ser Arg Tyr Lys Asp Ser Gly Lys Arg Gly Leu Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

```
Ser Asp Ile Ile Phe Phe Arg Arg Ser Val Pro Gly His Ser Arg Lys
            100                 105                 110

Val Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 87
<211> LENGTH: 157
<212> TYPE: PRT
<213> ORGANISM: artificial sequence
<220> FEATURE:
<223> OTHER INFORMATION: Synthetic sequence

<400> SEQUENCE: 87

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Gly Asp Ser Gly Ala Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Glu Arg Asp Val Pro Gly His Ser Gly Lys
            100                 105                 110

Val Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 88
<211> LENGTH: 157
<212> TYPE: PRT
<213> ORGANISM: artificial sequence
<220> FEATURE:
<223> OTHER INFORMATION: Synthetic sequence

<400> SEQUENCE: 88

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Gly Asp Ser Arg Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80
```

```
Ile Ser Phe Lys Glu Met Asn Pro Pro Asp Asn Ile Lys Asp Thr Lys
                85                  90                  95

Ser Asp Ile Ile Phe Phe Gln Arg Ala Val Pro Gly His Asn Arg Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

```
<210> SEQ ID NO 89
<211> LENGTH: 157
<212> TYPE: PRT
<213> ORGANISM: artificial sequence
<220> FEATURE:
<223> OTHER INFORMATION: Synthetic sequence

<400> SEQUENCE: 89

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Ser Asp Ser Leu Ala Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asp Val Pro Gly His Ser Arg Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

```
<210> SEQ ID NO 90
<211> LENGTH: 157
<212> TYPE: PRT
<213> ORGANISM: artificial sequence
<220> FEATURE:
<223> OTHER INFORMATION: Synthetic sequence

<400> SEQUENCE: 90

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Ser Asp Ser Arg Ala Arg Gly Leu Ala Val Thr Ile
    50                  55                  60
```

```
Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ala Arg Ser Val Pro Gly His Gly Arg Lys
            100                 105                 110

Thr Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 91
<211> LENGTH: 157
<212> TYPE: PRT
<213> ORGANISM: artificial sequence
<220> FEATURE:
<223> OTHER INFORMATION: Synthetic sequence

<400> SEQUENCE: 91

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Ser Asp Ser Arg Ala Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Asn Val Pro Gly His Gly Arg Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 92
<211> LENGTH: 157
<212> TYPE: PRT
<213> ORGANISM: artificial sequence
<220> FEATURE:
<223> OTHER INFORMATION: Synthetic sequence

<400> SEQUENCE: 92

His Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Lys Asp
            20                  25                  30

Met Thr Ala Ser Asp Cys Arg Ala Asn Ala Pro Arg Thr Ile Phe Ile
        35                  40                  45
```

Ile Ser Phe Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ile Arg Ser Val Pro Gly Ala Asp Asn Lys
            100                 105                 110

Phe Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 93
<211> LENGTH: 157
<212> TYPE: PRT
<213> ORGANISM: artificial sequence
<220> FEATURE:
<223> OTHER INFORMATION: Synthetic sequence

<400> SEQUENCE: 93

Asp Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Ala Asp
            20                  25                  30

Met Thr Asp Asn Pro Cys Arg Ser Asn Ala Pro Arg Thr Ile Phe Ile
        35                  40                  45

Ile Ser Phe Tyr Lys Asp Ser Gln Pro Arg Gly Ile Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Leu Arg Ser Val Pro Gly Pro Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 94
<211> LENGTH: 157
<212> TYPE: PRT
<213> ORGANISM: artificial sequence
<220> FEATURE:
<223> OTHER INFORMATION: Synthetic sequence

<400> SEQUENCE: 94

His Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Ala Asp
            20                  25                  30

```
Met Glu Ala Ser Pro Cys Arg Asp Asn Ala Pro Arg Thr Ile Phe Ile
        35                  40                  45

Ile Ser Phe Tyr Lys Asp Ser Gln Pro Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Leu Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 95
<211> LENGTH: 157
<212> TYPE: PRT
<213> ORGANISM: artificial sequence
<220> FEATURE:
<223> OTHER INFORMATION: Synthetic sequence

<400> SEQUENCE: 95

Leu Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Ala Asp
            20                  25                  30

Met Thr Ser Ser Pro Cys Arg Ser Arg Ala Pro Arg Thr Ile Phe Ile
        35                  40                  45

Ile Ser Phe Tyr Lys Asp Ser Gln Pro Arg Gly Phe Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ile Arg Ser Val Pro Gly His Asp Asn Lys
            100                 105                 110

Ile Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 96
<211> LENGTH: 157
<212> TYPE: PRT
<213> ORGANISM: artificial sequence
<220> FEATURE:
<223> OTHER INFORMATION: Synthetic sequence

<400> SEQUENCE: 96

His Phe Gly Lys Leu Glu Ser Lys Leu Ser Val Ile Arg Asn Leu Asn
1               5                   10                  15
```

Asp Gln Val Leu Phe Ile Asp Gln Gly Asn Arg Pro Leu Phe Thr Asp
20 25 30

Met Glu Ser Lys Pro Cys Arg Asp Ser Ala Pro Arg Thr Ile Phe Ile
35 40 45

Ile Ser Met Tyr Lys Asp Ser Gln Pro Arg Gly Ile Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Ile Arg Ser Val Pro Gly His Asp Asn Lys
100 105 110

Phe Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 97
<211> LENGTH: 157
<212> TYPE: PRT
<213> ORGANISM: artificial sequence
<220> FEATURE:
<223> OTHER INFORMATION: Synthetic sequence

<400> SEQUENCE: 97

Tyr Phe Gly Lys Leu Glu Ser Lys Leu Ser Val Ile Arg Asn Leu Asn
1 5 10 15

Arg Gln Val Leu Phe Ile Asp Gln Gly Asn Arg Pro Leu Phe Thr Asp
20 25 30

Met Thr Tyr Lys Asp Cys Arg Asp Asn Ala Pro Arg Thr Ile Phe Ile
35 40 45

Ile Ser Phe Tyr Lys Asp Ser Gln Pro Arg Gly Phe Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Ile Arg Ser Val Pro Gly Ala Asp Asn Lys
100 105 110

Ile Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 98
<211> LENGTH: 157
<212> TYPE: PRT
<213> ORGANISM: artificial sequence
<220> FEATURE:
<223> OTHER INFORMATION: Synthetic sequence

<400> SEQUENCE: 98

His Phe Gly Lys Leu Glu Ser Lys Leu Ser Val Ile Arg Asn Leu Asn
1 5 10 15

Gly Gln Val Leu Phe Ile Asp Gln Gly Asn Arg Pro Leu Phe Gly Asp
20 25 30

Met Glu Ala Ser Pro Cys Arg Asp Asn Ala Pro Arg Thr Ile Phe Ile
35 40 45

Ile Ser Phe Tyr Lys Asp Ser Gln Pro Arg Gly Met Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Ile Arg Ser Val Pro Gly Ala Asp Asn Lys
100 105 110

Leu Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 99
<211> LENGTH: 157
<212> TYPE: PRT
<213> ORGANISM: artificial sequence
<220> FEATURE:
<223> OTHER INFORMATION: Synthetic sequence

<400> SEQUENCE: 99

His Phe Gly Lys Leu Glu Ser Lys Leu Ser Val Ile Arg Asn Leu Asn
1 5 10 15

Gly Gln Val Leu Phe Ile Asp Gln Gly Asn Arg Pro Leu Phe Thr Asp
20 25 30

Met Thr Ser Ser Asp Cys Arg Asp Lys Ala Pro Arg Thr Ile Phe Ile
35 40 45

Ile Ser Phe Tyr Lys Asp Ser Gln Pro Arg Gly Leu Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Leu Arg Ser Val Pro Gly Pro Asp Asn Lys
100 105 110

Phe Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 100
<211> LENGTH: 157
<212> TYPE: PRT
<213> ORGANISM: artificial sequence
<220> FEATURE:

<223> OTHER INFORMATION: Synthetic sequence

<400> SEQUENCE: 100

His Phe Gly Lys Leu Glu Ser Lys Leu Ser Val Ile Arg Asn Leu Asn
1 5 10 15

Gly Gln Val Leu Phe Ile Asp Gln Gly Asn Arg Pro Leu Phe Ala Asp
20 25 30

Met Glu Ser Asn Arg Cys Arg Asp Ser Ala Pro Arg Thr Ile Phe Ile
35 40 45

Ile Ser Met Tyr Lys Asp Ser Gln Pro Arg Gly Phe Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Leu Arg Ser Val Pro Gly His Asp Asn Lys
100 105 110

Ile Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 101
<211> LENGTH: 157
<212> TYPE: PRT
<213> ORGANISM: artificial sequence
<220> FEATURE:
<223> OTHER INFORMATION: Synthetic sequence

<400> SEQUENCE: 101

Tyr Phe Gly Lys Leu Glu Ser Lys Leu Ser Val Ile Arg Asn Leu Asn
1 5 10 15

Gly Gln Val Leu Phe Ile Asp Gln Gly Asn Arg Pro Leu Phe Thr Asp
20 25 30

Met Thr Ala Ser Pro Cys Arg Asp Asn Ala Pro Arg Thr Ile Phe Ile
35 40 45

Ile Ser Phe Tyr Lys Asp Ser Gln Pro Arg Gly Leu Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Leu Arg Ser Val Pro Gly His Asp Asn Lys
100 105 110

Ile Gln Phe Glu Ser Ser Ser Tyr Glu Gly Tyr Phe Leu Ala Cys Glu
115 120 125

Lys Glu Arg Ser Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 102
<211> LENGTH: 157
<212> TYPE: PRT
<213> ORGANISM: artificial sequence
<220> FEATURE:
<223> OTHER INFORMATION: Synthetic sequence

<400> SEQUENCE: 102

Asp Phe Gly Lys Leu Glu Ser Lys Leu Ser Val Ile Arg Asn Leu Asn
1 5 10 15

Asp Gln Val Leu Phe Ile Asp Gln Gly Asn Arg Pro Leu Phe Ala Asp
20 25 30

Met Lys Ser Asn Val Cys Arg Ala Asn Ala Pro Arg Thr Ile Phe Ile
35 40 45

Ile Ser Met Tyr Lys Asp Ser Gln Pro Arg Gly Met Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Ile Arg Ser Val Pro Gly Pro Asp Asn Lys
100 105 110

Leu Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 103
<211> LENGTH: 157
<212> TYPE: PRT
<213> ORGANISM: artificial sequence
<220> FEATURE:
<223> OTHER INFORMATION: Synthetic sequence

<400> SEQUENCE: 103

His Phe Gly Lys Leu Glu Ser Lys Leu Ser Val Ile Arg Asn Leu Asn
1 5 10 15

Gly Gln Val Leu Phe Ile Asp Gln Gly Asn Arg Pro Leu Phe Gly Asp
20 25 30

Met Glu Ala Ser Pro Cys Arg Ala Lys Ala Pro Arg Thr Ile Phe Ile
35 40 45

Ile Ser Ile Tyr Lys Asp Ser Gln Pro Arg Gly Phe Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Leu Arg Ser Val Pro Gly His Asp Asn Lys
100 105 110

Phe Gln Phe Glu Ser Ser Ser Tyr Glu Gly Tyr Phe Leu Ala Cys Glu
115 120 125

Lys Glu Arg Ser Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 104
<211> LENGTH: 157
<212> TYPE: PRT

```
<213> ORGANISM: artificial sequence
<220> FEATURE:
<223> OTHER INFORMATION: Synthetic sequence

<400> SEQUENCE: 104

His Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Ala Asp
            20                  25                  30

Met Ala Ser Asn Arg Cys Arg Ala Asn Ala Pro Arg Thr Ile Phe Ile
        35                  40                  45

Ile Ser Met Tyr Lys Asp Ser Gln Pro Arg Gly Phe Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ile Arg Ser Val Pro Gly Pro Asp Asn Lys
            100                 105                 110

Phe Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 105
<211> LENGTH: 157
<212> TYPE: PRT
<213> ORGANISM: artificial sequence
<220> FEATURE:
<223> OTHER INFORMATION: Synthetic sequence

<400> SEQUENCE: 105

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Ala Asp
            20                  25                  30

Met Lys Ala Lys Ala Cys Arg Ser Asn Ala Pro Arg Thr Ile Phe Ile
        35                  40                  45

Ile Ser Phe Tyr Lys Asp Ser Gln Pro Arg Gly Phe Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Leu Arg Ser Val Pro Gly Ala Asp Asn Lys
            100                 105                 110

Ile Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 106
<211> LENGTH: 157
```

<212> TYPE: PRT
<213> ORGANISM: artificial sequence
<220> FEATURE:
<223> OTHER INFORMATION: Synthetic sequence

<400> SEQUENCE: 106

```
His Phe Gly Lys Leu Glu Ser Lys Leu Ser Val Ile Arg Asn Leu Asn
1               5                   10                  15

His Gln Val Leu Phe Ile Asp Gln Gly Asn Arg Pro Leu Phe Thr Asp
            20                  25                  30

Met Ala Asp Asn Ala Cys Arg Asp Asn Ala Pro Arg Thr Ile Phe Ile
        35                  40                  45

Ile Ser Phe Tyr Lys Asp Ser Gln Pro Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ile Arg Ser Val Pro Gly Asp Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 107
<211> LENGTH: 157
<212> TYPE: PRT
<213> ORGANISM: artificial sequence
<220> FEATURE:
<223> OTHER INFORMATION: Synthetic sequence

<400> SEQUENCE: 107

```
Tyr Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Thr Asp
            20                  25                  30

Met Lys Ser Asn Leu Cys Arg Ser Asn Ala Pro Arg Thr Ile Phe Ile
        35                  40                  45

Ile Ser Phe Tyr Lys Asp Ser Gln Pro Arg Gly Ile Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ile Arg Ser Val Pro Gly Asp Asp Asn Lys
            100                 105                 110

Ile Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 108

<211> LENGTH: 157
<212> TYPE: PRT
<213> ORGANISM: artificial sequence
<220> FEATURE:
<223> OTHER INFORMATION: Synthetic sequence

<400> SEQUENCE: 108

```
His Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Arg Asp
            20                  25                  30

Met Ala Ala Ser His Cys Arg Asp Ser Ala Pro Arg Thr Ile Phe Ile
        35                  40                  45

Ile Ser Ile Tyr Lys Asp Ser Gln Pro Arg Gly Phe Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Leu Arg Ser Val Pro Gly His Asp Asn Lys
            100                 105                 110

Ile Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 109
<211> LENGTH: 157
<212> TYPE: PRT
<213> ORGANISM: artificial sequence
<220> FEATURE:
<223> OTHER INFORMATION: Synthetic sequence

<400> SEQUENCE: 109

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Ala Asp
            20                  25                  30

Met Ala Ser Asn Pro Cys Arg Tyr Lys Ala Pro Arg Thr Ile Phe Ile
        35                  40                  45

Ile Ser Met Tyr Lys Asp Ser Gln Pro Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Leu Arg Ser Val Pro Gly Ala Asp Asn Lys
            100                 105                 110

Leu Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 110
<211> LENGTH: 157
<212> TYPE: PRT
<213> ORGANISM: artificial sequence
<220> FEATURE:
<223> OTHER INFORMATION: Synthetic sequence

<400> SEQUENCE: 110

```
His Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Thr Asp
            20                  25                  30

Met Ala Ser Asn His Cys Arg Tyr Asn Ala Pro Arg Thr Ile Phe Ile
        35                  40                  45

Ile Ser Met Tyr Lys Asp Ser Gln Pro Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Leu Arg Ser Val Pro Gly Ala Asp Asn Lys
            100                 105                 110

Ile Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 111
<211> LENGTH: 157
<212> TYPE: PRT
<213> ORGANISM: artificial sequence
<220> FEATURE:
<223> OTHER INFORMATION: Synthetic sequence

<400> SEQUENCE: 111

```
His Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Ala Asp
            20                  25                  30

Met Thr Asp Asn Pro Cys Arg Ser Arg Ala Pro Arg Thr Ile Phe Ile
        35                  40                  45

Ile Ser Phe Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ile Arg Ser Val Pro Gly His Asp Asn Lys
            100                 105                 110

Phe Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 112
<211> LENGTH: 157
<212> TYPE: PRT
<213> ORGANISM: artificial sequence
<220> FEATURE:
<223> OTHER INFORMATION: Synthetic sequence

<400> SEQUENCE: 112

```
Tyr Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Thr Asp
            20                  25                  30

Met Thr Ala Ser His Cys Arg Ser Ser Ala Pro Arg Thr Ile Phe Ile
        35                  40                  45

Ile Ser Leu Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Leu Arg Ser Val Pro Gly His Asp Asn Lys
            100                 105                 110

Phe Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 113
<211> LENGTH: 157
<212> TYPE: PRT
<213> ORGANISM: artificial sequence
<220> FEATURE:
<223> OTHER INFORMATION: Synthetic sequence

<400> SEQUENCE: 113

```
Tyr Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Thr Asp
            20                  25                  30

Met Glu Tyr Arg Leu Cys Arg Ala Asn Ala Pro Arg Thr Ile Phe Ile
        35                  40                  45

Ile Ser Phe Tyr Lys Asp Ser His Pro Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Leu Arg Ser Val Pro Gly Asp Asp Asn Lys
            100                 105                 110

Leu Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 114
<211> LENGTH: 157
<212> TYPE: PRT
<213> ORGANISM: artificial sequence
<220> FEATURE:
<223> OTHER INFORMATION: Synthetic sequence

<400> SEQUENCE: 114

```
Tyr Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Thr Asp
            20                  25                  30

Met Glu Ser Ser Leu Cys Arg Asp Asn Ala Pro Arg Thr Ile Phe Ile
        35                  40                  45

Ile Ser Leu Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Leu Arg Ser Val Pro Gly Ala Asp Asn Lys
            100                 105                 110

Phe Gln Phe Glu Ser Ser Ser Tyr Glu Gly Tyr Phe Leu Ala Cys Glu
        115                 120                 125

Lys Glu Arg Ser Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 115
<211> LENGTH: 157
<212> TYPE: PRT
<213> ORGANISM: artificial sequence
<220> FEATURE:
<223> OTHER INFORMATION: Synthetic sequence

<400> SEQUENCE: 115

```
Tyr Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Lys Asp
            20                  25                  30

Met Glu Ala Asn Asp Cys Arg Ser Ser Ala Pro Arg Thr Ile Phe Ile
        35                  40                  45

Ile Ser Ile Tyr Lys Asp Ser Gln Pro Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ile Arg Ser Val Pro Gly Ala Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140
```

Gly Asp Arg Ser Ile Met Phe Thr Val Gln Asn Glu Asp
145 150 155

<210> SEQ ID NO 116
<211> LENGTH: 157
<212> TYPE: PRT
<213> ORGANISM: artificial sequence
<220> FEATURE:
<223> OTHER INFORMATION: Synthetic sequence

<400> SEQUENCE: 116

Asp Phe Gly Lys Leu Glu Ser Lys Leu Ser Val Ile Arg Asn Leu Asn
1 5 10 15

Asp Gln Val Leu Phe Ile Asp Gln Gly Asn Arg Pro Leu Phe Ala Asp
20 25 30

Met Lys Ala Ser Ala Cys Arg Ala Asn Ala Pro Arg Thr Ile Phe Ile
35 40 45

Ile Ser Met Tyr Lys Asp Ser Gln Pro Arg Gly Leu Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Leu Arg Ser Val Pro Gly His Asp Asn Lys
100 105 110

Phe Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 117
<211> LENGTH: 157
<212> TYPE: PRT
<213> ORGANISM: artificial sequence
<220> FEATURE:
<223> OTHER INFORMATION: Synthetic sequence

<400> SEQUENCE: 117

Tyr Phe Gly Lys Leu Glu Ser Lys Leu Ser Val Ile Arg Asn Leu Asn
1 5 10 15

Gly Gln Val Leu Phe Ile Asp Gln Gly Asn Arg Pro Leu Phe Gly Asp
20 25 30

Met Thr Ala Lys His Cys Arg Ala Arg Ala Pro Arg Thr Ile Phe Ile
35 40 45

Ile Ser Phe Tyr Lys Asp Ser Gln Pro Arg Gly Met Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Ile Arg Ser Val Pro Gly Ala Asp Asn Lys
100 105 110

Phe Gln Phe Glu Ser Ser Ser Tyr Glu Gly Tyr Phe Leu Ala Cys Glu
115 120 125

```
Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 118
<211> LENGTH: 157
<212> TYPE: PRT
<213> ORGANISM: artificial sequence
<220> FEATURE:
<223> OTHER INFORMATION: Synthetic sequence

<400> SEQUENCE: 118

Phe Phe Gly Lys Phe Glu Ser Lys Leu Ser Val Ile Arg Asn Leu Asn
1               5                   10                  15

Gly Gln Val Leu Phe Ile Asp Gln Gly Asn Arg Pro Leu Phe Thr Asp
            20                  25                  30

Met Glu Ser Lys Asp Cys Arg Asp Arg Ala Pro Arg Thr Ile Phe Ile
        35                  40                  45

Ile Ser Phe Tyr Lys Asp Ser Gln Pro Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Leu Arg Ser Val Pro Gly His Asp Asn Lys
            100                 105                 110

Leu Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 119
<211> LENGTH: 157
<212> TYPE: PRT
<213> ORGANISM: artificial sequence
<220> FEATURE:
<223> OTHER INFORMATION: Synthetic sequence

<400> SEQUENCE: 119

Phe Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Ala Asp
            20                  25                  30

Met Ala Ser Asn His Cys Arg Ala Asn Ala Pro Arg Thr Ile Phe Ile
        35                  40                  45

Ile Ser Leu Tyr Lys Asp Ser Gln Pro Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ile Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125
```

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 120
<211> LENGTH: 157
<212> TYPE: PRT
<213> ORGANISM: artificial sequence
<220> FEATURE:
<223> OTHER INFORMATION: Synthetic sequence

<400> SEQUENCE: 120

Tyr Phe Gly Lys Leu Glu Ser Lys Leu Ser Val Ile Arg Asn Leu Asn
1 5 10 15

Gly Gln Val Leu Phe Ile Asp Gln Gly Asn Arg Pro Leu Phe Ala Asp
20 25 30

Met Thr Ser Lys Arg Cys Arg Asp Asn Ala Pro Arg Thr Ile Phe Ile
35 40 45

Ile Ser Leu Tyr Lys Asp Ser Gln Pro Arg Gly Phe Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Ile Arg Ser Val Pro Gly His Asp Asn Lys
100 105 110

Ile Gln Phe Glu Ser Ser Ser Tyr Glu Gly Tyr Phe Leu Ala Cys Glu
115 120 125

Lys Glu Arg Asp Leu Phe Lys Leu Ile Leu Lys Lys Glu Asp Glu Leu
130 135 140

Gly Asp Arg Ser Ile Met Phe Thr Val Gln Asn Glu Asp
145 150 155

<210> SEQ ID NO 121
<211> LENGTH: 157
<212> TYPE: PRT
<213> ORGANISM: artificial sequence
<220> FEATURE:
<223> OTHER INFORMATION: Synthetic sequence

<400> SEQUENCE: 121

Leu Phe Gly Lys His Glu Ser Lys Leu Ser Val Ile Arg Asn Leu Asn
1 5 10 15

Gly Gln Val Leu Phe Ile Asp Gln Gly Asn Arg Pro Leu Phe Gly Asp
20 25 30

Met Glu Ser Ser Pro Cys Arg Tyr Asn Ala Pro Arg Thr Ile Phe Ile
35 40 45

Ile Ser Phe Tyr Lys Asp Ser Gln Pro Arg Gly Leu Ala Val Thr Ile
50 55 60

Ser Val Lys Cys Glu Lys Ile Ser Thr Leu Ser Cys Glu Asn Lys Ile
65 70 75 80

Ile Ser Phe Lys Glu Met Asn Pro Pro Asp Asn Ile Lys Asp Thr Lys
85 90 95

Ser Asp Ile Ile Phe Phe Ile Arg Ser Val Pro Gly His Asp Asn Lys
100 105 110

```
Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 122
<211> LENGTH: 157
<212> TYPE: PRT
<213> ORGANISM: artificial sequence
<220> FEATURE:
<223> OTHER INFORMATION: Synthetic sequence

<400> SEQUENCE: 122

```
Tyr Phe Gly Lys Leu Glu Ser Lys Leu Ser Val Ile Arg Asn Leu Asn
1               5                   10                  15

Ala Gln Val Leu Phe Ile Asp Gln Gly Asn Arg Pro Leu Phe Thr Asp
            20                  25                  30

Met Thr Ala Ser Pro Cys Arg Ser Ser Ala Pro Arg Thr Ile Phe Ile
        35                  40                  45

Ile Ser Leu Tyr Lys Asp Ser Gln Pro Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Leu Arg Ser Val Pro Gly Pro Asp Asn Lys
            100                 105                 110

Ile Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 123
<211> LENGTH: 157
<212> TYPE: PRT
<213> ORGANISM: artificial sequence
<220> FEATURE:
<223> OTHER INFORMATION: Synthetic sequence

<400> SEQUENCE: 123

```
Tyr Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Ala Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95
```

```
Ser Asp Ile Ile Phe Phe Leu Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 124
<211> LENGTH: 157
<212> TYPE: PRT
<213> ORGANISM: artificial sequence
<220> FEATURE:
<223> OTHER INFORMATION: Synthetic sequence

<400> SEQUENCE: 124

Tyr Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Ala Asp
            20                  25                  30

Met Thr Ser Ser Asp Cys Arg Asp Asn Ala Pro Arg Thr Ile Phe Ile
        35                  40                  45

Ile Ser Phe Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Leu Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 125
<211> LENGTH: 157
<212> TYPE: PRT
<213> ORGANISM: artificial sequence
<220> FEATURE:
<223> OTHER INFORMATION: Synthetic sequence

<400> SEQUENCE: 125

Tyr Phe Gly Lys Leu Glu Ser Lys Leu Ser Val Ile Arg Asn Leu Asn
1               5                   10                  15

Gly Gln Val Leu Phe Ile Asp Gln Gly Asn Arg Pro Leu Phe Ala Asp
            20                  25                  30

Met Glu Ser Ser Asp Cys Arg Asp Asn Ala Pro Arg Thr Ile Phe Ile
        35                  40                  45

Ile Ser Phe Tyr Lys Asp Ser Gln Pro Arg Gly Leu Ala Val Thr Ile
    50                  55                  60

Ser Val Lys Cys Glu Lys Ile Ser Thr Leu Ser Cys Glu Asn Lys Ile
65                  70                  75                  80
```

```
Ile Ser Phe Lys Glu Met Asn Pro Pro Asp Asn Ile Lys Asp Thr Lys
                85                  90                  95

Ser Asp Ile Ile Phe Phe Leu Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

```
<210> SEQ ID NO 126
<211> LENGTH: 157
<212> TYPE: PRT
<213> ORGANISM: artificial sequence
<220> FEATURE:
<223> OTHER INFORMATION: Synthetic sequence

<400> SEQUENCE: 126

Tyr Phe Gly Arg Tyr His Cys Thr Thr Ala Val Ile Arg Asn Ile Asn
1               5                   10                  15

Gln Gln Val Leu Phe Val Asp Lys Arg Gln Pro Val Phe Ala Asp Met
            20                  25                  30

Gly Tyr Thr Val Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Glu Val Pro Gly His Arg Lys Leu Glu
            100                 105                 110

Phe Glu Ser Ser Leu Tyr Glu Gly His Phe Leu Ala Cys Gln Lys Glu
        115                 120                 125

Asp Glu Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

```
<210> SEQ ID NO 127
<211> LENGTH: 157
<212> TYPE: PRT
<213> ORGANISM: artificial sequence
<220> FEATURE:
<223> OTHER INFORMATION: Synthetic sequence

<400> SEQUENCE: 127

Asp Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Ala Asp Met
            20                  25                  30

Gly Ser Ile Ala Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60
```

```
Val Lys Asp Ser Lys Met Tyr Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Ala Val Pro Gly Asp Asn Lys Ile Glu
            100                 105                 110

Phe Glu Ser Ser Leu Tyr Glu Gly His Phe Leu Ala Cys Gln Lys Glu
        115                 120                 125

Ala Thr Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 128
<211> LENGTH: 157
<212> TYPE: PRT
<213> ORGANISM: artificial sequence
<220> FEATURE:
<223> OTHER INFORMATION: Synthetic sequence

<400> SEQUENCE: 128

Tyr Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Arg Asp Met
            20                  25                  30

Ala Asp Thr Val Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Pro Val Pro Gly Ala Ser Lys Met Glu
            100                 105                 110

Phe Glu Ser Ser Leu Tyr Glu Gly His Phe Leu Ala Cys Gln Lys Glu
        115                 120                 125

Ala Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 129
<211> LENGTH: 157
<212> TYPE: PRT
<213> ORGANISM: artificial sequence
<220> FEATURE:
<223> OTHER INFORMATION: Synthetic sequence

<400> SEQUENCE: 129

His Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Lys Asp Met
            20                  25                  30

Glu Tyr Thr Val Gln Ser Ala Ser Glu Pro Gln Thr Arg Leu Ile Ile
        35                  40                  45
```

Tyr Met Tyr Lys Asp Ser Glu Val Arg Gly Leu Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Ile Lys Ala Val Pro Gly Asp Arg Lys Ile Glu
100 105 110

Phe Glu Ser Ser Leu Tyr Glu Gly His Phe Leu Ala Cys Gln Lys Glu
115 120 125

Asp Asn Ala Phe Lys Leu Ile Leu Lys Lys Lys Asp Glu Asn Gly Asp
130 135 140

Lys Ser Val Met Phe Thr Leu Thr Asn Leu His Gln Ser
145 150 155

<210> SEQ ID NO 130
<211> LENGTH: 157
<212> TYPE: PRT
<213> ORGANISM: artificial sequence
<220> FEATURE:
<223> OTHER INFORMATION: Synthetic sequence

<400> SEQUENCE: 130

Tyr Phe Gly Arg Leu His Cys Thr Thr Ala Val Ile Arg Asn Ile Asn
1 5 10 15

Ala Gln Val Leu Phe Val Asp Lys Arg Gln Pro Val Phe Ala Asp Met
20 25 30

Ala Asp Lys Gly Gln Ser Ala Ser Glu Pro Gln Thr Arg Leu Ile Ile
35 40 45

Tyr Met Tyr Lys Asp Ser Glu Val Arg Gly Leu Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Leu Lys Pro Val Pro Gly Asp Thr Lys Met Glu
100 105 110

Phe Glu Ser Ser Leu Tyr Glu Gly His Phe Leu Ala Cys Gln Lys Glu
115 120 125

Phe Gly Ala Phe Lys Leu Ile Leu Lys Lys Lys Asp Glu Asn Gly Asp
130 135 140

Lys Ser Val Met Phe Thr Leu Thr Asn Leu His Gln Ser
145 150 155

<210> SEQ ID NO 131
<211> LENGTH: 157
<212> TYPE: PRT
<213> ORGANISM: artificial sequence
<220> FEATURE:
<223> OTHER INFORMATION: Synthetic sequence

<400> SEQUENCE: 131

Tyr Phe Gly Arg Leu His Cys Thr Thr Ala Val Ile Arg Asn Ile Asn
1 5 10 15

Glu Gln Val Leu Phe Val Asp Lys Arg Gln Pro Val Phe Ala Asp Met
20 25 30

```
Gly Asp Arg His Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Pro Val Pro Gly Ala Ser Lys Leu Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 132
<211> LENGTH: 157
<212> TYPE: PRT
<213> ORGANISM: artificial sequence
<220> FEATURE:
<223> OTHER INFORMATION: Synthetic sequence

<400> SEQUENCE: 132

His Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Arg Asp Met
            20                  25                  30

Gly Ala Ile Gly Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Pro Val Pro Gly Asp Ser Lys Leu Glu
            100                 105                 110

Phe Glu Ser Ser Leu Tyr Glu Gly His Phe Leu Ala Cys Gln Lys Glu
        115                 120                 125

Val Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 133
<211> LENGTH: 157
<212> TYPE: PRT
<213> ORGANISM: artificial sequence
<220> FEATURE:
<223> OTHER INFORMATION: Synthetic sequence

<400> SEQUENCE: 133

His Phe Gly Arg Leu His Cys Thr Thr Ala Val Ile Arg Asn Ile Asn
1               5                   10                  15
```

```
Ser Gln Val Leu Phe Val Asp Lys Arg Gln Pro Val Phe Thr Asp Met
            20                  25                  30

Gly Ser Ile Val Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Gly Val Pro Gly Asp Asn Lys Ile Glu
            100                 105                 110

Phe Glu Ser Ser Leu Tyr Glu Gly His Phe Leu Ala Cys Gln Lys Glu
        115                 120                 125

Asp Arg Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 134
<211> LENGTH: 157
<212> TYPE: PRT
<213> ORGANISM: artificial sequence
<220> FEATURE:
<223> OTHER INFORMATION: Synthetic sequence

<400> SEQUENCE: 134

Tyr Phe Gly Arg Leu His Cys Thr Thr Ala Val Ile Arg Asn Ile Asn
1               5                   10                  15

Ser Gln Val Leu Phe Val Asp Lys Arg Gln Pro Val Phe Arg Asp Met
            20                  25                  30

Glu Asp Thr Pro Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Arg Val Pro Gly Asp Ser Lys Leu Glu
            100                 105                 110

Phe Glu Ser Ser Leu Tyr Glu Gly His Phe Leu Ala Cys Gln Lys Glu
        115                 120                 125

Phe Glu Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 135
<211> LENGTH: 157
<212> TYPE: PRT
<213> ORGANISM: artificial sequence
<220> FEATURE:
<223> OTHER INFORMATION: Synthetic sequence
```

<400> SEQUENCE: 135

His Phe Gly Arg Leu His Cys Thr Thr Ala Val Ile Arg Asn Ile Asn
1 5 10 15

Ala Gln Val Leu Phe Val Asp Lys Arg Gln Pro Val Phe Gly Asp Met
20 25 30

Thr Ala Thr Val Gln Ser Ala Ser Glu Pro Gln Thr Arg Leu Ile Ile
35 40 45

Tyr Phe Tyr Lys Asp Ser Glu Val Arg Gly Leu Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Ile Lys Pro Val Pro Gly Asp Ser Lys Leu Glu
100 105 110

Phe Glu Ser Ser Leu Tyr Glu Gly His Phe Leu Ala Cys Gln Lys Glu
115 120 125

Asp Asn Ala Phe Lys Leu Ile Leu Lys Lys Lys Asp Glu Asn Gly Asp
130 135 140

Lys Ser Val Met Phe Thr Leu Thr Asn Leu His Gln Ser
145 150 155

<210> SEQ ID NO 136
<211> LENGTH: 157
<212> TYPE: PRT
<213> ORGANISM: artificial sequence
<220> FEATURE:
<223> OTHER INFORMATION: Synthetic sequence

<400> SEQUENCE: 136

Asn Phe Gly Arg Leu His Cys Thr Thr Ala Val Ile Arg Asn Ile Asn
1 5 10 15

Asn Gln Val Leu Phe Val Asp Lys Arg Gln Pro Val Phe Lys Asp Met
20 25 30

Glu Tyr Thr Leu Gln Ser Ala Ser Glu Pro Gln Thr Arg Leu Ile Ile
35 40 45

Tyr Phe Tyr Lys Asp Ser Glu Val Arg Gly Leu Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Ile Lys Pro Val Pro Gly Asp Asn Lys Leu Glu
100 105 110

Phe Glu Ser Ser Leu Tyr Glu Gly His Phe Leu Ala Cys Gln Lys Glu
115 120 125

Tyr Glu Ala Phe Lys Leu Ile Leu Lys Lys Lys Asp Glu Asn Gly Asp
130 135 140

Lys Ser Val Met Phe Thr Leu Thr Asn Leu His Gln Ser
145 150 155

<210> SEQ ID NO 137
<211> LENGTH: 157
<212> TYPE: PRT
<213> ORGANISM: artificial sequence
<220> FEATURE:

<223> OTHER INFORMATION: Synthetic sequence

<400> SEQUENCE: 137

Tyr Phe Gly Arg Leu His Cys Thr Thr Ala Val Ile Arg Asn Ile Asn
1 5 10 15

Gly Gln Val Leu Phe Val Asp Lys Arg Gln Pro Val Phe Ala Asp Met
20 25 30

Glu Ala Thr Arg Gln Ser Ala Ser Glu Pro Gln Thr Arg Leu Ile Ile
35 40 45

Tyr Phe Tyr Lys Asp Ser Glu Val Arg Gly Leu Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Ile Lys Gly Val Pro Gly Ala Asn Lys Met Glu
100 105 110

Phe Glu Ser Ser Leu Tyr Glu Gly His Phe Leu Ala Cys Gln Lys Glu
115 120 125

Asp Gly Ala Phe Lys Leu Ile Leu Lys Lys Lys Asp Glu Asn Gly Asp
130 135 140

Asn Ser Val Met Phe Thr Leu Thr Asn Leu His Gln Ser
145 150 155

<210> SEQ ID NO 138
<211> LENGTH: 157
<212> TYPE: PRT
<213> ORGANISM: artificial sequence
<220> FEATURE:
<223> OTHER INFORMATION: Synthetic sequence

<400> SEQUENCE: 138

Asn Phe Gly Arg Leu His Cys Thr Thr Ala Val Ile Arg Asn Ile Asn
1 5 10 15

Gly Gln Val Leu Phe Val Asp Lys Arg Gln Pro Val Phe Ala Asp Met
20 25 30

Arg Ala Ile Leu Gln Ser Ala Ser Glu Pro Gln Thr Arg Leu Ile Ile
35 40 45

Tyr Phe Tyr Lys Asp Ser Glu Val Arg Gly Leu Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Leu Lys Gly Val Pro Gly Asp Asn Lys Leu Glu
100 105 110

Phe Glu Ser Ser Leu Tyr Glu Gly His Phe Leu Ala Cys Gln Lys Glu
115 120 125

Asp Arg Ala Phe Lys Leu Ile Leu Lys Lys Lys Asp Glu Asn Gly Asp
130 135 140

Lys Ser Val Met Phe Thr Leu Thr Asn Leu His Gln Ser
145 150 155

<210> SEQ ID NO 139
<211> LENGTH: 157
<212> TYPE: PRT
<213> ORGANISM: artificial sequence
<220> FEATURE:
<223> OTHER INFORMATION: Synthetic sequence

<400> SEQUENCE: 139

Tyr Phe Gly Arg Leu His Cys Thr Thr Ala Val Ile Arg Asn Ile Asn
1               5                   10                  15

Ala Gln Val Leu Phe Val Asp Lys Arg Gln Pro Val Phe Ala Asp Met
            20                  25                  30

Glu Ala Thr Ala Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Gly Val Pro Gly Ala Ser Lys Met Glu
            100                 105                 110

Phe Glu Ser Ser Leu Tyr Glu Gly His Phe Leu Ala Cys Gln Lys Glu
        115                 120                 125

Asp Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 140
<211> LENGTH: 157
<212> TYPE: PRT
<213> ORGANISM: artificial sequence
<220> FEATURE:
<223> OTHER INFORMATION: Synthetic sequence

<400> SEQUENCE: 140

Leu Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Ala Asp Met
            20                  25                  30

Gly Ala Thr Leu Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Pro Val Pro Gly Asp Thr Lys Met Glu
            100                 105                 110

Phe Glu Ser Ser Leu Tyr Glu Gly His Phe Leu Ala Cys Gln Lys Glu
        115                 120                 125

Ala Ser Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 141
<211> LENGTH: 157
<212> TYPE: PRT

```
<213> ORGANISM: artificial sequence
<220> FEATURE:
<223> OTHER INFORMATION: Synthetic sequence

<400> SEQUENCE: 141

Asn Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Glu Asp Met
            20                  25                  30

Ala Tyr Thr Val Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Gly Val Pro Gly Asp Ser Lys Met Glu
            100                 105                 110

Phe Glu Ser Ser Leu Tyr Glu Gly His Phe Leu Ala Cys Gln Lys Glu
        115                 120                 125

Tyr Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 142
<211> LENGTH: 157
<212> TYPE: PRT
<213> ORGANISM: artificial sequence
<220> FEATURE:
<223> OTHER INFORMATION: Synthetic sequence

<400> SEQUENCE: 142

Asp Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Lys Asp Met
            20                  25                  30

Glu Ser Lys Pro Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Ala Val Pro Gly Ala Ser Lys Leu Glu
            100                 105                 110

Phe Glu Ser Ser Leu Tyr Glu Gly His Phe Leu Ala Cys Gln Lys Glu
        115                 120                 125

Ala Asn Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 143
<211> LENGTH: 157
```

<212> TYPE: PRT
<213> ORGANISM: artificial sequence
<220> FEATURE:
<223> OTHER INFORMATION: Synthetic sequence

<400> SEQUENCE: 143

```
Leu Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Ala Asp Met
            20                  25                  30

Gly Asp Lys Val Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Pro Val Pro Gly Asp Asn Lys Leu Glu
            100                 105                 110

Phe Glu Ser Ser Leu Tyr Glu Gly His Phe Leu Ala Cys Gln Lys Glu
        115                 120                 125

Asp Glu Ala Phe Lys Leu Ile Leu Lys Thr Lys Asp Glu Asn Gly Asp
    130                 135                 140

Lys Ser Val Met Phe Thr Leu Thr Asn Leu His Gln Ser
145                 150                 155
```

<210> SEQ ID NO 144
<211> LENGTH: 157
<212> TYPE: PRT
<213> ORGANISM: artificial sequence
<220> FEATURE:
<223> OTHER INFORMATION: Synthetic sequence

<400> SEQUENCE: 144

```
Tyr Phe Gly Arg His His Cys Thr Thr Ala Val Ile Arg Asn Ile Asn
1               5                   10                  15

Gln Gln Val Leu Phe Val Asp Lys Arg Gln Pro Val Phe Arg Asp Met
            20                  25                  30

Ala Ala Thr Arg Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Gly Val Pro Gly Asp Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 145

<211> LENGTH: 157
<212> TYPE: PRT
<213> ORGANISM: artificial sequence
<220> FEATURE:
<223> OTHER INFORMATION: Synthetic sequence

<400> SEQUENCE: 145

Asn Phe Gly Arg Leu His Cys Thr Thr Ala Val Ile Arg Asn Ile Asn
1               5                   10                  15

Gln Gln Val Leu Phe Val Asp Lys Arg Gln Pro Val Phe Thr Asp Met
            20                  25                  30

Glu Ser Ile Gly Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Ala Val Pro Gly Ala Asn Lys Leu Glu
            100                 105                 110

Phe Glu Ser Ser Leu Tyr Glu Gly His Phe Leu Ala Cys Gln Lys Glu
        115                 120                 125

Asp Ser Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 146
<211> LENGTH: 157
<212> TYPE: PRT
<213> ORGANISM: artificial sequence
<220> FEATURE:
<223> OTHER INFORMATION: Synthetic sequence

<400> SEQUENCE: 146

Phe Phe Gly Arg His His Cys Thr Thr Ala Val Ile Arg Asn Ile Asn
1               5                   10                  15

Gly Gln Val Leu Phe Val Asp Lys Arg Gln Pro Val Phe Gly Asp Met
            20                  25                  30

Gly Asp Arg Val Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Ala Val Pro Gly Asp Ser Lys Ile Glu
            100                 105                 110

Phe Glu Ser Ser Leu Tyr Glu Gly His Phe Leu Ala Cys Gln Lys Glu
        115                 120                 125

Asp Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 147
<211> LENGTH: 157
<212> TYPE: PRT
<213> ORGANISM: artificial sequence
<220> FEATURE:
<223> OTHER INFORMATION: Synthetic sequence

<400> SEQUENCE: 147

```
Val Phe Gly Arg His His Cys Thr Thr Ala Val Ile Arg Asn Ile Asn
1               5                   10                  15

Gly Gln Val Leu Phe Val Asp Lys Arg Gln Pro Val Phe Lys Asp Met
            20                  25                  30

Thr Tyr Ile Asp Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Ala Val Pro Gly Asp Thr Lys Met Glu
            100                 105                 110

Phe Glu Ser Ser Leu Tyr Glu Gly His Phe Leu Ala Cys Gln Lys Glu
        115                 120                 125

Ala Gln Ala Phe Lys Leu Ile Leu Lys Lys Lys Asp Glu Ile Gly Asp
    130                 135                 140

Lys Ser Val Met Phe Thr Leu Thr Asn Leu His Gln Ser
145                 150                 155
```

<210> SEQ ID NO 148
<211> LENGTH: 157
<212> TYPE: PRT
<213> ORGANISM: artificial sequence
<220> FEATURE:
<223> OTHER INFORMATION: Synthetic sequence

<400> SEQUENCE: 148

```
Asn Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Ala Asp Met
            20                  25                  30

Thr Ala Thr Arg Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Gln Val Pro Gly Ala Asn Lys Ile Glu
            100                 105                 110

Phe Glu Ser Ser Leu Tyr Glu Gly His Phe Leu Ala Cys Gln Lys Glu
        115                 120                 125

Phe Arg Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 149
<211> LENGTH: 157
<212> TYPE: PRT
<213> ORGANISM: artificial sequence
<220> FEATURE:
<223> OTHER INFORMATION: Synthetic sequence

<400> SEQUENCE: 149

```
Asp Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Gly Asp Met
            20                  25                  30

Ala Tyr Ile Gly Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Ala Val Pro Gly His Ser Lys Ile Glu
            100                 105                 110

Phe Glu Ser Ser Leu Tyr Glu Gly His Phe Leu Ala Cys Gln Lys Glu
        115                 120                 125

Ser Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 150
<211> LENGTH: 157
<212> TYPE: PRT
<213> ORGANISM: artificial sequence
<220> FEATURE:
<223> OTHER INFORMATION: Synthetic sequence

<400> SEQUENCE: 150

```
Tyr Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Arg Asp Met
            20                  25                  30

Gly Ser Ile Ala Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Pro Val Pro Gly Ala Thr Lys Leu Glu
            100                 105                 110

Phe Glu Ser Ser Leu Tyr Glu Gly His Phe Leu Ala Cys Gln Lys Glu
        115                 120                 125

Asp Gly Ala Phe Lys Leu Ile Leu Lys Lys Lys Asp Glu Asn Gly Asp
    130                 135                 140

Asn Ser Val Met Phe Thr Leu Thr Asn Leu His Gln Ser
145                 150                 155
```

<210> SEQ ID NO 151
<211> LENGTH: 157
<212> TYPE: PRT
<213> ORGANISM: artificial sequence
<220> FEATURE:
<223> OTHER INFORMATION: Synthetic sequence

<400> SEQUENCE: 151

Tyr Phe Gly Arg Leu His Cys Thr Thr Ala Val Ile Arg Asn Ile Asn
1 5 10 15

Glu Gln Val Leu Phe Val Asp Lys Arg Gln Pro Val Phe Thr Asp Met
20 25 30

Glu Ala Ile Gly Gln Ser Ala Ser Glu Pro Gln Thr Arg Leu Ile Ile
35 40 45

Tyr Phe Tyr Lys Asp Ser Glu Val Arg Gly Leu Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Ile Lys Gly Val Pro Gly Asp Arg Lys Met Glu
100 105 110

Phe Glu Ser Ser Leu Tyr Glu Gly His Phe Leu Ala Cys Gln Lys Glu
115 120 125

Asp Gly Ala Phe Lys Leu Ile Leu Lys Lys Lys Asp Glu Asn Gly Asp
130 135 140

Lys Ser Val Met Phe Thr Leu Thr Asn Leu His Gln Ser
145 150 155

<210> SEQ ID NO 152
<211> LENGTH: 157
<212> TYPE: PRT
<213> ORGANISM: artificial sequence
<220> FEATURE:
<223> OTHER INFORMATION: Synthetic sequence

<400> SEQUENCE: 152

Phe Phe Gly Arg Leu His Cys Thr Thr Ala Val Ile Arg Asn Ile Asn
1 5 10 15

Asn Gln Val Leu Phe Val Asp Lys Arg Gln Pro Val Phe Glu Asp Met
20 25 30

Glu Tyr Arg Leu Gln Ser Ala Ser Glu Pro Gln Thr Arg Leu Ile Ile
35 40 45

Tyr Met Tyr Lys Asp Ser Glu Val Arg Gly Leu Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Leu Lys Pro Val Pro Gly Ala Ser Lys Leu Glu
100 105 110

Phe Glu Ser Ser Leu Tyr Glu Gly His Phe Leu Ala Cys Gln Lys Glu
115 120 125

Ser Asp Ala Phe Lys Leu Ile Leu Lys Lys Lys Asp Glu Asn Gly Asp
130 135 140

Lys Ser Val Met Phe Thr Leu Thr Asn Leu His Gln Ser
145 150 155

<210> SEQ ID NO 153
<211> LENGTH: 157
<212> TYPE: PRT
<213> ORGANISM: artificial sequence
<220> FEATURE:
<223> OTHER INFORMATION: Synthetic sequence

<400> SEQUENCE: 153

Asn Phe Gly Arg Leu His Cys Thr Thr Ala Val Ile Arg Asn Ile Asn
1 5 10 15

Asn Gln Val Leu Phe Val Asp Lys Arg Gln Pro Val Phe Ala Asp Met
20 25 30

Glu Asp Arg Leu Gln Ser Ala Ser Glu Pro Gln Thr Arg Leu Ile Ile
35 40 45

Tyr Met Tyr Lys Asp Ser Glu Val Arg Gly Leu Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Leu Lys Gly Val Pro Gly Asp Asn Lys Met Glu
100 105 110

Phe Glu Ser Ser Leu Tyr Glu Gly His Phe Leu Ala Cys Gln Lys Glu
115 120 125

Asp His Ala Phe Lys Leu Ile Leu Lys Lys Lys Asp Glu Asn Gly Asp
130 135 140

Lys Ser Val Met Phe Thr Leu Thr Asn Leu His Gln Ser
145 150 155

<210> SEQ ID NO 154
<211> LENGTH: 157
<212> TYPE: PRT
<213> ORGANISM: artificial sequence
<220> FEATURE:
<223> OTHER INFORMATION: Synthetic sequence

<400> SEQUENCE: 154

Tyr Phe Gly Arg Leu His Cys Thr Thr Ala Val Ile Arg Asn Ile Asn
1 5 10 15

Ala Gln Val Leu Phe Val Asp Lys Arg Gln Pro Val Phe Arg Asp Met
20 25 30

Gly Tyr Ile Leu Gln Ser Ala Ser Glu Pro Gln Thr Arg Leu Ile Ile
35 40 45

Tyr Leu Tyr Lys Asp Ser Glu Val Arg Gly Leu Ala Val Thr Leu Ser
50 55 60

Val Lys Glu Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Leu Lys Pro Val Pro Gly Asp Thr Lys Ile Glu
100 105 110

Phe Glu Ser Ser Leu Tyr Glu Gly His Phe Leu Ala Cys Gln Lys Glu
115 120 125

Asp Asn Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 155
<211> LENGTH: 157
<212> TYPE: PRT
<213> ORGANISM: artificial sequence
<220> FEATURE:
<223> OTHER INFORMATION: Synthetic sequence

<400> SEQUENCE: 155

Tyr Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Gly Asp Met
            20                  25                  30

Ala Asp Thr Ala Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Pro Val Pro Gly Asp Ser Lys Met Glu
            100                 105                 110

Phe Glu Ser Ser Leu Tyr Glu Gly His Phe Leu Ala Cys Gln Lys Glu
        115                 120                 125

Ala Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 156
<211> LENGTH: 157
<212> TYPE: PRT
<213> ORGANISM: artificial sequence
<220> FEATURE:
<223> OTHER INFORMATION: Synthetic sequence

<400> SEQUENCE: 156

Asp Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Glu Asp Met
            20                  25                  30

Ala Tyr Ile Ala Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Pro Val Pro Gly Asp Ser Lys Ile Glu
            100                 105                 110

```
Phe Glu Ser Ser Leu Tyr Glu Gly His Phe Leu Ala Cys Gln Lys Glu
        115                 120                 125

Ala Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 157
<211> LENGTH: 157
<212> TYPE: PRT
<213> ORGANISM: artificial sequence
<220> FEATURE:
<223> OTHER INFORMATION: Synthetic sequence

<400> SEQUENCE: 157

Asn Phe Gly Arg Leu His Cys Thr Thr Ala Val Ile Arg Asn Ile Asn
1               5                   10                  15

Glu Gln Val Leu Ser Val Asp Lys Arg Gln Pro Val Phe Arg Asp Met
            20                  25                  30

Lys Tyr Ile Leu Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Gly Val Pro Gly Asp Asn Lys Met Glu
            100                 105                 110

Phe Glu Ser Ser Leu Tyr Glu Gly His Phe Leu Ala Cys Gln Lys Glu
        115                 120                 125

Tyr Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 158
<211> LENGTH: 157
<212> TYPE: PRT
<213> ORGANISM: artificial sequence
<220> FEATURE:
<223> OTHER INFORMATION: Synthetic sequence

<400> SEQUENCE: 158

Asp Phe Gly Arg Leu His Cys Thr Thr Ala Val Ile Arg Asn Ile Asn
1               5                   10                  15

Glu Gln Val Leu Phe Val Asp Lys Arg Gln Pro Val Phe Thr Asp Met
            20                  25                  30

Ala Tyr Ile Leu Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Glu Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95
```

```
Asp Leu Ile Phe Phe Ile Lys Ala Val Pro Gly Asp Ser Lys Leu Glu
            100                 105                 110

Phe Glu Ser Ser Leu Tyr Glu Gly His Phe Leu Ala Cys Gln Lys Glu
        115                 120                 125

Asp Thr Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 159
<211> LENGTH: 157
<212> TYPE: PRT
<213> ORGANISM: artificial sequence
<220> FEATURE:
<223> OTHER INFORMATION: Synthetic sequence

<400> SEQUENCE: 159

Asp Phe Gly Arg Leu His Cys Thr Thr Ala Val Ile Arg Asn Ile Asn
1               5                   10                  15

Asn Gln Val Leu Phe Val Asp Lys Arg Gln Pro Val Phe Lys Asp Met
            20                  25                  30

Glu Ser Thr Ala Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Gly Val Pro Gly Ala Ser Lys Leu Glu
            100                 105                 110

Phe Glu Ser Ser Leu Tyr Glu Gly His Phe Leu Ala Cys Gln Lys Glu
        115                 120                 125

Ala Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 160
<211> LENGTH: 157
<212> TYPE: PRT
<213> ORGANISM: artificial sequence
<220> FEATURE:
<223> OTHER INFORMATION: Synthetic sequence

<400> SEQUENCE: 160

His Phe Gly Arg Leu His Cys Thr Thr Ala Val Ile Arg Asn Ile Asn
1               5                   10                  15

Glu Gln Val Leu Phe Val Asp Lys Arg Gln Pro Val Phe Ala Asp Met
            20                  25                  30

Glu Ala Ile Gly Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Glu Ser Lys Met Ser Thr Leu Ser Cys Lys Asn Lys Ile Ile
65                  70                  75                  80
```

```
Ser Phe Glu Glu Met Asp Pro Pro Glu Asn Ile Asp Asp Ile Gln Ser
                85                  90                  95

Asp Leu Ile Phe Phe Ile Lys Gly Val Pro Gly Asp Thr Lys Leu Glu
            100                 105                 110

Phe Glu Ser Ser Leu Tyr Ala Gly His Phe Leu Ala Cys Gln Lys Glu
        115                 120                 125

Asp Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 161
<211> LENGTH: 157
<212> TYPE: PRT
<213> ORGANISM: artificial sequence
<220> FEATURE:
<223> OTHER INFORMATION: Synthetic sequence

<400> SEQUENCE: 161

Ile Phe Gly Arg Leu His Cys Thr Thr Ala Val Ile Arg Asn Ile Asn
1               5                   10                  15

Glu Gln Val Leu Phe Val Asp Lys Arg Gln Pro Val Phe Lys Asp Met
            20                  25                  30

Arg Tyr Ile Val Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Glu Val Pro Gly Ala Ser Lys Leu Glu
            100                 105                 110

Phe Glu Ser Ser Leu Tyr Glu Gly His Phe Leu Ala Cys Gln Lys Glu
        115                 120                 125

Asp Glu Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 162
<211> LENGTH: 157
<212> TYPE: PRT
<213> ORGANISM: artificial sequence
<220> FEATURE:
<223> OTHER INFORMATION: Synthetic sequence

<400> SEQUENCE: 162

Tyr Phe Gly Arg Leu His Cys Thr Thr Ala Val Ile Arg Asn Ile Asn
1               5                   10                  15

Ala Gln Val Leu Phe Val Asp Lys Arg Gln Pro Val Phe Thr Asp Met
            20                  25                  30

Gly Tyr Thr Leu Gln Ser Ala Ser Glu Pro Gln Thr Arg Leu Ile Ile
        35                  40                  45

Tyr Leu Tyr Lys Asp Ser Glu Val Arg Gly Leu Ala Val Thr Leu Ser
    50                  55                  60
```

```
Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Pro Val Pro Gly His Asn Lys Ile Glu
            100                 105                 110

Phe Glu Ser Ser Leu Tyr Glu Gly His Phe Leu Ala Cys Gln Lys Glu
        115                 120                 125

Asp Arg Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

```
<210> SEQ ID NO 163
<211> LENGTH: 157
<212> TYPE: PRT
<213> ORGANISM: artificial sequence
<220> FEATURE:
<223> OTHER INFORMATION: Synthetic sequence

<400> SEQUENCE: 163

Asn Phe Gly Arg Leu His Cys Thr Thr Ala Val Ile Arg Asn Ile Asn
1               5                   10                  15

Asn Gln Val Leu Phe Val Asp Lys Arg Gln Pro Val Phe Arg Asp Met
            20                  25                  30

Ala Ser Thr Ala Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Gly Val Pro Gly Ala Asn Lys Ile Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

```
<210> SEQ ID NO 164
<211> LENGTH: 157
<212> TYPE: PRT
<213> ORGANISM: artificial sequence
<220> FEATURE:
<223> OTHER INFORMATION: Synthetic sequence

<400> SEQUENCE: 164

Asp Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Glu Asp Met
            20                  25                  30

Lys Asp Arg Ala Gln Ser Ala Ser Glu Pro Gln Thr Arg Leu Ile Ile
        35                  40                  45
```

```
Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Ala Val Pro Gly His Ser Lys Met Glu
            100                 105                 110

Phe Glu Ser Ser Leu Tyr Glu Gly His Phe Leu Ala Cys Gln Lys Glu
        115                 120                 125

Asp Glu Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 165
<211> LENGTH: 157
<212> TYPE: PRT
<213> ORGANISM: artificial sequence
<220> FEATURE:
<223> OTHER INFORMATION: Synthetic sequence

<400> SEQUENCE: 165

Asn Phe Gly Arg Leu His Cys Thr Thr Ala Val Ile Arg Asn Ile Asn
1               5                   10                  15

Glu Gln Val Leu Phe Val Asp Lys Arg Gln Pro Val Phe Ala Asp Met
            20                  25                  30

Thr Asp Ile Ala Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Glu Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Pro Val Pro Gly Asp Ile Lys Met Glu
            100                 105                 110

Phe Glu Ser Ser Leu Tyr Glu Gly His Phe Leu Ala Cys Gln Lys Glu
        115                 120                 125

Tyr Gly Ala Phe Lys Leu Ile Leu Lys Lys Lys Asp Glu Asn Gly Asp
    130                 135                 140

Asn Ser Val Met Phe Thr Leu Thr Asn Leu His Gln Ser
145                 150                 155


<210> SEQ ID NO 166
<211> LENGTH: 157
<212> TYPE: PRT
<213> ORGANISM: artificial sequence
<220> FEATURE:
<223> OTHER INFORMATION: Synthetic sequence

<400> SEQUENCE: 166

Tyr Phe Gly Arg Leu His Cys Thr Thr Ala Val Ile Arg Asn Ile Asn
1               5                   10                  15

Glu Gln Val Leu Phe Val Asp Lys Arg Gln Pro Val Phe Ala Asp Met
            20                  25                  30
```

```
Thr Asp Thr Leu Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Gly Val Pro Gly Asp Asn Lys Met Glu
            100                 105                 110

Phe Glu Ser Ser Leu Tyr Glu Gly His Phe Leu Ala Cys Gln Lys Glu
        115                 120                 125

Asp Thr Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 167
<211> LENGTH: 157
<212> TYPE: PRT
<213> ORGANISM: artificial sequence
<220> FEATURE:
<223> OTHER INFORMATION: Synthetic sequence

<400> SEQUENCE: 167

Tyr Phe Gly Arg Leu His Cys Thr Thr Ala Val Ile Arg Asn Ile Asn
1               5                   10                  15

Glu Gln Val Leu Phe Val Asp Lys Arg Gln Pro Val Phe Ala Asp Met
            20                  25                  30

Thr Asp Thr Leu Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Gly Val Pro Gly Asp Asn Lys Met Glu
            100                 105                 110

Phe Glu Ser Ser Leu Tyr Glu Gly His Phe Leu Ala Cys Gln Lys Glu
        115                 120                 125

Asp Thr Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 168
<211> LENGTH: 157
<212> TYPE: PRT
<213> ORGANISM: artificial sequence
<220> FEATURE:
<223> OTHER INFORMATION: Synthetic sequence

<400> SEQUENCE: 168

Tyr Phe Gly Arg Leu His Cys Thr Thr Ala Val Ile Arg Asn Ile Asn
1               5                   10                  15
```

```
Glu Gln Val Leu Phe Val Asp Lys Arg Gln Pro Val Phe Ala Asp Met
            20                  25                  30

Thr Asp Thr Leu Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Gly Val Pro Gly Asp Asn Lys Met Glu
            100                 105                 110

Phe Glu Ser Ser Leu Tyr Glu Gly His Phe Leu Ala Cys Gln Lys Glu
        115                 120                 125

Asp Thr Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 169
<211> LENGTH: 157
<212> TYPE: PRT
<213> ORGANISM: artificial sequence
<220> FEATURE:
<223> OTHER INFORMATION: Synthetic sequence

<400> SEQUENCE: 169

His Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Lys Asp Met
            20                  25                  30

Lys Tyr Ile Val Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Ala Val Pro Gly His Ser Lys Ile Glu
            100                 105                 110

Phe Glu Ser Ser Leu Tyr Glu Gly His Phe Leu Ala Cys Gln Lys Glu
        115                 120                 125

Asp Ser Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155


<210> SEQ ID NO 170
<211> LENGTH: 157
<212> TYPE: PRT
<213> ORGANISM: artificial sequence
<220> FEATURE:
<223> OTHER INFORMATION: Synthetic sequence
```

<400> SEQUENCE: 170

His Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Lys Asp Met
            20                  25                  30

Lys Tyr Ile Val Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Ala Val Pro Gly His Ser Lys Ile Glu
            100                 105                 110

Phe Glu Ser Ser Leu Tyr Glu Gly His Phe Leu Ala Cys Gln Lys Glu
        115                 120                 125

Asp Ser Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 171
<211> LENGTH: 157
<212> TYPE: PRT
<213> ORGANISM: artificial sequence
<220> FEATURE:
<223> OTHER INFORMATION: Synthetic sequence

<400> SEQUENCE: 171

Tyr Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Glu Asp Met
            20                  25                  30

Lys Ala Lys Ala Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Pro Val Pro Gly Ala Ser Lys Met Glu
            100                 105                 110

Phe Glu Ser Ser Leu Tyr Glu Gly His Phe Leu Ala Cys Gln Lys Glu
        115                 120                 125

Asp Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 172
<211> LENGTH: 157
<212> TYPE: PRT
<213> ORGANISM: artificial sequence
<220> FEATURE:

<223> OTHER INFORMATION: Synthetic sequence

<400> SEQUENCE: 172

Tyr Phe Gly Arg Leu His Cys Thr Thr Ala Val Ile Arg Asn Ile Asn
1 5 10 15

Gly Gln Val Leu Phe Val Asp Lys Arg Gln Pro Val Phe Glu Asp Met
20 25 30

Lys Ala Lys Ala Gln Ser Ala Ser Glu Pro Gln Thr Arg Leu Ile Ile
35 40 45

Tyr Phe Tyr Lys Asp Ser Glu Val Arg Gly Leu Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Ile Lys Pro Val Pro Gly Ala Ser Lys Met Glu
100 105 110

Phe Glu Ser Ser Leu Tyr Glu Gly His Phe Leu Ala Cys Gln Lys Glu
115 120 125

Asp Gly Ala Phe Lys Leu Ile Leu Lys Lys Lys Asp Glu Asn Gly Asp
130 135 140

Lys Ser Val Met Phe Thr Leu Thr Asn Leu His Gln Ser
145 150 155

<210> SEQ ID NO 173
<211> LENGTH: 157
<212> TYPE: PRT
<213> ORGANISM: artificial sequence
<220> FEATURE:
<223> OTHER INFORMATION: Synthetic sequence

<400> SEQUENCE: 173

Tyr Phe Gly Arg Leu His Cys Thr Thr Ala Val Ile Arg Asn Ile Asn
1 5 10 15

Gly Gln Val Leu Phe Val Asp Lys Arg Gln Pro Val Phe Glu Asp Met
20 25 30

Lys Ala Lys Ala Gln Ser Ala Ser Glu Pro Gln Thr Arg Leu Ile Ile
35 40 45

Tyr Phe Tyr Lys Asp Ser Glu Val Arg Gly Leu Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Ile Lys Pro Val Pro Gly Ala Ser Lys Met Glu
100 105 110

Phe Glu Ser Ser Leu Tyr Glu Gly His Phe Leu Ala Cys Gln Lys Glu
115 120 125

Asp Gly Ala Phe Lys Leu Ile Leu Lys Lys Lys Asp Glu Asn Gly Asp
130 135 140

Lys Ser Val Met Phe Thr Leu Thr Asn Leu His Gln Ser
145 150 155

<210> SEQ ID NO 174
<211> LENGTH: 157
<212> TYPE: PRT
<213> ORGANISM: artificial sequence
<220> FEATURE:
<223> OTHER INFORMATION: Synthetic sequence

<400> SEQUENCE: 174

Leu Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Gly Asp Met
            20                  25                  30

Gly Ser Ile Pro Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys His Val Pro Gly Ala Thr Lys Met Glu
            100                 105                 110

Phe Glu Ser Ser Leu Tyr Glu Gly His Phe Leu Ala Cys Gln Lys Glu
        115                 120                 125

Asp Asn Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 175
<211> LENGTH: 157
<212> TYPE: PRT
<213> ORGANISM: artificial sequence
<220> FEATURE:
<223> OTHER INFORMATION: Synthetic sequence

<400> SEQUENCE: 175

Leu Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Gly Asp Met
            20                  25                  30

Gly Ser Ile Pro Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys His Val Pro Gly Ala Thr Lys Met Glu
            100                 105                 110

Phe Glu Ser Ser Leu Tyr Glu Gly His Phe Leu Ala Cys Gln Lys Glu
        115                 120                 125

Asp Asn Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 176
<211> LENGTH: 157
<212> TYPE: PRT

<213> ORGANISM: artificial sequence
<220> FEATURE:
<223> OTHER INFORMATION: Synthetic sequence

<400> SEQUENCE: 176

```
Tyr Phe Gly Arg Leu His Cys Thr Thr Ala Val Ile Arg Asn Ile Asn
1               5                   10                  15

Ser Gln Val Leu Phe Val Asp Lys Arg Gln Pro Val Phe Thr Asp Met
            20                  25                  30

Ala Tyr Thr Val Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Ala Val Pro Gly Asp Ser Lys Leu Glu
            100                 105                 110

Phe Glu Ser Ser Leu Tyr Glu Gly His Phe Leu Ala Cys Gln Lys Glu
        115                 120                 125

Asp Asn Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 177
<211> LENGTH: 157
<212> TYPE: PRT
<213> ORGANISM: artificial sequence
<220> FEATURE:
<223> OTHER INFORMATION: Synthetic sequence

<400> SEQUENCE: 177

```
Tyr Phe Gly Arg Leu His Cys Thr Thr Ala Val Ile Arg Asn Ile Asn
1               5                   10                  15

Ser Gln Val Leu Phe Val Asp Lys Arg Gln Pro Val Phe Thr Asp Met
            20                  25                  30

Ala Tyr Thr Val Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Ala Val Pro Gly Asp Ser Lys Leu Glu
            100                 105                 110

Phe Glu Ser Ser Leu Tyr Glu Gly His Phe Leu Ala Cys Gln Lys Glu
        115                 120                 125

Asp Asn Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 178
<211> LENGTH: 157

<212> TYPE: PRT
<213> ORGANISM: artificial sequence
<220> FEATURE:
<223> OTHER INFORMATION: Synthetic sequence

<400> SEQUENCE: 178

```
Tyr Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Thr Asp Met
            20                  25                  30

Gly Ala Arg Val Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Tyr Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Pro Val Pro Gly Asp Asn Lys Leu Glu
            100                 105                 110

Phe Glu Ser Ser Leu Tyr Glu Gly His Phe Leu Ala Cys Gln Lys Glu
        115                 120                 125

Ser Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 179
<211> LENGTH: 157
<212> TYPE: PRT
<213> ORGANISM: artificial sequence
<220> FEATURE:
<223> OTHER INFORMATION: Synthetic sequence

<400> SEQUENCE: 179

```
Tyr Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Thr Asp Met
            20                  25                  30

Gly Ala Arg Val Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Tyr Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Pro Val Pro Gly Asp Asn Lys Leu Glu
            100                 105                 110

Phe Glu Ser Ser Leu Tyr Glu Gly His Phe Leu Ala Cys Gln Lys Glu
        115                 120                 125

Ser Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 180

<211> LENGTH: 157
<212> TYPE: PRT
<213> ORGANISM: artificial sequence
<220> FEATURE:
<223> OTHER INFORMATION: Synthetic sequence

<400> SEQUENCE: 180

Asp Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Gly Asp Met
            20                  25                  30

Lys Ala Thr Gly Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Ala Val Pro Gly Ala Asn Lys Leu Glu
            100                 105                 110

Phe Glu Ser Ser Leu Tyr Glu Gly His Phe Leu Ala Cys Gln Lys Glu
        115                 120                 125

Ala Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 181
<211> LENGTH: 157
<212> TYPE: PRT
<213> ORGANISM: artificial sequence
<220> FEATURE:
<223> OTHER INFORMATION: Synthetic sequence

<400> SEQUENCE: 181

Asp Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Gly Asp Met
            20                  25                  30

Lys Ala Thr Gly Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Ile Lys Ala Val Pro Gly Ala Asn Lys Leu Glu
            100                 105                 110

Phe Glu Ser Ser Leu Tyr Glu Gly His Phe Leu Ala Cys Gln Lys Glu
        115                 120                 125

Ala Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 182
<211> LENGTH: 157
<212> TYPE: PRT
<213> ORGANISM: artificial sequence
<220> FEATURE:
<223> OTHER INFORMATION: Synthetic sequence

<400> SEQUENCE: 182

```
Asp Phe Gly Arg Leu His Cys Thr Thr Ala Val Ile Arg Asn Ile Asn
1               5                   10                  15

Ser Gln Val Leu Phe Val Asp Lys Arg Gln Pro Val Phe Arg Asp Met
            20                  25                  30

Gly Ser Ile His Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Ala Val Pro Gly Ala Asn Lys Leu Glu
            100                 105                 110

Phe Glu Ser Ser Leu Tyr Glu Gly His Phe Leu Ala Cys Gln Lys Glu
        115                 120                 125

Asp Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 183
<211> LENGTH: 157
<212> TYPE: PRT
<213> ORGANISM: artificial sequence
<220> FEATURE:
<223> OTHER INFORMATION: Synthetic sequence

<400> SEQUENCE: 183

```
Asp Phe Gly Arg Leu His Cys Thr Thr Ala Val Ile Arg Asn Ile Asn
1               5                   10                  15

Ser Gln Val Leu Phe Val Asp Lys Arg Gln Pro Val Phe Arg Asp Met
            20                  25                  30

Gly Ser Ile His Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Ala Val Pro Gly Ala Asn Lys Leu Glu
            100                 105                 110

Phe Glu Ser Ser Leu Tyr Glu Gly His Phe Leu Ala Cys Gln Lys Glu
        115                 120                 125

Asp Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 184
<211> LENGTH: 157
<212> TYPE: PRT
<213> ORGANISM: artificial sequence
<220> FEATURE:
<223> OTHER INFORMATION: Synthetic sequence

<400> SEQUENCE: 184

```
Tyr Phe Gly Arg Leu His Cys Thr Thr Ala Val Ile Arg Asn Ile Asn
1               5                   10                  15

Glu Gln Val Leu Phe Val Asp Lys Arg Gln Pro Val Phe Lys Asp Met
            20                  25                  30

Lys Asp Lys Leu Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Gly Val Pro Gly Asp Asn Lys Leu Glu
            100                 105                 110

Phe Glu Ser Ser Leu Tyr Glu Gly His Phe Leu Ala Cys Gln Lys Glu
        115                 120                 125

Phe Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 185
<211> LENGTH: 157
<212> TYPE: PRT
<213> ORGANISM: artificial sequence
<220> FEATURE:
<223> OTHER INFORMATION: Synthetic sequence

<400> SEQUENCE: 185

```
Tyr Phe Gly Arg Leu His Cys Thr Thr Ala Val Ile Arg Asn Ile Asn
1               5                   10                  15

Glu Gln Val Leu Phe Val Asp Lys Arg Gln Pro Val Phe Lys Asp Met
            20                  25                  30

Lys Asp Lys Leu Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Gly Val Pro Gly Asp Asn Lys Leu Glu
            100                 105                 110

Phe Glu Ser Ser Leu Tyr Glu Gly His Phe Leu Ala Cys Gln Lys Glu
        115                 120                 125

Phe Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 186
<211> LENGTH: 157
<212> TYPE: PRT
<213> ORGANISM: artificial sequence
<220> FEATURE:
<223> OTHER INFORMATION: Synthetic sequence

<400> SEQUENCE: 186

```
Tyr Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Ala Asp Met
            20                  25                  30

Ala Ser Thr His Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Gly Val Pro Gly Ala Asn Lys Ile Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

<210> SEQ ID NO 187
<211> LENGTH: 157
<212> TYPE: PRT
<213> ORGANISM: artificial sequence
<220> FEATURE:
<223> OTHER INFORMATION: Synthetic sequence

<400> SEQUENCE: 187

```
Tyr Phe Gly Arg Leu His Cys Thr Thr Ala Val Ile Arg Asn Ile Asn
1               5                   10                  15

Gly Gln Val Leu Phe Val Asp Lys Arg Gln Pro Val Phe Ala Asp Met
            20                  25                  30

Ala Ser Thr His Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Gly Val Pro Gly Ala Asn Lys Ile Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140
```

Lys Ser Val Met Phe Thr Leu Thr Asn Leu His Gln Ser
145 150 155

<210> SEQ ID NO 188
<211> LENGTH: 157
<212> TYPE: PRT
<213> ORGANISM: artificial sequence
<220> FEATURE:
<223> OTHER INFORMATION: Synthetic sequence

<400> SEQUENCE: 188

Tyr Phe Gly Arg Leu His Cys Thr Thr Ala Val Ile Arg Asn Ile Asn
1 5 10 15

Gly Gln Val Leu Phe Val Asp Lys Arg Gln Pro Val Phe Ala Asp Met
20 25 30

Ala Ser Thr His Gln Ser Ala Ser Glu Pro Gln Thr Arg Leu Ile Ile
35 40 45

Tyr Phe Tyr Lys Asp Ser Glu Val Arg Gly Leu Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Leu Lys Gly Val Pro Gly Ala Asn Lys Ile Glu
100 105 110

Phe Glu Ser Ser Leu Tyr Glu Gly His Phe Leu Ala Cys Gln Lys Glu
115 120 125

Asp Asp Ala Phe Lys Leu Ile Leu Lys Lys Lys Asp Glu Asn Gly Asp
130 135 140

Lys Ser Val Met Phe Thr Leu Thr Asn Leu His Gln Ser
145 150 155

<210> SEQ ID NO 189
<211> LENGTH: 157
<212> TYPE: PRT
<213> ORGANISM: artificial sequence
<220> FEATURE:
<223> OTHER INFORMATION: Synthetic sequence

<400> SEQUENCE: 189

Tyr Phe Gly Arg Leu His Cys Thr Thr Ala Val Ile Arg Asn Ile Asn
1 5 10 15

Ser Gln Val Leu Phe Val Asp Lys Arg Gln Pro Val Phe Gly Asp Met
20 25 30

Lys Tyr Ile Val Gln Ser Ala Ser Glu Pro Gln Thr Arg Leu Ile Ile
35 40 45

Tyr Phe Tyr Lys Asp Ser Glu Val Arg Gly Leu Ala Val Thr Leu Ser
50 55 60

Val Lys Asp Ser Lys Met Ser Thr Leu Ser Cys Lys Asn Lys Ile Ile
65 70 75 80

Ser Phe Glu Glu Met Asp Pro Pro Glu Asn Ile Asp Asp Ile Gln Ser
85 90 95

Asp Leu Ile Phe Phe Leu Lys Gly Val Pro Gly Asp Thr Lys Met Glu
100 105 110

Phe Glu Ser Ser Leu Tyr Glu Gly His Phe Leu Ala Cys Gln Lys Glu
115 120 125

Ser Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 190
<211> LENGTH: 157
<212> TYPE: PRT
<213> ORGANISM: artificial sequence
<220> FEATURE:
<223> OTHER INFORMATION: Synthetic sequence

<400> SEQUENCE: 190

Tyr Phe Gly Arg Leu His Cys Thr Thr Ala Val Ile Arg Asn Ile Asn
1               5                   10                  15

Ser Gln Val Leu Phe Val Asp Lys Arg Gln Pro Val Phe Gly Asp Met
            20                  25                  30

Lys Tyr Ile Val Gln Ser Ala Ser Glu Pro Gln Thr Arg Leu Ile Ile
        35                  40                  45

Tyr Phe Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Leu Lys Gly Val Pro Gly Asp Thr Lys Met Glu
            100                 105                 110

Phe Glu Ser Ser Leu Tyr Glu Gly His Phe Leu Ala Cys Gln Lys Glu
        115                 120                 125

Ser Gly Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 191
<211> LENGTH: 157
<212> TYPE: PRT
<213> ORGANISM: artificial sequence
<220> FEATURE:
<223> OTHER INFORMATION: Synthetic sequence

<400> SEQUENCE: 191

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Gly Asp Ser Val Pro Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ala Arg Ala Val Pro Gly His Ser Arg Lys
            100                 105                 110

```
Thr Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 192
<211> LENGTH: 157
<212> TYPE: PRT
<213> ORGANISM: artificial sequence
<220> FEATURE:
<223> OTHER INFORMATION: Synthetic sequence

<400> SEQUENCE: 192

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Ser Asp Ser Arg Ala Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Ala Arg Ser Val Pro Gly His Gly Arg Lys
            100                 105                 110

Thr Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 193
<211> LENGTH: 157
<212> TYPE: PRT
<213> ORGANISM: artificial sequence
<220> FEATURE:
<223> OTHER INFORMATION: Synthetic sequence

<400> SEQUENCE: 193

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Lys Tyr Ser Asp Ser Arg Ala Arg Gly Leu Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95
```

-continued

```
Ser Asp Ile Ile Phe Phe Ala Arg Asp Val Pro Gly His Ser Gly Lys
            100                 105                 110

Arg Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

INTERLEUKIN-18 MIMICS AND METHODS OF USE

CROSS-REFERENCE

This application claims the benefit of U.S. Provisional Application No. 62/847,190 filed May 13, 2019, which application is incorporated herein by reference in its entirety.

INCORPORATION BY REFERENCE OF SEQUENCE LISTING PROVIDED AS A TEXT FILE

A Sequence Listing is provided herewith as a text file, "SMCH-002_SeqList_ST25.txt" created on Oct. 12, 2020 and having a size of 241 KB. The contents of the text file are incorporated by reference herein in their entirety.

INTRODUCTION

Interleukin 18 (IL-18) is a pro-inflammatory cytokine that can stimulate T cells, NK cells, and myeloid cells. IL-18 has been proposed as an immunotherapeutic agent for the treatment of cancer, given its ability to stimulate anti-tumor immune cells. However, the clinical efficacy of IL-18 has been limited.

Thus, there is a need for compositions and methods that provide effective IL-18 signaling activity to treat and prevent cancer and other diseases and disorders. The present invention addresses this need.

SUMMARY

The present disclosure provides methods for making and using protein mimics ("IL-18 mimics") of Interleukin 18 variant polypeptides. Protein mimics of IL-18 variants are referred to herein as "Interleukin 18 mimic polypeptides", "Interleukin 18 mimics", or "IL-18 mimics" (e.g., DR mimics or D2D mimics), or an "Interleukine 18 neoleukin," Unlike IL-18 variants (e.g., DR IL-18 or D2D IL-18 variants, IL-18 mimics are proteins designed to recapitulate the binding properties and binding sites of IL-18 variants, but are otherwise unrelated in topology or amino acid sequence. Thus, while IL-18 variants generally have high overall sequence identity (e.g., 85% or more) with wild type IL-18 (e.g., wild type human IL-18), IL-18 mimics do not. Provided are methods of making and methods of using IL-18 mimics. In some cases the methods are methods of making an IL-18 mimic of a parent IL-18 protein, where the parent IL-18 protein is an IL-18 variant (e.g., a DR IL-18 variant, a D2D IL-18 variant, and the like).

In some cases, an IL-18 mimic is a mimic of a parent IL-18 protein where the parent IL-18 protein is a "decoy resistant" (DR) IL-18 variant. Decoy resistant IL-18 variants (DR IL-18 variants) are variants/mutants of IL-18 that bind to IL-18 receptor (IL-18R), thereby inducing/enhancing/stimulating IL-18 signaling activity, but exhibit little to no binding to the inhibitory IL-18 binding protein (IL-18BP). DR IL-18 variants are therefore IL-18R agonists that are resistant to inhibition by IL-18BP.

In some cases, an IL-18 mimic is a mimic of a parent IL-18 protein where the parent IL-1.8 protein is a "decoy-to-the-decoy" (D2D) IL-18 variant. D2D IL-18 variants are variants/mutants of IL-18 that bind to IL-18BP but exhibit little to no binding to IL-18R. D2D IL-18 variants bind IL-18BP (but do not signal), thereby antagonizing the effect of IL-18BP on IL-18. Thus, D2D IL-18 variants can be used to increase signaling through IL-18R because they act by inhibiting an inhibitor.

Therefore, in some cases an IL-18 mimic is a DR IL-18 mimic and in some cases an IL-18 mimic is a D2D IL-18 mimic. The present disclosure provides methods of making and methods of using IL-18 mimics (e.g., DR IL-18 mimics and D2D IL-18 mimics).

In some embodiments, IL-18 mimics (e.g., DR IL-18 mimics, D2D IL-18 mimics) are used for the treatment and prevention of a disease or disorder. In various embodiments, the disease or disorder is cancer or an infectious disease, such as poxviruses that encode an IL-18BP ortholog, a metabolic disease or disorder (including obesity and diabetes), or macular degeneration (e.g., wet macular degeneration, e.g., wet age-related macular degeneration, e.g., the IL-18 mimic can be used as an anti-angiogenic—as an illustrative example in some cases an IL-18 mimic can attenuate Choroidal neovascularization). Thus, methods are provided that include administering an IL-18 mimic (e.g., a DR IL-18 mimic, a D2D IL-18 mimic) to treat or prevent a disease or disorder, such as, but not limited to, cancer, or infectious disease, a metabolic disease or disorder, or macular degeneration (e.g., wet macular degeneration such as wet age-related macular degeneration).

In some embodiments, a method comprises administering to a subject in need thereof a composition comprising at least one IL-18 mimic. In some embodiments, a method comprises administering to a subject in need thereof a composition comprising at least one IL-18 mimic, and a composition comprising an additional agent. In some such embodiments, the additional agent comprises an immunotherapeutic agent, e.g., an altered T-cell, a chimeric antigen receptor T-cell (CAR-T), an armored CAR-T cell, a virus, an antigen, a vaccine, an antibody, an immune checkpoint inhibitor, a small molecule, a chemotherapeutic agent, a stem cell, and the like. In some embodiments, a composition comprising at least one IL-18 mimic is used in a method to increase immune system activity before, during, or after infection by a bacterium, virus, or other pathogen. In some embodiments, a composition comprising at least one IL-18 mimic is used in a method to increase the number and/or activity of immune cells in vitro, in vivo or ex vivo, such as the number and/or activity of T cells, NK cells, and/or myeloid cells.

In some cases an IL-18 mimic is computationally designed, and said computationally designing includes using a IL-18 variant polypeptide's primary amino acid sequence in defining a structure that is fed into a mimetic design protocol that (i) detects core secondary structure elements that compose the target template, and (ii) produces resulting de novo mimetic backbones. In some cases, the core secondary structure elements are idealized by reconstruction using loops from a clustered database of highly ideal fragments. In some cases, the computationally designing includes combinatorially recombining solutions for pairs of connected secondary structures to produce fully connected backbones. In some cases the computationally designing includes combining information on hotspots, compatible built-fragment amino acids and layers to facilitate flexible backbone design and filtering.

BRIEF DESCRIPTION OF THE DRAWINGS

The following detailed description of embodiments of the disclosure will be better understood when read in conjunction with the appended drawings. It should be understood that the invention is not limited to the precise arrangements and instrumentalities of the embodiments shown in the drawings.

(FIG. 1A) The IL-18 pathway (including IL-18 and its receptor subunits) is upregulated in both activated and dysfunctional tumor T cell programs, as seen in RNAseq expression analysis for cytokines and receptors in CD8+ TILs. Genes are assigned "activation" and "dysfunction" scores in comparison to naïve T cells. Yellow highlights indicate IL-18 cytokine, IL-18R1 (Rα), and IL-18RAP (Rβ). Data are adapted from Singer et al. (Singer, M. et al., 2016, Cell, 166:1500-1511, e1509). (FIG. 1B) The IL-18 receptor subunits IL-18Rα and IL-18Rβ are part of a gene expression program associated with chronic antigen exposure, as seen after infection with LCMV (left; CD4) or VSV-OVA (right; CD8). Data are from the ImmGen database.

(FIG. 2A) IL-18BP mediates Interferon-γ (IFN-γ) driven negative feedback of IL-18, reminiscent of the immune checkpoint PD-L1. A schematic of the IL-18/IFN-γ/IL-18BP feedback loop is depicted. Black arrows indicate stimulation, red circuits indicate inhibition. (FIG. 2B) IL-18BP is upregulated in gastric and breast cancer, as seen in data from the TCGA and Oncomine databases. (FIG. 2C) PD-1 and IL-18BP expression is strongly correlated in bulk breast and gastric cancer samples (from TCGA database). R=0.78 and 0.65, respectively.

(FIG. 3A) A structure-guided library to randomize residues on the IL-18:IL-18BP interface was designed and introduced into a yeast-display system. Yeast clones were selected using magnetic and fluorescence cell sorting for binding to IL-18Rα and counter-selected against IL-18BP. (FIG. 3B) Summary of directed evolution to generate IL-18BP resistant IL-18 variants. Blue text indicates positive selection conditions, red text shows counterselection. (FIG. 3C) Flow cytometric analysis of yeast-displayed WT IL-18 (left) or variants after directed evolution (right). Y-axes show IL-18BP binding, x-axes show IL-18Rα binding. After 5 rounds of directed evolution, the remaining clones greatly preferred IL-18Rα to IL-18BP.

FIG. 4 depicts results from example experiments, demonstrating a summary of the sequences of decoy-resistant human IL-18 ("DR-IL-18", also called "DR-18") variants. The position of each mutated position and the corresponding residue in the mature form of wild-type human IL-18 is indicated at the top of the table. hC4 through hE12 represent sequences obtained after selection with directed evolution. hCS1-hCS4 are consensus sequences derived from the selected sequences. Shaded residues represent the five most conserved mutations observed.

(FIG. 5A) Yeast-displayed DR-IL-18 variants hCS1-hCS4 and A8 are capable of binding hIL-18Rα with comparable binding isotherms as WT human IL-18 (left), By contrast, very little binding is observed with the same variants and hIL-18BP (right). (FIG. 5B) Representative surface plasmon resonance sensorgrams between immobilized biotinylated hIL-18BP and the DR-IL-18 variants. Recombinant hIL-18 (left) binds IL-18BP with exquisitely high affinity, $K_D$=2.0 pM, whereas hCS1 (right) shows greatly attenuated binding, with a much faster off-rate and $K_D$=15.2 nM, This data is summarized in Tables 6 and 7.

(FIG. 6A) Recombinant IL-18BP inhibits biotinylated IL-18Rα from binding yeast-displayed WT IL-18, but does not affect the DR-IL-18 variants hCS1-4 and A8 (left). By contrast, IL-18BP effectively neutralizes the IL-18 E42A, K89A and E42A/K89A previously described (Kim et al., 2001, Proc. Natl. Acad. Sci., 98(6): 3304-3309) (right) [E42 and K89 of Kim et al. are E6 and K53 of SEQ ID NO: 30, respectively]. Biotinylated IL-18Rα was kept at a fixed concentration of 100 nM for all samples. (FIG. 6B) WT IL-18 and hCS1, hCS3, and hCS4 stimulate IL-18 HEK-Blue reporter cells with comparable potency and efficacy (left). Wild-type IL-18 is highly sensitive to application of recombinant IL-18BP in this assay (IC50=3 nM), whereas hCS1 and hCS3 are not inhibited by recombinant IL-18BP, even at IL-18BP concentrations of 1 μM (Right). hIL-18 was kept at a fixed concentration of 5 nM and hCS1 and hCS3 at 2.5 nM.

FIG. 7A through FIG. 7C depict results from experiments demonstrating engineering additional human IL-18 variants for independence to IL-18BP (version 2 variants) using yeast display. (FIG. 7A) Summary of the positions in human IL-18 randomized in the version 2.0 library. Degenerate codons and the set of encoded amino acids are given for each position. (FIG. 7B) Summary of directed evolution to generate version 2.0 IL-18BP resistant IL-18 variants. Blue text indicates positive selection conditions, red text shows counterselection. (FIG. 7C) Flow cytometric analysis of progress in creating version 2.0 DR-IL-18 variants. Yeast obtained after rounds 1, 4, and 6 were stained simultaneously with 250 nM IL-18BP streptavidin-PE tetramers or 100 nM IL-18Rα directly labeled with AlexaFluor647. Y-axes show IL-18BP binding, x-axes show IL-18Rα binding. After 6 rounds of directed evolution, the remaining clones greatly preferred IL-18Rα to IL-18BP.

FIG. 8 depicts results from example experiments, demonstrating a summary of the sequences of version 2.0 decoy-resistant human IL-18 (DR-IL-18) variants. The position of each mutated position and the corresponding residue in the mature form of wild-type human IL-18 is indicated at the top of the table. Shaded rows indicate recurrent sequence variants obtained in both round 5 and round 6.

FIG. 9A through FIG. 9D depicts results from example experiments, demonstrating biophysical characterization of version 2.0 human DR-IL-18 variants. (FIG. 9A) Yeast-displayed version 2.0 DR-IL-18 variants are capable of binding hIL-18Rα with comparable binding isotherms as WT human IL-18. (FIG. 9B) By contrast, very little binding is observed with the same variants and hIL-18BP. (FIG. 9C) Thermal stability of the version 2.0 DR-IL-18 variants was assessed by heating the yeast-displayed variants across a range of temperatures for 15 minutes, followed by staining with hIL-18Rα. The version 2.0 DR-IL-18 variants were more thermostable than WT IL-18 (Tm=47.6 C) and the first-generation consensus sequences (Tm=50.9 and 40.2 for hCS1 and hCS2, respectively). (FIG. 9D) Summary of the receptor binding properties and thermal stability of the second-generation DR-IL-18 variants. NBD=no binding detected. N.D.=value not determined.

FIG. 10A through FIG. 10C depict results from example experiments, demonstrating engineering murine IL-18 variants for independence to IL-18BP using yeast display. (FIG. 10A) Summary of directed evolution to generate IL-18BP resistant murine IL-18 variants. Blue text indicates positive selection conditions, red text shows counterselection. (FIG. 10B) Flow cytometric analysis of yeast-displayed murine IL-18 variants after 5 rounds of directed evolution. Y-axes show IL-18BP binding, x-axes show IL-18Rα binding. (FIG. 10C) Summary of the sequences of decoy-resistant murine IL-18 (DR-IL-18) variants. The position of each mutated position and the corresponding residue in the mature form of wild-type murine IL-18 is indicated at the top of the table. mC1 through mH3 represent sequences obtained after selection with directed evolution. mCS1 and mCS2 are consensus sequences derived from the selected sequences. Shaded residues represent the five most conserved mutations observed.

(FIG. 11A) Yeast-displayed DR-IL-18 variants mA7, mB1, mC1, mE8, mCS1, and mCS2 are capable of binding mIL-18Rα with comparable binding isotherms as WT murine IL-18 (left). By contrast, very little binding is observed with the same variants and mIL-18BP (right). (FIG. 11B) Representative surface plasmon resonance sensorgrams between immobilized biotinylated mIL-18BP and the murine DR-IL-18 variants. Recombinant mIL-18 (left) binds mIL-18BP with high affinity, $K_D$=0.8 pM, whereas mCS2 (right) shows greatly decreased binding with a $K_D$ value greater than 10 μM. This data is summarized in Tables 8 and 9.

(FIG. 12A) Schematic of study design. Mice were administered vehicle (PBS), mIL-18 (1 mg/kg), or the DR-IL-18 variant mCS2 (1 mg/kg) once daily for seven total doses (depicted as syringes). Blood samples were taken five hours post-injection two days prior to the experiment, and on days 0, 3, and 6. (FIG. 12B) Peripheral blood cell counts for CD4, CD8, NK cells, and monocytes at day 0, day 3, and day 6. Both IL-18 and mCS2 expanded NK cells and monocytes to a similar degree by day 3. For each time point (day), left bar is PBS, middle bar is IL-18, and right bar is mCS2. (FIG. 12C) CD69 expression on peripheral CD4, CD8, and NK cells. mCS2, but not IL-18 stimulated CD69 expression on CD4 and CD8 cells. Both IL-18 and mCS2 increased CD69 on NK cells, but mCS2 treatment caused sustained CD69 expression evident at day 6, in comparison to IL-18, which reverted to baseline CD69 levels. For each time point (day), left bar is PBS, middle bar is IL-18, and right bar is mCS2. (FIG. 12D) Serum cytokine levels for interferon-γ (IFN-γ), MIP-1b, and G-CSF. mCS2 treatment yielded higher levels of IFN-γ, MIP-1b, and G-CSF than mIL-18 treatment.

(FIG. 14A) Tumor growth spider plots for mice bearing Yummer1.7 melanoma tumors treated with saline (control), WT IL-18 (0.32 mg/kg), the DR-IL-18 variant mCS2 (0.32 mg/kg), anti-PD1 (8 mg/kg), IL-18+ anti-PD1, or mCS2+ anti-PD-1 twice per week. (FIG. 14B) Survival curves from the same groups as in (FIG. 11A). mCS2 was effective as a monotherapy and synergized in combination with anti-PD1 in this model.

(FIG. 15B) Survival curves from the same groups as in (FIG. 15A).

(FIG. 18A) Tumor immunophenotyping experiments from mice treated twice weekly for four doses with saline, WT IL-18, or the DR-IL-18 variant mCS2. DR-IL-18 treatment resulted in increased numbers of CD8 and NK cells per mg of tumor (upper left two panels) and increased expression of activation markers granzyme B and KLRG1 on CD8 and NK cells (upper right two panels). DR-IL-18 treatment did not improve the CD8:Treg ratio compared to saline treatment, whereas WT IL-18 made the ratio less favorable. However, DR-IL-18 treatment increased the ratio of CD8 cells to inhibitory myeloid populations including tumor associated macrophages (TAM), and monocytic and granulocyte myeloid derived suppressor cells (mMDSCs and gMDSCs). (FIG. 18B) Serum Luminex cytokine measurements from the same mice as (FIG. 18A) taken 24 hours after the $4^{th}$ treatment dose. DR-IL-18 shows a dramatically altered secondary cytokine release profile from treatment with WT IL-18, notably increasing Interferon-gamma, IL-7, and IL-15 levels by more than 100-fold.

(FIG. 19A) Tumor growth spider plots from mice bearing B2m-deficient Yummer1.7 tumors treated with saline, anti-PD1+ anti-CTLA4, the DR-IL-18 variant mCS2, or mCS2 with depletion of NK cells with anti-NK1.1 antibodies. DR-IL-18 demonstrated strong efficacy in terms of tumor growth and survival (FIG. 19B), curing 60% of treated mice in this model that is completely resistant to even combination treatment with anti-CTLA4+ anti-PD1. This efficacy is NK cell dependent since administration of anti-NK1.1 abrogates the mCS2 treatment effect. (FIG. 19C) NK cells isolated from B2m-deficient Yummer1.7 are dysfunctional and show diminished proliferation (Ki67 staining) and function (Interferon-gamma secretion). However, treatment with DR-IL-18 reverses this phenotype to enable robust proliferation and cytokine secretion.

FIG. 20A through FIG. 20C depicts example experiments demonstrating engineering of human IL-18 variants as IL-18BP antagonists (or "decoys-to-the-decoy", D2D) using yeast display. These variants bind IL-18BP but do not signal, thereby antagonizing the effect of IL-18BP on endogenous IL-18 (FIG. 20A) Summary of the positions in human IL-18 randomized in the D2D library. Degenerate codons and the set of encoded amino acids are given for each position. (FIG. 20B) Summary of directed evolution to generate D2D IL-18 variants that bind and neutralize IL-18BP, but do not signal through the IL-18R. Blue text indicates positive selection conditions, red text shows counter-selection. (FIG. 20C) Flow cytometric analysis of progress in creating D2D hIL-18 variants. Yeast obtained after rounds 1-4 were stained with 1 nM of mouse IL-18BP (left panel), 1 nM human IL-18BP (middle panel), or 1 μM IL18Rα plus 1 μM IL18Rβ. Selected variants show enhanced IL-18BP binding across rounds of selection without increases in IL18Rα or IL18Rβ binding.

FIG. 21 depicts results from example experiments demonstrating a summary of the sequences of D2D human IL-18 variants. The position of each mutated position and the corresponding residue in the mature form of wild-type human IL-18 is indicated at the top of the table.

FIG. 22A through FIG. 22C depict results from example experiments demonstrating biophysical characterization of the human decoy-to-the-decoy (D2D) IL-28 variants. (FIG. 22A) Yeast-displayed D2D IL-8 variants 5-B02, 5-E08, 5-F10, 5-F02, 5-F01, hD2D-CS1, hD2D-CS2, and hD2D-CS3 are capable of binding hIL-18RBP with comparable binding isotherms as WT human IL-18. (FIG. 22*b*) By contrast, very little binding is observed with the same variants and hIL-18Rα (FIG. 11C) Summary of the receptor binding properties of the D2D IL-18 variants. NBD=no binding detected, FIG. 2.3 depicts results from example experiments demonstrating a summary of the sequences of D2D murine IL-18 variants. The position of each mutated position and the corresponding residue in the mature form of wild-type murine IL-18 is indicated at the top of the table.

C57BL/6 mice were infected with $10^6$ PFU of Vaccinia virus (VACV) intraperitoneally (IP) and administered 1 mg/kg WT mIL-18 or mCS2 IP. Mice were sacrificed and viral titers were measured in the blood and ovaries by RT-PCR on day 3 post-infection. (B) Quantification of VACV viral copies in ovaries and blood of treated mice at day 3 post infection. Treatment with CS2 showed a significant reduction of viral titers, whereas WT IL-18 was not effective. *$p<0.05$, $p<0.01$, *$p<0.001$.

Figure 30A:
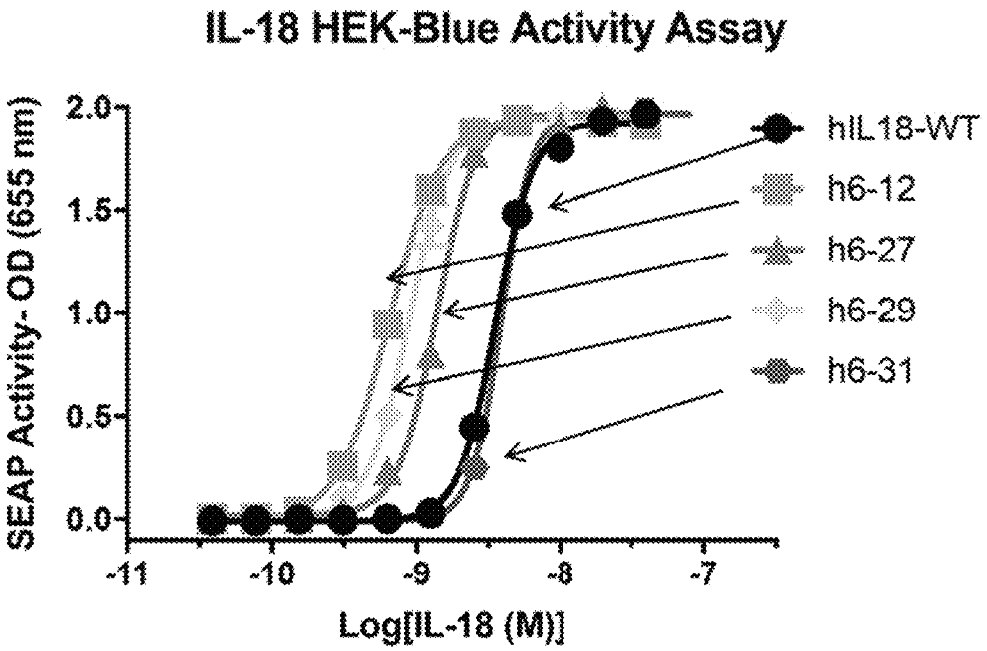

FIG. 30A depicts data demonstrating that the second generation human DR-IL-18 variants are active. (FIG. 30A) WT IL-18 and h6-12, h6-27, h6-29, and h6-31 stimulate IL-18 HEK-Blue reporter cells. 116-12, h6-27, and h6-29 show enhanced potency compared to WT hIL-18, whereas h6-31 has equivalent potency as WT hIL-18. The data demonstrate, therefore, that all tested second generation human DR-IL-18 variants actively signal through IL-18R.

FIG. 31 depicts a schematic diagram, according to embodiments of the present disclosure, for designing IL-18 mimic proteins e.g., a DR IL-18 mimic, a D2D IL-18 mimic).

DETAILED DESCRIPTION

As noted above, the present disclosure provides methods for making and using protein mimics ("IL-18 mimics") of Interleukin 18 variant polypeptides. Protein mimics of IL-18 variants are referred to herein as "Interleukin 18 mimic polypeptides", "Interleukin 18 mimics", or "IL-18 mimics" (e.g., DR mimics or D2D mimics). Unlike IL-18 variants (e.g., DR IL-18 or D2D IL-18 variants), IL-18 mimics are proteins designed to recapitulate the binding properties and binding sites of IL-18 variants, but are otherwise unrelated in topology or amino acid sequence. Thus, while IL-18 variants generally have high overall sequence identity (e.g., 85% or more) with wild type IL-18 (e.g., wild type human IL-18), IL-18 mimics do not. Provided are methods of making and methods of using IL-18 mimics.

In some cases, an IL-18 mimic is a mimic of a "decoy resistant" (DR) IL-18 variant. Decoy resistant IL-18 variants (DR IL-18 variants) are variants/mutants of IL-18 that bind to IL-18 receptor (IL-18R), thereby inducing/enhancing/stimulating IL-18 signaling activity, but exhibit little to no binding to the inhibitory IL-18 binding protein (IL-18BP). DR IL-18 variants are therefore IL-18R agonists that are resistant to inhibition by IL-18BP.

In some cases, an IL-18 mimic is a mimic of a "decoy-to-the-decoy" (D2D) IL-18 variant. D2D IL-18 variants are variants/mutants of IL-18 that bind to IL-18BP but exhibit little to no binding to IL-18R. D2D IL-18 variants bind IL-18BP (but do not signal), thereby antagonizing the effect of IL-18BP on IL-18. Thus, D2D IL-18 variants can be used to increase signaling through IL-18R because they act by inhibiting an inhibitor.

Therefore, in some cases an IL-18 mimic is a DR IL-18 mimic and in some cases an IL-18 mimic is a D2D IL-18 mimic. The present disclosure provides methods of making and methods of using IL-18 mimics (e.g., DR IL-18 mimics and D2D IL-18 mimics).

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112

Definitions

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present disclosure may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, synthetic antibodies, chimeric antibodies, and a humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, New York; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, an "immunoassay" refers to any binding assay that uses an antibody capable of binding specifically to a target molecule to detect and quantify the target molecule.

By the term "specifically binds," as used herein with respect to an IL-18 mimic or variant, is meant an IL-18 mimic or variant that recognizes and binds to a specific receptor, such as IL-18R, or to IL-18BP. In some instances, the IL-18 mimic or Variant exhibits substantially reduced binding to IL-18BP. For example, an IL-18 mimic or variant that specifically binds to a receptor from one species may also bind to that receptor from one or more species. But, such cross-species reactivity does not itself alter the classification of an IL-18 mimic or variant as specific. In another example, an IL-18 mimic or variant that specifically binds to a receptor may also bind to different allelic forms of the receptor. However, such cross reactivity does not itself alter the classification of an IL-18 mimic or variant as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an IL-18 mimic or variant recognizes and binds to a specific protein structure rather than to proteins generally.

By the term "applicator," as the term is used herein, is meant any device including, but not limited to, a hypodermic syringe, a pipette, an iontophoresis device, a patch, and the like, for administering the compositions of the disclosure to a subject.

"Cancer," as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues, including the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), and hematopoietic system (e.g., lymphoma, myeloma, leukemia, acute lymphocytic leukemia, chronic lymphocytic leukemia, acute myeloid leukemia, chronic myeloid leukemia, etc.).

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic, prophylactic, or other desired benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system, Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein, polypeptide or peptide, refers to a subsequence of a larger protein, polypeptide or peptide. A "fragment" of a protein, polypeptide, or peptide can be at least about 5 amino acids in length; for example, at least about 10 amino acids in length; at least about 20 amino acids in length; at least about 50 amino acids in length; at least about 100 amino acids in length; at least about 200 amino acids in length; or at least about 300 amino acids in length (and any integer value in between).

The term "gene" refers to a nucleic acid (e.g., DNA) sequence that includes coding sequences necessary for the production of a polypeptide, precursor, or RNA (e.g., mRNA). The polypeptide may be encoded by a full-length coding sequence or by any portion of the coding sequence so long as the desired activity or functional property (e.g., enzymatic activity, receptor binding, signal transduction, immunogenicity, etc.) of the full-length or fragment is retained. The term also encompasses the coding region of a structural gene and the sequences located adjacent to the coding region on both the 5' and 3' ends for a distance of about 2 kb or more on either end such that the gene corresponds to the length of the full-length mRNA and 5' regulatory sequences which influence the transcriptional properties of the gene. Sequences located 5' of the coding region and present on the mRNA are referred to as 5'-untranslated sequences. The 5'-untranslated sequences usually contain the regulatory sequences. Sequences located 3' or downstream of the coding region and present on the mRNA are referred to as 3'-untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

"Homologous", "identical," or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Instructional material," as that term is used herein, includes a publication, a recording, a diagram, or any other medium of expression which can be used to communicate the usefulness of the nucleic acid, peptide, polypeptide, and/or compound of the disclosure in the kit for identifying or alleviating or treating the various diseases or disorders recited herein. Optionally, or alternately, the instructional material may describe one or more methods of identifying or alleviating the diseases or disorders in a cell or a tissue of a subject. The instructional material of the kit may, for example, be affixed to a container that contains the nucleic acid, polypeptide, and/or compound of the disclosure or be shipped together with a container that contains the nucleic acid, polypeptide, and/or compound. Alternatively, the instructional material may be shipped separately from the container with the intention that the recipient uses the instructional material and the compound cooperatively.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "label" when used herein refers to a detectable compound or composition that is conjugated directly or indirectly to a probe to generate a "labeled" probe. The label may be detectable by itself (e.g., radioisotope labels or fluorescent labels) or, in the case of an enzymatic label, may catalyze chemical alteration of a substrate compound or composition that is detectable (e.g., avidin-biotin), In some instances, primers can be labeled to detect a PCR product.

By the term "modulating," as used herein, is meant mediating a detectable increase or decrease in the activity and/or level of a mRNA, polypeptide, or a response in a subject compared with the activity and/or level of a mRNA, polypeptide or a response in the subject in the absence of a treatment or compound, and/or compared with the activity and/or level of a mRNA, polypeptide, or a response in an otherwise identical but untreated subject. The term encompasses activating, inhibiting and/or otherwise affecting a native signal or response thereby mediating a beneficial therapeutic, prophylactic, or other desired response in a subject, for example, a human.

A "mutation," "mutant," or "variant," as used herein, refers to a change in nucleic acid or polypeptide sequence relative to a reference sequence (which may be a naturally-occurring normal or the "wild-type" sequence), and includes translocations, deletions, insertions, and substitutions/point mutations. A "mutant" or "variant" as used herein, refers to either a nucleic acid or protein comprising a mutation.

A "nucleic acid" refers to a polynucleotide and includes poly-ribonucleotides and poly-deoxyribonucleotides. Nucleic acids according to the present disclosure may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present disclosure contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present disclosure may be a peptide nucleic acid (PNA). (See U.S. Pat. No. 6,156,501 which is hereby incorporated by reference in its entirety.) The disclosure also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

The terms "patient," "subject," "individual," and the like are used interchangeably herein, and refer to any animal, or cells thereof whether in vivo, in vitro or in situ, amenable to the methods described herein. In certain non-limiting embodiments, the patient, subject or individual is a human.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, mutant polypeptides, variant polypeptides, or a combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to exhibit non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

To "prevent" a disease or disorder as the term is used herein, means to reduce the severity or frequency of at least one sign or symptom of a disease or disorder that is to be experienced by a subject.

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

As used herein, "substantially purified" refers to being essentially free of other components. For example, a substantially purified polypeptide is a polypeptide which has been separated from other components with which it is normally associated in its naturally occurring state.

As used herein, the terms "therapy" or "therapeutic regimen" refer to those activities taken to prevent, treat or alter a disease or disorder, e.g., a course of treatment intended to reduce or eliminate at least one sign or symptom of a disease or disorder using pharmacological, surgical, dietary and/or other techniques. A therapeutic regimen may include a prescribed dosage of one or more compounds or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound or composition that will elicit the biological, physiologic, clinical or medical response of a cell, tissue, organ, system, or subject that is being sought by the researcher, veterinarian, medical doctor or other clinician. The term "therapeutically effective amount" includes that amount of a compound or composition that, when administered, is sufficient to prevent development of, or treat to some extent, one or more of the signs or symptoms of the disorder or disease being treated. The therapeutically effective amount will vary depending on the compound or composition, the disease and its severity and the age, weight, etc., of the subject to be treated.

To "treat" a disease or disorder as the term is used herein, means to reduce the frequency or severity of at least one sign or symptom of a disease or disorder experienced by a subject. The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), e.g., slowing or arresting their development (e.g., halting the growth of tumors, slowing the rate of tumor growth, halting the rate of cancer cell proliferation, and the like); or (c) relieving the disease symptom(s), i.e., causing regression of the disease and/or symptom(s) (e.g., causing decrease in tumor size, reducing the number of cancer cells present, and the like). Those in need of treatment include those already inflicted (e.g., those with cancer, those with an infection, those with a metabolic disorder, those with macular degeneration, etc.) as well as those in which prevention is desired (e.g., those with increased susceptibility to cancer, those with an increased likelihood of infection, those suspected of having cancer, those suspected of harboring an infection, those with increased susceptibility for metabolic disease, those with increased susceptibility for macular degeneration, etc.).

As used herein, the term "wild-type" refers to a gene or gene product isolated from a naturally occurring source. A wild-type gene is that which is most frequently observed in a population and is thus arbitrarily designated the "normal" or "wild-type" form of the gene. In contrast, the term "modified," "variant," or "mutant" refers to a gene or gene product that possesses modifications in sequence and/or functional properties (i.e., altered characteristics) when compared to the wild-type gene or gene product.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

As summarized above, provided are methods for making and methods for using protein mimics ("IL-18 mimics") of parent proteins such as Interleukin 18 variants (IL-18 variants). In some cases a parent protein is an IL-18 variant that is a "decoy resistant" IL-18 variant, and in some cases a parent protein is an IL-18 variant that is a "decoy-to-the-decoy" IL-18 variant. Decoy resistant (DR) IL-18 variants ("DR IL-18 variants") are variants/mutants of IL-18 that bind to IL-18 receptor (IL-18R), thereby inducing/enhancing/stimulating IL-18 signaling activity, but exhibit little to no binding to the inhibitory IL-18 binding protein (IL-18BP). D2D ("decoy-to-the-decoy") IL-18 variants ("D2D IL-18 variants") are variants/mutants of IL-18 that bind to IL-18BP but exhibit little to no binding to IL-18R.

Therefore, in some cases an IL-18 mimic is a DR IL-18 mimic and in some cases an IL-18 mimic is a D2D IL-18 mimic. The present disclosure provides methods of making (e.g., designing and producing) and methods of using IL-18 mimics DR IL-18 mimics and D2D IL-18 mimics).

IL-18 mimics can be produced by any suitable means known or later discovered in the field, e.g., produced from eukaryotic or prokaryotic cells (e.g., encoded by a nucleic acid such as an RNA or DNA), synthesized in vitro, etc. In some cases an IL-18 mimic is produced by introducing a nucleic acid encoding the IL-18 mimic into a eukaryotic cell line that has been engineered for this purpose (the expression of protein from introduced nucleic acids). Various commercial synthetic apparatuses are available, for example, automated synthesizers by Applied Biosystems, Inc., Beckman Coulter, etc. By using synthesizers, naturally occurring amino acids may be substituted with unnatural amino acids. The particular sequence and the manner of preparation will be determined by convenience, economics, purity required, and the like.

IL-18 Mimics and Computational Design

To make IL-18 mimics, a computational protein design method can be used in which the structural elements that interact with the desired receptor/subunit(s) (e.g., IL-18Rα in the case of DR IL-18 mimics, IL-BP in the case of D2D IL-18 mimics) are fixed in space, and an idealized de novo globular protein structure is built to support these elements.

De novo design has been used previously to support short linear epitopes (see, e.g., Procko, E. et al. A computationally designed inhibitor of an Epstein-Barr viral Bcl-2 protein induces apoptosis in infected cells. *Cell* 157, 1644-1656 (2014); Chevalier, A. et al. Massively parallel de novo protein design for targeted therapeutics. *Nature* 550, 74-79 (2017); Jacobs, T. M. et al. Design of structurally distinct proteins using strategies inspired by evolution. *Science* 352, 687-690 (2016); and Correia, B. E. et al. Proof of principle for epitope-focused vaccine design. *Nature* 507, 201-206 (2014). It was recently demonstrated that more complex binding interfaces can also be supported (e.g., by using a parametric construction of disembodied helices coupled with knowledge-based loop closure)—see, e.g., Silva et al., Nature. 2019 January; 565(7738):186-191; and Boyken, S. E. et al. De novo design of protein homo-oligomers with modular hydrogen-bond network-mediated specificity. Science 352, 680-687 (2016).

Thus, to generate a DR IL-18 mimic, a de novo stable idealized protein can be designed with an interaction surface that mimics that of IL-18 for IL-18Rα (or mimics that of a parent protein such as a DR IL-18 variant for IL-18Rα), but: (i) entirely lacks the IL-18BP interaction surface, or (ii) mimics the modified IL-18BP interaction surface of a parent protein such as a DR IL-18 variant. Likewise, to generate a D2D IL-18 mimic, a de novo stable idealized protein can be designed with an interaction surface that mimics that of IL-18 for IL-18BP (or mimics that of a parent protein such as a D2D IL-18 variant for IL-18BP), but: (i) entirely lacks the IL-18Rα interaction surface, or (ii) mimics the modified IL-18Rα interaction surface of a parent protein such as a D2D IL-18 variant.

For structural details about the interaction between IL-18 and IL-18R or IL-18BP, see Tsutsumi et al, Nat Commun. 2014 Dec. 15; 5:5340; and Wei et al., FEBS Lett. 2014 Nov. 3; 588(21):3838-43. For example, IL-18 binds to IL-18Rα via α-helix I, which is stabilized by interactions with IL-18Rα. IL-18 binds to IL-18BP via the IL-18Rα-D3 binding site. Thus, for example, a DR IL-18 mimic might in some cases include a sequence designed to mimic IL-18 α-helix I, but not include an IL-18Rα-D3 binding site that mimics a DR IL-18 variant instead of mimicking that region of a wild type IL-18 protein. As another example, a D2D IL-18 mimic might in some cases include a sequence designed to mimic an IL-18Rα-D3 binding site, but not include an IL-18 α-helix I or instead include a IL-18 α-helix I that mimics a D2D IL-18 variant instead of mimicking that region of a wild type IL-18 protein.

For detailed methods on how computational design can be achieved, see Silva et al., Nature. 2019 January; 565(7738): 186-191. For example, design of de novo cytokine mimetics can begin by defining the structure of human IL-18 (or e.g., an IL18 variant such as a DR IL-18 variant or a D2D IL-18 variant) in the complex with its binding partner (e.g., human IL-18Rα or human IL-18BP) as the template for the design. After inspection, the residues composing the binding site can be defined as hotspots (see, e.g., examples section below describing amino acid positions that were selected for mutagenesis). The structure can be fed into a mimetic design protocol (e.g., one that is programmed in PyRosetta), which can automatically detect the core secondary structure elements that compose the target template and produce the resulting de novo mimetic backbones. In brief, a mimetic building algorithm can work as follows. For the first generation of designs, each of the core elements can be idealized by reconstruction using loops from a clustered database of highly ideal fragments (fragment size=4 amino acids). After idealization, the mimetic building protocol can reconnect the idealized elements by pairs in all possible combinations. To do this, it can use combinatorial fragment assembly of sequence-agnostic fragments from the database, followed by Cartesian-constrained backbone minimization for potential solutions (that is, where the N and C ends of the built fragment are close enough to link the two secondary structures). After minimization, the solutions can be verified to contain highly ideal fragments (that is, that every overlapping fragment that composes the two connected elements is also contained within the database) and that no backbone clashes with the target (context) receptor. Successful solutions can be profiled using the same database of fragments in order to determine the most probable amino acids at each position (this information can be encoded as metadata on each design). Next, solutions for pairs of connected secondary structures can be combinatorially recombined (e.g., by using graph theory-connected components) to produce fully connected backbones. Since the number of solutions grows exponentially with each pair of elements, at each fragment combination step the designs can be ranked to favor those with shorter interconnections between pairs of secondary structure core elements (that is, effectively with shorter loops), and in some cases only the top are solutions kept. Fully connected backbone solutions can be profiled by layer (interface, core, non-core surface, surface) in order to restrict the identities of the possible amino acids to be layer-compatible.

The information on hotspots, compatible built-fragment amino acids and layers can be combined (hotspot has precedence to amino acid probability, and amino acid probability can take precedence to layer) and output as Rosetta refiles (specific for a given de novo mimic backbone result). These backbones and their corresponding refiles can be passed to RosettaScripts for flexible backbone design and filtering.

For a second generation of designs, two approaches can be followed. In the first approach, Rosetta sequence redesigns of the best first generation optimized design can be executed (G1_neo2_40_1F). In the second approach, new mimetics can be engineered using G1_neo2_40_1F as the target template. The mimetic design protocol in this second generation can be similar to the one described for the first generation, but with two key differences. First, the core elements (that is, those that are secondary structures) can be built by discovering parametric equations of repetitive phi and psi angles (omega fixed to 180°) that result in secondary structures that recapitulated each of the target helices as close as possible. Second, a 'pitch' on the phi and psi angles can be allowed every 3rd residue in order to allow the helices the possibility to have curvature (final angle parameters: H1: phi=−60.4, psi=−45.8, phi_pitch=−1.0, psi_pitch=2.0; H2: phi=−64.5, psi=−38.4, phi_pitch=4.0, psi_pitch=8.0; H3: phi=−64.6, psi=−40.6, phi_pitch 0.0, psi_pitch=0.0; H4: phi=−64.3, psi=−41.7, phi_pitch=0.0, psi_pitch=0.0). By using these parametric equations, the algorithm can variate the length of each of the core-elements up to ±8 amino acids (compared to the input template). Reductions in the size of the core elements should not be allowed to remove hotspots from the binding site. All length variations of the core elements can be reconnected with loops from a clustered database of highly ideal loops (fragment size of 7 amino acids). The rest of the design algorithm can be in essence similar to the one followed in the generation one. However, the implementation of the second generation algorithm can be more convenient, because the input PDB can incorporate PDBInfoLabels metadata to define the hotspots, and subsequently, it can use this information to integrate the loop amino acids-preferences, layers, and hotspots into the final output(s) as PDBInfoLabels metadata. This information can be conveniently used for the subsequent step of sequence design with RosettaScripts. The Rosetta energy functions used for sequence design can be 'talaris2013' and 'talaris2014', for the first and second generation of designs, respectively. The databases of highly ideal fragments used for the design of the backbones for the de novo mimetics can be constructed with the Rosetta application 'kcenters_clustering_of_fragments' using an extensive database of non-redundant (publicly available) protein structures from the RCSB protein data bank (e.g., the 4-mer database that can be used in the first generation of designs, or the 7-mer database that can be used for the second generation designs).

As noted above, computational design (e.g., design of de novo cytokine mimetics—IL-18 mimics) can begin by defining the structure of human IL-18 (or e.g., an IL-18 variant such as a DR IL-18 variant or a D2D IL-18 variant) in the complex with its binding partner (e.g., human IL-18Rα or human IL-18BP) as the template for the design. Mimetic backbones (scaffolds) with a given secondary structure(s) can be used when generating amino acid sequences of potential mimic proteins. Any convenient structure can be used as a scaffold. In some cases the scaffold used for designing a mimic protein includes a structural feature selected from the group consisting of: a beta trefoil fold, a four-helix bundle, an IL-1 family fold, an IL-17 family fold, a cysteine-knot, a knottin fold, an immunoglobulin domain, a fibronectin domain, an ankyrin repeat, a leucin rich repeat, a beta barrel, an inhibitor cystine knot, or any combination thereof. In some cases the scaffold used for designing a mimic protein includes a structural feature selected from the group consisting of: a beta trefoil fold, a four-helix bundle, a cysteine-knot, a knottin fold, an immunoglobulin domain, a fibronectin domain, an ankyrin repeat, a leucin rich repeat, a beta barrel, an inhibitor cystine knot, or any combination thereof.

The above structural features are known in the art for example the four-helix bundle family (four α-helix bundle family) is present in a number of cytokines—and the cytokines with this feature can be divided into three sub-families (the IL-2 subfamily, the Interferon (IFN) subfamily, and the IL-10 subfamily. The IL-2 subfamily contains several non-immunological cytokines including erythropoietin (EPO) and thrombopoietin (TPO). Furthermore, four-α-helix bundle cytokines can be grouped into long-chain and short-chain cytokines. The IL-1 family cytokines primarily include IL-1 and IL-18; while the IL-17 family cytokines have a specific effect in promoting proliferation of T-cells that cause cytotoxic effects. The cysteine-knot cytokines include members of the Transforming growth factor beta superfamily, including TGF-β1, TGF-β1 and TGF-β3.

Given that mimetic backbones (scaffolds) with any of the above structure(s) can be used when generating amino acid sequences of potential IL-18 mimic proteins, the designed mimic protein can include any of the above structural features. For example, in some cases a IL-18 mimic protein includes a structural feature selected from the group consisting of: a beta trefoil fold, a four-helix bundle, an IL-1 family fold, an IL-17 family fold, a cysteine-knot, a knottin fold, an immunoglobulin domain, a fibronectin domain, an ankyrin repeat, a leucin rich repeat, a beta barrel, an inhibitor cystine knot, or any combination thereof. In some cases a IL-18 mimic protein includes a structural feature selected from the group consisting of: a beta trefoil fold, a four-helix bundle, a cysteine-knot, a knottin fold, an immunoglobulin domain, a fibronectin domain, an ankyrin repeat, a leucin rich repeat, a beta barrel, an inhibitor cystine knot, or any combination thereof.

Likewise, in some cases a scaffold used for designing a mimic protein includes a topology selected from: HHH, EHEE, HEE, EEHE, and HEEH, wherein H indicates an α-helix and E indicates a β-strand (see, e.g., Chevalier et al., Nature. 2017 Oct. 5; 550(7674):74-79; "Massively parallel de novo protein design for targeted therapeutics"). Thus, the designed mimic protein can include a topology selected from: HHH, EHEE, HEE, EEHE, and HEEH, wherein H indicates an α-helix and E indicates a β-strand. In some cases a scaffold used for designing a mimic protein includes a Tumor Necrosis Factor Superfamily (TNFSF) scaffold. Thus, the designed mimic protein can include a Tumor Necrosis Factor Superfamily (TNFSF) scaffold.

IL-18 variants (which can be used as 'parent proteins' herein—i.e., starting proteins used for the design of other proteins such as IL-18 mimics) generally have 85% or more amino acid sequence identity (e.g., 90% or more, 92% or more, 93% or more, 94% or more, 95% or more, 96% or more, 97% or more, 98% or more, or 99% or more sequence identity) with wild type IL-18 (e.g., wild type human IL-18). To the contrary, IL-18 mimics (e.g., DR or D2D IL-18 mimics) have 84% or less amino acid sequence identity (e.g., 80% or less, 70% or less, 60% or less, 50% or less, 40% or less, 30% or less, 20% or less, 10% or less, 5% or less, or 2% or less sequence identity) with wild type IL-18 (e.g., wild type human IL-18). Likewise, DR IL-18 mimics have 84% or less amino acid sequence identity (e.g., 80% or less, 70% or less, 60% or less, 50% or less, 40% or less, 30% or less, 20% or less, 10% or less, 5% or less, or 2% or less sequence identity) with DR IL-18 variants, and in some cases D2D IL-18 mimics have 84% or less amino acid sequence identity (e.g., 80% or less, 70% or less, 60% or less, 50% or less, 40% or less, 30% or less, 20% or less, 10% or less, 5% or less, or 2% or less sequence identity) with D2D IL-18 variants.

As such, in some cases IL-18 mimics (e.g., DR or D2D IL-18 mimics) have 50% or less amino acid sequence identity (e.g., 40% or less, 30% or less, 20% or less, 10% or less, 5% or less, or 2% or less sequence identity) with wild type IL-18 (e.g., wild type human IL-18). Likewise, in some cases DR IL-18 mimics have 50% or less amino acid sequence identity (e.g., 40% or less, 30% or less, 20% or less, 10% or less, 5% or less, or 2% or less sequence identity) with DR IL-18 variants, and in some cases D2D IL-18 mimics have 50% or less amino acid sequence identity (e.g., 40% or less, 30% or less, 20% or less, 10% or less, 5% or less, or 2% or less sequence identity) with D2D IL-18 variants With reference to FIG. 31, a flow chart of an embodiment of the present method is shown. Inputs can be provided for computation. Inputs can include, e.g., (1) structural information for IL-18 binding interactions as the template for design (e.g., an IL-18 variant such as a DR IL-18 variant or a D2D IL-18 variant binding with IL-18R or IL-18BP); and/or (2) amino acid position information for IL-18 variant polypeptide(s) that are known to exhibit desired binding properties (e.g., DR variants that bind to IL-18R but not IL-18BP, or D2D variants that bind to IL-18BP but not IL-18R). Computation can include one or more of (i.e., any combination of one or more of the following): hotspot identification; detection of core secondary structure elements; production of de novo mimetic backbones; reconstruction using loops from a clustered database of highly ideal fragments; reconnection of idealized elements by pairs in all possible combinations; combinatorial fragment assembly; Cartesian-constrained backbone minimization for potential solutions; verification that potential solutions contain highly ideal fragments; verification that the backbones do not clash with the target; determination of the most probable amino acids at each position; combinatorial recombination to produce fully connected backbones; design ranking to favor those with shorter interconnections between pairs of secondary structure core elements; restriction of identities of possible amino acids to be layer-compatible; combination of compatible built-fragment amino acids and layers; flexible backbone design and filtering; sequence redesigns of the best first generation optimized design; discovery of parametric equations of repetitive phi and psi angles that result in secondary structures that recapitulate target helices as close as possible; variation of the length of each of the core-elements (e.g., in some cases up to ±8 amino acids); reconnection of length variations of the core elements with loops from a clustered database of highly ideal loops; incorporation of PDBInfoLabels metadata to define the hotspots; integration of the loop amino acids-preferences, layers, and hotspots into a final output (e.g., as PDBInfoLabels metadata); and any combination thereof. The output can include amino acid sequence(s) of IL-18 mimic protein(s), e.g., DR mimic(s) and/or D2D mimic(s).

Computer Controlled Systems

Aspects of the present disclosure include computer controlled systems for practicing the subject methods. Such systems can include one or more computers for complete automation or partial automation of a system for practicing methods described herein. In some embodiments, a subject system include a computer having a computer readable storage medium with a computer program stored thereon, where the computer program when loaded on the computer includes instructions for implementing one or more aspects of the computational design as discussed above, e.g., one or more of: hotspot identification; detection of core secondary structure elements; production of de novo mimetic backbones; reconstruction using loops from a clustered database of highly ideal fragments; reconnection of idealized elements by pairs in all possible combinations; combinatorial fragment assembly; Cartesian-constrained backbone minimization for potential solutions; verification that potential solutions contain highly ideal fragments; verification that the backbones do not clash with the target; determination of the most probable amino acids at each position; combinatorial recombination to produce fully connected backbones; design ranking to favor those with shorter interconnections between pairs of secondary structure core elements; restriction of identities of possible amino acids to be layer-compatible; combination of compatible built-fragment amino acids and layers; flexible backbone design and filtering; sequence redesigns of the best first generation optimized design; discovery of parametric equations of repetitive phi and psi angles that result in secondary structures that recapitulate target helices as close as possible; variation of the length of each of the core-elements (e.g., in some cases up to ±8 amino acids); reconnection of length variations of the core elements with loops from a clustered database of highly ideal loops; incorporation of PDBInfoLabels metadata to define the hotspots; integration of the loop amino acids-preferences, layers, and hotspots into a final output (e.g., as PDBInfoLabels metadata); and any combination thereof.

In some embodiments, a subject system include a computer having a computer readable storage medium with a computer program stored thereon, where the computer program when loaded on the computer implements one or more aspects of the computational design as discussed above, e.g., one or more of: hotspot identification; detection of core secondary structure elements; production of de novo mimetic backbones; reconstruction using loops from a clustered database of highly ideal fragments; reconnection of idealized elements by pairs in all possible combinations; combinatorial fragment assembly; Cartesian-constrained backbone minimization for potential solutions; verification that potential solutions contain highly ideal fragments; verification that the backbones do not clash with the target; determination of the most probable amino acids at each position; combinatorial recombination to produce fully connected backbones; design ranking to favor those with shorter interconnections between pairs of secondary structure core elements; restriction of identities of possible amino acids to be layer-compatible; combination of compatible built-fragment amino acids and layers; flexible backbone design and filtering; sequence redesigns of the best first generation optimized design; discovery of parametric equations of repetitive phi and psi angles that result in secondary structures that recapitulate target helices as close as possible; variation of the length of each of the core-elements (e.g., in some cases up to ±8 amino acids); reconnection of length variations of the core elements with loops from a clustered database of highly ideal loops; incorporation of PDBInfo-Labels metadata to define the hotspots; integration of the loop amino acids-preferences, layers, and hotspots into a final output (e.g., as PDBInfoLabels metadata); and any combination thereof.

In some embodiments, the memory includes instructions, which when executed by the processor, cause the processor to implement one or more aspects of the computational design as discussed above, e.g., one or more of: hotspot identification; detection of core secondary structure elements; production of de novo mimetic backbones; reconstruction using loops from a clustered database of highly ideal fragments; reconnection of idealized elements by pairs in all possible combinations; combinatorial fragment assembly; Cartesian-constrained backbone minimization for potential solutions; verification that potential solutions contain highly ideal fragments; verification that the backbones do not clash with the target; determination of the most probable amino acids at each position; combinatorial recombination to produce fully connected backbones; design ranking to favor those with shorter interconnections between pairs of secondary structure core elements; restriction of identities of possible amino acids to be layer-compatible; combination of compatible built-fragment amino acids and layers; flexible backbone design and filtering; sequence redesigns of the best first generation optimized design; discovery of parametric equations of repetitive phi and psi angles that result in secondary structures that recapitulate target helices as close as possible; variation of the length of each of the core-elements (e.g., in some cases up to ±8 amino acids); reconnection of length variations of the core elements with loops from a clustered database of highly ideal loops; incorporation of PDBInfoLabels metadata to define the hotspots; integration of the loop amino acids-preferences, layers, and hotspots into a final output (e.g., as PDBInfoLabels metadata); and any combination thereof.

In some cases the memory includes instructions, which when executed by the processor, cause the processor to implement one or more aspects of the computational design as discussed above, e.g., one or more of: hotspot identification; detection of core secondary structure elements; production of de novo mimetic backbones; reconstruction using loops from a clustered database of highly ideal fragments; reconnection of idealized elements by pairs in all possible combinations; combinatorial fragment assembly; Cartesian-constrained backbone minimization for potential solutions; verification that potential solutions contain highly ideal fragments; verification that the backbones do not clash with the target; determination of the most probable amino acids at each position; combinatorial recombination to produce fully connected backbones; design ranking to favor those with shorter interconnections between pairs of secondary structure core elements; restriction of identities of possible amino acids to be layer-compatible; combination of compatible built-fragment amino acids and layers; flexible backbone design and filtering; sequence redesigns of the best first generation optimized design; discovery of parametric equations of repetitive phi and psi angles that result in secondary structures that recapitulate target helices as close as possible; variation of the length of each of the core-elements (e.g., in some cases up to ±8 amino acids); reconnection of length variations of the core elements with loops from a clustered database of highly ideal loops; incorporation of PDBInfo-Labels metadata to define the hotspots; integration of the loop amino acids-preferences, layers, and hotspots into a final output (e.g., as PDBInfoLabels metadata); and any combination thereof.

Systems may include a display and operator input device. Operator input devices may, for example, be a keyboard, mouse, or the like. The processing module includes a processor which has access to a memory having instructions stored thereon for performing the steps of the subject methods. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques. The processor may be any suitable analog or digital system. In some embodiments, the processor includes analog electronics which provide feedback control, such as for example negative feedback control.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

In some embodiments, systems according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the subject systems and other external devices such as a computer terminal (for example, at a physician's office or in hospital environment) that is configured for similar complementary data communication.

In some embodiments, the communication interface is configured for infrared communication, Bluetooth® communication, or any other suitable wireless communication protocol to enable the subject systems to communicate with other devices such as computer terminals and/or networks, communication enabled mobile telephones, personal digital assistants, or any other communication devices which the user may use in conjunction.

In some embodiments, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the subject systems are configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen.

In some embodiments, the communication interface is configured to automatically or semi-automatically communicate data stored in the subject systems, e.g., in an optional data storage unit, with a network or server device using one or more of the communication protocols and/or mechanisms described above.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows 10, Windows NT°, Windows XP, Windows 7, Windows 8, iOS, Sun Solaris, Linux, OS/400, Compaq Tru64 Unix, SGI IRIX, Siemens Reliant Unix, Ubuntu, Zorin OS and others.

For all descriptions below that refer to an IL-18 variant polypeptide, the same can be said for a subject IL-18 mimic. For example, when referring to the binding characteristics, methods of use, utilities, etc. of an IL-18 variant polypeptide, the same can be true for an IL-18 mimic, which is designed to behave like an IL-18 variant—but with a de novo designed primary amino acid sequence. Properties such as stability e.g., thermostability, stability in the blood, and the like can of course be different and in many cases are improved relative to the IL-18 variant polypeptide that was used to design the IL-18 mimic.

DR IL-18 Variants

In some embodiments, a subject IL-18 mimic mimics an IL-18 variant polypeptide, or a fragment thereof, that specifically binds to IL-18R, and exhibits substantially reduced binding IL-18BP. In some embodiments, a subject IL-18 mimic that binds to IL-18R, but does not bind substantially to IL-18BP, is useful for providing IL-18 signaling activity that is uninhibited by the presence and activity of IL-18BP.

In some embodiments, the IL-18 variant polypeptide (and therefore the IL-18 mimic) is resistant to or independent of negative regulation by IL-18BP polypeptide. In some embodiments, IL-18BP polypeptide is unable to substantially bind to the IL-18 variant polypeptide. The IL-18 variant polypeptides of the disclosure exhibit decreased binding affinity to IL-18BP, as compared with the WT IL-18 polypeptide. In some embodiments, the IL-18 variant polypeptide exhibits increased binding affinity to IL-18R, as compared with the WT IL-18 polypeptide. In some embodiments, the IL-18 variant polypeptide exhibits similar binding affinity to IL-18R, as compared with the WT IL-18 polypeptide. In some embodiments, the IL-18 variant polypeptide exhibits decreased binding affinity to IL-18R, as compared with the WT IL-18 polypeptide.

In some embodiments, the IL-18 mimic is an inhibitor of IL-18BP, wherein the inhibitor inhibits or reduces IL-18BP expression, activity, or both. In certain embodiments, an IL-18 mimic binds IL-18BP, thereby reducing or preventing IL-18BP from inhibiting IL-18 and IL-18 signaling.

In some embodiments, IL-18 variant polypeptides (and therefore. IL-18 mimics) are useful for the treatment or prevention of a disease or disorder. In various embodiments, the disease or disorder is cancer or a metabolic disease or disorder, including obesity and diabetes (e.g., a subject method can cause a decrease in body fat). Thus, in some embodiments, provided is a method of administering at least one IL-18 mimic, to treat or prevent a disease or disorder, such as, but not limited to, cancer or a metabolic disease or disorder.

In some embodiments, the IL-18 variant polypeptide binds to IL-18R and exhibits substantially reduced binding to IL-18BP. In some embodiments, the IL-18 variant polypeptide that binds to IL-18R and exhibits substantially reduced binding to IL-18BP binds to IL-18BP with a binding affinity that is about 0.000000000001% to about 95% of the binding affinity of wild-type IL-18 to IL-18BP.

In some embodiments, the IL-18 variant polypeptide that binds to IL-18R and exhibits substantially reduced binding to IL-18BP binds to IL-18BP with a binding affinity that is about 95% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 90% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 85% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 80% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 75% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 70% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 65% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 60% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 55% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 50% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 45% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 40% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 35% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 30% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 25% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 20% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 15% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 1.0% of the binding affinity of wild-type IL-18 to IL-18BP.

In some embodiments, the IL-18 variant polypeptide that binds to IL-18R and exhibits substantially reduced binding to IL-18BP binds to IL-18BP with a binding affinity that is about 5% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 4% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 3% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 2% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 1% of the binding affinity of wild-type IL-18 to IL-18BP.

In some embodiments, the IL-18 variant polypeptide that binds to IL-18R and exhibits substantially reduced binding to IL-18BP binds to IL-18BP with a binding affinity that is about 0.1% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.01% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.0001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.00001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.000001% of the binding affinity of wild-type IL-18 to IL-18BP, In some embodiments, the IL-18 variant polypeptide that binds to IL-18R and exhibits substantially reduced binding to IL-18BP binds to IL-18BP with a binding affinity that is about 0.0000001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.00000001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.000000001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.0000000001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.00000000001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.000000000001% of the binding affinity of wild-type IL-18 to IL-18BP.

In some embodiments, a subject IL-18 variant polypeptide (a DR-IL-18) that binds to IL-18R and exhibits substantially reduced binding to IL-18BP has a $K_D$ for IL-18BP that is 10 nM or greater (higher $K_D$ means lower binding affinity). In some embodiments, a subject DR-IL-18 variant polypeptide has a $K_D$ for IL-18BP that is 20 nM or greater (e.g., 50 nM or greater, 100 nM or greater, 500 nM or greater, or 1 μM or greater).

In some embodiments, the IL-18 variant polypeptide binds to IL-18R and exhibits substantially reduced binding to IL-18BP. In some embodiments, the variant polypeptide that binds to IL-18R and exhibits substantially reduced binding to IL-18BP has an IL-18BP/IL-18R dissociation constant ratio that is about at least 2-fold higher than the IL-18BP/IL-18R dissociation constant ratio of wild-type IL-18 (note that an increased dissociation constant ratio implies a relative decrease in IL-18BP binding relative to IL-18R binding). In some embodiments, the variant polypeptide that binds to IL-18R and exhibits substantially reduced binding to IL-18BP has an IL-18BP/IL-18R dissociation constant ratio that is about at least 20-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 200-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 2,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 20,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 200,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 2,000,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 20,000,000-fold higher than the IL-18BP/IL-18R dissociation constant ratio of wild-type IL-18.

In some embodiments, the IL-18 variant polypeptide binds to IL-18R and exhibits substantially reduced binding to IL-18BP. In some embodiments, the variant polypeptide that binds to IL-18R and exhibits substantially reduced binding to IL-18BP has an IL-18BP/IL-18R dissociation constant ratio that is about at least 3-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 30-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 300-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 3,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 30,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 300,000-told higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 3,000,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 30,000,000-fold higher than the IL-18BP/IL-18R dissociation constant ratio of wild-type IL-18.

In some embodiments, the IL-18 variant polypeptide binds to IL-18R and exhibits substantially reduced binding to IL-18BP. In some embodiments, the variant polypeptide that binds to IL-18R and exhibits substantially reduced binding to IL-18BP has an IL-18BP/IL-18R dissociation constant ratio that is about at least 5-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 50-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 500-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 5,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 50,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 500,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 5,000,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 50,000,000-fold higher than the IL-18BP/IL-18R dissociation constant ratio of wild-type IL-18.

In some embodiments, the IL-18 variant polypeptide binds to IL-18R and exhibits substantially reduced binding to IL-18BP. In some embodiments, the variant polypeptide that binds to IL-18R and exhibits substantially reduced binding to IL-18BP has an IL-18BP/IL-18R dissociation constant ratio that is about at least 10-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 100-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 1000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 10,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 100,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 1,000,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 10,000,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 100,000,000-fold higher than the IL-18BP/IL-18R dissociation constant ratio of wild-type IL-18.

In some embodiments, a subject IL-18 variant polypeptide (a DR-IL-18) that binds to IL-18R and exhibits substantially reduced binding to IL-18BP has an inhibitor constant (Ki) for IL-18BP that is greater than 3 nM (e.g., 5 nM or more, 10 mM or more, 50 nM or more, 100 nM or more, 500 nM or more, 750 nM or more, or 1 μM or more). In some embodiments, a subject DR-IL-18 variant polypeptide has a Ki for IL-18BP that is 500 nM or more. In some embodiments, a subject DR-IL-18 variant polypeptide has a Ki for IL-18BP that is 1 μM or more.

In some embodiments, a subject IL-18 variant polypeptide (a DR-IL-18) that binds to IL-18R and exhibits substantially reduced binding to IL-18BP has a Ki for IL-18BP that is greater than 200 nM (e.g., 500 nM or more, 750 nM or more, or 1 μM or more). In some embodiments, a subject DR-IL-18 variant polypeptide has a Ki for IL-18BP that is 1 μM or more.

In some embodiments, a subject IL-18 variant polypeptide (a DR-IL-18) that binds to IL-18R and exhibits substantially reduced binding to IL-18BP has an inhibitor constant (Ki) for IL-18BP that is at least 2-fold higher than the Ki of wild type IL-18 for IL-18BP (i.e., the Ki of the subject IL-18 variant polypeptide for IL-18BP is at least 2-fold relative to the Ki of WT IL-18 for IL-18BP). For example, in some cases a subject DR-IL-18 variant polypeptide has a Ki for IL-18BP that is at least 5-fold higher (e.g., at least 10-fold, at least 50-fold, at least 100-fold, at least 200-fold, at least 500-fold, or at least 1000-folder higher) than the Ki of wild type IL-18 for IL-18BP.

In some embodiments, a subject IL-18 variant polypeptide (a DR-IL-18) that binds to IL-18R and exhibits substantially reduced binding to IL-18BP has an $EC_{50}$ for IL-18BP that is at least 2-fold higher than the $EC_{50}$ of wild type IL-18 for IL-18BP (i.e., the $EC_{50}$ of the subject IL-18 variant polypeptide for IL-18BP is at least 2-fold relative to the $EC_{50}$ of WT IL-18 for IL-18BP). For example, in some cases a subject DR-IL-18 variant polypeptide has a $EC_{50}$ for IL-18BP that is at least 5-fold higher (e.g., at least 10-fold, at least 50-fold, at least 100-fold, at least 200-fold, at least 500-fold, or at least 1000-folder higher) than the $EC_{50}$ of wild type IL-18 for IL-18BP.

In various embodiments, the IL-18 variant polypeptide comprises a mutation relative to a wild-type (WT) IL-18 polypeptide. In some embodiments, the WT IL-18 polypeptide comprises the amino acid sequence of SEQ ID NO: 30. In other embodiments, the WT IL-18 polypeptide comprises the amino acid sequence of SEQ ID NO: 31. Unless otherwise specified, the term "X" is used below to represent any amino acid.

In various embodiments, the human IL-18 variant polypeptide, or fragment thereof, comprises at least one mutation (e.g., at least 2, at least 3, at least 4, at least 5, or at least 6 mutations) selected from the group consisting of Y1X, L5X, K8X, M51X, K53X, S55X, Q56X, P57X, G59X, M60X, E77X, Q103X, S105X, D110X, N111X, M113X, V153X, and N155X, wherein X denotes any amino acid. In various embodiments, the human IL-18 variant polypeptide, or fragment thereof, comprises at least 4 mutations selected from the group consisting of Y1X, L5X, K8X, M51X, K53X, S55X, Q56X, P57X, G59X, M60X, E77X, Q103X, S105X, D110X, N111X, M113X, V153X, and N155X. In various embodiments, the human IL-18 variant polypeptide, or fragment thereof, comprises at least 6 mutations selected from the group consisting of Y1X, L5X, K8X, M51X, K53X, S55X, Q56X, P57X, G59X, M60X, E77X, Q103X, S105X, D110X, N111X, M113X, V153X, and N155X. In various embodiments, the human IL-18 variant polypeptide, or fragment thereof, comprises at least one mutation (e.g., at least 2, at least 3, at least 4, at least 5, or at least 6 mutations) selected from the group consisting of Y1X, L5X, K8X, S55X, Q56X, P57X, G59X, E77X, Q103X, S105X, D110X, N111X, M113X, V153X, and N155X. In some embodiments, a human IL-18 variant polypeptide, or fragment thereof, comprises at least one mutation (e.g., at leak 2, at least 3, at least 4, at least 5, or at least 6 mutations) selected from the group consisting of Y1H, Y1R, L5H, L5I, L5Y, K8Q, K8R, M51T, M51K, M51D, M51N, M51E, M51R, K53R, K53G, K53S, K53T, S55K, S55R, Q56E, Q56A, Q56R, Q56V, Q56G, Q56K, Q56L, P57L, P57G, P57A, P57K, G59T, G59A, M60K, M60Q, M60R, M60L, E77D, Q103E, Q103K, Q103P, Q103A, Q103R, S105R, S105D, S105K, S105N, S105A, D110H, D110K, D110N, D110Q, D110E, D110S, D110G, N111H, N111Y, N111D, N111R, N111S, N111G, M113V, M113R, M113T, M113K, V153I, V153T, V153A, N155K, and N155H. In some embodiments, a human IL-18 variant polypeptide comprises at least one IL-18 variant polypeptide, or fragment thereof, selected from the group consisting of hCS1 (SEQ ID NO: 34), hCS2 (SEQ ID NO: 35), hCS3 (SEQ IL) NO: 36), hCS4 (SEQ IL) NO: 37), hC4 (SEQ ID NO: 38), hA8 (SEQ ID NO: 39), hD6 (SEQ ID NO: 40), h1112 (SEQ ID NO: 41), hB11 (SEQ ID NO: 42), hC3 (SEQ ID NO: 43), hC2 (SEQ ID NO: 44), hG10 (SEQ NO: 45), hG1 (SEQ ID NO: 46), hF1 (SEQ NO: 47), hD2 (SEQ ID NO: 48), hA1 (SEQ ID NO: 49), hB3

(SEQ ID NO: 50), hB4 (SEQ ID NO: 51), MD (SEQ ID NO: 52), 11145 (SEQ ID NO: 53), h144 (SEQ ID NO: 54), hE1 (SEQ ID NO: 55), hG2 (SEQ ID NO: 56), hB9 (SEQ ID NO: 57), hE12 (SEQ ID NO: 58), hC5 (SEQ ID NO: 59), 5-18 (SEQ ID NO: 73), 5-29 (SEQ ID NO: 74), 5-8 (SEQ ID NO: 75), 5-6 (SEQ ID NO: 76), 5-27 (SEQ ID NO: 77), 5-20 (SEQ ID NO: 78), 5-2 (SEQ ID NO: 79), 5-9 (SEQ ID NO: 80), 5-42 (SEQ ID NO: 81), 5-13 (SEQ ID NO: 82), 5-12 (SEQ ID NO: 83), 5-1 (SEQ ID NO: 84), 5-33 (SEQ ID NO: 85), 5-21 (SEQ ID NO: 86), 6-31 (SEQ ID NO: 87), 6-20 (SEQ ID NO: 88), 6-12 (SEQ ID NO: 89), 6-27 (SEQ ID NO: 90), 6-29 (SEQ ID NO: 91), 5-26 (SEQ ID NO: 191), 5-17 (SEQ ID NO: 192), 5-41 (SEQ ID NO: 193), or a fragment thereof.

In some cases a subject DR-IL-18 variant, or fragment thereof, includes at least one mutation (e.g., at least 2, at least 3, or at least 4 mutations) selected from the group consisting of M51X, M60X, S105X, D110X, and N111 X, relative to SEQ ID NO: 30. In some cases a subject DR-IL-18 variant, or fragment thereof, includes at least 3 mutations selected from the group consisting of M51X, M60X, S105X, D110X, and N111X, relative to SEQ ID NO: 30. In some cases a subject DR-IL-18 variant, or fragment thereof, includes at least one mutation (e.g., at least 2, at least 3, or at least 4 mutations) selected from the group consisting of $M51X_1$, $M60X_2$, $S105X_3$, $D110X_4$, and $N111X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, includes at least 3 mutations (e.g., at least 2, at least 3, or at least 4 mutations) selected from the group consisting of $M51X_1$, $M60X_2$, $S105X_3$, $D110X_4$, and $N111X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, includes at least one mutation (e.g., at least 2, at least 3, or at least 4 mutations) selected from the group consisting of $M51X_1$, $M60X_2$, $S105X_3$, $D110X_4$, and $N111X_5$, relative to SEQ ID NO: 30, where $X_1$ is T or K; $X_2$ is K or L; $X_3$ is D, N, or A; $X_4$ is K, N, S, or G; and $X_5$ is H, Y, G, or R.

In some cases a subject DR-IL-18 variant, or fragment thereof, includes the mutations M51X, M60X, S105X, D110X, and N111X, relative to SEQ ID NO: 30. For example, in some cases a subject DR-IL-18 variant, or fragment thereof, includes the mutations $M51X_1$, $M60X_2$, $S105X_3$, $D110X_4$, and $N111X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, S, or G; and $X_5$ is H, D, Y, R, S, or G. In some cases a subject DR-IL-18 variant, or fragment thereof, includes the mutations $M51X_1$, $M60X_2$, $S105X_3$, $D110X_4$, and $N111X_5$, relative to SEQ ID NO: 30, where $X_1$ is T or K; $X_2$ is K or L; $X_3$ is D, N, or A; $X_4$ is K, N, S, or G; and $X_5$ is H, Y, G, or R. In other words, in some cases a subject DR-IL-18 variant, or fragment thereof, includes the mutations {M51T or M51K}; {M60K or M60L}; {S105D, S105N, S105A}; {D110K, D110N, D110S, or D110G}; and {N111H, N111Y, N111R, or N111G}, relative to SEQ ID NO: 30.

In some cases a subject DR-IL-18 variant, or fragment thereof, includes at least one mutation (e.g., at least 2, at least 3, or at least 4 mutations) selected from the group consisting of M51X, K53X, Q56X, S105X, and N111X, relative to SEQ ID NO: 30. In some cases a subject DR-IL-18 variant, or fragment thereof, includes at least 3 mutations selected from the group consisting of M51X, K53X, Q56X, S105X, and N111X, relative to SEQ ID NO: 30. In some cases a subject DR-IL-18 variant, or fragment thereof, includes at least one mutation (e.g., at least 2, at least 3, or at least 4 mutations) selected from the group consisting of $M51X_1$, $K53X_2$, $Q56X_3$, $S105X_4$, and $N111X_5$, relative to SEQ ID NO: 30; where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, includes at least 3 mutations selected from the group consisting of $M51X_1$, $K53X_2$, $Q56X_3$, $S105X_4$, and $N111X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, includes at least one mutation (e.g., at least 2, at least 3, or at least 4 mutations) selected from the group consisting of $M51X_1$, $K53X_2$, $Q56X_3$, $S105X_4$, and $N111X_5$, relative to SEQ ID NO: 30, where $X_1$ is K; $X_2$ is G or S; $X_3$ is G, R, or L; $X_4$ is S, N, or G; and $X_5$ is G or R.

In some cases a subject DR-IL-18 variant, or fragment thereof, includes the mutations M51X, K53X, Q56X, S105X, and N111X, relative to SEQ ID NO: 30. For example, in some cases a subject DR-IL-18 variant, or fragment thereof, includes the mutations $M51X_1$, $K53X_2$, $Q56X_3$, $S105X_4$, and $N111X_5$, relative to SEQ ID NO: 30, where $X_1$ is E, R, or K; $X_2$ is G, S, or T; $X_3$ is E, A, R, V, G, K, or L; $X_1$ is N, S, K, or G; and $X_5$ is R, S, G, or D. In some cases a subject DR-IL-8 variant, or fragment thereof, includes the mutations $M51X_1$, $K53X_2$, $Q56X_3$, $S105X_4$, and $N111X_5$; relative to SEQ ID NO: 30, where $X_1$ is K; $X_2$ is G or S; $X_3$ is G, R, or L; $X_4$ is S, N, or G; and $X_5$ is G or R. In other words, in some cases a subject DR-IL-18 variant, or fragment thereof, includes the mutations {M51K}; {K53G or K53S}; {Q56G, Q56R, or Q56L}; {D100S, D110N, or D110G}; and {N111R, or N111G}, relative to SEQ ID NO: 30.

In some cases a subject DR-IL-18 variant, or fragment thereof, includes at least one mutation (e.g., at least 2, at least 3, or at least 4 mutations) selected from the group consisting of M51X, K53X, Q56X, D110X, and N111X, relative to SEQ ID NO: 30. In some cases a subject DR-IL-18 variant, or fragment thereof, includes at least 3 mutations selected from the group consisting of M51X, K53X, Q56X, D110X, and N111X, relative to SEQ ID NO: 30. In some cases a subject DR-IL-18 variant, or fragment thereof, includes at least one mutation (e.g., at least 2, at least 3, or at least 4 mutations) selected from the group consisting of $M51X_1$, $K53X_2$, $Q56X_3$, $D110X_4$, and $N111X_5$, relative to SEQ ID NO: 30, where $X_1$ is $E, R, or K; $X_2$ is G, S, or T; $X_3$ is E, A, R, V, G, K, or L; $X_4$ is N, S, K, or G; and $X_5$ is R, S, or D. In some cases a subject DR-IL-18 variant, or fragment thereof, includes at least 3 mutations selected from the group consisting of $M51X_1$, $K53X_2$, $Q56X_3$, $D110X_4$, and $N111X_5$, relative to SEQ ID NO: 30, where $X_1$ is E, R, or K; $X_2$ is G, S, or T; $X_3$ is E, A R, V, G, K, or L; $X_4$ is N, S, K, or G; and $X_5$ is R, S, G, or D. In some cases a subject DR-IL-18 variant, or fragment thereof, includes at least one mutation (e.g., at least 2, at least 3, or at least 4 mutations) selected from the group consisting of $M51X_1$, $K53X_2$, $Q56X_3$, $D110X_4$, and $N111X_5$, relative to SEQ ID NO: 30, where $X_1$ is K; $X_2$ is G or 5; $X_3$ is G, R, or L; $X_4$ is S, N, or G; and $X_5$ is G or R.

In some cases a subject DR-IL-18 variant, or fragment thereof, includes the mutations M51X, K53X, Q56X, D110X, and N111X, relative to SEQ ID NO: 30. For example, in some cases a subject DR-IL-18 variant, or fragment thereof, includes the mutations $M51X_1$, $K53X_2$, $Q56X_3$, $D110X_4$, and $N111X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, includes the mutations $M51X_1$, $K53X_2$, $Q56X_3$, $D110X_4$, and $N111X_5$ relative to SEQ ID NO: 30, where $X_1$ is K; $X_2$ is G or S; $X_3$ is G, R, or L; $X_4$ is S, N, or G; and $X_5$ is G or R. In other words, in some cases a subject DR-IL-18 variant, or fragment thereof, includes the mutations {M51K}; {K53G} or {K53S}, {Q56G, Q56R, or Q56L}; {D110S, D110N, or D110G}; and {N111R, or N111G}, relative to SEQ ID NO: 30.

In some cases a subject DR-IL-18 variant, or fragment thereof, comprises an amino acid sequence having 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30. As such in some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) relative to wild type IL-18 (e.g., human IL-18).

In some cases a subject DR-IL-18 variant, or fragment thereof, comprises an amino acid sequence having 85% or more sequence identity (e.g., 90% or more, 92% or more, 93% or more, 94% or more, 95% or more, 96% or more, 97% or more, 98% or more, or 99% or more sequence identity) with the amino acid sequence set forth in any one of SEQ ID NOs: 34-59, 73-91, and 191-193. As such in some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the amino acid sequence set forth in any one of SEQ ID NOs: 34-59, 73-91, and 191-193; and (ii) includes at least one mutation (e.g., at least 2, at least 3, at least 4, at least 5, or at least 6 mutations) relative to wild type IL-18 (e.g., human IL-18).

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of Y1X, L5X, K8X, M5X, K53X, S55X, Q56X, P57X, G59X, M60X, E77X, Q103X, S105X, D110X, N111X, M113X, V153X, and N155X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 4 mutations selected from the group consisting of Y1X, L5X, K8X, M51X, K53X, 555X, Q56X, P57X, G59X, M60X, E77X, Q103X, S105X, D110X, N111X, M113X, V153X, and N155X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 6 mutations selected from the group consisting of Y1X, L5X, K8X, M51X, K53X, S55X, Q56X, P57X, G59X, M60X, E77X, Q103X, S105X, D110X, N111X, M113X, V153X, and N155X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of Y1X, L5X, K8X, S55X, Q56X, P57X, G59X, E77X, Q103X, S105X, D110X, N111 X, M113X, V153X, and N155X, relative to SEQ ID NO: 30.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51X, M60X, S105X, D110X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of M51X, M60X, S105X, D110X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of $M51X_1$, $M60X_2$, $S105X_3$, $D110X_4$, and $N111X_5$ relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, 5, or G. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of $M51X_1$, $M60X_2$, $S105X_3$, $D110X_4$, and $N111X_5$ relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51$X_1$, M60$X_2$, S105$X_3$, D110$X_4$, and N111$X_5$, relative to SEQ ID NO: 30, where $X_1$ is T or K; $X_2$ is K or L; $X_3$ is D, N, or A; $X_4$ is K, N, S, or G; and $X_5$ is H, Y, G, or R.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51X, M60X, S105X, D110X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, M60$X_2$, S105$X_3$, D110$X_4$, and N111$X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, M60$X_2$, S105$X_3$, D110$X_4$, and N111$X_5$, relative to SEQ ID NO: 30, where $X_1$ is T or K; $X_2$ is K or L; $X_3$ is D, N, or A; $X_4$ is K, N, S, or G; and $X_5$ is H, Y, G, or R.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51X, K53X, Q56X, S105X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of M51X, K53X, Q56X, S105X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51$X_1$, K53$X_2$, Q56$X_3$, S105$X_4$, and N111$X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of M51$X_1$, K53$X_2$, Q56$X_3$, S105$X_4$, and N111$X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51$X_1$, K53$X_2$, Q56$X_3$, S105$X_4$, and N111$X_5$, relative to SEQ ID NO: 30, where $X_1$ is K; $X_2$ is G or S; $X_3$ is G, R, or L; $X_4$ is S, N, or G; and $X_5$ is G or R.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or ore sequence identity) with the wild type human IL-18 amino acid sequence set forth as SEQ ID NO: 30; and (ii) includes the mutations M51X, K53X, Q56X, S105X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, K53$X_2$, Q56$X_3$, S105$X_4$, and N111$X_5$ relative to SEQ ID NO: 30, where $X_1$ is E, R, or K; $X_2$ is G, S, or T; $X_3$ is E, A, R, G, K, or L; $X_4$ is N, S, K, or G; and $X_5$ is R, S, G, or D. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, K53$X_2$, Q56$X_3$, S105$X_4$, and N111$X_5$, relative to SEQ ID NO: 30, where $X_1$ is K; $X_2$ is G or S; $X_3$ is G, R, or L; $X_4$ is S, N, or G; and $X_5$ is G or R.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51X, K53X, Q56X, D110X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of M51X, K53X, Q56X, D110X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51$X_1$, K53$X_2$, Q56$X_3$, D110$X_4$, and N111$X_5$, relative to SEQ ID NO: 30, where $X_1$ is E, R, or K; $X_2$ is G, S, or T; $X_3$ is E, A, R, V, G, K, or L; $X_4$ is N, S K, or G; and $X_5$ is R, S, G, or D. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of M51$X_1$, K53$X_2$, Q56$X_3$, D110$X_1$, and N111$X_5$, relative to SEQ ID NO: 30, where $X_1$ is F, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51$X_1$, K53$X_2$, Q56$X_3$, D110$X_4$, and N111 $X_5$, relative to SEQ ID NO: 30, where $X_1$ is K; $X_2$ is G or S; $X_3$ is G, R, or L; $X_4$ is 5, N, or Gr; and $X_5$ is G or R.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51X, K53X, Q56X, D110X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, K53$X_2$, Q56$X_3$, D110$X_4$, and N111$X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, K53$X_2$, Q56$X_3$, D110$X_4$, and N111$X_5$, relative to SEQ ID NO: 30, where $X_1$ is K; $X_2$ is G or S; $X_3$ is G, R, or L; $X_4$ is S, N, or G; and $X_5$ is G or R.

In some embodiments, the murine IL-18 variant polypeptide comprises at least one mutation (e.g., at least 2, at least 3, at least 4, at least 5, or at least 6 mutations) selected from the group consisting of N1X, M50X, Y51X, K52X, S54X, E55X, V56X, R57X, G58X, L59X, R104X, N109X, and L151X, wherein X denotes any amino acid. In some embodiments, a murine IL-18 variant polypeptide, or fragment thereof, comprises at least one mutation (e.g., at least 2, at least 3, at least 4, at least 5, or at least 6 mutations) selected from the group consisting of N1H, N1Y, M50A, M50S, M50V, M50G, M50T, Y51R, K52V, K52S, K52T, K52G, K52A, S54R, S54K, S54G, S54N, E55R, E55H, E55N, E55D, E55G, V56L, V56M, V56R, V56A, V56S, V56Q, R57G, R57K, G58A, L59K, L59R, L59V, R104K, R104L, R104Q, R104S, N109D, and L151V. In some embodiments, a murine IL-18 variant polypeptide comprises at least one variant selected from the group consisting of mCS1 (SEQ ID NO: 60), mCS2 (SEQ ID NO: 61), mC1 (SEQ ID NO: 62), mA12 (SEQ ID NO: 63), mE8 (SEQ ID NO: 64), mC10 (SEQ ID NO: 65), mB7 (SEQ ID NO: 66), mB1 (SEQ ID NO: 67), mD1 (SEQ ID NO: 68), mH7 (SEQ ID NO: 69), mA7 (SEQ ID NO: 70), mE1 (SEQ ID NO: 71), and mH3 (SEQ ID NO: 72), or a fragment thereof.

D2D IL-18 Variants

In various embodiments, a subject IL-18 mimic is used for treating or preventing a disease or disorder where a diminished activity or level of IL-18BP is desired. The indications for such an agent are encompassed by the indications elaborated for a DR-IL-18 variant above. Non-limiting examples of diseases or disorders where a diminished activity or level of IL-18BP is desired which can be treated or prevented with the compositions and methods of the disclosure include cancer, infectious disease, metabolic diseases or disorders, and macular degeneration.

In some embodiments, an IL-18 variant polypeptide binds to IL-18BP, but does not substantially bind to or interact with the IL-18R (e.g., IL-18Rα and IL-18Rβ). This variant, a "decoy-to-the-decoy" (D2D), serves to bind to IL-18BP and thus prevent IL-18BP from inhibiting endogenously-produced or therapeutically-introduced IL-18. The "decoy-to-the-decoy" could be engineered using nearly the same yeast display selection strategies described elsewhere herein, but instead positively selecting for IL-18BP binding, and counter-selected against substantially binding to IL-18Rα.

In various embodiments, the IL-18 variant polypeptide that binds to and inhibits IL-18BP, comprises a mutation relative to a wild-type (WI) IL-18 polypeptide. In some embodiments, the WT IL-18 polypeptide comprises the amino acid sequence of SEQ ID NO: 30. In other embodiments, the WT IL-18 polypeptide comprises the amino acid sequence of SEQ ID NO: 31.

In various embodiments, the IL-18 variant polypeptide that binds to and inhibits IL-18BP comprises a human IL-18 variant polypeptide, or fragment thereof, comprising at least one mutation (e.g., at least 2, at least 3, at least 4, at least 5, or at least 6 mutations) selected from the group consisting of Y1X, L5X, D17X, E31X, T34X, D35X, S36X, D37X, D40X, N41X, M51X, Q56X, M60X, Q103X, H109X, M113X, and R131X, wherein X denotes any amino acid. In some embodiments, the IL-18 variant polypeptide that binds to and inhibits IL-18BP comprises a human IL-18 variant polypeptide, or fragment thereof, comprising at least one mutation (e.g., at least 2, at least 3, at least 4, at least 5, or at least 6 mutations) selected from the group consisting of Y1D, Y1F, Y1H, Y1L, L5F, L5H, D17A, D17G, D17R, D17H, E31A, E31T, E31G, E31K, E31R, T34A, T34K T34E, D35S, D35A, D35Y, S36N, S36K, S36R, D37P, D37A, D37R, D37H, D37L, D37V, D40Y D40S, D40A, N41K, N41S, N41R, M51F, M51L, M51I, Q56H, M60L, M60F, M60I, Q103L, Q103I, H109A, H109P, H109D, M113L, M113I, M113F, and R131S. In some embodiments, the IL-18 variant polypeptide that binds to and inhibits IL-18BP comprises a human IL-18 variant polypeptide, or fragment thereof, selected from the group consisting of hD2D-5F12 (SEQ ID NO: 92), hD2D-5F11 (SEQ ID NO: 93), hD2D-5F10 (SEQ ID NO: 94), hD2D-5F08 (SEQ ID NO: 95), hD2D-5F06 (SEQ ID NO: 96), hD2D-5F04 (SEQ ID NO: 97), hD2D-5F02 (SEQ ID NO: 98), hD2D-5F01 (SEQ ID NO: 99), hD2D-5E10 (SEQ ID NO: 100), hD2D-5E08 (SEQ ID NO: 101), hD2D-5E03 (SEQ ID NO: 102), hD2D-5E02 (SEQ ID NO: 103), hD2D-5D10 (SEQ ID NO: 104), hD2D-5D08 (SEQ ID NO: 105), hD2D-5D06 (SEQ ID NO: 106), hD2D-5D05 (SEQ ID NO: 107), hD2D-5D03 (SEQ ID NO: 108), hD2D-5D02 (SEQ ID NO: 109), hD2D-5C10 (SEQ ID NO: 110), hD2D-5C09 (SEQ ID NO: 111), hD2D-5C08 (SEQ ID NO: 112), hD2D-5C05 (SEQ ID NO: 113), hD2D-5C04 (SEQ ID NO: 114), hD2D-5C03 (SEQ ID NO: 115), hD2D-5B11 (SEQ ID NO: 116), hD2D-5B10 (SEQ ID NO: 117), hD2D-5B06 (SEQ ID NO: 118), hD2D-5B05 (SEQ ID NO: 119), hD2D-5B02 (SEQ ID NO: 120), hD2D-5A09 (SEQ ID NO: 121), hD2D-5A02 (SEQ ID NO: 122), hD2D-CS1 (SEQ ID NO: 123), hD2D-CS2 (SEQ ID NO: 124), hD2D-CS3 (SEQ ID NO: 125), or a fragment thereof.

In some cases a subject D2D-IL-18 variant, or fragment thereof, includes at least one mutation (e.g., at least 2, at least 3, or at least 4 mutations) selected from the group consisting of D17X, E30X, and Q103X, relative to SEQ ID NO: 30, In some cases a subject D2D-IL-18 variant, or fragment thereof, includes at least one mutation (e.g., at least 2, at least 3, or at least 4 mutations) selected from the group consisting of D17$X_1$, E30$X_2$, and Q103$X_3$, relative to SEQ ID NO: 30, where $X_1$ is G, H, R, or A; $X_2$ is A, T, G, K, or R; and $X_3$ is I or L. In some cases a subject D2D-IL-18 variant, or fragment thereof, includes at least one mutation (e.g., at least 2, at least 3, or at least 4 mutations) selected from the group consisting of D17G, E30A, and (Q103L or Q103I).

In some cases a subject D2D-IL-18 variant, or fragment thereof, includes the mutations D17X, E30X, and Q103X, relative to SEQ ID NO: 30. For example, in some cases a subject D2D-IL-18 variant, or fragment thereof, includes the mutations D17$X_1$, E30$X_2$, and Q103$X_3$, relative to SEQ ID NO: 30, where $X_1$ is G, H, R, or A; $X_2$ is T, G, K, or R; and $X_3$ is I or L. In some cases a subject D2D-IL-18 variant, or fragment thereof, includes the mutations D17G, E30A, and (Q103L or Q103I).

In some cases a subject D2D-IL-18 variant, or fragment thereof, includes at least one mutation (e.g., at least 2, at least 3, or at least 4 mutations) selected from the group consisting of D17X, E30X, D35X, M51X, and Q103X, relative to SEQ ID NO: 30. In some cases a subject D2D-IL-18 variant, or fragment thereof, includes at least one mutation (e.g., at least 2, at least 3, or at least 4 mutations) selected from the group consisting of D17$X_1$, E30$X_2$, D35$X_3$, M51$X_4$, and Q103$X_3$ relative to SEQ ID NO: 30, where $X_1$ is G, H, R, or A; $X_2$ is A, T, G, K, or R; $X_3$ is S, A, or Y; $X_4$ is F, I, or tr; and $X_5$ is I or L. In some cases a subject D2D-IL-18 variant, or fragment thereof, includes at least one mutation (e.g., at least 2, at least 3, or at least 4 mutations) selected from the group consisting of D17G, E30A, D35S, M51F, and (Q103L or Q103I), relative to SEQ ID NO: 30.

In some cases a subject D2D-IL-18 variant, or fragment thereof, includes the mutations D17X, E30X, D35X, M51X, and Q103X, relative to SEQ ID NO: 30. For example, in some cases a subject D2D-IL-18 variant, or fragment thereof, includes the mutations D17$X_1$, E30$X_2$, D35$X_3$, M51$X_4$, and Q103$X_3$, relative to SEQ ID NO: 30, where $X_1$ is G, H, R, or A; $X_2$ is A, T, G, K, or R; $X_3$ is S, A, or Y; $X_4$ is F, I, or L; and $X_5$ is I or L. In some cases a subject D2D-IL-18 variant, or fragment thereof, includes the mutations D17G, E30A, D35S, M51F, and (Q103L or Q103I), relative to SEQ ID NO: 30.

In some cases a subject D2D-IL-18 variant, or fragment thereof, comprises an amino acid sequence having 85% or more sequence identity (e.g., 90% or more, 92% or more, 93% or more, 94% or more, 95% or more. 96% or more, 97% or more, 98% or more, or 99% or more sequence identity) with the wild type human IL-18 amino acid sequence set forth as SEQ ID NO: 30. As such in some cases a subject D2D-IL-18 variant, or fragment thereof, comprises an amino acid sequence that (i) has 85% or more sequence identity (e.g., 90% or more, 92% or more, 93% or more, 94% or more, 95% or more, 96% or more 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) relative to wild type IL-18 (e.g., human IL-18).

In some cases a subject D2D-IL-18 variant, or fragment thereof, comprises an amino acid sequence having 85% or more sequence identity (e.g., 90% or more, 92% or more, 93% or more, 94% or more, 95% or more, 96% or more, 97% or more, 98% or more, or 99% or more sequence identity) with the amino acid sequence set forth in any one of SEQ ID NOs: 126-190, As such in some cases a subject D2D-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the amino acid sequence set forth in any one of SEQ ID NOs: 126-190; and (ii) includes at least one mutation (e.g., at least 2, at least 3, at least 4, at least 5, or at least 6 mutations) relative to wild type IL-18 (e.g., human IL-18).

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of Y1X, L5X, D17X, E31X, T34X, D35X, S36X, D37X, D40X, N41X, M51X, Q56X, M60X, Q103X, H109X, M113X, and R131X.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or ore sequence identity)

with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17X, E30X, and Q103X, relative to SEQ NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17$X_1$, E30$X_2$, and Q103$X_3$, relative to SEQ ID NO: 30, where $X_1$ is G, H, R, or A; $X_2$ is A, T. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17G, E30A, and (Q103L or Q103I).

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17X, E30X, and Q103X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17$X_1$, E30$X_2$, and Q103$X_3$, relative to SEQ ID NO: 30, where $X_1$ is G, H, R, or A; $X_2$ is A, T. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17G, E30A, and (Q103L or Q103I).

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17X, E30X, D35X, M51X, and Q103X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17$X_1$, E30$X_2$, D35$X_3$, M51 $X_4$, and Q103$X_3$, relative to SEQ ID NO: 30, where $X_1$ is G, H, R, or A; $X_2$ is A, T, G, K, or R; $X_3$ is S, A, or Y; $X_4$ is F, I, or L; and $X_5$ is I or L. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17G, E30A, D35S, M51F, and (Q103L or Q103I), relative to SEQ ID NO: 30.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17X, E30X, D35X, M51X, and Q103X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17$X_1$, E30$X_2$, D35$X_3$, M51 $X_4$, and Q103$X_3$, relative to SEQ ID NO: 30, where $X_1$ is G, H, R, or A; $X_2$ is A, T, G, K, or R; $X_3$ is S, A, or Y; $X_4$ is F, I, or L; and $X_5$ is I or L. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17G, E30A, D35S, M51F, and (Q103L or Q103I), relative to SEQ ID NO: 30.

In some embodiments, the IL-18 variant polypeptide that binds to and inhibits IL-18BP comprises a murine IL-18 variant polypeptide comprising at least one mutation (e.g., at least 2, at least 3, at least 4, at least 5, or at least 6 mutations) selected from the group consisting of N1X, L5X, D17X, E30X, T33X, D34X, I35X, D36X, M50X, Q102X, R104, H108X, N109X, M111X, D129X, and D130X, wherein X denotes any amino acid. In some embodiments, the IL-18 variant polypeptide that binds to and inhibits IL-18BP comprises a murine IL-18 variant polypeptide, or fragment thereof, comprising at least one mutation (e.g., at least 2, at least 3, at least 4, at least 5, or at least 6 mutations) selected from the group consisting of N1Y, N1D, N1H, N1L, N1F, N1V, N1I, L5Y, L5H, D17Q, D17G, D17A, D17E, D17S, D17N, E30A, E30R, E30K, E30T, E30G, T33G, T33A, T33E, T33R, T33K, D34Y, D34S, D34A, I35T, I35K, I35R, D36V, D36A, D36G, D36H, D36P, D36R, D36I M50F, M50L, Q102L, Q102I, R104E, R104A, R104P, R104G, R104Q, R104H, H108D, H108A, N109R, N109S, N109T, N109I, M111L, M111I, D129A, D129F, D129V, D129Y, D129S, D130E, D130T, D130G, D130N, D130R, D130S, D130Q, and D130H. In some embodiments, the IL-18 variant polypeptide that binds to and inhibits IL-18BP comprises a murine IL-18 variant polypeptide, or fragment thereof, selected from the group consisting of mD2D-A5 (SEQ ID NO: 126), mD2D-A6 (SEQ ID NO: 127), mD2D-A7 (SEQ ID NO: 128), mD2D-A8 (SEQ ID NO: 129), mD2D-A9 (SEQ ID NO: 130), mD2D-All (SEQ ID NO: 131), mD2D-A12 (SEQ ID NO: 132), mD2D-B4 (SEQ ID NO: 133), mD2D-B7 (SEQ ID NO: 134), mD2D-B11 (SEQ ID NO: 135), mD2D-B12 (SEQ ID NO: 136), mD2D-C1 (SEQ ID NO: 137), mD2D-C3 (SEQ ID NO: 138), mD2D-CS (SEQ ID NO: 139), mD2D-C6 (SEQ ID NO: 140), mD2D-C9 (SEQ ID NO: 141), mD2D-C10 (SEQ ID NO: 142), mD2D-C11 (SEQ ID NO: 143), mD2D-D1 (SEQ ID NO: 144), mD2D-D9 (SEQ ID NO: 145), mD2D-D12 (SEQ ID NO: 146), mD2D-E3 (SEQ ID NO: 147), mD2D-E4 (SEQ ID NO: 148), mD2D-E5 (SEQ ID NO: 149), mD2D-E7 (SEQ ID NO: 150), mD2D-E8 (SEQ ID NO: 151), mD2D-E9 (SEQ ID NO: 152), mD2D-E10 (SEQ ID NO: 153), mD2D-E11 (SEQ ID NO: 154), mD2D-E12 (SEQ ID NO: 155), mD2D-F3 (SEQ ID NO: 156), mD2D-F4 (SEQ ID NO: 157), mD2D-F5 (SEQ ID NO: 158), mD2D-F7 (SEQ IL) NO: 159), mD2D-F8 (SEQ ID NO: 160), mD2D-F9 (SEQ ID NO: 161), mD2D-G1 (SEQ ID NO: 162), mD2D-G7 (SEQ ID NO: 163), mD2D-G9 (SEQ ID NO: 164), mD2D-H7 (SEQ ID NO: 165), mD2D-E1 (SEQ IL) NO: 166), mD2D-G8 (SEQ ID NO: 167), mD2D-H3 (SEQ ID NO: 168), mD2D-A10 (SEQ ID NO: 169), mD2D-H1 (SEQ ID NO: 170), mD2D-F12 (SEQ ID NO: 171), mD2D-G10 (SEQ ID NO: 172), mD2D-G12 (SEQ ID NO: 173), mD2D-E2 (SEQ ID NO: 174), mD2D-G11 (SEQ ID NO: 175), mD2D-C4 (SEQ ID NO: 176), mD2D-F11 (SEQ ID NO: 177), mD2D-C2 (SEQ ID NO: 178), mD2D-F10 (SEQ ID NO: 179), mD2D-A2 (SEQ ID NO: 180), mD2D-F6 (SEQ ID NO: 181), mD2D-A1 (SEQ ID NO: 182), mD2D-E6 (SEQ ID NO: 183), mD2D-D4 (SEQ ID NO: 184), mD2D-D6 (SEQ ID NO: 185), mD2D-A3 (SEQ ID NO: 186), mD2D-A4 (SEQ ID NO: 187), mD2D-B10 (SEQ ID NO: 188), mD2D-B8 (SEQ ID NO: 189), mD2D-B9 (SEQ IL) NO: 190), or a fragment thereof.

In some embodiments, the IL-18 variant polypeptide that binds to IL-18BP and exhibits substantially reduced binding to IL-18R. In some embodiments, IL-18BP inhibitor that binds to IL-18BP and exhibits substantially reduced binding to IL-18R binds to IL-18R with a binding affinity that is about 0.000000000001% to about 95% of the binding affinity of wild-type IL-18 to IL-18R.

In some embodiments, the IL-18 variant polypeptide that binds to IL-18BP and exhibits substantially reduced binding to IL-18R binds to IL-18R with a binding affinity that is about 95% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 90% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 85% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 80% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 75% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 70% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 65% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 60% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 55% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 50% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 45% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 40% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 35% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 30% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 25% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 20% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 15% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 10% of the binding affinity of wild-type IL-18 to IL-18R.

In some embodiments, the IL-18 variant polypeptide that binds to IL-18BP and exhibits substantially reduced binding to IL-18R binds to IL-18R with a binding affinity that is about 5% the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 4% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 3% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 2% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 1% of the binding affinity of wild-type IL-18 to IL-18R.

In some embodiments, the IL-18 variant polypeptide that binds to IL-18BP and exhibits substantially reduced binding to IL-18R binds to IL-18R with a binding affinity that is about 0.1% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.01% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.0001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.00001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.000001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.0000001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.00000001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.000000001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.0000000001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.00000000001% of the binding affinity of wild-type IL-18 to IL-1 SR. In some embodiments, the IL-18 variant polypeptide that binds to IL-18BP and exhibits substantially reduced binding to IL-18R binds to IL-18R with a binding affinity that is about 0,000000000001% of the binding affinity of wild-type IL-18 to IL-18R.

One of skill in the art will realize that diminishing the amount or activity of a molecule that itself increases the amount or activity of IL-18BP can serve in the compositions and methods of the present disclosure to decrease the amount or activity of IL-18BP.

One of skill in the art will appreciate that inhibitors of IL-18BP can be administered acutely (e.g., over a short period of time, such as a day, a week or a month) or chronically (e.g., over a long period of time, such as several months or a year or more). One of skill in the art will appreciate that inhibitors of IL-18BP can be administered singly or in any combination with other agents. Further, IL-18BP inhibitors can be administered singly or in any combination in a temporal sense, in that they may be administered concurrently, and/or before, and/or after each other. One of ordinary skill in the art will appreciate, based on the disclosure provided herein, that IL-18BP inhibitor compositions can be used to treat or prevent a disease or disorder in a subject in need thereof, and that an inhibitor composition can be used alone or in any combination with another agent to affect a therapeutic result.

In various embodiments, any of the inhibitors of IL-18BP of the disclosure described herein can be administered alone or in combination with other inhibitors of other molecules associated with a disease or disorder disclosed herein or known in the art.

It will be appreciated by one of skill in the art, when armed with the present disclosure including the methods detailed herein, that the invention is not limited to treatment of a disease or disorder that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing a disease or disorder in a subject, in that an IL-18BP inhibitor composition, as discussed previously elsewhere herein, can be administered to a subject prior to the onset of the disease or disorder, thereby preventing the disease or disorder from developing. The preventive methods described herein also include the treatment of a subject that is in remission for the prevention of a recurrence of a disease or disorder.

One of skill in the art, when armed with the disclosure herein, would appreciate that the prevention of a disease or disorder encompasses administering to a subject an IL-18BP inhibitor composition as a preventative measure against the disease or disorder. As more fully discussed elsewhere herein, methods of decreasing the level or activity of IL-18BP encompass a wide plethora of techniques for decreasing not only IL-18BP activity, but also for decreasing expression of a nucleic acid encoding IL-18BP, including either a decrease in transcription, a decrease in translation, or both.

Additionally, as disclosed elsewhere herein, one skilled in the art would understand, once armed with the teaching provided herein, that the present disclosure encompasses a method of preventing a wide variety of diseases, disorders and pathologies where a decrease in expression and/or activity of IL-18BP mediates, treats or prevents the disease, disorder or pathology. Methods for assessing whether a disease relates to the levels or activity of IL-18BP are known in the art. Further, the disclosure encompasses treatment or prevention of such diseases discovered in the future.

Compositions and Methods of Treatment and Prevention

In various embodiments, the present disclosure includes methods using compositions comprising an activator of IL-18 activity (e.g., an IL-18 mimic), such as signaling activity through at least one IL-18R, and methods of increasing IL-18 activity, such as signaling through at least one IL-18R, in a cell, tissue, organ, system, or subject in need thereof. In various embodiments, the activator of IL-18 activity compositions, and methods of treatment of the disclosure, increase the amount of IL-18R signaling, the amount of immune cell activity, or both. In various embodiments, the diseases and disorders in which an increase in IL-18R signaling may improve therapeutic outcomes include, but are not limited to cancer, infectious diseases, macular degeneration, and metabolic diseases or disorders.

The following are non-limiting examples of cancers that can be treated or prevented by the methods and compositions of the disclosure: acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytornalmalignant glioma, cerebral astrocytoma/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromnal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocvtoma of bone and osteosarcoma, medulloblastoma, medulloepithelioma, melanoma, Merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, and Wilms Tumor.

Thus, non-limiting examples of cancers that can be treated or prevented by the methods and compositions of the disclosure include solid tumor cancers, liquid cancers, blood cancers, teratomas, sarcomas, and carcinomas.

In some embodiments, the methods of the present disclosure are useful for treating or preventing a tumor or cancer that is resistant to immune checkpoint inhibitors (ICIs). Exemplary immune checkpoint inhibitors include, but is not limited to, anti-PD1 (e.g., nivolumab), anti-CTLA4 (e.g., ipilimumab), anti-TIM3, anti-TIGIT, anti-LAG3, anti-B7H3, anti-B7H4, anti-VISTA, anti-ICOS, anti-GITR, anti-41BB, anti-OX40, and anti-CD40. Examples of targets of immune checkpoint inhibitors include but are not limited to: PD-L1, PD1, CTLA4, TIM3, TIGIT, LAG3, B7H3, B7H4, VISTA, ICOS, GITR, 41BB, OX40, and CD40. Thus, examples of immune checkpoint inhibitors include agents that inhibit proteins such as: PD-L1, PD1, CTLA4, TIM3, TIGIT, LAG3, B7H3, B7H4, VISTA, ICOS, GITR, 41BB, OX40, or CD40. In some cases, a subject IL-18 variant polypeptide (e.g., a DR-IL-18 variant, a D2D-IL-18 variant) is co-administered with an immune checkpoint inhibitor (e.g., an agent that inhibits PD-L1, PD1, CTLA4, TIM3, TIGIT, LAG3, B7H3, B7H4, VISTA, ICOS, GITR, 41BB, OX40, or CD40, or any combination thereof).

Fusions/Conjugations

In some embodiments, an IL-18 variant polypeptide (or a subject IL-18 mimic) of the present disclosure is fused to another protein, i.e., an IL-18 variant polypeptide or a fragment thereof (or an IL-18 mimic) can be fused in frame with a second polypeptide (a fusion partner). In some embodiments, the second polypeptide (the fusion partner) is capable of increasing the overall size of the fusion protein, e.g., so that the fusion protein will not be cleared from the circulation rapidly. In some cases, a IL-18 variant polypeptide or a fragment thereof is not fused to a second polypeptide.

In some embodiments, the second polypeptide (the fusion partner for a IL-18 variant polypeptide or a fragment thereof) is part or whole of an immunoglobulin Fe region (i.e., an antibody Fc sequence). In other embodiments, the second polypeptide is any suitable polypeptide that is substantially similar to Fe, e.g., providing increased size, multimerization domains, and/or additional binding or interaction with Ig molecules. In some embodiments, the second polypeptide is part or whole of Human Serum Albumin (HSA). In some embodiments, the second polypeptide is part or whole of an antibody, antibody fragment, camelid antibody or "nanobody" or other affinity reagent that binds to or interacts with HSA. These fusion proteins can facilitate purification, multimerization, and show an increased half-life in vivo. Fusion proteins having disulfide-linked multimeric structures can also, in some cases, be more efficient in binding and neutralizing other molecules.

When fused to a heterologous polypeptide, the portion corresponding to the IL-18 variant polypeptide or a fragment thereof can be referred to as the "IL-18 variant polypeptide portion" of a subject IL-18 variant polypeptide. In some cases, the "IL-18 variant polypeptide portion" can be 100 amino acids or more in length (e.g., 110 amino acids or more, 125 amino acids or more, 150 amino acids or more, 90 amino acids or more, 95 amino acids or more, 100 amino acids or more, 105 amino acids or more, 110 amino acids or more, 115 amino acids or more, 120 amino acids or more, 125 amino acids or more, 130 amino acids or more, 140 amino acids or more, or 150 amino acids or more), up to full-length IL-18, and can further be fused to a heterologous polypeptide.

In some cases, IL-18 variant polypeptide portion of a IL-18 variant polypeptide has a length in a range of from 100 amino acids to 157 amino acids (e.g., from 100 amino acids to 150 amino acids, from 100 amino acids to 140 amino acids, from 140 amino acids to 157 amino acids, from 140 amino acids to 150 amino acids, from 145 amino acids to 157 amino acids, or from 150 amino acids to 157 amino acids).

In some cases, the second polypeptide is a marker sequence (e.g., an affinity tag), such as a peptide that facilitates purification of the fused polypeptide. For example, the marker amino acid sequence can be a hexa-histidine peptide, such as the tag provided in a pQE vector (QIAGEN, Inc., 9259 Eton Avenue, Chatsworth, Calif., 91311), among others, many of which are commercially available. As described in Gent et al., Proc. Natl. Acad. Sci. USA 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., Cell 37: 767, 1984. The addition of peptide moieties to facilitate handling of polypeptides are familiar and routine techniques in the art.

A subject IL-18 variant polypeptide can be modified, e.g., joined/conjugated to a wide variety of other oligopeptides, proteins, and/or non-protein moieties for a variety of purposes. For example, post-translationally modified, for example by prenylation, acetylation, amidation, carboxylation, glycosylation, PEGylation (covalent attachment of polyethylene glycol (PEG) polymer chains), etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. In some embodiments, a subject IL-18 variant polypeptide has one or more phosphorylated amino acid residues, e.g. phosphotyrosine, phosphoserine, or phosphothreonine.

In some other embodiments, IL-18 variant polypeptides of the disclosure include reagents further modified to improve their resistance to proteolytic degradation or to optimize solubility properties or to render them more suitable as a therapeutic agent. For example, variants of the present disclosure further include analogs containing residues other than naturally occurring L-amino acids, e.g. D-amino acids or non-naturally occurring synthetic amino acids. D-amino acids may be substituted for some or all of the amino acid residues.

Co-Administration and Multi-Specific IL-18 Variant Polypeptides

As noted elsewhere in this disclosure, in some cases an IL-18 variant polypeptide (or an IL-18 mimic) is administered with an additional agent. The terms "co-administration", "co-administer", and "in combination with" include the administration of two or more therapeutic agents (e.g., a subject IL-18 mimic such as a DR-IL-18 mimic or a D2D IL-18 mimic in combination with an additional agent) either simultaneously, concurrently or sequentially within no specific time limits. In some embodiments, the agents are present in the cell or in the subject's body at the same time or exert their biological or therapeutic effect at the same time. In some embodiments, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours; 4 hours. 6 hours, 12 hours; 24 hours, 48 hours. 72 hours, 96 hours, 1 week; 2 weeks, 3 weeks, 4 weeks, 5 weeks, 6 weeks, 8 weeks, or 12 weeks after) the administration of a second therapeutic agent.

In some cases, a subject IL-18 variant (or a subject IL-18 mimic such as a DR-IL-18 mimic or a D2D IL-18 mimic) (e.g., formulated as a pharmaceutical composition co-administered with a cancer therapeutic drug, therapeutic drug to treat an infection, or cancer-directed antibody. Such administration may involve concurrent (i.e. at the same time), prior, or subsequent administration of the drug/antibody with respect to the administration of an agent or agents of the disclosure. A person of ordinary skill in the art would have no difficulty determining the appropriate timing, sequence and dosages of administration for particular drugs and compositions of the present disclosure.

In some embodiments, treatment is accomplished by administering a combination (co-administration) of a subject IL-18 variant (or a subject IL-18 mimic such as a DR-IL-18 mimic or a D2D IL-18 mimic) with another agent (e.g., an immune stimulant, an agent to treat chronic infection, a cytotoxic agent, an anti-cancer agent, etc.). One example class of cytotoxic agents that can be used are chemotherapeutic agents. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine and vinorelbine tartrate.

A subject IL-18 variant (or a subject IL-18 mimic such as a DR-IL-18 mimic or a D2D IL-18 mimic) need not be, but is optionally formulated with one or more agents that potentiate activity, or that otherwise increase the therapeutic effect. In some embodiments, treatment is accomplished by administering a combination (co-administration) of a subject IL-18 variant (or a subject IL-18 mimic such as a DR-IL-18 mimic or a D2D IL-18 mimic) and an agent that opsonizes a target cell. Thus, also envisioned herein are compositions (and methods that use the compositions) that include: (a) a subject IL-18 variant (or a subject IL-18 mimic such as a DR-IL-18 mimic or a D2D IL-18 mimic); and (b) an agent that opsonizes the target cell. In some cases, that agent that opsonizes the target cell is Rituximab. In some cases, that agent that opsonizes the target cell is Cetuximab.

An "agent that opsonizes a target cell" (an "opsonizing agent") is any agent that can bind to a target cell (e.g., a cancer cell, a cell harboring an intracellular pathogen, etc.) and opsonize the target cell (e.g., mark the target cell for phagocytosis and/or for antibody-dependent cell mediated cytotoxicity (ADCC)). For example, any antibody that can bind to a target cell (e.g., a cancer cell such as a tumor cell), where the antibody has an FC region, is considered to be an agent that opsonizes a target cell. In some cases, the agent that opsonizes a target cell is an antibody that binds to a target cell (e.g., an anti-tumor antibody, an anti-cancer antibody, an anti-infection antibody, and the like).

For example antibodies selective for tumor cell markers, radiation, surgery, and/or hormone deprivation, see Kwon et al., Proc. Natl. Acad. Sci U.S.A., 96: 15074-9, 1999. Angiogenesis inhibitors can also be combined with the methods of the disclosure. A number of antibodies are currently in clinical use for the treatment of cancer, and others are in varying stages of clinical development. For example, there are a number of antigens and corresponding monoclonal antibodies for the treatment of B cell malignancies. One target antigen is CD20. Rituximab is a chimeric unconjugated monoclonal antibody directed at the CD20 antigen. CD20 has an important functional role in B cell activation, proliferation, and differentiation. The CD52 antigen is targeted by the monoclonal antibody alemtuzumab, which is indicated for treatment of chronic lymphocytic leukemia. CD22 is targeted by a number of antibodies, and has recently demonstrated efficacy combined with toxin in chemotherapy-resistant hairy cell leukemia. Two new monoclonal antibodies targeting CD20, tositumomab and ibritumomab, have been submitted to the Food and Drug Administration (FDA). These antibodies are conjugated with radioisotopes. Alemtuzumab (Campath) is used in the treatment of chronic lymphocytic leukemia; Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer.

Monoclonal antibodies useful in the methods of the disclosure that have been used in solid tumors include, without limitation, edrecolomab and trastuzumab (herceptin). Edrecolomab targets the 17-1A antigen seen in colon and rectal cancer, and has been approved for use in Europe for these indications. Trastuzumab targets the HER-2/neu antigen. Cetuximab (Erbitux) is also of interest for use in the methods of the disclosure. The antibody binds to the EGF receptor (EGFR), and has been used in the treatment of solid tumors including colon cancer and squamous cell carcinoma of the head and neck (SCCHN).

A subject IL-18 variant polypeptide (or a subject IL-18 mimic such as a DR-IL-18 mimic or a D2D IL-18 mimic) can be combined with any of the above mentioned agents (e.g., agents such as antibodies that opsonize a target cell). Thus, in some cases, a subject IL-18 variant polypeptide (or a subject IL-18 mimic such as a DR-IL-18 mimic or a D2D IL-18 mimic) is used in a combination therapy (is co-administered) with one or more opsonizing agents selective for cancer cells, e.g., tumor cells. In some cases, a subject IL-18 variant polypeptide (or a subject IL-18 mimic such as a DR-IL-18 mimic or a D2D IL-18 mimic) is used in a combination therapy (is co-administered) with one or more of: cetuximab (binds EGFR), panitumumab (binds EGER), rituximab (binds CD20), trastuzumab (binds HER2), pertuzumab (binds HER2), alemtuzumab (binds CD52), brentuximab (binds CD30), tositumomab, ibritumomab, gemtuzumab, ibritumomab, and edrecolomab (binds 17-1A), or a combination thereof.

In some cases, a subject IL-18 variant polypeptide (e or a subject IL-18 mimic such as a DR-IL-18 mimic or a D2D IL-18 mimic) is co-administered with a cancer cell opsonizing agent (e.g., one that comprises an antigen binding region that targets CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGER, PDGFRA, AXL, TWEAKR, PTHR2, HAVCR2 (TIM3), GD2 ganglioside, MUC1, mucin CanAg, mesothelin, endoglin, Lewis-4 antigen, CEA, CEACAM1, CEACAM5, CA-125, PSMA, BATF, EGER2, TAG-72, gelatinase B, glypican 3, nectin-4, BCMA, CSFIR, SLAME7, integrin $\alpha_v\beta_3$, TYRP1, GPNMB, CLDN18.2, FOLR1, CCR4, CXCR4, MICA, C242 antigen, DLL3, DLL4, EGFL7, vimentin, fibronectin extra domain-B, TROP-2, LRRC15, FAP, SLITRK6, NOTCH2, NOTCH3, Tenascin-3, STEAP1, or NRP1, or any combination thereof).

In some cases, a subject IL-18 variant polypeptide or a subject IL-18 mimic such as a DR-IL-18 mimic or a D2D IL-18 mimic) is co-administered with and agent that targets one or more antigens selected from: CD19, CD20, CD22, CD24, CD25, CD30, CD33, CD38, CD44, CD47, SIRPA, CD52, CD56, CD70, CD96, CD97, CD99, CD123, CD279 (PD-1), CD274 (PD-L1), EGFR, 17-1A, HER2, CD117, C-Met, PTHR2, and HAVCR2 (TIM3).

In some cases, a subject IL-18 variant polypeptide (or a subject IL-18 mimic such as a DR-IL-18 mimic or a D2D IL-18 mimic) is used in a combination therapy (is co-administered) with any convenient immunomodulatory agent (e.g., an anti-CTLA4 antibody, an anti-PD-1 antibody, an anti-PD-L1 antibody, a TIGIT antibody, a TIM3 antibody, a LAG3 antibody, a VISTA antibody, a B7H3 antibody, a B7H4 antibody, a CD40 agonist, a 4-1BB modulator (e.g., a 41BB-agonist), an OX-40 modulator (e.g., an OX-40 agonist), a GITR modulator (e.g., a GITR agonist), a CD47 binding agent such as an anti-CD47 antibody or a high affinity CD47 binding agent, a SIRPA binding agent such as an anti-SIRPA antibody or high affinity SIRPA binding agent, and the like), a TGFbeta antagonist such as an anti-TGFbeta antibody, a cytokine or a cytokine variant including IL-1, IL-2, IL-10, IL-12, IL-15, IL-18, IL-21, IL-33, Interferon alpha, Interferon beta, interferon gamma, TNF, TRAIL, lymphotoxin, LIGHT/TNSF14, or an agonist of a Toll Like Receptor including TIR2, TLR4, TLR5, TLR7, TLR9, an agonist of an inflammasome, an agonist of the STING/cGAS pathway, or an agonist of the RIG-I pathway, an antagonist of the adenosine receptors A2aR/A2bR, an antagonist of the Aryl hydrocarbon receptor, an antagonist of IDO and/or TDO, or an oncolytic virus.

In some cases, a subject IL-18 variant polypeptide or a subject IL-18 mimic such as a DR-IL-18 mimic or a D2D IL-18 mimic) is used in a combination therapy (is co-administered) with an inhibitor of BTLA and/or CD160. In some cases, a subject IL-18 variant polypeptide (or a subject IL-18 mimic such as a DR-IL-18 mimic or a D2D IL-18 mimic) is used in a combination therapy (is co-administered) with an anti-CD47/SIRPA agent (e.g., anti-CD47, anti-SIRPA, a high affinity CD47 binding agent, a high affinity SIRPA binding agent, and the like). In some cases, a subject IL-18 variant polypeptide (or a subject IL-18 mimic such as a DR-IL-18 mimic or a D2D IL-18 mimic) is used in a combination therapy (is co-administered) with an inhibitor of TIM3 and/or CEACAM1.

As noted above, in some cases a subject IL-18 variant polypeptide (or a subject IL-18 mimic such as a DR-IL-18 mimic or a D2D IL-18 mimic) is fused to another protein (i.e., a "fusion partner", a "second polypeptide"). In some embodiments, the second polypeptide (the fusion partner for a subject IL-18 variant polypeptide) specifically binds to a target molecule other than the target molecule bound by the IL-18 variant polypeptide portion of the fusion protein (e.g., other than IL-18R for variants that bind IL-18R; or other than IL-18BP for variants that bind to IL-18BP).

Thus, in some embodiments, a subject IL-18 variant polypeptide (or a subject IL-18 mimic such as a DR-IL-18 mimic or a D2D IL-18 mimic) is multispecific (e.g., bispecific). The terms "multispecific" or "bispecific" are commonly used when referring to agents (e.g., ligands or antibodies) that recognize two or more different antigens by virtue of possessing at least one region (e.g., a ligand or a Fab of a first antibody) that is specific for a first target, and at least a second region (e.g., a ligand or a Fab of a second antibody) that is specific for a second target. A bispecific agent specifically binds to two targets and is thus one type of multispecific agent.

In some embodiments, a subject IL-18 variant polypeptide (or a subject IL-18 mimic such as a DR-IL-18 mimic or a D2D IL-18 mimic) is multi-specific (e.g., bispecific), such that a first region of the polypeptide includes a subject IL-18 variant polypeptide sequence (i.e., the first region includes a IL-18 variant polypeptide) (or a subject IL-18 mimic such as a DR-IL-18 mimic or a D2D IL-18 mimic), and a second region that specifically binds to another target molecule (e.g., an antigen). For example, in some cases, a IL-18 variant polypeptide is fused to a second polypeptide that binds specifically to a target molecule other than the target molecule bound by the IL-18 variant polypeptide.

Any one of the agents discussed above in the context of co-administration can be conjugated to a subject IL-18 variant polypeptide. The term "co-administration" as used herein is meant to encompass such conjugated compounds. For example, when agent 1 is co-administered with agent 2, the term is meant to encompass embodiments where agent 1 and agent 2 are not conjugated to one another, and is also meant to encompass embodiments where agent 1 and agent 2 are conjugated to one another (e.g., where agent 1 and agent 2 are both proteins and agent 1 is fused to agent 2).

In some cases, the second region of a multi-specific IL-18 variant polypeptide is a checkpoint inhibitor. In some cases, the second region of a multi-specific IL-18 variant polypeptide inhibits one or more proteins selected from: PD-L1, PD1, CTLA4, TIM3, TIGIT, LAG3, B7H3, B7H4, VISTA, ICOS, GITR, 41BB, OX40, and CD40.

In some cases, the second region of a multi-specific IL-18 variant polypeptide is a cancer cell opsonizing agent. In some cases, the second region of a multi-specific IL-18 variant polypeptide targets one or more proteins selected from: CD19, CD20, CD22, CD24, CD25, CD30, CD33, CD38, CD44, CD47, SIRPA, CD52, CD56, CD70, CD96, CD97, CD99, CD123, CD279 (PD-1), CD274 (PD-L1), EGFR, 17-1A, HER2, CD117, C-Met, PTHR2, and HAVCR2 (TIM3). In some cases, the second region of a multi-specific IL-18 variant polypeptide is an opsonizing agent that targets one or more proteins selected from: CD19, CD20, CD22, CD24, CD25, CD30, CD33, CD38, CD44, CD47, SIRPA, CD52, CD56, CD70, CD96, CD97, CD99, CD123, CD279 (PD-1), CD274, (PD-L1), EGFR, 17-1A, HER2, CD117, C-Met, PTHR2, and HAVCR2 (TIM3).

For example, in some cases, the second region of a multi-specific IL-18 variant polypeptide includes an ectodomain, e.g., an ectodomain from PD-1 PD-L1, CD47 (e.g., a high affinity CD47 variant/polypeptide), or SIRPA. (e.g., a high affinity SIRPA variant/polypeptide). In some cases, the second region of a multi-specific IL-18 variant polypeptide specifically binds an antigen selected from: CTLA-4, Lag-3, BTLA, Tim-3, CD244, CD40, CD40L, CD47, SIRPA, PD-1, and PD-L1.

In some embodiments, a subject IL-18 variant polypeptide includes a linker (e.g., a linker polypeptide). For example, in some embodiments, a subject IL-18 variant polypeptide and a fusion partner are separated by a linker (e.g., a linker polypeptide). A linker polypeptide may have any of a variety of amino acid sequences. Proteins can be joined by a linker polypeptide can be of a flexible nature (e.g., a flexible linker polypeptide), although other chemical linkages are not excluded. Suitable linkers include polypeptides of between about 6 amino acids and about 40 amino acids in length, or between about 6 amino acids and about 25 amino acids in length. These linkers can be produced by using synthetic, linker-encoding oligonucleotides to couple the proteins. Peptide linkers with a degree of flexibility can be used. The linking peptides may have virtually any amino acid sequence, bearing in mind that the in some case, linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

In some embodiments the IL-18 variant polypeptide is co-administered with an engineered immune cell such as a CAR-T or CAR-NK cell or T or NK cell transduced with an engineered T cell receptor. In other embodiments, the IL-18 variant polypeptide is co-administered with an oncolytic virus.

In some embodiments, a nucleic acid encoding an IL-18 variant polypeptide is included within an engineered ("altered") immune cell such as a CAR-T or CAR-NK cell or T or NK cell transduced with an engineered T cell receptor. In this instance, the engineered cell (e.g., altered T cell, altered NK cell) would secrete the IL-18 variant polypeptide. The ability to secrete the IL-18 variant peptide can be regulated in a contextual manner (e.g., turned on within the tumor microenvironment), for instance, by a synthetic NOTCH receptor.

In some embodiments, a nucleic acid encoding an IL-18 variant polypeptide is included within an oncolytic virus. In this instance, cells infected by the oncolytic virus would secrete the IL-18 variant polypeptide.

In some embodiments, the method of the present disclosure is useful for treating or preventing a tumor or cancer tumors that have lost surface expression of MHC class I; such as a tumor that has lost B2m, the MHC locus, or has mutations in other members of the antigen presentation and/or antigen loading complex, such as tapasin.

Metabolic diseases and disorders include various metabolic and endocrine-related diseases and disorders. The following are non-limiting examples of metabolic and endocrine-related diseases and disorders that can be treated or prevented by the methods and compositions of the disclosure: obesity, diabetes, prediabetes, type II diabetes, mature onset diabetes of the young (MODY), hyperglycemia, metabolic syndrome, dyslipidemia, hypertriglyceridemia, and hypercholesterolemia.

Non-limiting examples of other diseases and disorders that can be treated or prevented using the compositions and methods of the disclosure include viral infections, bacterial infections, parasitic infections, and low immune activity. In some embodiments, the viral infection is at least one of a pox virus, a smallpox virus, molluscum contagiosum, HPV infection, and warts caused by a virus. In some embodiments, the infection is a systemic infection. In some embodiments, the viral infection is a vaccinia virus infection. In some embodiments, the viral infection is a systemic vaccinia virus infection. In some embodiments, the bacterial infection is sepsis. In some embodiments, the low immune activity is neutropenia, for example, as may occur with chemotherapy.

Non-limiting examples of other diseases and disorders that can be treated or prevented using the compositions and methods of the disclosure include macular degeneration. For example, in some cases the disease or disorder is wet macular degeneration, and in some cases the disease or disorder is wet age-related macular degeneration. In some such cases, the IL-18 variant can be used as an anti-angiogenic. For example, a subject IL-18 variant polypeptide can in some cases attenuate choroidal neovascularization.

Thus, the present disclosure relates to the prevention and treatment of a disease or disorder by administration of a therapeutically effective amount of an IL-18 variant polypeptide (or a subject IL-18 mimic such as a DR-IL-18 mimic or a D2D IL-18 mimic), a recombinant IL-18 variant polypeptide, an active IL-18 variant polypeptide fragment IL-18 variant peptide, etc.), an activator of IL-18 variant expression or activity, or a nucleic acid DNA, cDNA, mRNA, etc.) that encodes at least one IL-18 variant polypeptide (or a subject IL-18 mimic such as a DR-IL-18 mimic or a D2D IL-18 mimic), to a cell, tissue, organ, or subject in need thereof, for the treatment or prevention of a disease or disorder, or its associated signs, symptoms or pathologies.

In some embodiments, a composition of the disclosure is administered to a cell, tissue, organ, system, or subject to treat or prevent a disease or disorder. In some embodiments, a human IL-18 variant polypeptide is administered to a cell, tissue, organ, system, or subject. In some embodiments, a nucleic acid (e.g., DNA, cDNA, mRNA, etc.) encoding at least one human IL-18 variant polypeptide (or a subject IL-18 mimic such as a DR-IL-18 mimic or a D2D IL-18 mimic) is administered to a cell, tissue, organ, system, or subject.

In some embodiments, the method comprises administering to a subject, cell, or tissue, an isolated nucleic acid molecule encoding on or more of the IL-18 variant peptides described herein (or a subject IL-18 mimic such as a DR-IL-18 mimic or a D2D IL-18 mimic).

It will be understood by one skilled in the art that an increase in the level of IL-18 signaling through the IL-18R encompasses an increase in the amount of IL-18 or IL-18 variant polypeptide available for binding to and activating IL-18R. This can be accomplished by increasing the level or activity of IL-18 which includes, but is not limited to, the direct or indirect administration of IL-18, the direct or indirect administration of an IL-18 variant polypeptide, and the direct or indirect administration of an inhibitor of IL-18BP, as well as increasing transcription, translation, or both, of a nucleic acid encoding IL-18 or an IL-18 variant polypeptide; and it also includes increasing any activity of IL-18 or IL-18 variant polypeptide as well.

The increased level of IL-18 signaling, including by using an IL-18 variant polypeptide, can be assessed using a wide variety of methods, including those disclosed herein, as well as methods known in the art or to be developed in the future. That is, the routineer would appreciate, based upon the disclosure provided herein, that increasing the level or activity of IL-18 signaling can be readily assessed using methods that assess the level of a nucleic acid (e.g., mRNA) encoding IL-18 or an IL-18 variant polypeptide or fragment thereof, the level of IL-18 or an IL-18 variant polypeptide or fragment polypeptide, and/or the level of IL-18 or an IL-18 variant polypeptide or fragment activity in a biological sample obtained from a subject.

One skilled in the art, based upon the disclosure provided herein, would understand that the invention is useful in subjects who, in whole (e.g., systemically) or in part (e.g., locally, cell, tissue, organ), are being or will be, treated for a disease or disorder where an increase in IL-18 signaling activity would be beneficial. The skilled artisan will appreciate, based upon the teachings provided herein, that the diseases and disorders treatable by the compositions and methods described herein encompass any disease or disorder wherein an increase in IL-18 signaling will promote a positive biologic, physiologic, clinical or therapeutic outcome.

One of skill in the art will realize that in addition to increasing IL-18 signaling directly, diminishing the amount or activity of a molecule that itself diminishes the amount or activity of IL-18 signaling can also serve to increase the amount or activity of IL-18 signaling. Thus, an activator of IL-18 activity can include, but should not be construed as being limited to, a chemical compound, a protein, a peptidomimetic, an antibody, a ribozyme, and an antisense nucleic acid molecule. One of skill in the art would readily appreciate, based on the disclosure provided herein, that an activator of IL-18 activity encompasses a compound that increases the level of IL-18 signaling. Additionally, an activator of IL-18 activity encompasses a compound that inhibits the level or activity of a molecule that itself diminishes the amount or activity of IL-18 signaling (i.e., IL-18BP). Contemplated in the present disclosure are IL-18BP antagonists that include (but are not limited to) monoclonal antibodies, small molecular therapeutics that neutralize IL-18BP, and an engineered IL-18 variant that binds to IL-18BP but does not substantially bind to or interact with the IL-18R by inhibiting IL-18BP in this manner, the activity of endogenously-produced IL-18 is enhanced through distribution.

The skilled artisan will also appreciate, once armed with the teachings of the present disclosure, that an increase in the level of IL-18 signaling includes an increase in IL-18 level or IL-18 activity (e.g., receptor binding activity, receptor signaling activity, etc.). Thus, increasing the level or activity of IL-18 signaling includes, but is not limited to, increasing the amount of available IL-18 polypeptide or IL-18 variant polypeptide, increasing transcription, translation, or both, of a nucleic acid encoding IL-18 polypeptide or an IL-18 variant polypeptide; and it also includes increasing any activity of an IL-18 polypeptide or IL-18 variant polypeptide as well. The activator of IL-18 activity compositions and methods of the disclosure can selectively activate IL-18 signaling, or can activate both IL-18 signaling and another molecule or pathway. Thus, the present disclosure relates to administration of an activator of IL-18 activity, a recombinant activator of IL-18 activity polypeptide, an active activator of IL-18 activity polypeptide fragment, or an activator of IL-18 signaling pathway component expression or activity.

One of skill in the art will also appreciate administration can be acute (e.g., over a short period of time, such as a day, a week or a month) or chronic (e.g., over a long period of time, such as several months or a year or more). Further, an activator of IL-18 activity, such as an IL-18 variant polypeptide or fragment thereof, (or an IL-18 mimic) or a nucleic acid (e.g., DNA, cDNA, mRNA, etc.) encoding an IL-18 variant polypeptide, or fragment thereof, (or an IL-18 mimic) can be administered singly or in any combination thereof, in a temporal sense, in that they may be administered simultaneously, before, and/or after each other. One of ordinary skill in the art will appreciate, based on the disclosure provided herein, that a activator of IL-18 activity, a activator of IL-18 activity polypeptide, a recombinant activator of IL-18 activity polypeptide, or an active activator of IL-18 activity polypeptide fragment can be used alone or in any combination with another activator of IL-18 activity, activator of IL-18 activity polypeptide, recombinant activator of IL-18 activity polypeptide, or active activator of IL-18 activity polypeptide fragment to effect a therapeutic result.

In some embodiments, a method comprises administering to a subject in need thereof a composition comprising at least one IL-18 variant polypeptide, and administering to the subject a composition comprising an additional agent. In one such embodiment, the additional agent comprises an immunotherapeutic agent comprising at least one selected from the group including, but not limited to an altered T-cell, a chimeric antigen receptor T-cell (CAR-T), an armored CAR-T cell, a virus, an antigen, a vaccine, an antibody, an immune checkpoint inhibitor, a small molecule, a chemotherapeutic agent, and a stem cell. In some embodiments, a composition comprising at least one IL-18 variant polypeptide is used in a method to increase immune system activity before, during, or after infection by a bacterium, virus, or other pathogen. In some embodiments, a composition comprising at least one IL-18 variant polypeptide is used in a method to increase the number and/or activity of immune cells in vitro, in vivo or ex vivo, such as the number and/or activity of T cells, NK cells, and/or myeloid cells.

In some embodiments, the additional agent comprises an inhibitor of one or more cytokines. In some embodiments, the inhibitor of one or more cytokines comprises a chemical compound, a protein, a peptide, a peptidomimetic, an antibody, a ribozyme, a small molecule chemical compound, or an antisense nucleic acid molecule (e.g., siRNA, miRNA, etc.) that inhibits the expression, activity, or both of one or more cytokines. In some embodiments, the inhibitor inhibits the expression, activity, or both of IL-17, IL-5, or IL-3. In some embodiments, the administration of a cytokine inhibitor decreases toxicity. In some embodiments, the administration of a cytokine inhibitor increases efficacy of an administered IL-18 variant polypeptide or IL-18BP inhibitor.

As used herein, the term "pharmaceutically-acceptable carrier" means a chemical composition with which an appropriate IL-18 signaling modulator may be combined and which, following the combination, can be used to administer the appropriate IL-18 signaling modulator thereof, to a subject.

Pharmaceutical Compositions and Administration

Compositions comprising a polypeptide (e.g., an IL-18 mimic), a polypeptide fragment, an activator of IL-18 signaling level or activity, or an inhibitor of IL-18BP level or activity, as described elsewhere herein can be formulated and administered to a subject, as now described. By way of non-limiting examples, a composition identified as an activator of IL-18 activity, including IL-18 variant polypeptides (or IL-18 mimics), recombinant IL-18 variant polypeptides, and active IL-18 variant polypeptide fragments, for the treatment and/or prevention of a disease or disorder can be formulated and administered to a subject, as now described.

The disclosure encompasses the preparation and use of pharmaceutical compositions comprising a composition useful for the treatment or prevention of a disease or disorder, disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art. In various embodiments, the active ingredient is a polypeptide, a polypeptide fragment, an activator of IL-18 signaling level or activity, an inhibitor of IL-18BP level or activity, or a combination thereof, as elsewhere described herein.

As used herein, the term "pharmaceutically-acceptable carrier" means a chemical composition with which an appropriate IL-18 signaling modulator thereof, may be combined and which, following the combination, can be used to administer the appropriate modulator (e.g., activator, inhibitor, etc.) thereof, to a subject.

In some embodiments, pharmaceutical compositions can include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

The pharmaceutical compositions useful for practicing the invention may be administered to deliver a dose of between about 0.1 ng/kg/day and 100 mg/kg/day, or more.

In various embodiments, the pharmaceutical compositions useful in the methods of the disclosure may be administered, by way of example, systemically, parenterally, or topically, such as, in oral formulations, inhaled formulations, including solid or aerosol, and by topical or other similar formulations. In addition to the appropriate therapeutic composition, such pharmaceutical compositions may contain pharmaceutically acceptable carriers and other ingredients known to enhance and facilitate drug administration. Other possible formulations, such as nanoparticles, liposomes, other preparations containing the active ingredient, and immunologically based systems may also be used to administer an appropriate modulator thereof, according to the methods of the disclosure.

A carrier may bear a subject agent (e.g., IL-18 mimic) in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear a IL-18 variant polypeptide (or IL-18 mimic) by non-covalent associations, such as non-covalent bonding or by encapsulation. The nature of the carrier can be either soluble or insoluble for purposes of the disclosure.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Compositions can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this disclosure can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Pharmaceutical compositions that are useful in the methods of the disclosure may be prepared, packaged, or sold in formulations suitable for oral, rectal, vaginal, parenteral, topical, pulmonary, intranasal, buccal, intravenous, transdermal, intralesional, subcutaneous, intramuscular, ophthalmic, intrathecal and other known routes of administration. Other contemplated formulations include projected nanoparticles, liposomal preparations, other preparations containing the active ingredient, and immunologically-based formulations.

A pharmaceutical composition of the disclosure may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the disclosure may further comprise one or more additional pharmaceutically active agents.

Controlled- or sustained-release formulations of a pharmaceutical composition of the disclosure may be made using conventional technology.

A formulation of a pharmaceutical composition of the disclosure suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

Pharmaceutically acceptable excipients used in the manufacture of pharmaceutical compositions include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Liquid formulations of a pharmaceutical composition of the disclosure may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the disclosure may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the disclosure may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the disclosure may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, intramuscular, intracisternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In some embodiments of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent Formulations for topical administration may further comprise one or more of the additional ingredients described herein.

A pharmaceutical composition of the disclosure may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the disclosure formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers. The formulations described herein as being useful for pulmonary delivery are also useful for intranasal delivery of a pharmaceutical composition of the disclosure. Another formulation suitable for intranasal administration is a coarse powder comprising the active ingredient and having an average particle from about 0.2 to 500 micrometers.

Such a formulation is administered in the manner in which snuff is taken i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the disclosure may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the disclosure may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically—administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the disclosure are known in the art and described, for example in Genaro, ed., 1985, Remington's Pharmaceutical Sciences, Mack Publishing Co., Easton, Pa., which is incorporated herein by reference.

Typically dosages of the compound of the disclosure which may be administered to an animal, preferably a human, range in amount from about 0.001 mg to about 1000 mg per kilogram of body weight of the animal. The precise dosage administered will vary depending upon any number of factors, including, but not limited to, the type of animal and type of disease or disorder being treated, the age of the animal and the route of administration. Preferably, the dosage of the compound will vary from about 0.1 mg to about 10 mg per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease or disorder being treated, the type and age of the animal, etc.

Experimental

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

EXAMPLE 1

IL-18 Variant Polypeptides

IL-18 is a pro-inflammatory cytokine that can stimulate T, NK, and myeloid cells. It has been proposed as an immunotherapeutic agent for cancer given its ability to stimulate anti-tumor immune cells. As demonstrated herein, the therapeutic efficacy of recombinant IL-18 treatment is greatly limited by upregulation of its natural endogenous soluble inhibitor IL-18BP. The present disclosure is based, in part, on the development of variants of both human and mouse IL-18 that are almost entirely independent of IL-18BP. The cytokine variants exhibit altered relative preference for the receptors (IL-18Rα and IL-18BP) by hundreds of thousands to over a million-fold. These variants have potent anti-tumor activity in preclinical tumor models, both as monotherapies and in combination with immune checkpoint inhibitors such as anti-PD-1. As an additional application, IL-18 also has a well-established anti-obesity role and it is demonstrated herein that administration of the variants greatly reduces body fat composition compared to WT IL-18 treatment. The new variants thus have indications in endocrinology/metabolism/obesity in addition to tumor immunotherapies.

Also described herein are an additional set of IL-18 variants that act as IL-18BP antagonists by exclusively binding IL-18BP with absent or greatly reduced binding IL-18Rα. It is envisaged that these proteins could be used to enhance the activity of endogenous IL-18 by neutralizing IL-18BP.

The materials and methods employed in these experiments are now described.

Protein Expression and Purification

Human IL-18, mouse IL-18 (amino acids 1-157) and variants thereof, were assembled as gBlocks (Integrated DNA Technologies, IDT) and cloned into a pET28a-smt vector for expression of N-terminal sumo-tagged and C-terminal hexahistidine-tagged proteins in *E. coli* BL21 (DE3) Rosetta strain, Protein expression was induced with 0.5 mM IPTG at 16° C. for 20 hours. The fusion proteins were first purified using Ni-chelating resins, followed by cleavage of the sumo tag with sumo protease. Proteins were then separated from aggregates by successive ammonium sulfate cuts, with aggregates precipitating at 20% ammonium sulfate and the target proteins at 70% ammonium sulfate. Protein pellets were resuspended and applied to Ni-chelating resins again to remove sumo tags, and were subjected to an endotoxin removal wash with 0.1% Triton X-114. Finally, eluted protein was buffer exchanged to PBS by PD-10 column (GE Healthcare). Protein sample was tested for monodispersity by size exclusion chromatography using an FPLC (Bio-Rad) and SEC650 column (Bio-Rad).

Human IL-18Rα ectodomain (amino acids 19-329), IL-18Rβ ectodomain (amino acids 15-356), and IL-18BP (amino acids 31-194), were secreted and purified via a baculovirus expression system. In brief, all construct sequences were cloned into the pAcBN-BH3 vector (BD Biosciences) with an N-terminal gp67 signal peptide and a C-terminal AviTag™ and hexahistidine tag. Spodoptera frugiperda (Sf9) insect cells cultured at 27° C. in SF900 II SFM medium (Invitrogen) were transfected with the plasmid constructs to establish high-titer recombinant virus, which was subsequently amplified. Trichopulsia ni (High-Five) insect cells (Invitrogen) grown in Insect Xpress medium (Lonza) at 27° C. were infected with the viruses to express recombinant protein. Three days after infection, proteins were extracted via Ni-NTA (QIAGEN) affinity chromatography, concentrated, and purified to >98% homogeneity with SEC650 sizing column (Bio-Rad) equilibrated in 10 mM HEPES (pH 7.5) and 150 mM NaCl.

Mouse IL-18Rα ectodomain (amino acids 19-329) and IL-18BP (amino acids 31-194) were produced as secreted proteins using the Expi293 expression system (Therm Fisher). In brief, all construct sequences were cloned into the BacMam expression vector pEZT_D_Lux with an N-terminal H7 signal peptide and a C-terminal AviTag™ and hexahistidine tag. Expi293 cells cultured at 37° C. in Expi293 expression medium (Thermo Fisher) were transfected with plasmids using the ExpiFectamine 293 Transfection Kit (Thermo Fisher) according to the manufacturer's instructions. Cells were harvested 3-5 days after transfection. Protein purification procedures were the same as with the human proteins.

For protein biotinylation, a C-terminal biotin acceptor peptide (AviTag)-GLNDIFEAQKIEWHE was fused to all IL-18 receptor constructs, Protein biotinylation was carried out with soluble BirA ligase enzyme in 0.1 mM Bicine (pH 8.3), 10 mM ATP, 10 mM magnesium acetate, and 0.5 mM biotin (Sigma). Proteins were purified by size exclusion on a SEC650 column, as described above.

Yeast Display of IL-18

Human and mouse IL-18 gene block (IDT) were synthesized and cloned into the vector pYAL and displayed on the Saccharomyces cerevisiae strain EBY100, Individual colonies of IL-18 yeast were grown overnight at 30° C. in SDCAA liquid media and induced in SGCAA liquid media for 1 day at 20° C. IL-18 display levels on yeast were verified by flow cytometry using an anti-cMyc tag antibody (anti-myc-PE; Cell Signaling Technologies). Receptor staining with biotinylated IL-18Rα (with or without IL-18Rβ) or biotinylated IL-18BP was performed in PBS supplemented with 0.5% BSA and 2 mM EDTA (PBE) on ice. All analysis was performed on a Sony SA3800 flow cytometer.

Human IL-18 Library Construction and Selection

For the first human decoy-resistant IL-18 library, fourteen hIL-18Rα and hIL-8BP contact residues in hIL-18 (Table 1) were identified from homologous positions by aligning the structure of hIL-18/hIL-18Rα/hIL-18Rβ complex (Protein Data Bank (PDB ID) code 3OW4) to the structure of IL-18/IL-18BP (PDB ID 3F62). A library randomizing these residues was constructed using assembly PCR with the degenerate primers listed in Table 2. The library had a theoretical diversity of ~$1.96\times10^{11}$ unique protein sequences. The PCR products were further amplified with primers having homology to the pYAL vector and co-electroporated together with linearized pYAL into EBY100 yeast. The resulting library contained $2.5\times10^8$ transformants.

For the second V2.0 human decoy-resistant IL-18 library, eleven hIL-18Rα and hIL-18BP contact residues in hIL-18 were selected to randomize, with a theoretical diversity of $3.44\times10^9$ variants (described in FIG. 7A). A library randomizing these residues was constructed using assembly PCR with the degenerate primers and co-electroporated with pYAL into EBY100 yeast. The resulting library had a diversity of $6\times10^8$ transformants.

TABLE 1

First Human IL-18 library design

| Residue | Codon | Potential residues |
|---|---|---|
| 1Y | YNT | Y, F, S, C, L, P, H, R |
| L5 | NWT | L, F, I, Y, H, N, V, D |
| 8K | MRA | K, R, R, Q |
| 51M | RNS | M, I, T, N, K, S, R, V, A, D, E, G |
| 53K | ARA | K, R |
| 55S | RRW | S, R, G, G, N, K, D, E |
| 59G | RNA | G, E, A, V, I, T, K, R |
| 60M | VDG | M, K, R, L, Q, R, V, E, G |
| 103Q | VAW | Q, K, E, D, N, H |
| 105S | RRW | S, K, R, N, D, E, G, G |
| 110D | VAW | D, E, K, N, Q, H |
| 111N | NAT | N, D, H, Y |
| 153V | RHT | V, A, D, I, T, N |
| 155N | VAW | N, K, D, E, Q, H |

TABLE 2

First human IL-18 library assembly primers

| Primer | Sequence (5' to 3') |
|---|---|
| hIL18Lib1 | CATTTTCATTAAGATGCAGTTACTTCGCTGTTTTTCAAT ATTTTCTGTTATTGCTAGC (SEQ ID NO: 1) |
| hIL18Lib2 | AATTACGGATGACCGAAAGTYKGGATTCAWNCTTGCC GAAANRTGCTAAAACGCTAGCAATAACAGAAAATATT GAAAAA (SEQ ID NO: 2) |
| hIL18Lib3 | ACTTTCGGTCATCCGTAATTTGAACGACCAAGTCCTTTT TATTGACCAGGG (SEQ ID NO: 3) |
| hIL18Lib4 | ACTATCCGTCATATCCTCGAATAAGGGACGATTGCCCT GGTCAATAAAAAGGACT (SEQ ID NO: 4) |
| hIL18Lib5 | CTTATTCGAGGATATGACGGATAGTGATTGCCGTGACA ACGCCC (SEQ ID NO: 5) |
| hIL18Lib6 | ACTGAGATTGTTACCGCCHBTNYACGGGGTTGWYYATC TYTATASNYAGAGATGATGAAAATTGTACGAGGGGCGT TGTCACGG (SEQ ID NO: 6) |
| hIL18Lib7 | GGCGGTAACAATCTCAGTTAAGTGCGAAAAAATCTCGA CACTTTCTTGTGAA (SEQ ID NO: 7) |
| hIL18Lib8 | GGTTCATTTCCTTGAACGAAATGATCTTGTTTTCACAAG AAAGTGTCGAGATT (SEQ ID NO: 8) |
| hIL18Lib9 | CATTTCGTTCAAGGAAATGAACCCGCCGGATAATATCA AGGATACAAAATCAGATATTATTT (SEQ ID NO: 9) |
| hIL18Lib10 | TGATGAGCTCTCGAATTGCATCTTATNWTBGTGTCCAG GCACWYYACGWTBGAAGAAAATAATATCTGATTTTGT ATCCTTGATATTA (SEQ ID NO: 10) |
| hIL18Lib11 | ATAAGATGCAATTCGAGAGCTCATCATACGAAGGTTAC TTTTTAGCCTGCG (SEQ ID NO: 11) |
| hIL18Lib12 | AATTAACTTAAACAGGTCGCGCTCCTTCTCGCAGGCTA AAAAGTAACCTT (SEQ ID NO: 12) |

TABLE 2-continued

First human IL-18 library assembly primers

| Primer | Sequence (5' to 3') |
|---|---|
| hIL18Lib13 | GCGACCTGTTTAAGTTAATTCTTAAGAAAGAAGATGAG TTGGGGGATCG (SEQ ID NO: 13) |
| hIL18Lib14 | CCAGAACCACCGTCCTCWTBCTGADYGGTAAACATGAT GCTACGATCCCCCAACTCATCTT (SEQ ID NO: 14) |
| hIL18Lib15 | GAGGACGGTGGTTCTGGATCCGAACAAAAGCTTATCTC CGAAGAAGACTTGG (SEQ ID NO: 15) |
| hIL18Lib16 | CCACCAGATCCACCACCACCCAAGTCTTCTTCGGAGAT AAG (SEQ ID NO: 16) |

For both libraries, transformed yeast were recovered and expanded in liquid synthetic dextrose medium with casamino acids (SDCAA) medium at 30° C. and induced by dilution 1:10 into liquid synthetic galactose medium with casamino acids (SGCAA) medium and cultured at 20° C. for 24 hours. Appropriate numbers of induced yeast were used in each round to ensure at least 10-fold coverage of the expected diversity of the library at each step, and not less than $10^8$ cells. All selection steps were carried out at 4° C. using PBE buffer (PBS with 0.5% BSA and 2 mM EDTA). For the first generation library, each round's selection reagents are listed in Table 3. For round 1, yeast were counter-selected with anti-Cy5/AlexaFluor647 microbeads (Miltenyi) and an LS MACS column (Miltenyi) to remove non-specific bead binders. Positive selection was performed by labeling yeast with 1 μM biotinylated hIL-18Rα for 1 hour at 4° C., followed by magnetic selection with SA/AlexaFluor 647 microbeads and an LS MACS column. For round 2, counter-selection was performed with 1 μM biotinylated IL-18BP, with positive selection identical to round 1. For rounds 3-5, selection was performed by incubating yeast with 100 nM (rounds 3-4) or 10 nM (round 5) biotinylated IL-18Rα and 250 nM pre-formed, biotin-capped hIL-18BP/SA-PE tetramers. After competition binding, yeast were washed and labeled with SA AlexaFluor 647 to detect IL-18Rα. Display levels were determined by staining with AlexaFluor 488-conjugated anti-cMyc (Cell Signaling Technologies), and the top 1% of display-normalized IL-18Rα binders (out of IL-18BP non-binders) were isolated using FACS with a Sony SA3800 cell sorter. After each round of selection, recovered yeast were expanded in SDCAA medium at 30° C. overnight and later induced at 20° C. by a 1:10 dilution into SGCAA medium for 24 hours.

The V2.0 human DR-IL-18 library was selected in a similar fashion, with specific selection steps elaborated in FIG. 7B.

Mouse IL-18 Library Construction and Selection

Construction and selection procedures are similar to human IL-18, with the following changes. Library construction was informed by an in-silico modeled mouse IL-18/receptor complex structure (predicted by Phyer2.0). Thirteen positions were chosen for randomization (Table 3) using primers described in Table 4. Co-electroporation with pYAL yielded a library of $4\times10^8$ transformants. Selection reagents used for each round are listed in Table 5.

TABLE 3

| Mouse IL-18 library design | | |
|---|---|---|
| Residue | Codon | Potential residues |
| 1N | NWT | F, Y, L, H, I, N, V, D |
| 50M | RNS | M, I, T, N, K, S, R, V, A, D, E, G |
| 51Y | NRN | Y, K, R, D, E |
| 52K | VNS | L, P, H, Q, R, I, M, T, N, K, S, V, A, D, E, G |
| 54S | RRW | S, R, G, G, N, K, D, E |
| 55E | VRN | E, K, N, R, S, R, H |
| 56V | VNV | V, S, P, T, A, K, R |
| 57R | RVW | R, D, E, S, T |
| 58G | RNA | G, E, A, V, I, T, K, R |
| 59L | VDR | L, K, R, Q, R, V, E, G |
| 104R | NDH | R, D, E, N, Y, F, I, L, V |
| 109N | NAT | N, D, H, Y |
| 151L | VHY | L, V, A, D, I, T, N |

TABLE 4

| Mouse IL-18 library assembly primers | |
|---|---|
| Primer | Sequence (5' to 3') |
| mIL18lib1 | CATTTTCATTAAGATGCAGTTACTTCGCTGTTTTTCAATCATTTTTGTTATTGCTAGCGTTT (SEQ ID NO: 17) |
| mIL18lib2 | TTGTACAGTGAAGTCGGCCAAAAWNTGCTAAAACGCTAGCAATAACAGAAAATAT (SEQ ID NO: 18) |
| mIL18lib3 | GCCGACTTCACTGTACAACCGCAGTAATACGGAATATAAATGACCAAGTTCTCTTCGTT (SEQ ID NO: 19) |
| mIL18lib4 | TTGATCAATATCAGTCATATCCTCGAACACAGGCTGTCTTTTGTCAACGAAGAGAACTTGGTCATTT (SEQ ID NO: 20) |
| mIL18lib5 | GTGTTCGAGGATATGACTGATATTGATCAAAGTGCCAGTGAACCCCAGACCAGA (SEQ ID NO: 21) |
| mIL18lib6 | TCACAGAGAGGGTCACAGCYHBTNYWBYBNBNYBWYYGTCSNBNYNSNYGTATATTATCAGTCTGGTCTGGGGTTCAC (SEQ ID NO: 22) |
| mIL18lib7 | GCTGTGACCCTCTCTGTGAAGGATAGTAAAATGTCTACCCTCTCCTGTAAGAACAAGA (SEQ ID NO: 23) |
| mIL18lib8 | GTATATCATCAATATTTTCAGGTGGATCCATTTCCTCAAAGGAAATGATCTTGTTCTTACAGGAGAGGG (SEQ ID NO: 24) |

TABLE 4-continued

| Mouse IL-18 library assembly primers | |
|---|---|
| Primer | Sequence (5' to 3') |
| mIL18lib9 | AATGGATCCACCTGAAAATATTGATGATATACAAAGTGATCTCATATTCTTTCAGAAANDHGTTCCAGGACACNATAAGATGGAGTTTGAATCTTCACT (SEQ ID NO: 25) |
| mIL18lib10 | CCTTTTGGCAAGCAAGAAAGTGTCCTTCATACAGTGAAGATTCAAACTCCATCTTAT (SEQ ID NO: 26) |
| mIL18lib11 | CTTTCTTGCTTGCCAAAAGGAAGATGATGCTTTCAAACTCATTCTGAAAAAAAAGGATGA (SEQ ID NO: 27) |
| mIL18lib12 | CCACCACTTTGATGTAAGTTAGTRDBAGTGAACATTACAGATTTATCCCCATTTTCATCCTTTTTTTCAGAATGAG (SEQ ID NO: 28) |
| mIL18lib13 | ACTAACTTACATCAAAGTGGTGGTTCTGGATCCGAACAAAAGCTTATCTCCGAAGAAGA (SEQ ID NO: 19) |

TABLE 5

| Summary of library selection reagents | | | | |
|---|---|---|---|---|
| | Human IL-18 library selection | | Mouse IL-18 library selection | |
| | Counter-selection | Positive Selection | Counter-selection | Positive Selection |
| Round1 | SA-beads alone | 1 μM hIL-18Rα-SA-beads | — | 1000 nM IL-18Ra-SA-beads |
| Round2 | 1 μM IL-18BP | 1 μM IL-18Rα-SA-beads | — | 1 μM IL-18Rα |
| Round3 | 1 μM IL-18BP | 100 nM hIL-18Rα | 1 μM IL-18BP | 1 μM IL-18Rα |
| Round4 | 1 μM IL-18BP | 10 nM hIL-18Rα | 1 μM IL-18BP | 100 nM IL-18Rα |
| Round5 | 250 nM IL-18BP tetramer | 10 nM hIL-18Rα | 1 μM IL-18BP | 10 nM IL-18Rα |
| Round6 | — | — | 250 nM IL-18BP tetramer | 200 nM IL-18Rα |

Surface Plasmon Resonance

Experiments were conducted using a Biacore T100 and carried out at 25° C. Biotinylated IL-18Rα or IL-18BP were immobilized onto a Biacore biotin capture chip (Series S CAP sensor chip. GE Healthcare) to yield an Rmax of ~50 RU (IL-18Rα) or ~10 RU (IL-18BP), Measurements were made with serial dilutions of the IL-18 variants in HEPES buffered Saline-P+ buffer (10 mM HEPES pH 7.4, 150 mM NaCl, 0.005% surfactant P20). The surface was regenerated by three 60-sec injections of regeneration buffer (3/4 (v/v) 8M guanidine hydrochloride with ¼ (v/v) 1M sodium hydroxide). Experiments were performed in multiple channels simultaneously for increased observations. All data were analyzed with the Biacore T100 evaluation software version 2.0 with a 1:1 Langmuir binding model.

Cell Lines

HEK-Blue IL-18 sensor cells (InvivoGen) were maintained in complete media (DMEM containing 10% heat-inactivated FBS, 2 mM L-glutamine, 50 U/mL penicillin, and 50 ug/mL streptomycin) supplemented with 100 μg/mL Normocin, 30 μg/mL Blasticidin, 180 μg/mL Zeocin, and 200 μg/mL Hygromycin. YUMMER1.7 melanoma cells were cultured and prepared as previously described (Wang et al., 2017, Pigment Cell Melanoma Res., 30(4):428-435).

HEK-Blue Cytokine Activity Assay

For cytokine activity measurements, 50,000 HEK-Blue IL-18 sensor cells per well of a flat-bottom 96-well plate were incubated with recombinant human IL-18 at successively decreasing concentrations in a total volume of 200 μL of complete media. After 20-24 hours of incubation at 37° C. and 5% $CO_2$, 30 μL of cell culture supernatant was mixed with 170 μL QUANTI-Blue detection media (InvivoGen) and incubated at 37° C. and 5% $CO_2$ until a color change from pink to blue was detectable (0.5-4 hours). Levels of alkaline phosphatase were quantified using a spectrophotometer at 655 nm wavelength. Cytokine activity was determined by calculating the relative absorbance value (percentage of the maximal absorbance value measured at 655 nm) for each cytokine in the assay.

For IL-18BP blockade experiments, a fixed concentration of recombinant human IL-18 was pre-incubated with recombinant human IL-18BP at successively decreasing concentrations for 1 hour at 4° C. Subsequently, the protein mixture was added to the HEK-Blue IL-18 sensor cells and the assay was performed as described.

Mice

C57BL/6 wild type mice (6-9 weeks old) from Jackson Laboratory were used for in vivo mouse experiments. Experimental groups were matched by weight, sex, and age. All animal experiments were conducted in compliance with approval from the Yale Institutional Animal Care and Use Committee.

In Vivo Pharmacodynamic and Pharmacokinetic Studies

Mice (n=9 per group) received daily intraperitoneal (i.p.) injections of 1 mg/kg recombinant IL-18 (WT or variant mCS2), or PBS as vehicle control. On day 1, day 4, and day 7 of the experiment, 3 mice per group were sacrificed 5 hours post-injection for blood collection via cardiac puncture, and subsequent analysis of blood plasma or white blood cells (see mouse IL-18BP ELISA, Luminex-based multiplex immunoassay for mouse cytokine analysis, as well as immunophenotyping via flow cytometry) was performed. Throughout the 7 days of the experiment, body temperatures were monitored daily using the Rodent thermometer BIO-TK8851 (Bioseb) and the RET 3 rectal probe for mice (Braintree Scientific Inc.). Body weights were monitored daily.

Plasma Preparation from Whole Blood

Plasma preparation from whole blood was performed using EDTA-coated Microtainer Plasma Separator Tubes (BD) according to manufacturer's instruction. Plasma samples were frozen once at −20° C. before being used for analytical assays.

IFN-γ and IL-18BP ELISA

To measure levels of human IFN-γ in cell culture supernatant, the Human IFN-γ ELISA MAX Deluxe Set (BioLegend) with a sensitivity of 4 pg/mL and a detection range of 7.8-500 pg/mL was used according to the manufacturer's instructions. For quantification of human IL-18BP in cell culture supernatant, the Quantikine Human IL-18BP Immunoassay (R&D Systems) with a sensitivity of 7.52 pg/mL and a detection range of 26.6-1,700 pg/mL, was used. Mouse IL-18BP levels in blood plasma were quantified using the Mouse IL-18BP ELISA Kit (R&D systems) with a sensitivity of 0.156 ng/mL and a detection range of 0.156-10 ng/mL. All assays including sample preparation were performed according to manufacturer's instructions.

Luminex-Based Multiplex Immunoassay for Mouse Cytokine Analysis

To quantify a variety of mouse cytokine levels in blood plasma including IFN-γ and IL-12, the luminex-based Bio-Plex Pro multiplex immunoassay (Bio-Rad) was performed using the Bio-Plex 200 System (Bio-Rad). Cytokines of interest were analyzed using the Bio-Plex Pro Mouse Cytokine Standard 23-Plex (Group I) reconstituted in DMEM, following the manufacturer's instructions.

Immunophenotyping Via Flow Cytometry

For white blood cell analysis, 100 μL of whole blood were collected into an EDTA-coated Microtainer Plasma Separator Tube (BD) additionally containing 50 μL Heparin-solution, and mixed by inverting several times. Red blood cell lysis was performed by adding ACK Lysing Buffer (VWR) and incubating for 3-5 minutes at room temperature. After adding MACS buffer (2 mM EDTA, 2% FBS, in PBS), white blood cells were collected by centrifugation (5 minutes, 400×g, 4° C.) and aspiration of the supernatant. White blood cells were washed once with cold MACS buffer, and collected again as described. The cell pellet was resuspended in 200 μL MACS buffer containing 10% (v/v) rat serum (STEMCELL Technologies Inc.) and specific fluorescently-labeled antibodies to stain for subsequent flow cytometric analysis. Staining was performed for 30 minutes at 4° C. using the following antibodies: αCD4-AF700 (BioLegend), αCD8-APC (BioLegend), B220-APC-Cy7 (BioLegend), CD11b-PB (BioLegend), NK1.1-PE (BioLegend), NKp46-PE. (BioLegend), and CD69-FITC (BioLegend). Thereafter, white blood cells were washed twice with MACS buffer as described before. Finally, the cells were resuspended in 100 μL MACS buffer and samples were acquired using the flow cytometer (Sony SA3800). An aliquot of 10 μL was taken to perform cell counting using the Invitrogen Countess II Automated Cell Counter (Thermo Fisher Scientific), FlowJo v10.3 software was used for data analysis, and cells were gated for leukocytes and single events using the forward and side scatter.

Tumor Treatment Experiments $0.5\times10^6$ YUMMER1.7 cells were implanted subcutaneously into C57BL/6.1 mice. 7 days after implantation, when tumors were approximately 50 mg, treatment was initiated. Mice were divided into treatment cohorts which included: 1) vehicle (saline), 2) anti-PD1 (rat clone RMP1-14, Bio X Cell, West Lebanon, New Hampshire, US), 3) wildtype IL-18, 4) mCS2, 5) wild type IL-18+ anti-PD-1, and 6) CS2 IL-18+ anti-PDT Anti PD-1, wild type IL-18, and mCS2 IL-18 were administered via intraperitoneal injection twice weekly at 8 mg/kg, 0.32 mg/kg, and 0.32 mg/kg, respectively. Mice were monitored for signs of clinical toxicity, and tumor growth was tracked twice weekly using caliper measurements. Mice were euthanized when the tumor diameter reached or exceeded 1.5 cm in greatest dimension; this was considered the endpoint for survival analyses.

B2m-deficient YUMMER1.7 studies were conducted in a similar fashion, with the minor changes. $1.0\times10^6$ cells were engrafted, as tumors grew slower than the parental strain. Treatments consisted of saline, anti-PD1 plus anti-CTLA4, and mCS2 given at the same schedule and dose as the studies above.

The results of the experiments are now described.

The IL-18 Axis as a Target for Cancer Immunotherapy

Figure 1A:
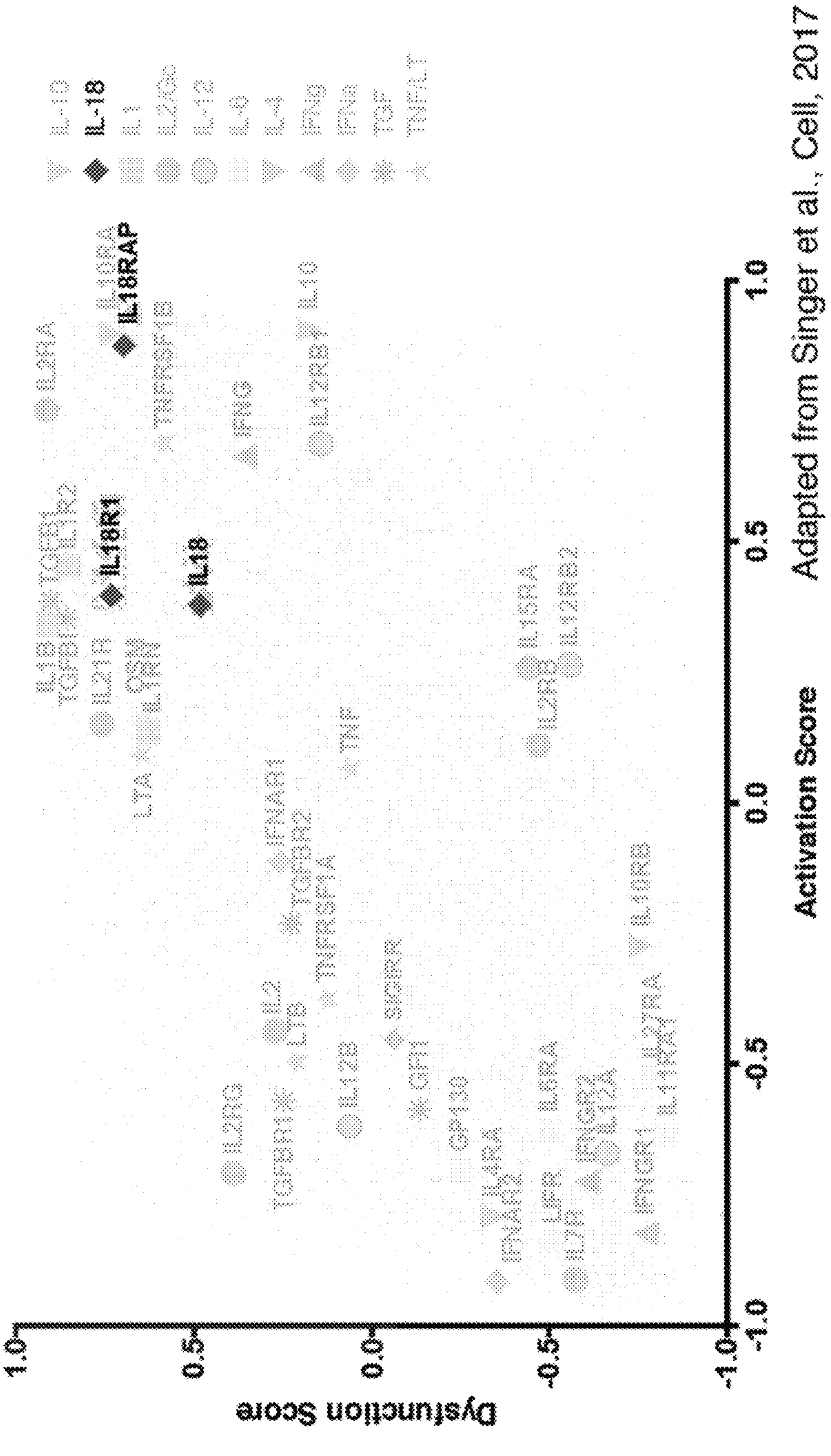
FIG. 1A and FIG. 1B depict results from example experiments, demonstrating the IL-18 pathway is a target for tumor immunotherapy.
Figure 1B:
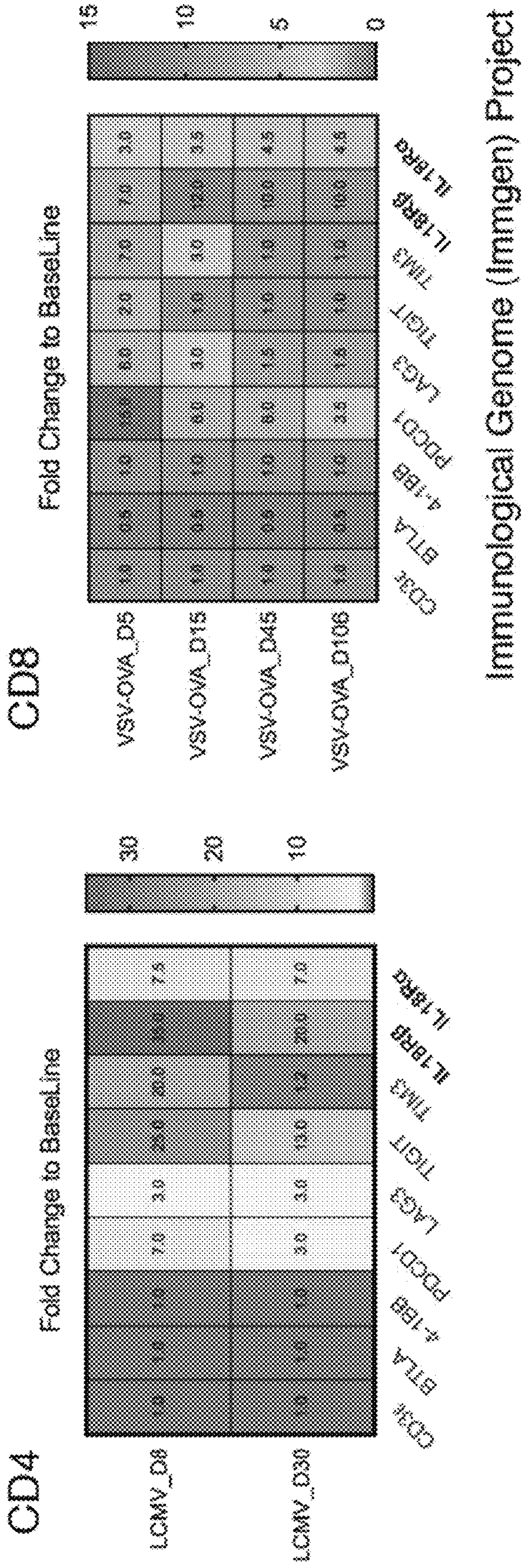

To identify potential signaling nodes for immunotherapeutic intervention, single cell RNAseq data from tumor infiltrating lymphocytes was analyzed for the expression of cytokine pathway components (Singer et al., 2016, Cell, 166:1500-1511, el 509). As seen in FIG. 1A, the receptor subunits for IL-18 IL-18Rα (i.e., IL-18R1) and IL-18Rβ (i.e., IL-18RAP)—as well as IL-18 itself were upregulated in both activated and dysfunctional lymphocyte programs. Further analysis of the Immunological Genome (ImmGen) database revealed that expression of both IL-18 receptor subunits correlated with expression of T cell "exhaustion" markers in CD4 and CD8 cells including PD-1, Tim3, Lag3, and TIGIT following chronic antigen exposure (FIG. 1B). These expression features suggested that the IL-18 pathway could be used to selectively stimulate activated and dysfunctional/exhausted T cells within tumors as an immunotherapeutic paradigm.

Figures 2A, 2B, 2C:
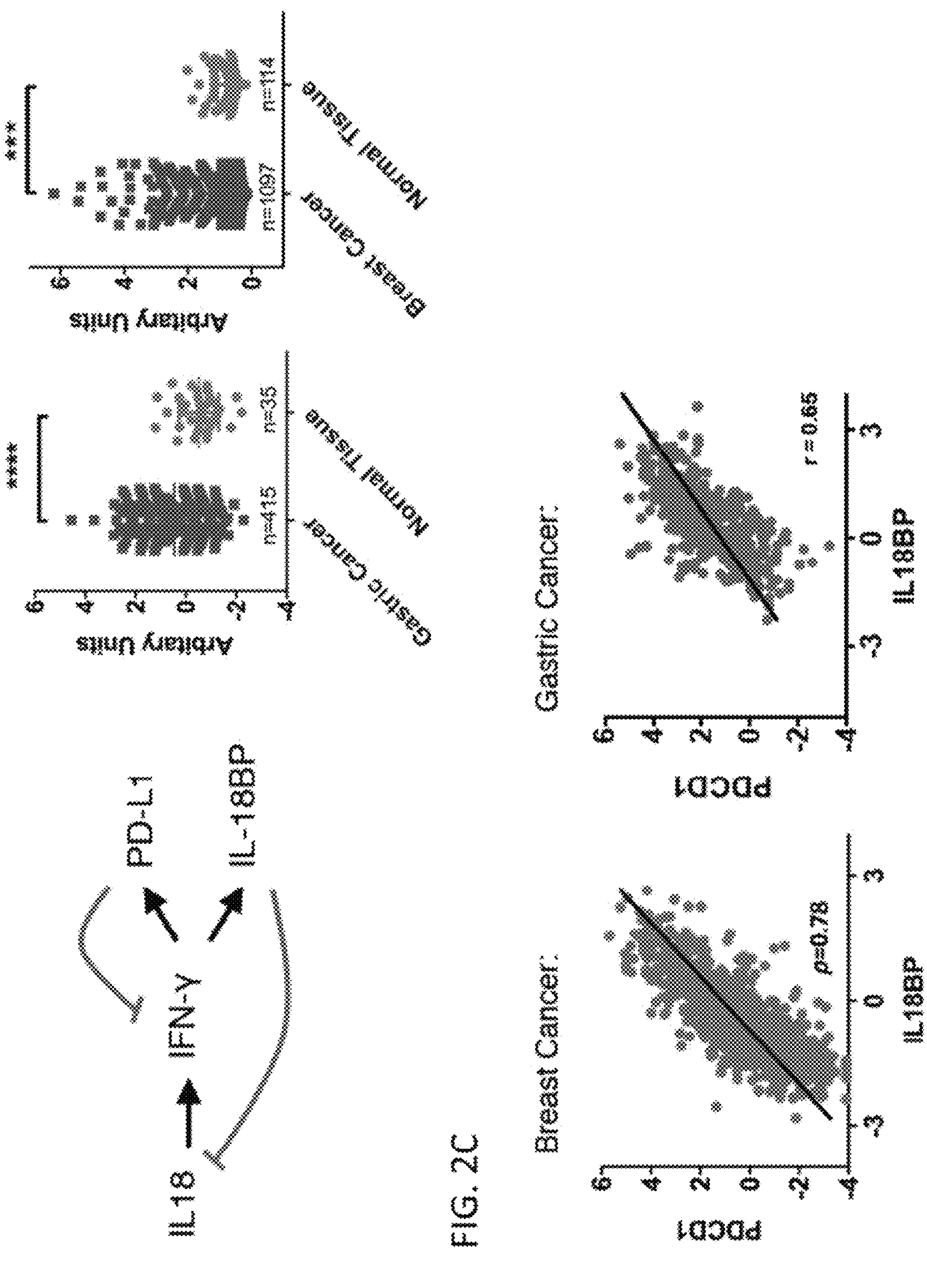
FIG. 2A through FIG. 2C depict results from example experiments, demonstrating IL-18BP has features of a "soluble immune checkpoint".

IL-18 is a Th1 cytokine initially termed "interferon-gamma-inducing-factor" (fan for its ability to robustly stimulate release of interferon gamma (IFN-γ) by T and NK cells. Feedback inhibition of IL-18 is achieved by IFN-γ-driven induction of IL-18BP, a high-affinity secreted decoy receptor for IL-18 that sterically hinders IL-18's ability to bind and activate its receptor (FIG. 2A). Without wishing to be bound by any particular theory, this mechanism is reminiscent of the induction of PD-L1 by IFN-γ, suggesting that IL-18BP may act as a "soluble immune checkpoint." Consistent with this hypothesis, it was found that IL-18BP is upregulated in several types of cancer, most notably breast, gastric, and brain cancer in the TCGA and Oncomine databases (FIG. 2B). Furthermore, IL-18BP expression strongly correlates with expression of the crucial immune checkpoint PD-1 in tumors (r=0.65 and 0.78 in gastric and breast cancer respectively, FIG. 2C), suggesting that IL-18BP may also contribute to tumor immune evasion and lymphocyte exhaustion.

Recombinant IL-18 has been administered to cancer patients in multiple clinical trials. It was found to be well-tolerated even at high doses of 2 mg/kg, with robust pharmacodynamics outputs including expansion of activated CD69 natural killer (NK) cells and dramatic increases in serum IFN-γ levels. However, a phase II trial of melanoma patients was discontinued due to lack of efficacy. Examination of the reported pharmacodynamics results from these clinical trials reveals that the effectiveness of rIL-18 wanes with repeated dosing, with tachyphylaxis seen with respect to peripheral NK cell activation/expansion and cytokine release (including IFN-γ and GM-CSF). The waning effectiveness of rIL-18 coincides with a profound increase in the serum levels of IL-18BP, more than two orders of magnitude over pre-treatment levels and often exceeding 100 ng/mL. Without wishing to be bound by any particular theory, it was hypothesized that IL-18BP limits the effectiveness of rIL-18 therapy and that IL-18 variants that are impervious to IL-18BP inhibition could be effective tumor immunotherapies. Additionally, inhibitors of IL-18BP will likely be effective for tumor immunotherapy.

Engineering IL-18 Variants that are Resistant to IL-18BP Inhibition (Human DR-IL-18 Variants)

Figure 3A:
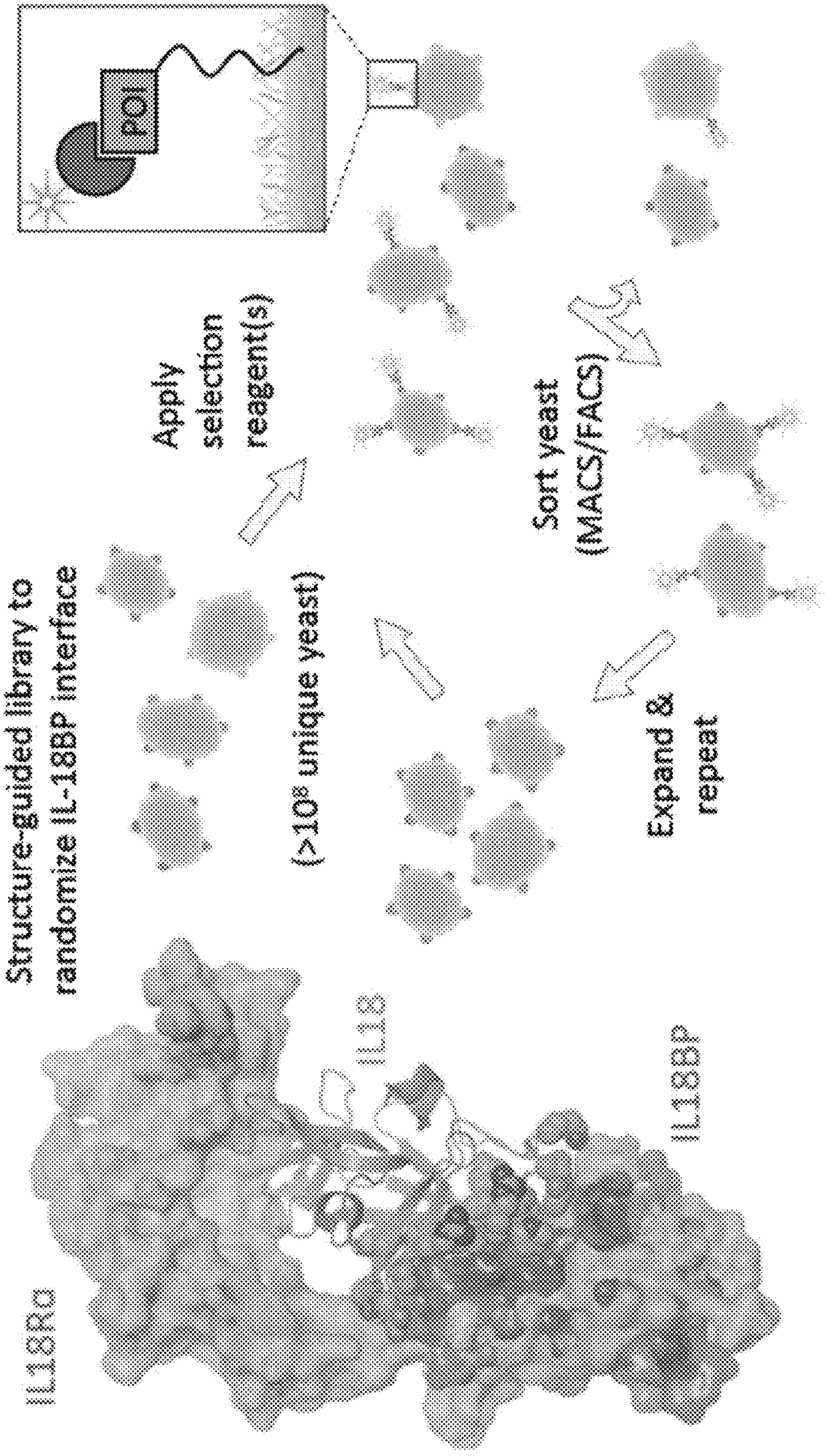
FIG. 3A through FIG. 3C depict results from example experiments, demonstrating engineering human IL-18 variants for independence to IL-18BP using yeast display.
Figure 3C:
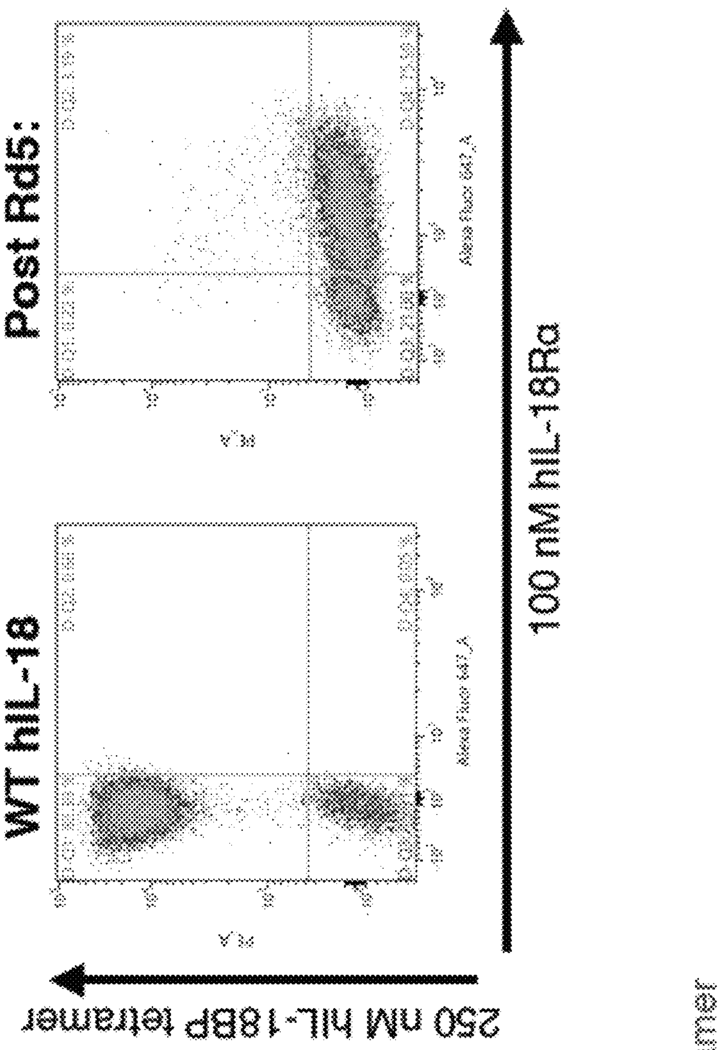
Figure 3B:
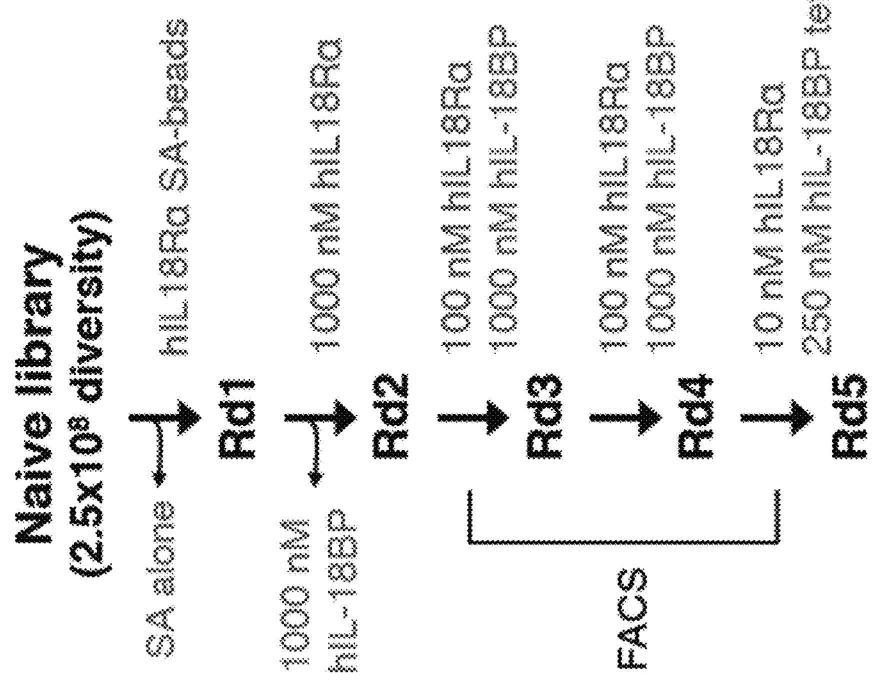

To obtain variants of IL-18 that can signal through IL-18Rα/IL-18Rβ, but are impervious to inhibition by IL-18BP, directed evolution with yeast surface display was utilized. The structure of the ternary signaling complex of human IL-18:IL-18Rα:IL-18Rβ (PDB=3OW4) was first analyzed, and residues of IL-18 that have a shared interface with the signaling complex and IL-18BP were identified (FIG. 3A). As the structure of hIL-18:hIL-18BP has not been determined, a related complex between IL-18 and a viral (ectromelia virus) orthologue of IL-18BP was utilized (PDB=3F62). A combinatorial library randomizing this set of residues to a defined set of alternatives (see Table 1) was created using degenerate oligonucleotide primers and assembly PCR. This library was electroporated into yeast together with the N-terminal yeast display vector pYAL to obtain a library with $2.5\times10^8$ transformants. Using this library, directed evolution was performed by conducting successive rounds of selection using magnetic and fluorescent cell sorting (FACS) with recombinant hIL-18Rα and counterselection with hIL-18BP, as summarized in FIG. 3B. After five rounds of selection, the clear majority of the library clones had completely swapped their relative preference for hIL-18BP and hIL-18Rα as compared to WT hIL-18 (FIG. 3C). These clones were designated as "DR-hIL-18" variants, where "DR" stands for "decoy-resistant."

Figure 5A:
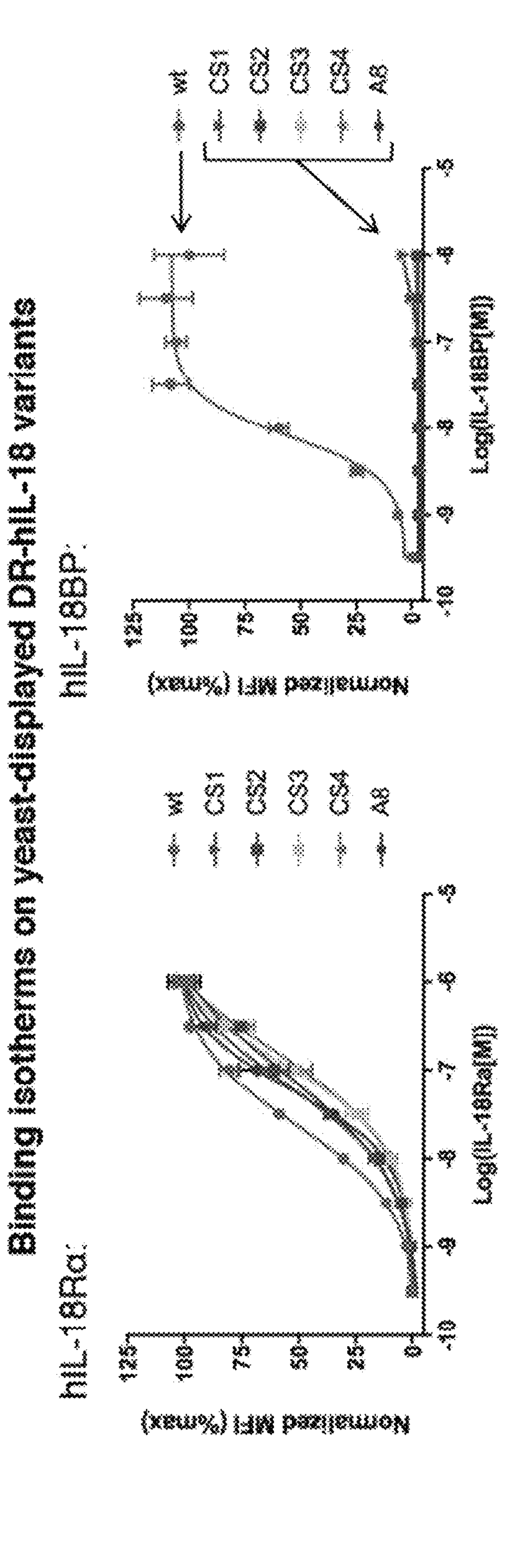
FIG. 5A and FIG. 5B depict results from example experiments, demonstrating biophysical characterization of human DR-IL-18 variants.
Figure 5B:
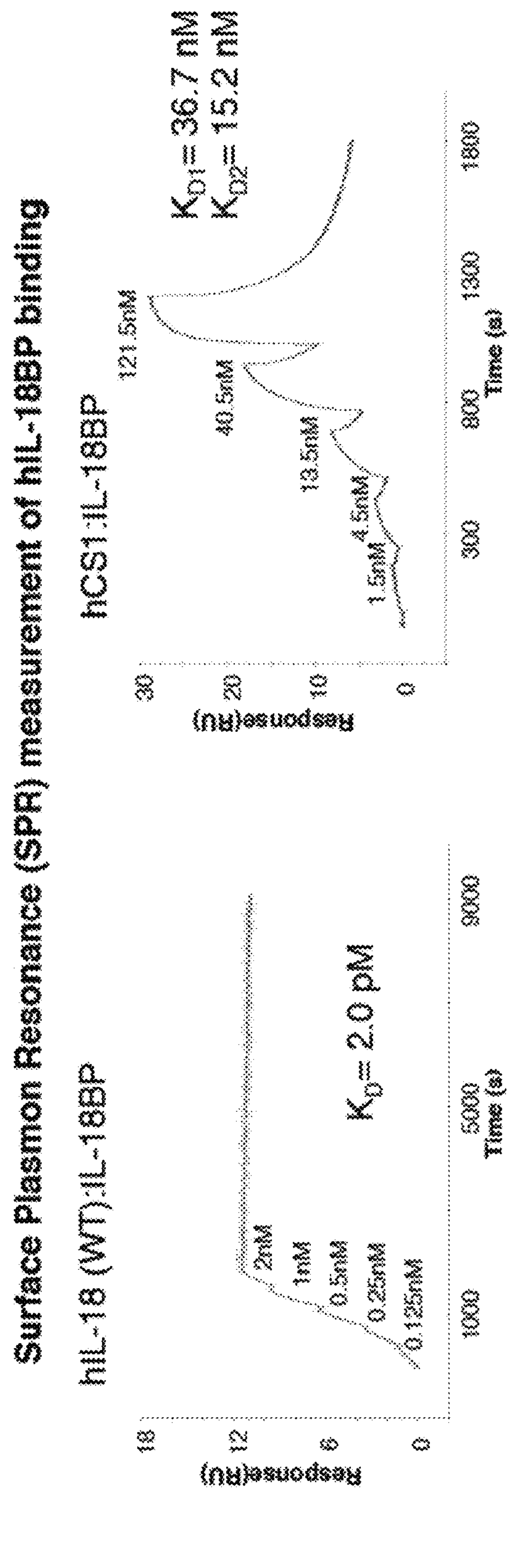

Sequencing of 96 clones from the post-round five pool revealed 21 unique sequences, which were analyzed to create four "consensus sequences", hCS1-4 (FIG. 4). To estimate the binding affinities of these variants for hIL-18Rα and hIL-18BP, binding isotherms were established for hIL-18Rα and IL-18BP binding using yeast-displayed cytokine variants and flow cytometry. As seen in FIG. 5A, the DR-hIL-18 variants bound hIL-18Rα with comparable affinity to WT IL-18, but showed severely attenuated binding to hIL-18BP, with apparent binding $EC_{50}$ values significantly greater than 1 μM. To additionally characterize the receptor binding activities of the DR-IL-18 variants, the cytokines were expressed recombinantly and surface plasmon resonance for IL-18Rα and IL-18BP was performed (see FIG. 5B for representative traces). These results are summarized in Tables 6 and 7 and demonstrate that the DR-hIL-18 variants have a dramatically decreased preference for IL-18BP compared to IL-18Rα, by several orders of magnitude.

TABLE 6

IL-18Rα and IL-18BP binding affinities of human IL-18 variants by on-yeast binding isotherms.

| IL-18 Variant | $K_D$ IL-18Rα (M) | $K_D$ IL-18BP (M) | $K_D$ ratio: IL-18BP/IL-18Rα | Dissociation Constant Ratio normalized to WT IL-18 |
|---|---|---|---|---|
| hIL-18 WT | 2.40E−08 | 7.08E−09 | 2.95E−01 | 1 |
| hA8 | 5.77E−08 | NBD | >3.47E−02 | >1.17E+03 |
| hH3 | 8.38E−08 | NBD | >2.39E+02 | >8.09E+02 |
| hB9 | 1.27E−07 | NBD | >1.57E+02 | >5.34E+02 |
| hCS1 | 6.44E−08 | 1.93E−05 | 3.00E+02 | 1.02E+03 |
| hCS2 | 9.15E−08 | NBD | >2.19E+02 | >7.41E+02 |
| hCS3 | 1.13E−07 | 1.16E−05 | 1.03E+02 | 3.48E+02 |
| hCS4 | 1.60E−07 | NBD | >1.25E+02 | >4.24E+02 |
| 6-31 | 4.1E−08 | NBD | 4.9E+02 | >7.2E+03 |
| 6-20 | N.D. | 3.4E−07 | — | — |
| 6-12 | 1.7E−08 | NBD | 1.2E+03 | >1.7E+04 |
| 6-27 | 4.2E−08 | NBD | 4.8E+02 | >7.0E+03 |
| 6-29 | 3.7E−08 | NBD | 5.4E+02 | >8.0E+03 |

NBD, no binding detected (20 μM used for ratio calculations)
—, value not determined

TABLE 7

IL-18Rα and IL-18BP binding affinities of human IL-18 variants by SPR

| IL-18 Variant | $K_D$ IL-18Rα (M) | $K_D$ IL-18BP (M) | $K_D$ ratio: IL-18BP/TL-18Rα | Dissociation Constant Ratio normalized to WT IL-18 |
|---|---|---|---|---|
| hIL-18 WT | 2.93E−09 | 1.90E−12 | 6.48E−04 | 1 |
| hA8 | — | — | — | — |
| hH3 | — | — | — | — |
| hB9 | — | — | — | — |
| hCS1 | 8.05E−09 | 1.94E−08 | 2.41E+00 | 3.72E+03 |
| hCS2 | 1.31E−08 | — | — | — |
| hCS3 | 8.18E−09 | 1.86E−08 | 2.27E+00 | 3.50E+03 |
| hCS4 | 4.38E−09 | 1.83E−07 | 4.18E+01 | 6.45E+04 |

—, value not determined

Functional Characterization of Human DR-IL-18 Variants

Figure 6A:
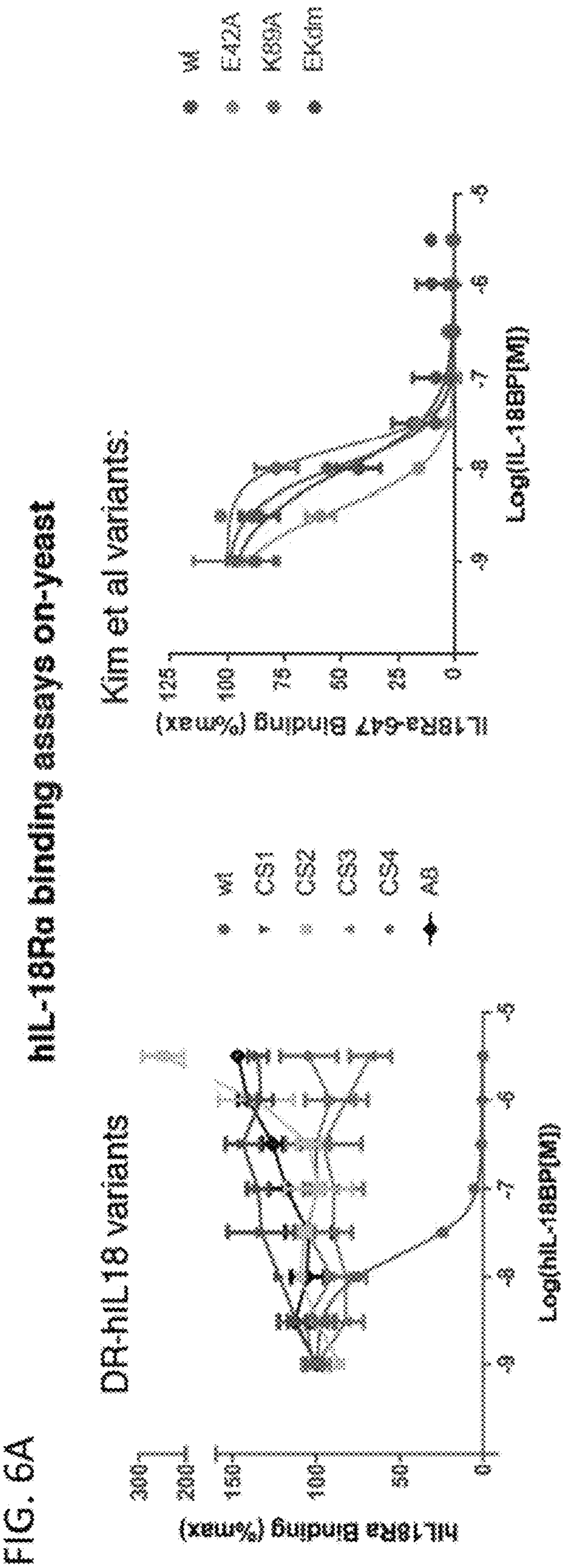
FIG. 6A and FIG. 6B depict results from example experiments, demonstrating human DR-IL-18 variants are not inhibited by IL-18BP.

A previous report from Kim et al (Kim et al., 2001, Proc Natl Acad Sci USA, 98(6):3304-9) described 3 hIL-8 variants with enhanced activity and purportedly decreased inhibition by IL-18BP: E42A, K89A, and E42A/K89A. These cytokine variants were displayed on yeast and IL-18BP inhibition of IL-18Rα binding was assessed by flow cytometry. As seen in FIG. 6A, while the DR-ML-18 variants were impervious to inhibition of hIL-18Rα binding by hIL-18BP, the Kim et al variants showed roughly equivalent hIL-18BP neutralization as compared to WT hIL-18. These results indicate that the DR-hIL-18 variants are IL-18BP independent, whereas the Kim et al variants are highly sensitive to IL-18BP inhibition, similar to WT hIL-18.

Figure 6B:
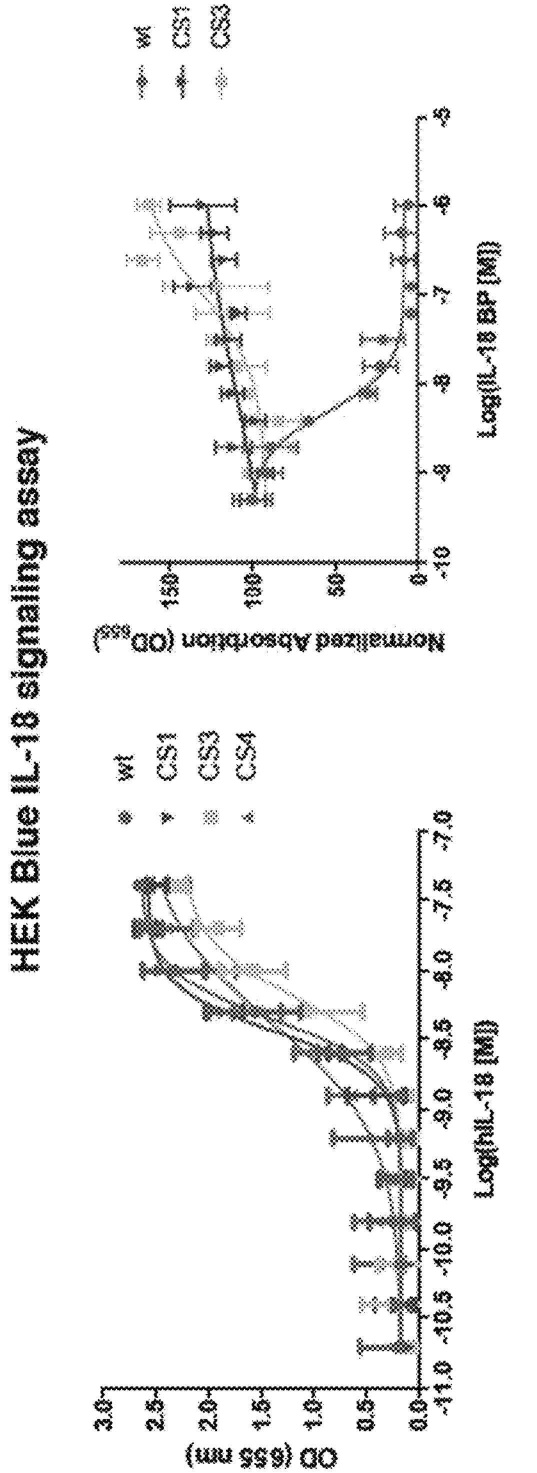

To confirm that the DR-hIL-18 could yield productive signaling through the IL-18 receptor in a cellular context, concentration-response experiments were performed using the HEK-blue IL-18 reporter cell line. In this system, IL-18R signaling is read-out by expression of secreted alkaline phosphatase (SEAP) downstream of a NFκb/AP1 promotor. In the absence of IL-18BP, DR-hIL-18 variants yielded signaling EC50 values commensurate with WT hIL-18, However, the DR-hIL-18 variants demonstrated virtually no inhibition by hIL-18BP, with no detectable inhibition at 1 μM IL-18BP (FIG. 6B). Taken together, these studies establish that the DR-hIL-18 variants are biologically active and impervious to IL-18BP neutralization in a cell signaling context.

Engineering and Characterization of Second-Generation Human IL-18 Variants that are Resistant to IL-18BP Inhibition (Human v2.0 DR-IL-18 Variants)

To obtain additional, potentially enhanced human DR-IL-18 variants, a second library of human IL-18 randomized at 11 positions (FIG. 7A) was designed and yeast was transformed as described above. The resulting library of $6\times10^8$ transformants was selected as outlined in (FIG. 7B), yielding a robust preference for IL-18Rα compared to IL-18BP with successive selection steps (FIG. 7C). 17 unique sequences were recovered after 5-6 rounds of selection (FIG. 8). (FIG. 9A) Compared to WT IL-18, clones 6-12, 6-27, 6-29, and 6-31 had equal or somewhat stronger binding to IL18Rα as measured by yeast-binding isotherms with biotinylated IL18Rα. (FIG. 9B) However, these clones did not show any appreciable binding to IL-18BP. (FIG. 9C) Measurement of thermal stability by applying a range of temperatures to the yeast-displayed clones showed that they were more thermal stable than WT IL-18 by 7-13° C. These results are summarized in (FIG. 9D).

Engineering IL-18 Variants that are Resistant to IL-18BP Inhibition (Murine DR-IL-18 Variants)

Figure 10B:
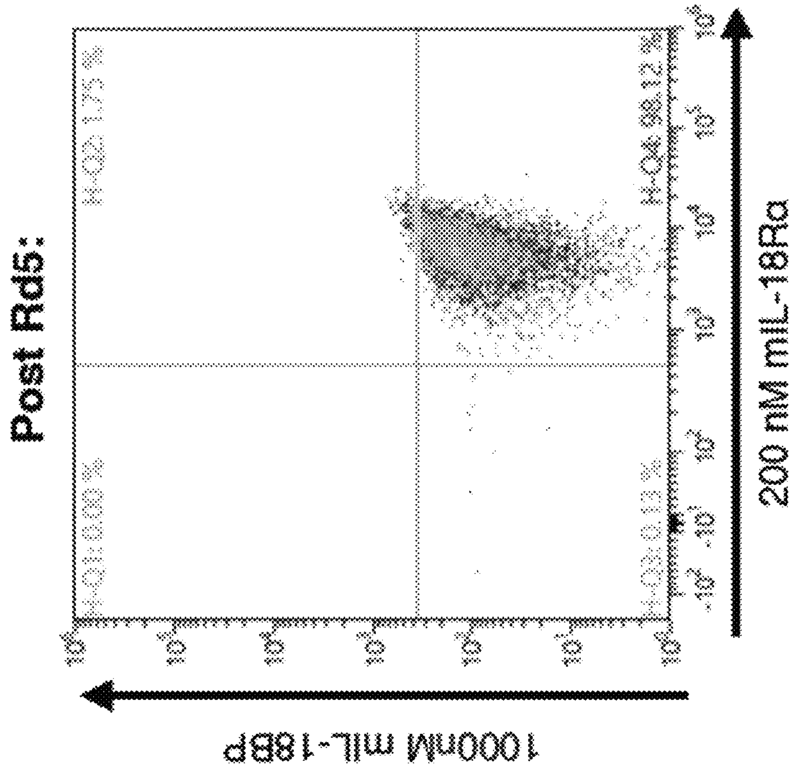
Figure 10A:
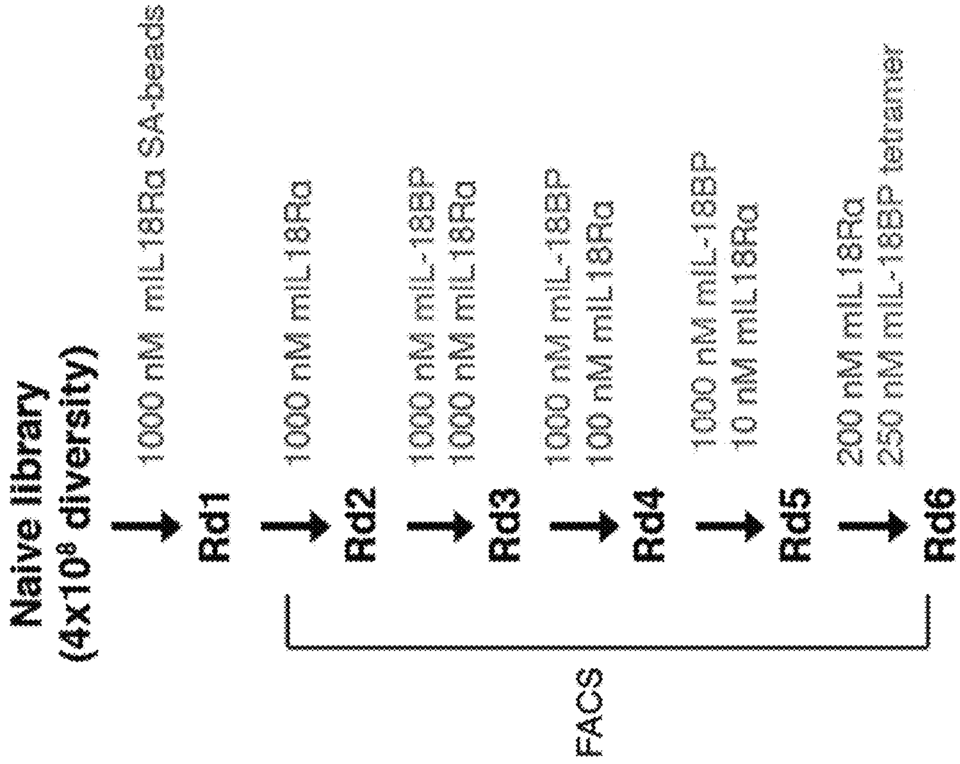
Figure 11A:
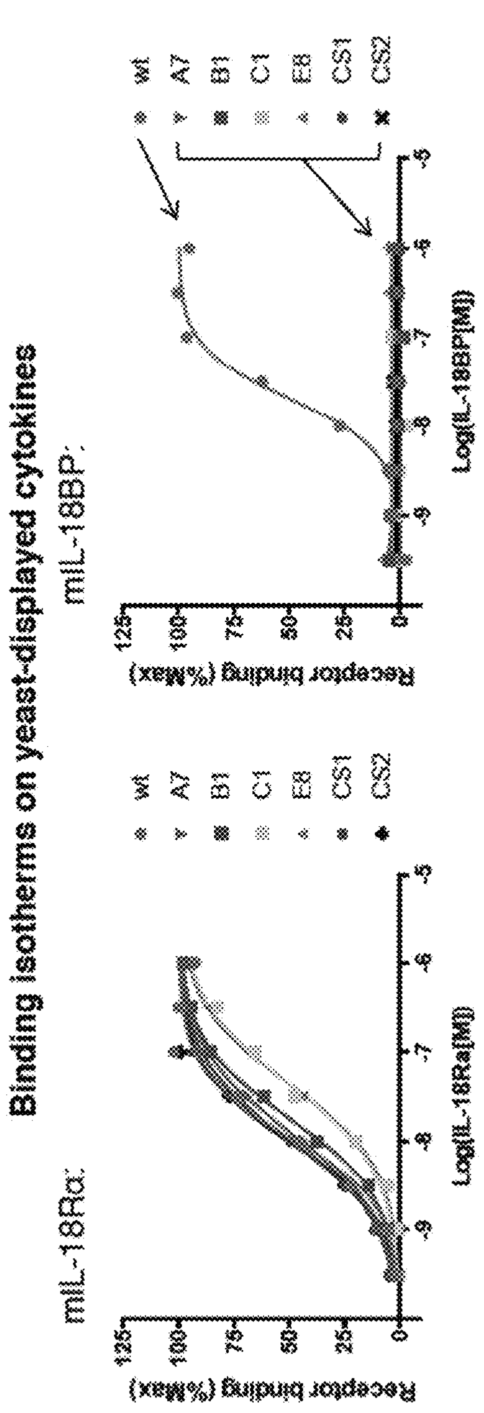
FIG. 11A and FIG. 11B depict results from example experiments, demonstrating biophysical characterization of murine DR-IL-18 variants.
Figure 11B:
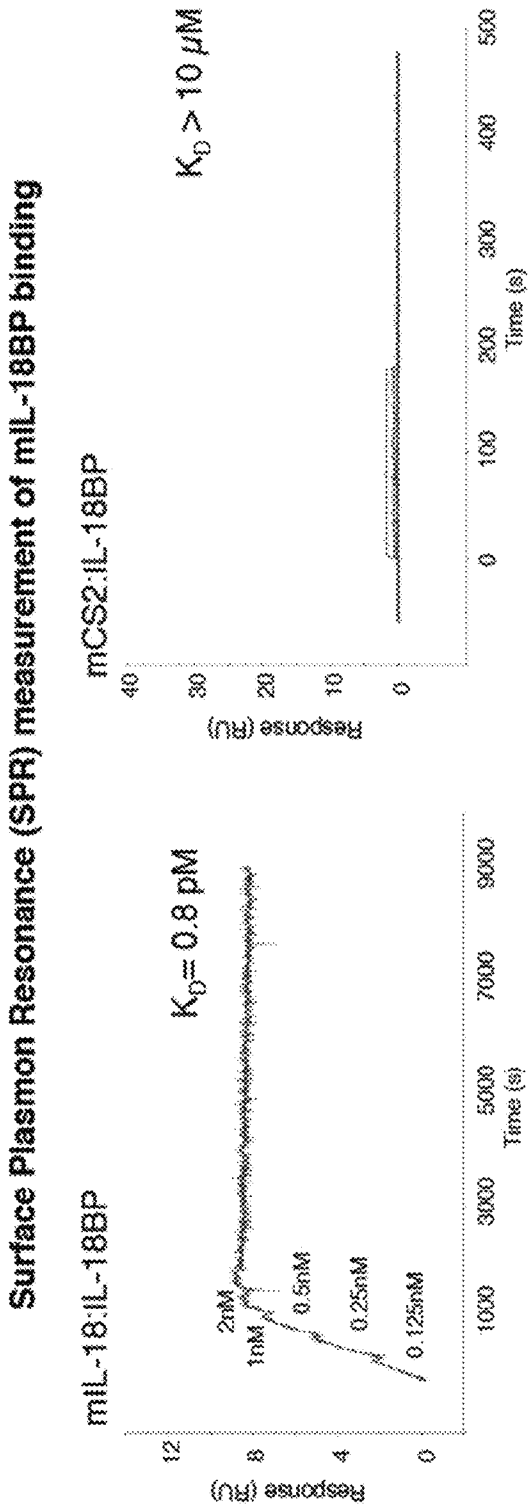

As the human and mouse interspecies cross-reactivity of IL-18 for IL-18Rα is poor, murine equivalents of the DR-IL-18 variants that could be used for studies in mice were created. Similar to the approach taken for hIL-18 above, a combinatorial library of mIL-18 variants randomizing a similar set of mIL-18Rα/mIL-18BP contact residues (Table 3) was created, yielding a library of $4\times10^8$ transformants. Directed evolution was performed on this library similar to how it was performed with the human IL-18 library; the selection strategy is summarized in FIG. 10A. After the completion of six rounds of selection, the remaining clones had a near-complete preference for mIL-18Rα over mIL-18BP (FIG. 10B). Analysis of 96 clones revealed 11 unique sequences, from which were derived two consensus sequences mCS1 and mCS2 (FIG. 10C). Yeast binding isotherms and surface plasmon resonance experiments confirmed these DR-IL-18 clones had an even greater independence for IL-18BP than the human IL-18 variants described herein, with the mIL-18BP binding KD's being well above 1 μM, with mIL-18Rα binding remaining roughly equal to WT mIL-18 (FIG. 11A, FIG. 11B, Tables 8 and 9).

TABLE 8

IL-18Rα and IL-18BP binding affinities of mouse IL-18 variants by on-yeast binding isotherms

| IL-18 Variant | $K_D$ IL-18Rα (M) | $K_D$ IL-18BP (M) | $K_D$ ratio: IL-18BP/IL-18Rα | Dissociation Constant Ratio normalized to WT IL-18 |
|---|---|---|---|---|
| mIL-18 WT | 1.13E−08 | 2.13E−09 | 1.88E−01 | 1 |
| mA7 | 1.35E−08 | NBD | >7.41E+02 | >3.93E+03 |
| mB1 | 1.79E−08 | NBD | >5.59E+02 | >2.96E+03 |
| mE8 | 4.20E−08 | NBD | >2.38E+02 | >1.26E+03 |
| mC1 | 4.30E−08 | NBD | >2.33E+02 | >1.23E+03 |
| mCS1 | 1.07E−08 | NBD | >9.35E+02 | >4.96E+03 |
| mCS2 | 1.13E−08 | NBD | >8.85E+02 | >4.69E+03 |

NBD, no binding detected (10 μM used for ratio calculations)

TABLE 9

IL-18Rα and IL-18BP binding affinities of mouse IL-18 variants by SPR

| IL-18 Variant | $K_D$ IL-18Rα (M) | $K_D$ IL-18BP (M) | $K_D$ ratio: IL-18BP/IL-18Rα | Dissociation Constant Ratio normalized to WT IL-18 |
|---|---|---|---|---|
| mIL-18 WT | 6.00E−10 | 1.10E−12 | 1.83E−03 | 1 |
| mA7 | 2.20E−10 | 1.39E−05 | 6.32E+04 | 3.45E+07 |
| mB1 | 7.00E−10 | 1.47E−05 | 2.10E+04 | 1.15E+07 |
| mE8 | 1.69E−09 | NBD | >1.78E+04 | >9.68E+06 |
| mC1 | 1.09E−09 | 2.87E−05 | 2.63E+04 | 1.44E+07 |
| mCS1 | 5.40E−10 | 3.80E−06 | 7.04E+03 | 3.84E+06 |
| mCS2 | 7.90E−11 | 1.05E−05 | 1.33E+05 | 7.25E+07 |

NBD, no binding detected (30 μM used for ratio calculations)

In Vivo Pharmacodynamic Studies of DR-IL-18 Variants

Figure 12A:
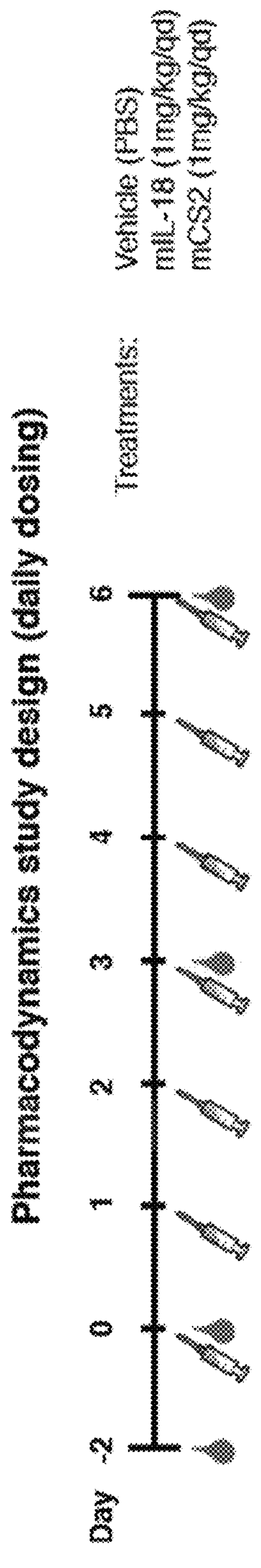
FIG. 12A through FIG. 12D depict results from example experiments, demonstrating pharmacodynamics of DR-IL-18 administered to mice.
Figure 12B:
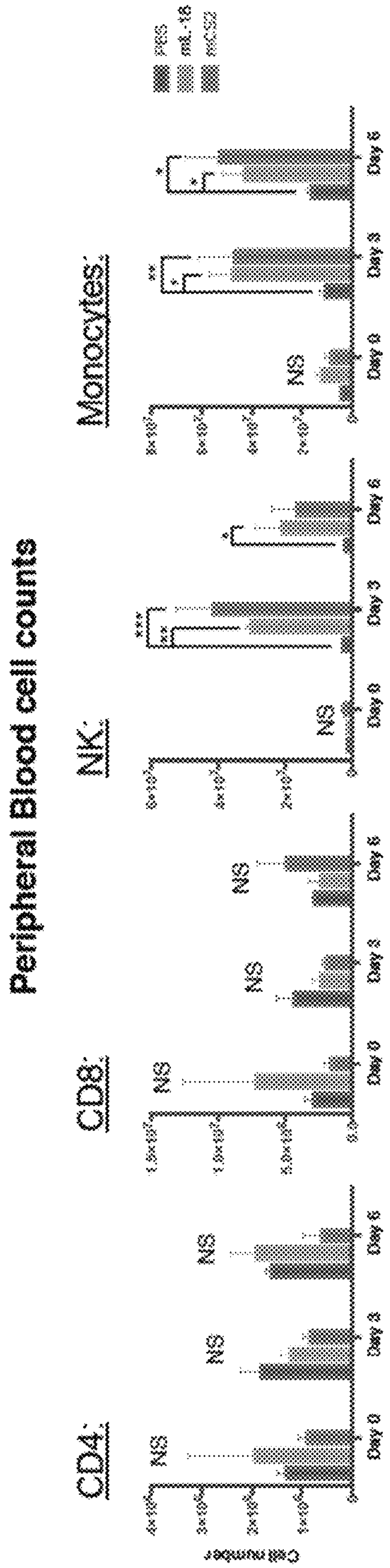
Figure 12C:
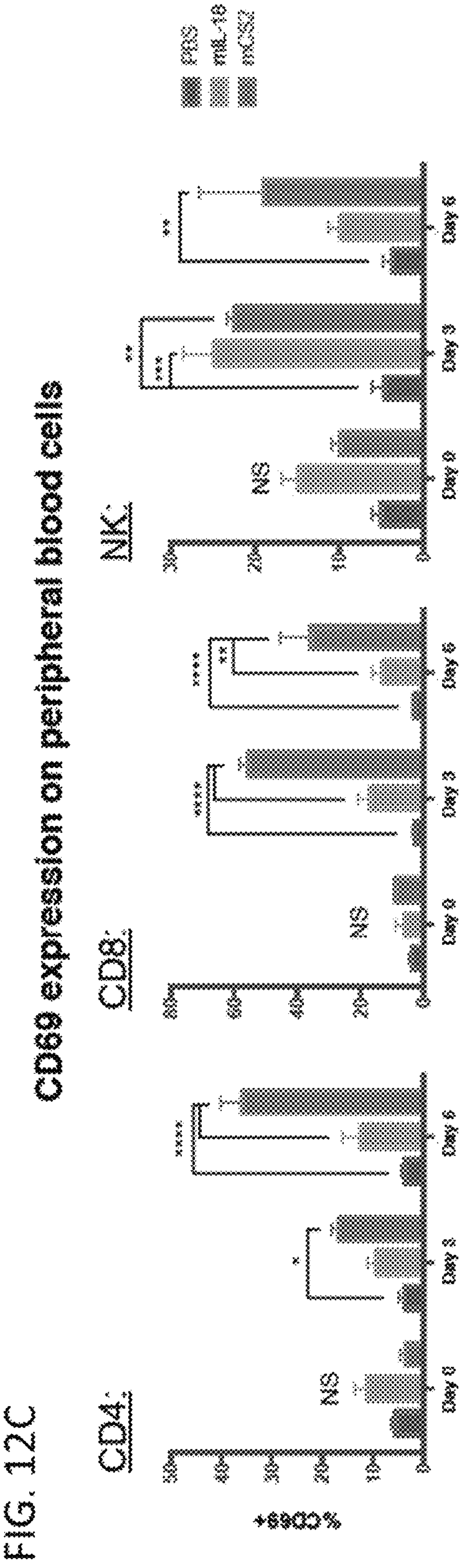
Figure 12D:
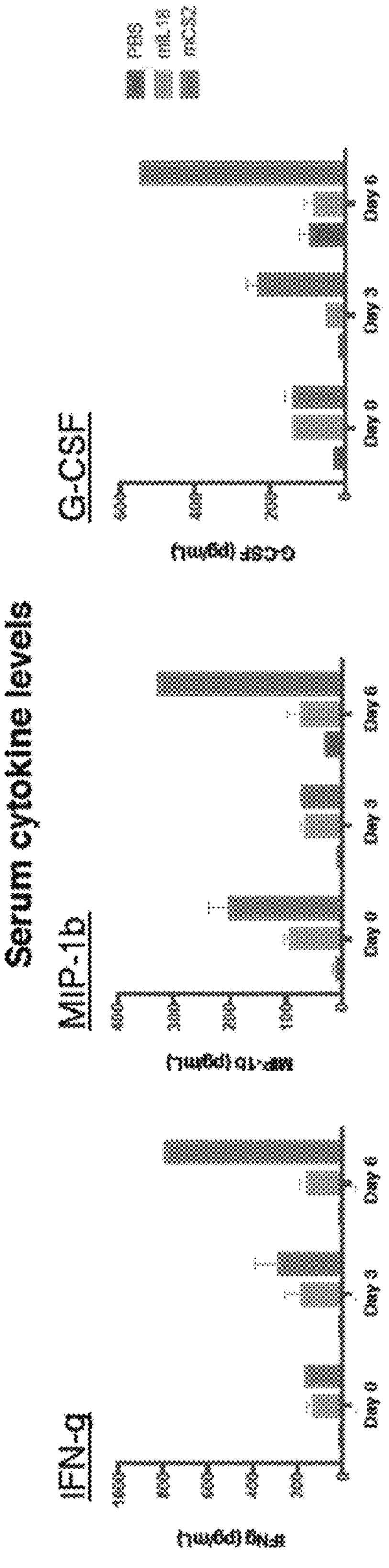

To assess the biologic effects of administration of the DR-IL-18 variants in vivo, pharmacodynamics studies were performed in mice, comparing WT mIL-18 to mCS2. In the first study, mice were treated with vehicle (PBS), mIL-18 (1 mg/kg/day), or mCS2 (1 mg/kg/day) for a total of seven injections (FIG. 12A). Analysis of peripheral blood phenotypes by flow cytometry showed that both WT mIL-18 and mCS2 increased peripheral NK cell numbers by over ten-fold, and peripheral monocyte counts by over five-fold compared to vehicle treatment; total CD4 and CD8 cell counts were not significantly affected (FIG. 12B). Examination of cellular activation status by CD69 induction revealed that mCS2 treatment dramatically increased CD69 levels on CD4 and CD8 cells compared to mIL-18 or vehicle treatment; reaching over 30% and over 50% positivity for CD4 and CD8 subsets, respectively (FIG. 12C). While both mIL-18 and mCS2 stimulated CD69 expression on peripheral NK cells to over 20% positive by day 3, the CD69 levels decreased to non-significant levels for mIL-18 by day 6, but remained significantly elevated with mCS2 treatment (FIG. 12C). Peripheral cytokine levels were also measured with a multiplexed Luminex panel. As seen in FIG. 12D, both mIL-18 and mCS2 increased serum IFN-g, MIP1b, and G-CSF compared to vehicle treatment, but mCS2 achieved much higher levels than mIL-18 by day 6 for each of these cytokines, as mIL-18 exhibited tachyphylaxis with plateaued or decreasing induced cytokine levels with subsequent administration.

Effect of mCS2 on Body Fat Composition

Figure 13:
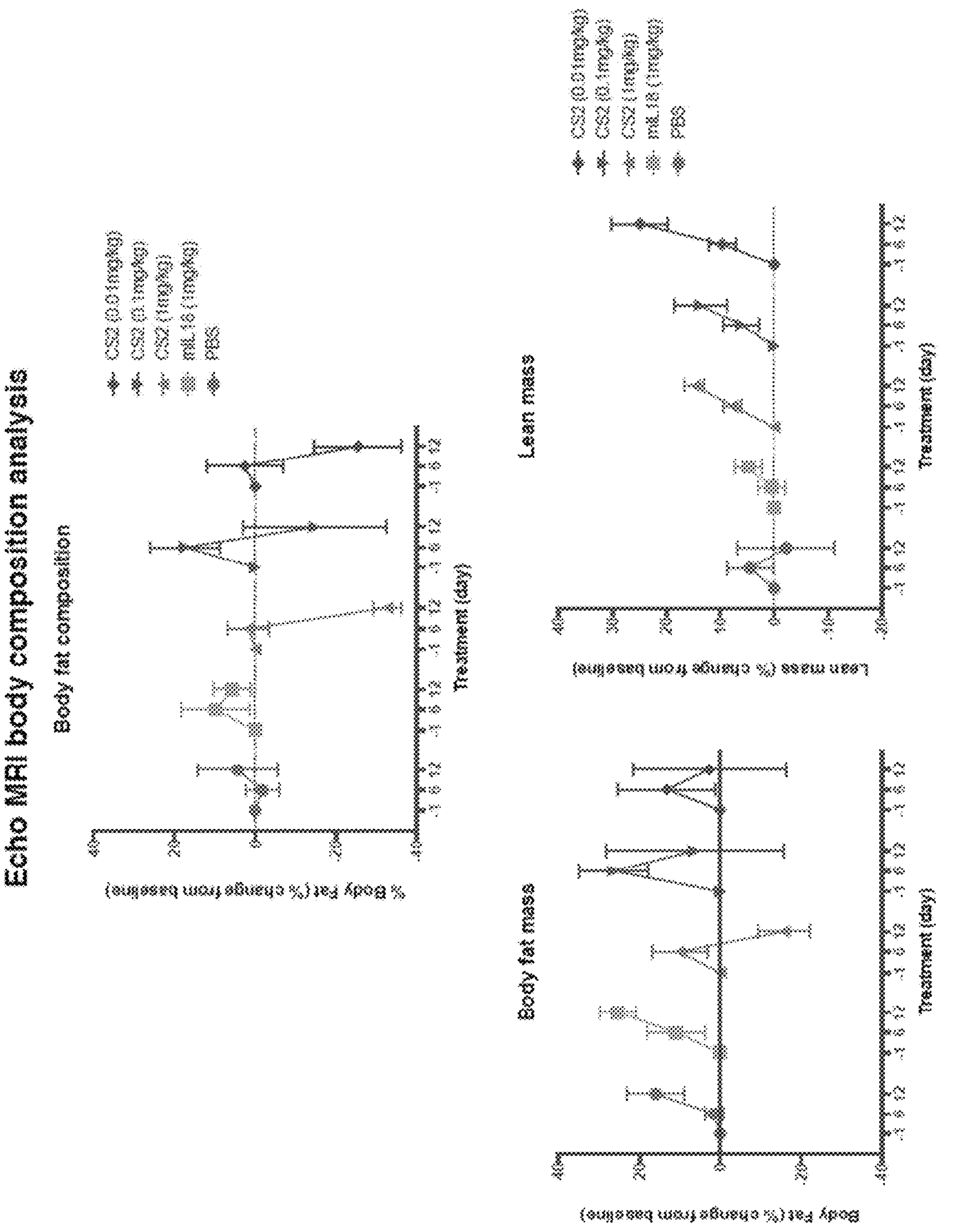
FIG. 13 depicts results from example experiments, demonstrating DR-IL-18 treatment decreases body fat composition in mice. Body fat and lean mass composition were measured in mice treated with 0.01, 0.1, or 1 mg/kg of the DR-IL-18 variant mCS2 or 1 mg/kg WT mIL-18 every three days. mCS2 treatment produced a significant decrease in body fat as a total percentage of body mass (top panel). This was manifested by decreases or stable fat mass (left panel), with concordant increases in lean mass (right panel). Vehicle treated and mIL-18 treated mice showed increases in body fat mass and stable lean mass over the same treatment period.

To assess the effect of the DR-IL-18 variants on body fat composition, we administered WT IL-18 at 1 mg/kg or 0.01, 0.1, or 1 mg/kg mCS2 by intraperitoneal injection to C57BL/6 mice every three days. Body fat and lean mass composition were monitored by echoMRI. All tested doses of mCS2 (1 mg/kg, 0.1 mg/kg, and 0.01 mg/kg) resulted in striking decreases in the overall percentage of body fat by day 12, while vehicle and mIL-18 treated mice did not have a significant change in total body fat composition (FIG. 13, top). Specifically, mCS2-treated mice had either reduced or stable levels of total fat mass during the experiment (FIG. 13, bottom left), but substantially increased their total lean mass (FIG. 13, bottom right). These results indicate that mCS2, and other variants disclosed herein, could be used to therapeutically decrease body fat composition (e.g., for treatment of obesity, diabetes, and/or metabolic syndrome).

Anti-Tumor Efficacy of DR-IL-18 Variants

Figure 14A:
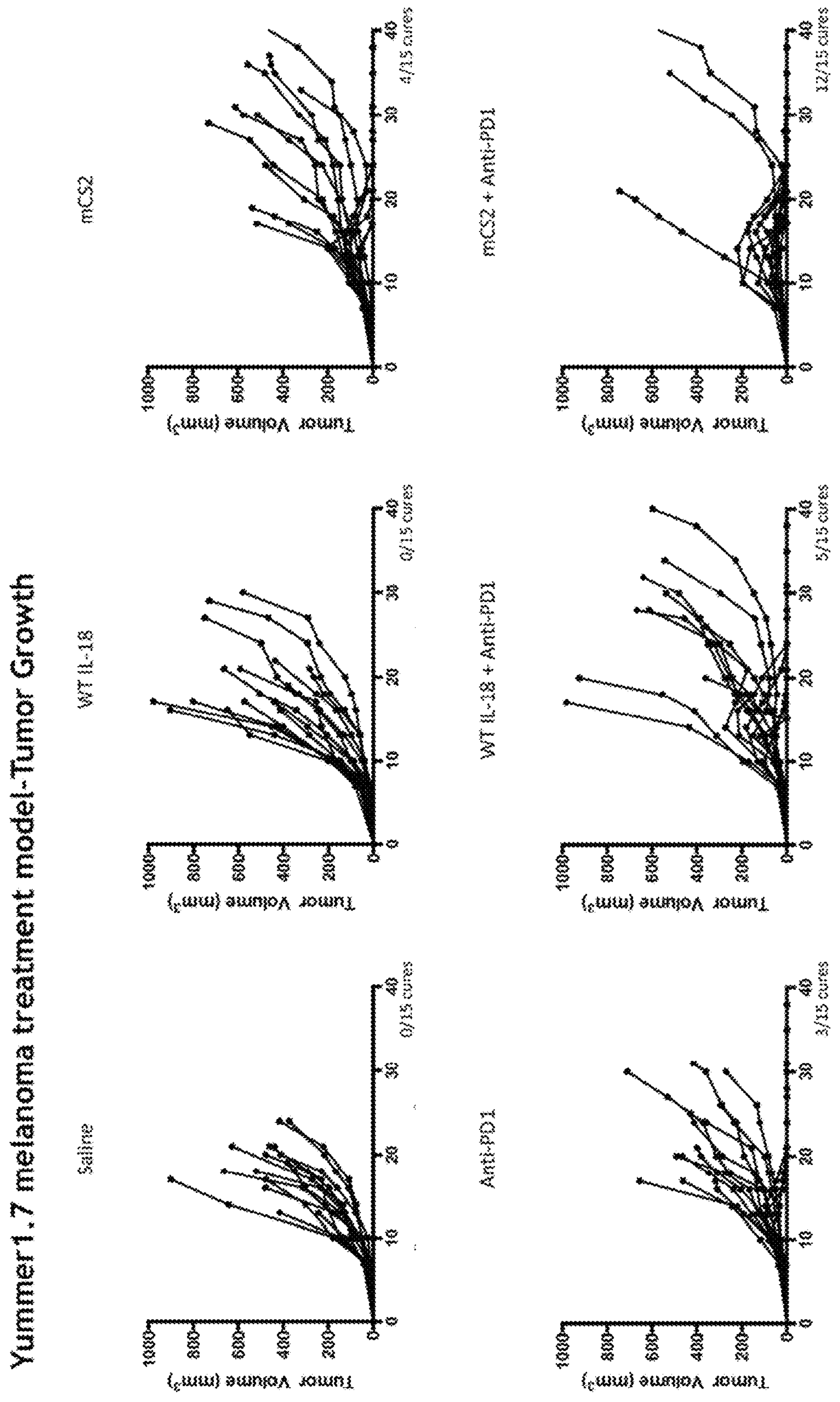
FIG. 14A through 14B depict results from example experiments, demonstrating DR-IL-18 is an effective immunotherapeutic in a melanoma model.
Figure 14B:
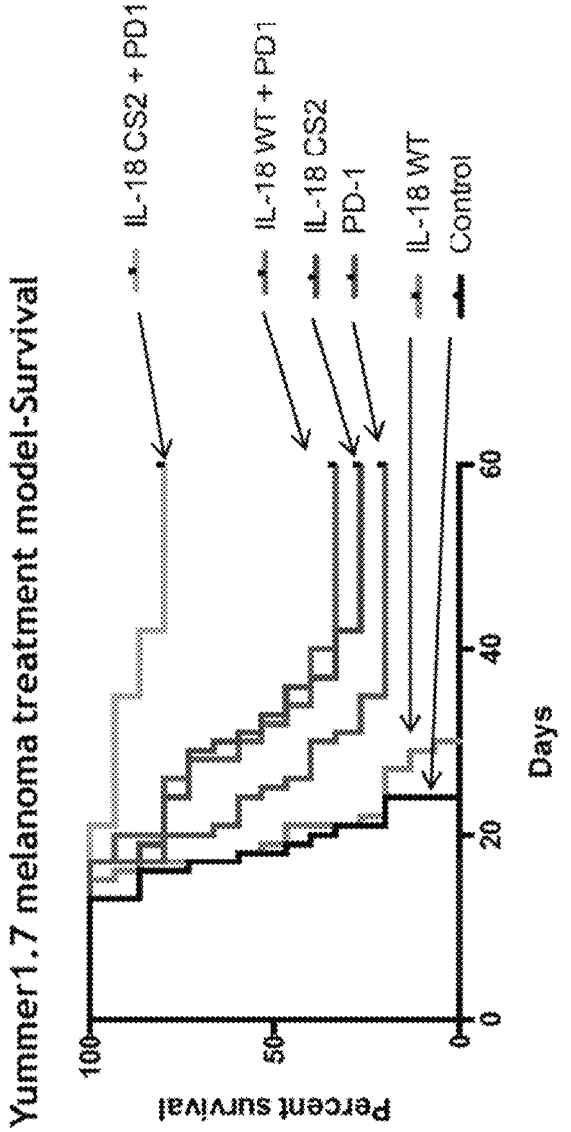

The anti-tumor efficacy of DR-IL-18 (mCS2) was assessed using the transplantable, syngenic YUMMER1.7 malignant melanoma tumor model. WT mIL-18 and mCS2 were administered to mice bearing YUMMER1.7 tumors biweekly at a dose of 0.32 mg/kg, with or without co-administration of anti-PD1 antibodies (8 mg/ka/q3d). Consistent with previous reports on its use in mice and humans, WT IL-18 did not affect tumor growth or survival compared to vehicle (saline and only marginally improved the efficacy anti-PD1 when administered in combination. However, mCS2 cured 27% of treated mice as a monotherapy and produced a partial response in another 27%, an effect commensurate with anti-PD1 treatment. The combination of mCS2 with anti-PD1 cured 80% of treated mice (FIG. 14A and FIG. 14B).

Figure 15A:
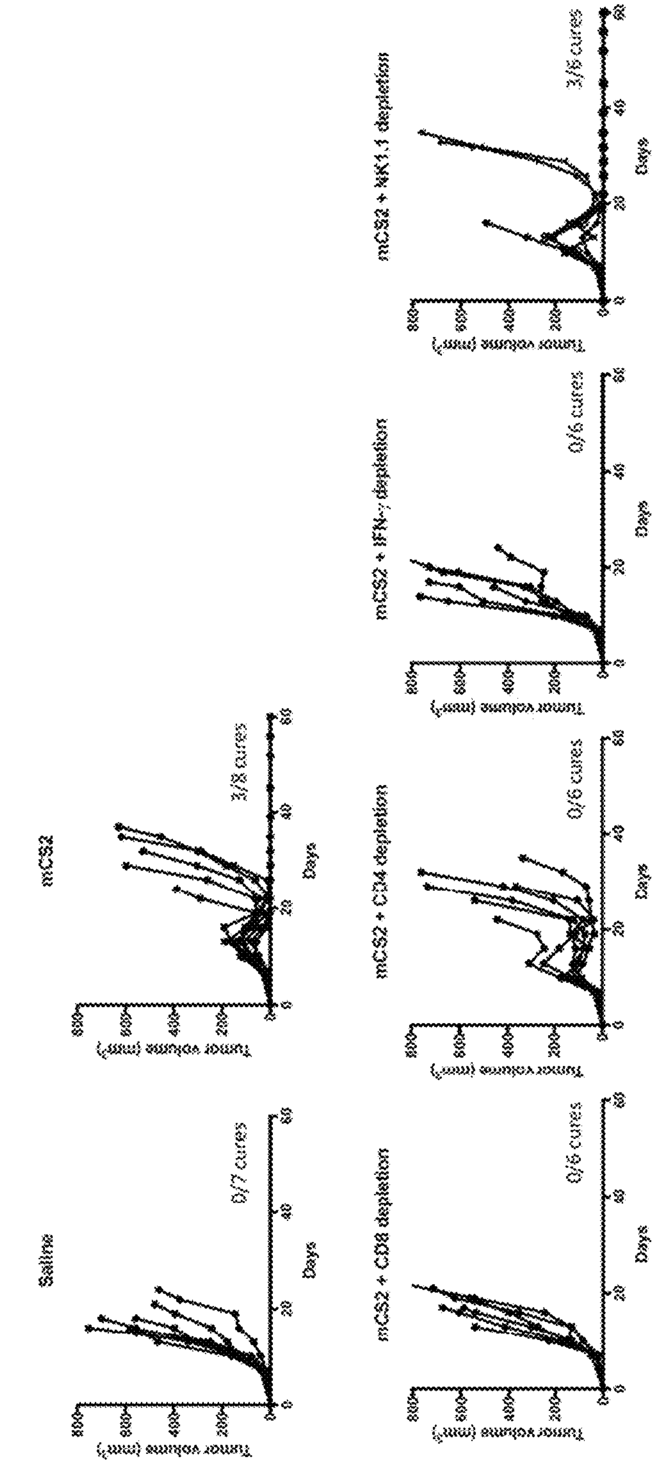
FIG. 15A and FIG. 15B depict results from example experiments that demonstrate that the effectiveness of DR-IL-18 in the melanoma model of FIG. 14 is dependent on CD4 and CD8 lymphocytes and interferon gamma (FIG. 15A.) Tumor growth spider plots for mice bearing Yummer1.7 melanoma tumors treated with saline (control), or the DR-IL-18 variant mCS2 (0.32 mg/kg) alone, or in combination with depleting antibodies against CD8, CD4, interferon gamma, or NK1.1.
Figure 15B:
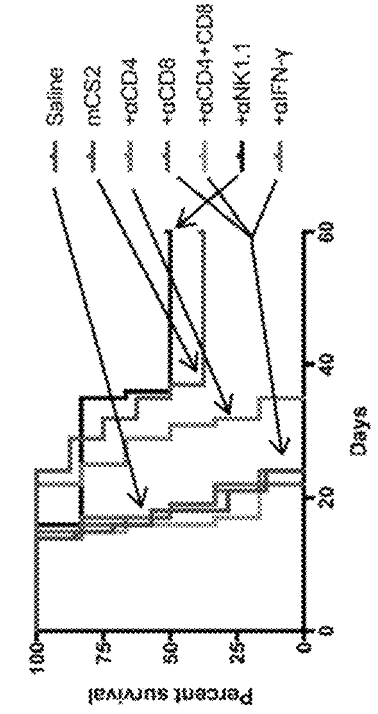

To establish the mechanism of action of DR-IL-18 on YUMMER1.7 tumors, cell depletion studies were performed using antibodies against CD8, CD4, NK1.1, and Interferon-gamma. As seen in FIG. 15A and FIG. 15B, depletion of CD8 cells or neutralization of Interferon-gamma completely abrogated the effectiveness of DR-IL-18. Depletion of CD4 cells did not affect the initial activity of DR-IL-18 in terms of tumor growth, however, in CD4 treated mice, therapeutic responses are not sustained, suggesting a role of CD4 cells in supporting and sustaining anti-tumor immunity. Depletion of NK cells did not affect tumor growth or survival in YUMMER1.7 cells.

Figure 16:
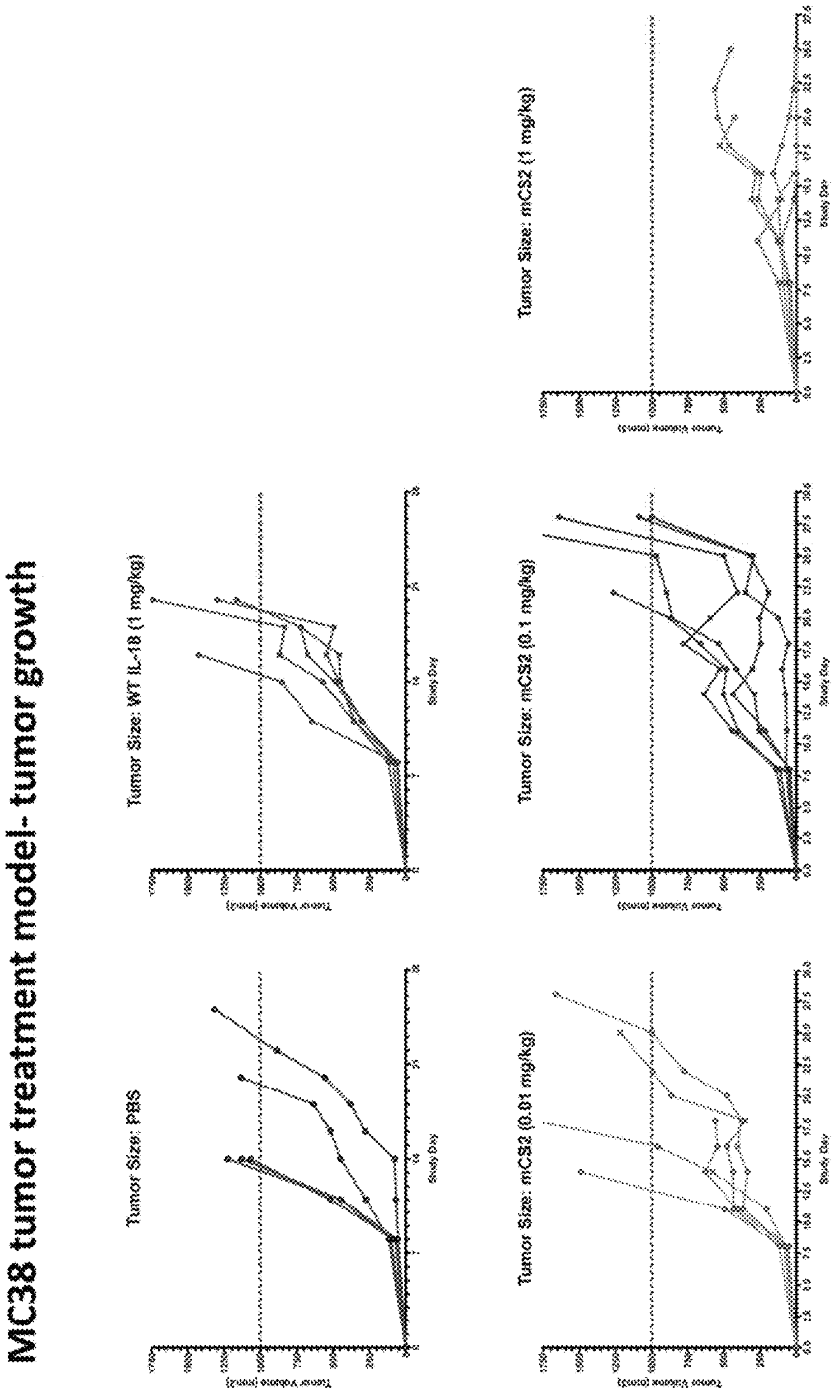
FIG. 16 depicts results from example experiments, demonstrating dose-dependent efficacy of DR-IL-18 in the MC38 tumor model. Tumor growth spider plots from mice bearing MC38 colon cancer tumors treated with PBS (control), 1.0 mg/kg WT IL-18, 1.0 mg/kg mCS2, 0.1 mg/kg mCS2, or 0.01 mg/kg mCS2 every three days. WT IL-18 was not efficacious at 1 mg/kg, whereas mCS2 showed partial efficacy at 0.1 mg/kg and maximal efficacy at 1.0 mg/kg.
Figure 17:
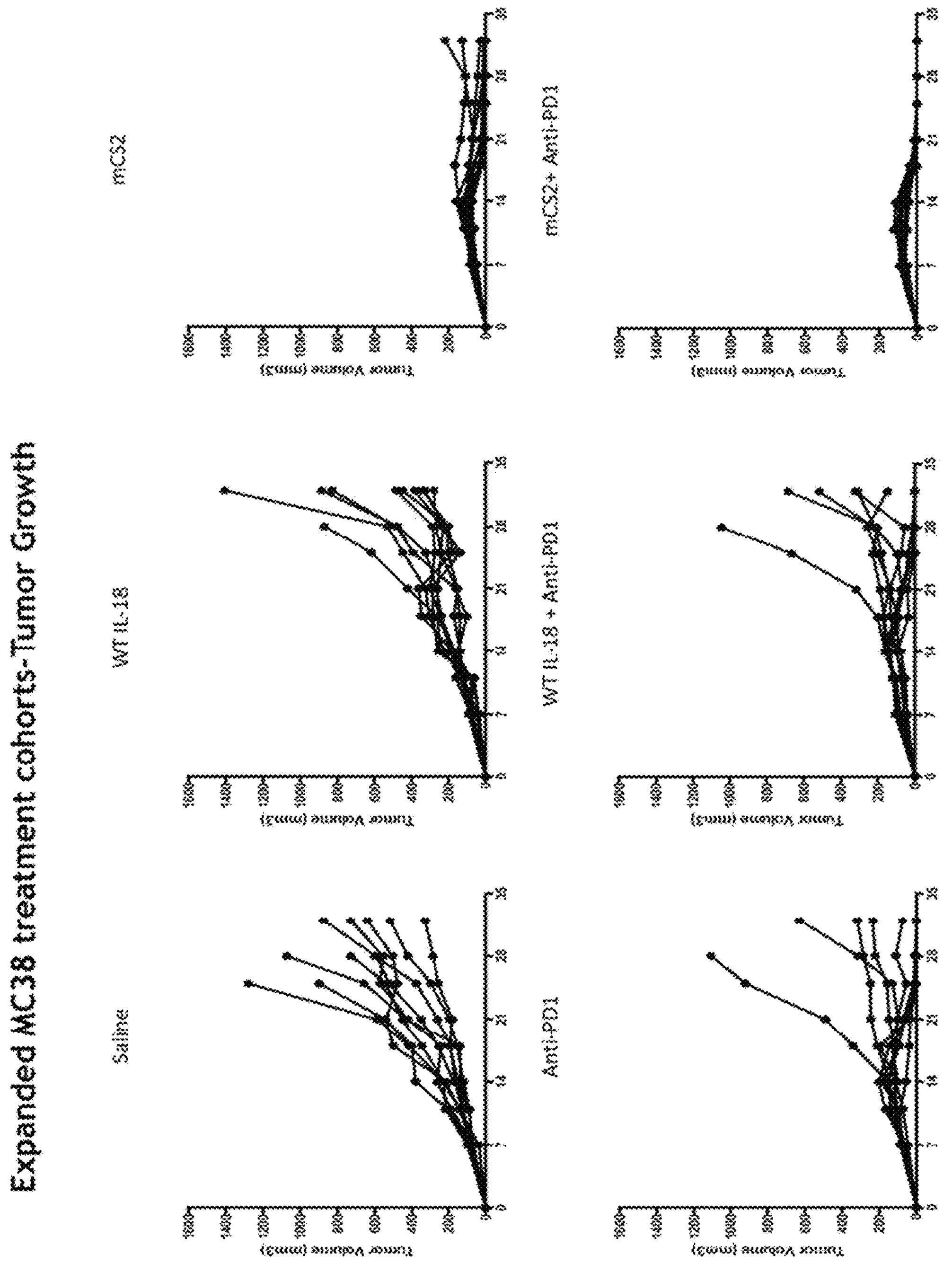
FIG. 17 depicts results from example experiments demonstrating the efficacy of DR-IL-18 alone in combination with the immune checkpoint inhibitor anti-PD1 in the MC38 tumor model. Tumor growth spider plots are shown from mice bearing MC38 colon cancer tumors treated with PBS (control), 0.32 mg/kg WT IL-18, 0.32 mg/kg of the DR-IL-18 variant mCS2, 5 mg/kg anti-PD1, the combinations of anti-PD1 with WT IL-18, or the combination of anti-PD1 with mCS2. All agents were dosed intraperitoneally twice per week for up to 6 total doses.

The activity of DR-IL-18 was additionally assessed in the immunogenic MC38 colorectal tumor model. A dose-finding study was first performed, administering saline, WT IL-18 (1 mg/kg twice weekly), or a range of DR-IL-18 doses from 0.01 mg/kg, 0.1 mg/kg, or 1 mg/kg twice weekly. As seen in FIG. 16, WT IL-18 had no effect on tumor growth, whereas DR-IL-18 (mCS2) showed dose-dependent efficacy, slowing tumor growth at 0.1 mg/kg and producing tumor regression at 1 mg/kg. The cohorts were then expanded and potential synergism with immune checkpoint inhibition was assessed. Again, WT IL-1S had no effect as a monotherapy and showed no enhancement of anti-PD1 efficacy. By contrast, DR-IL-18 showed robust monotherapeutic activity commensurate with or superior to anti-PD1, and the two therapies given together showed exceptional synergism, producing complete regression in all treated mice (FIG. 17).

Figure 18A:
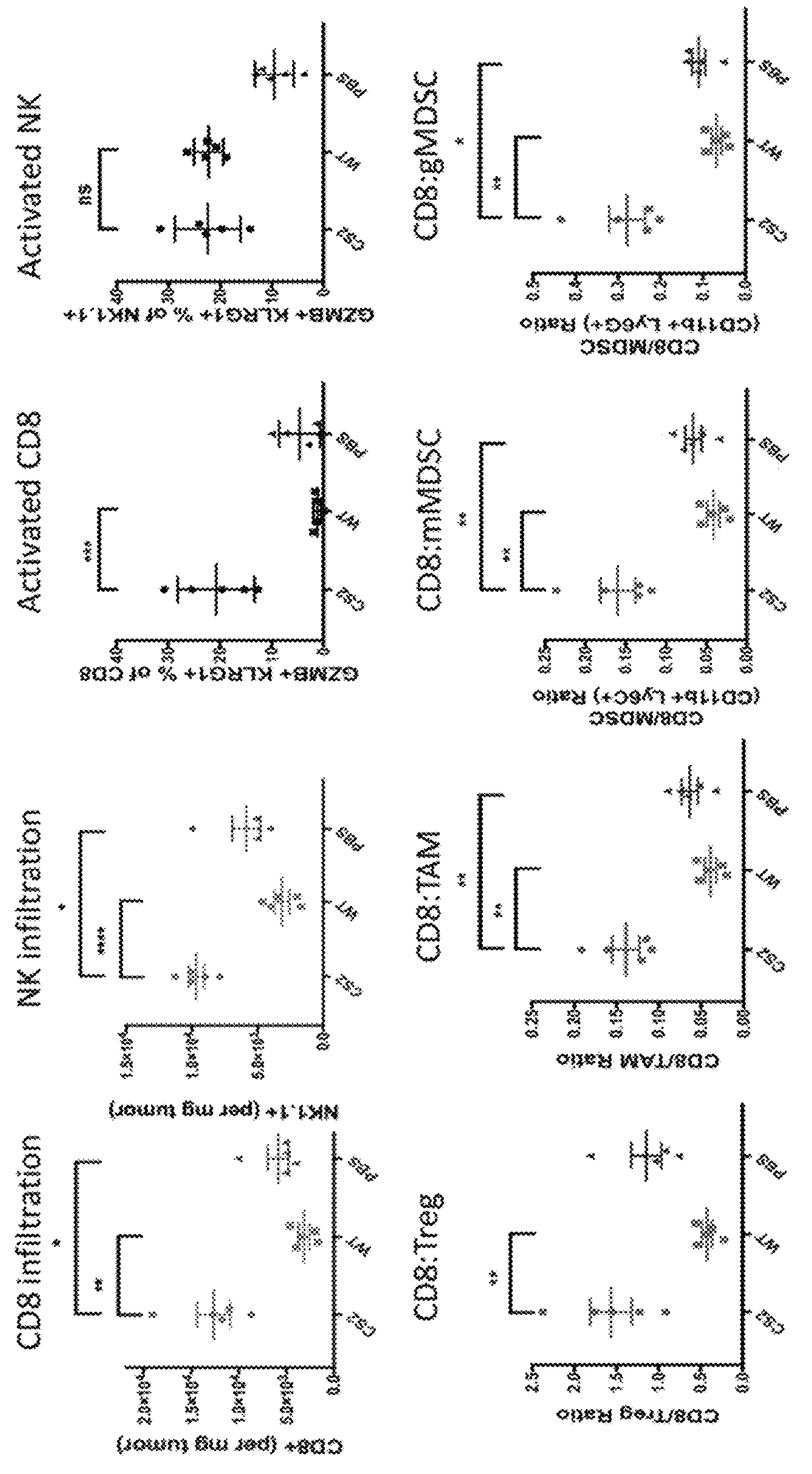
FIG. 18A and FIG. 18B depict results from example experiments that investigate the anti-tumor mechanism of DR-IL-18 in mice bearing MC38 tumors.
Figure 18B:
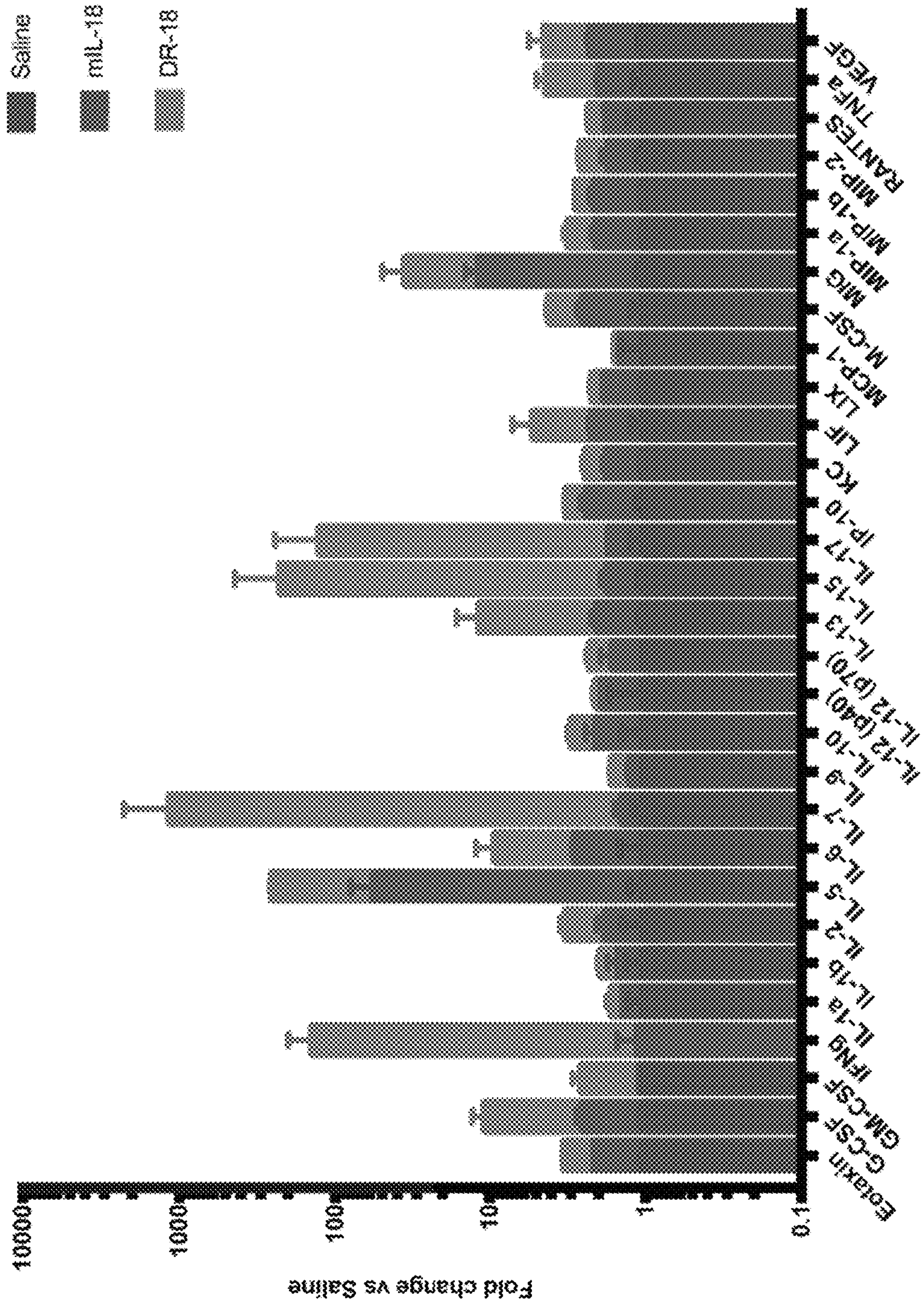

To further characterize the mechanism of DR-IL-18, flow cytometric studies were performed on the immune infiltrate of MC38 tumors from mice treated with saline, WT IL-18, or DR-IL-18 (mCS2). Relative to saline or WT IL-18, DR-IL-18 treatment increased CD8 and NK cell infiltration per mg of tumor and additionally resulting in upregulation of activation markers of effector cells such as granzyme B and KLRG1 (FIG. 18A, top row). Unlike other cytokine therapies such as IL-2 or IL-15, DR-IL-18 does not increase the CD8:Treg ratio within tumors compared to saline treatment. However, DR-IL-18 treatment leads to a more favorable tumor immune microenvironment, by increasing the ratio of CD8 cells to tumor associated macrophages (TAMs), and monocytic and granulocyte myeloids derived suppressor cells (MDSCs). The secondary cytokine release profile was also measured from serum of the same mice using a Luminex assay. As seen in FIG. 18B, DR-IL-18 treatment increased systemic levels of Interferon-gamma, IL-7, and IL-15 by over 100-fold relative to WT IL-18 treatment. Taken in aggregate, these results indicate that DR-IL-18 produces anti-tumor efficacy through a unique mechanism of action distinct from IL-2, IL-15, or WT IL-18 treatment.

Some of the secondary cytokines induced by DR-IL-18 therapy would be predicted to potentially contribute to toxicity and/or decreased effectiveness. For instance, IL-17 which is upregulated>100-fold by DR-IL-18 contributes to colitis and psoriasis and additionally stimulates granulocytes that can become immunosuppressive myeloid derived suppressor cells. IL-5 and IL-13 are type 2 cytokines also upregulated by DR-IL-18 and could contribute to allergy, exacerbation of asthma, or anaphylaxis. Th2 T cells do not contribute to immunotherapeutics responses and may promote immunosuppressive Treg development. As such, in certain instances the effectiveness and safety of DR-IL-18 could be enhanced by selective inhibition of undesired secondary cytokines such as IL-17, IL-5, and IL-13, for instance by a neutralizing antibody.

Figure 19B:
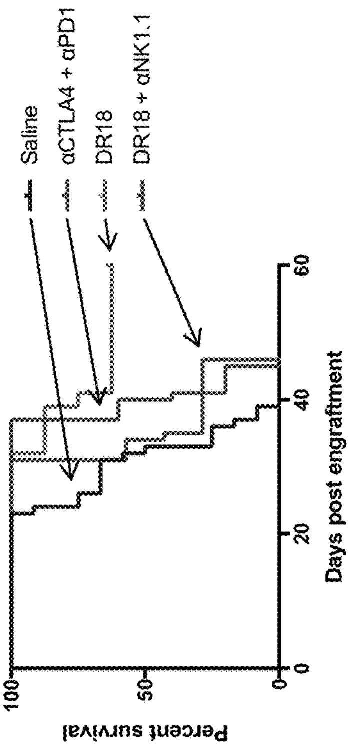
FIG. 19A through FIG. 19C depicts results from example experiments demonstrating the capability of DR-IL-18 to effectively treat tumors that are refractory to immune checkpoint inhibitors through loss of surface MHC class I expression.
Figure 19A:
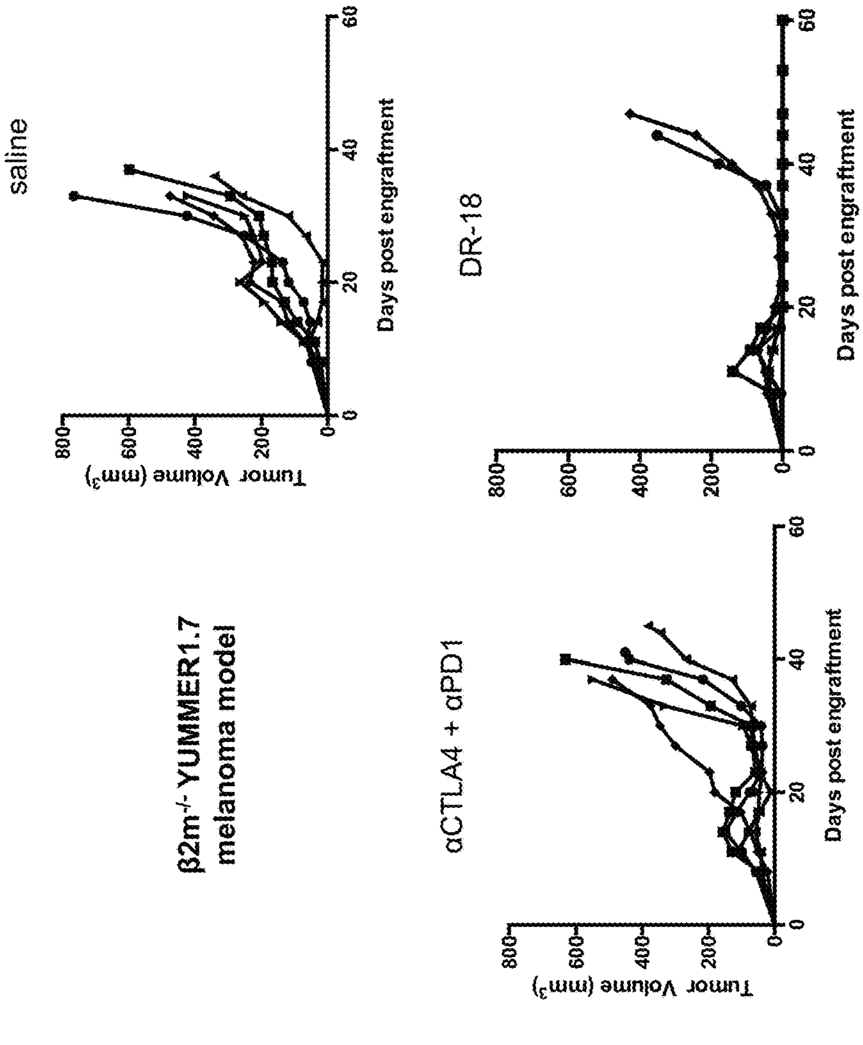
Figure 19C:
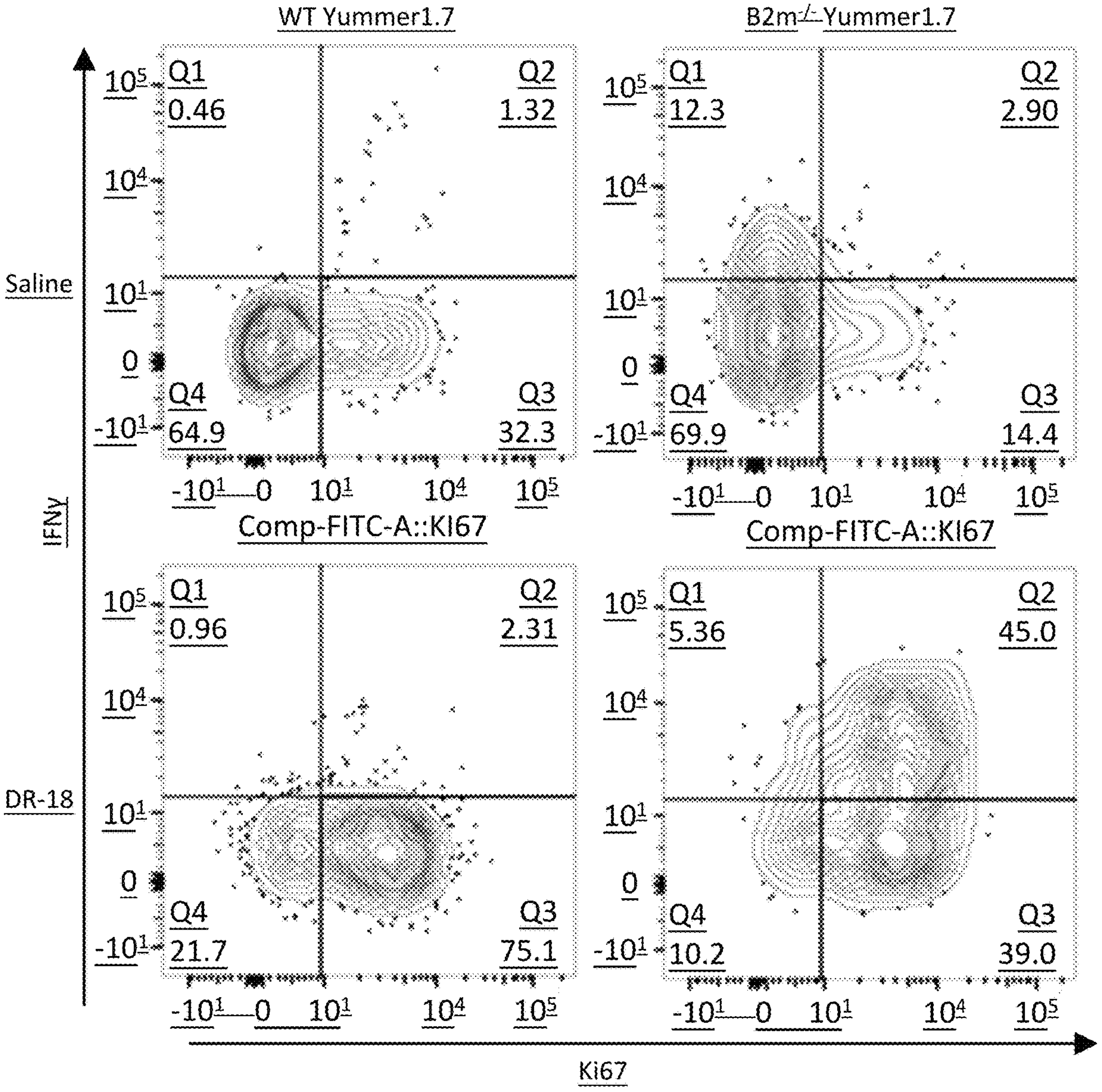

Many tumors are resistant to immune checkpoint inhibition, either at initial presentation (primary resistance) or after an initial response to treatment (secondary resistance). The most prevalent cause of resistance of checkpoint inhibitors is loss of antigen presentation through MHC class I. Loss of surface MHC class I is classically associated with NK-cell mediated cytolysis, however, NK cells can become exhausted within MHC I deficient tumors. As NK cells express the IL-18R and our previous results in MC38 indicated that NK cells are expanded and activated by DR-IL-18, we thus tested whether DR-IL-18 could stimulate NK cell attack against MHC deficient tumors. We used CRISPR/cas9 to knockout B2m in the Yummer1.7 cell line and found that implanted B2m-deficient YUMMER1.7 tumors were refractory to even combined treatment with both anti-CTLA4 and anti-PD1 (FIG. 19A and FIG. 19B), a combination that routinely cures close to 100% of parental Yummer1.7 tumors. However, single-agent treatment with DR-IL-18 (mCS2) cured 60% of B2m-deficient Yummer1.7 tumors in an NK-cell dependent fashion, as depletion with anti-NK1.1 abrogated the effect (FIG. 19A and FIG. 19B). Experiments were conducted to understand the effect that DR-IL-18 had on intratumoral NK cells in the setting of an MHC class I deficient tumor, Immunophenotyping studies were performed with flow cytometry on B2m-deficient Yummer.17 tumors from mice treated with saline or DR-IL-18. 24 hours after the 3rd dose of treatment, the mice were sacrificed, tumors were dissociated, and the cell suspension was treated with PMA/ionomycin for four hours. The proliferative index and functional capacity of the NK cells were then analyzed by intracellular flow cytometry with Ki67 and Interferon-gamma. As seen in FIG. 19C, NK cells from saline-treated B2m-deficient Yummer1.7 tumors had scant Interferon-gamma production and Ki67 levels, indicating an exhausted phenotype, By contrast, NK cells from tumors treated with DR-IL-18 had robust Interferon-gamma production and Ki67 levels, with the majority of NK cells being positive for both markers. These results thus establish that DR-IL-18 is effective in the treatment of MHC class I deficient tumors that are refractory to immune checkpoint blockade in an NK cell-dependent manner.

These results establish DR-IL-18 as a highly promising tumor immunotherapeutic, and provide strong evidence that IL-18BP greatly limits the effectiveness of IL-18 therapy, given the greatly improved activity of the mCS2 DR-IL-18 variant. From these results, it is predicted that other strategies, such as blocking IL-18BP with an antibody, small protein, and/or small molecule could augment IL-18 therapy and other immunotherapeutic regimens.

Efforts were undertaken to engineer an IL-18BP antagonist by creating a "decoy-to-the-decoy" (D2D), or IL-18 variants that specifically bind IL-18BP, but do not bind IL-18Rα and thus do not signal. The potential advantage of such an agent is that it would serve to neutralize IL-18BP and enhance the activity of endogenous IL-18, as opposed to driving IL-18R signaling systemically. IL-18 was thus randomized at contact positions for IL-18Rα (FIG. 20A) and a yeast-displayed library was prepared as described previously for human and mouse DR-IL-18. The resulting library of $3.9\times10^8$ transformants was selected for 3 rounds as indicated in (FIG. 20B), selecting for retained IL-18BP binding, while counterselecting against IL-18Rα. As seen in (FIG. 20C), each round of selection conferred enrichment for binding to IL-18BP (human and mouse), but without acquisition of IL-18Rα binding. 96 clones were sequenced, yielding 31 unique sequences, from which three consensus sequences hD2D-CS1, hD2D-CS2, and hD2D-CS3 were derived (FIG. 21). Biophysical characterization of the resulting clones indicated that they showed similar binding isotherms to IL-18BP as WT IL-18 (FIG. 22A), but with greatly decreased/absent binding to IL-18Rα (FIG. 22B). These data are summarized in (FIG. 22C). An identical selection process was performed for murine IL-18, creating a library of $2.0\times10^8$ transformants, which we selected to obtain 51 unique sequences (summarized in FIG. 23).

EXAMPLE 2

Binding Affinity Measurements of Second Generation Variants

Figure 24:
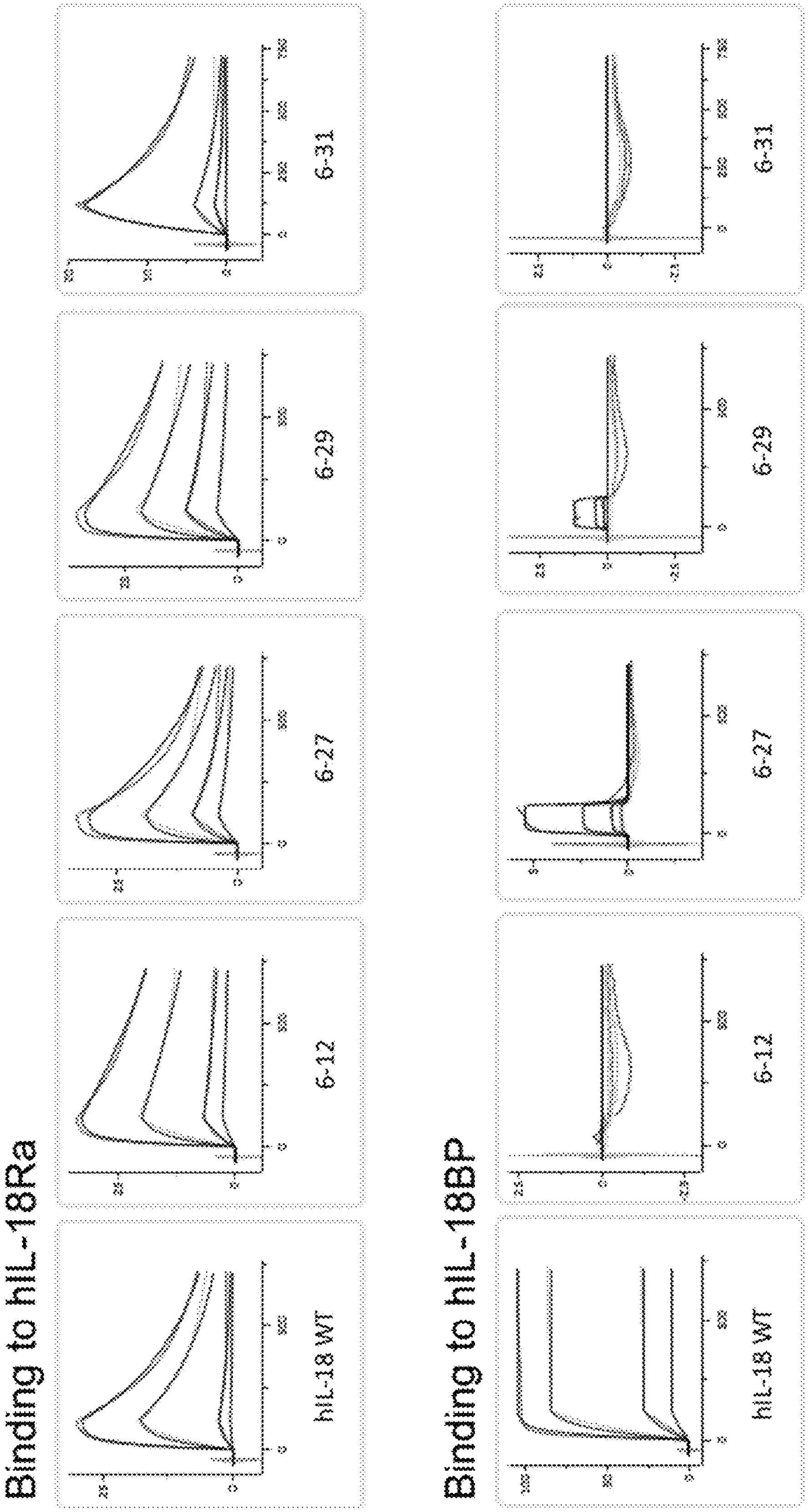
FIG. 24 depicts results from biophysical affinity measurements (sensorgrams) of the second-generation DR-IL-18 variants for binding to IL-18Rα and IL-18BP using Surface Plasmon Resonance (SPR). Top row: representative sensorgrams of the indicated IL-18 variants (soluble analytes) for hIL-18Ra (immobilized ligand). Bottom row: representative sensorgrams of the indicated IL-18 variants for human (hIL-18BP). The x axis is time in seconds and the y axis is Response Units (RU). The curves are the observed data over time for different concentrations (2-fold dilutions starting at 1 nM), superimposed with curves of best fit assuming a 1:1 langmuir binding model.

Surface Plasmon Resonance (SPR) was used to perform biophysical affinity measurements of second generation DR-IL-18 variants (binding to IL-18R vs IL-18BP). See FIG. 24 for the generated sensorgrams. Table 10 is a summary of the measured kinetics, Table 11 is a summary of the affinity measurements, and Table 12 is a general summary, including results for the dissociation constant ratios of the second generation DR-IL-18 variants.

TABLE 10

Summary of SPR data for second generation hDR-IL-18 variants (kinetics)

| Surface Ligand | Analyte | ka (1/Ms) | kd (1/s) | KD (M) Exp 2 | KD (M) Exp 1 | % Rmax |
|---|---|---|---|---|---|---|
| hIL-18Ra | hIL-18 | 5.55E+05 | 2.97E−03 | 5.36E−09 | 5.35E−09 | 32 |
| hIL-18Ra | 6-12 | 4.95E+05 | 9.10E−04 | 1.84E−09 | 2.24E−09 | 35 |
| hIL-18Ra | 6-27 | 6.31E+05 | 2.43E−03 | 3.85E−09 | 3.48E−09 | 35 |
| hIL-18Ra | 6-29 | 5.75E+05 | 1.19E−03 | 2.07E−09 | 2.65E−09 | 36 |
| hIL-18Ra | 6-31 | 2.18E+05 | 3.32E−03 | 1.52E−08 | 1.94E−08 | 19 |

TABLE 10-continued

Summary of SPR data for second generation hDR-IL-18 variants (kinetics)

| Surface Ligand | Analyte | ka (1/Ms) | kd (1/s) | KD (M) Exp 2 | KD (M) Exp 1 | % Rmax |
|---|---|---|---|---|---|---|
| hIL-18BP | hIL-18 | 5.18E+05 | 2.23E−07 | 4.30E−13 | 6.94E−13 | 48 |
| hIL-18BP | 6-12 | | Too weak to measure | | | −1 |
| hIL-18BP | 6-27 | | Too weak to measure | | | 2 |
| hIL-18BP | 6-29 | | Too weak to measure | | | 0 |
| hIL-18BP | 6-31 | | Too weak to measure | | | −1 |

TABLE 11

Summary of SPR data for second generation hDR-IL-18 variants (affinity)

| Sample | $KB_{apparent}$ hIL-18Ra (nM) | $KD_{apparent}$ hIL-18BP (nM) |
|---|---|---|
| hIL-18 | 5.4, 5.4 | <0.1 |
| 6-12 | 1.8. 2.2 | too weak |
| 6-27 | 3.9, 3.5 | too weak |
| 6-29 | 2.1, 2.7 | too weak |
| 6-31 | 15.2, 19.4 | too weak |

TABLE 12

Summary of SPR affinity measurements. Summary of the SPR affinity measurements of second generation hDR-IL-18 variants for IL-18Ra and IL-18BP. The IL-18 BP:Ra Dissociation Constant Ratio is the ratio of the KD for IL-18BP to the KD for IL-18Ra normalized to the same ratio of WT IL-18. A higher number for this ratio indicates that the IL-18 variant has an enhanced preference for binding IL-18Ra over IL-18BP compared to WT IL-18.

| Protein | SPR: $K_D$ Ra (nM) | SPR: $K_D$ BP (nM) | IL-18 BP:Ra Dissociation Constant Ratio |
|---|---|---|---|
| WT hIL-18 | 4.1* | 0.002 | 1 |
| hCS1 | 8.0* | 11.8* | 3,024 |
| hCS3 | 9.1* | 19.3* | 4,348 |
| hCS4 | 7.7* | 121* | 32,215 |
| 6-12 | 2.2 | >10,000 | >9,318,275 |
| 6-27 | 3.5 | >10,000 | >5,857,201 |
| 6-29 | 2.7 | >10,000 | >7,592,669 |
| 6-31 | 19.4 | >10,000 | >1,056,712 |
| WT mIL-18 | 0.60 | 0.0011 | 1 |
| mCS2 | 0.08 | 11,000 | >75,000,136 |
| A7, B1, C1, E8 | 0.22-1.7 | 14k-29k | 9.3m-35m |

*Average of 2 studies, k is a multiple of 1,000. m is a multiple of 1,000,000.

EXAMPLE 3

Efficacy for Cancer Treatment

Efficacy of DR-IL-18 variants was tested using multiple different cancer models, including models of colorectal tumors, breast cancer, melanoma, and WIC class I deficient tumors that are resistant to immune checkpoint inhibitors. The results show that DR-IL-18 variants with a bias to bind IL-18R and not IL-18BP can be used to treat a broad range of cancers (not limited to just those that were tested).

Figure 25A:
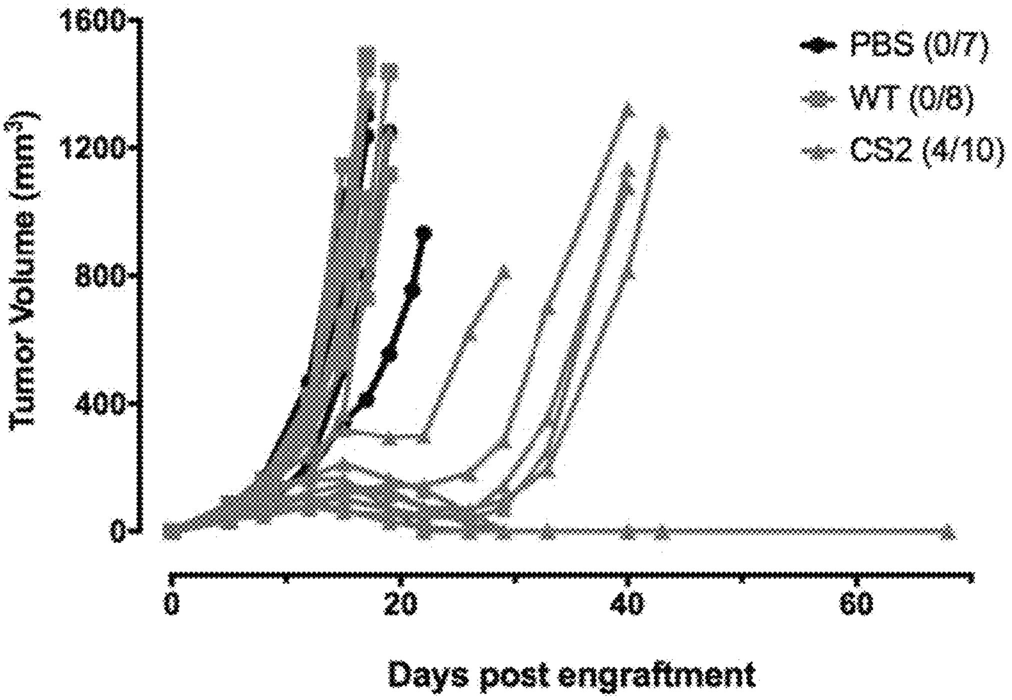
FIGS. 25A and 25B depict data demonstrating efficacy of DR-IL-18 on the CT26 colorectal tumor model. 250,000 CT26 cells were implanted subcutaneously and treatment initiated at day 7 once tumors were ~60 mm3 on average. WT IL-18 and mCS2 were dosed at 0.32 mg/kg twice weekly for a total of 5 doses. Anti-PD1 was given at 10 mg/kg at the same schedule. (A) Overlay of spider plots showing tumor growth of saline (PBS) treated animals in black lines (circles). WT IL-18 in blue lines (squares), and DR-IL-18 (mCS2) in pink (triangles). Only treatment with DR-IL-18, but not WT IL-18, resulted in tumor growth inhibition and tumor clearance in a subset of animals. (B) Survival curves for mice treated with anti-PD-1, WT IL-18, and DR-IL-18 (mCS2). Numbers of complete responses are indicated in parentheses, DR-IL-18, but not WT IL-18 resulted in prolonged survival and tumor clearance in 40% of mice, an improvement over the checkpoint inhibitor anti-PD-1.
Figure 25B:
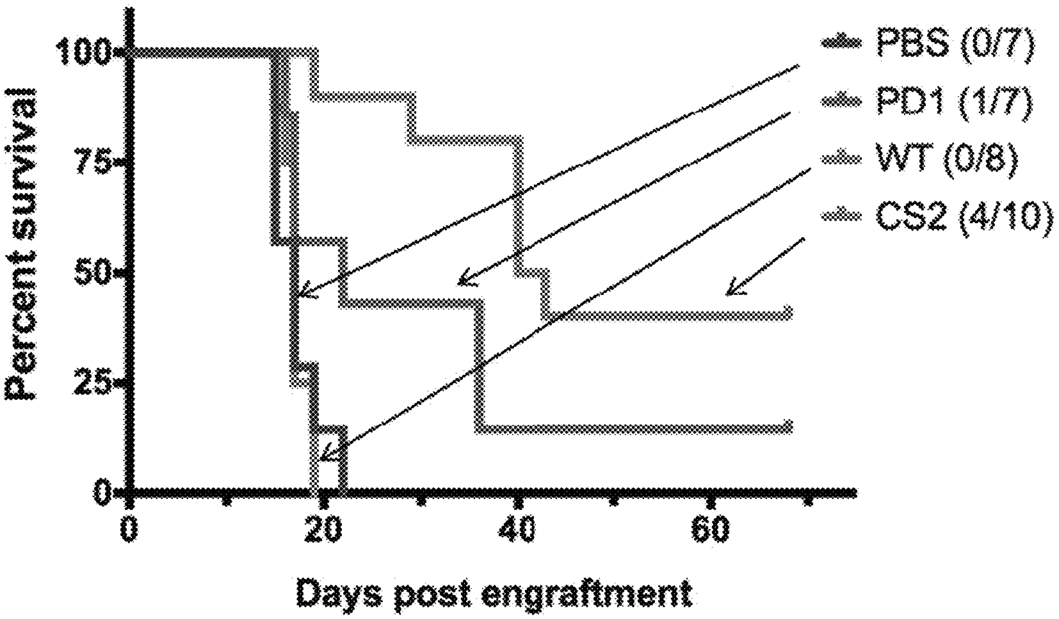

FIGS. 25A and 25B: data demonstrating efficacy of DR-IL-18 on the CT26 colorectal tumor model. 250,000 CT26 cells were implanted subcutaneously and treatment initiated at day 7 once tumors were ~60 mm3 on average. WT IL-18 and mCS2 were dosed at 0.32 mg/kg twice weekly for a total of 5 doses. Anti-PD1 was given at 10 mg/kg at the same schedule: (A) Overlay of spider plots showing tumor growth of saline (PBS) treated animals in black lines (circles), WT IL-18 in blue lines (squares), and DR-IL-18 (mCS2) in pink (triangles). Only treatment with DR-IL-18, but not WT IL-18, resulted in tumor growth inhibition and tumor clearance in a subset of animals. (B) Survival curves for mice treated with anti-PD-1, WT IL-18, and DR-IL-18 (mCS2). Numbers of complete responses are indicated in parentheses. DR-IL-18, but not WT IL-18 resulted in prolonged survival and tumor clearance in 40% of mice, an improvement over the checkpoint inhibitor anti-PD-1.

Figure 26A:
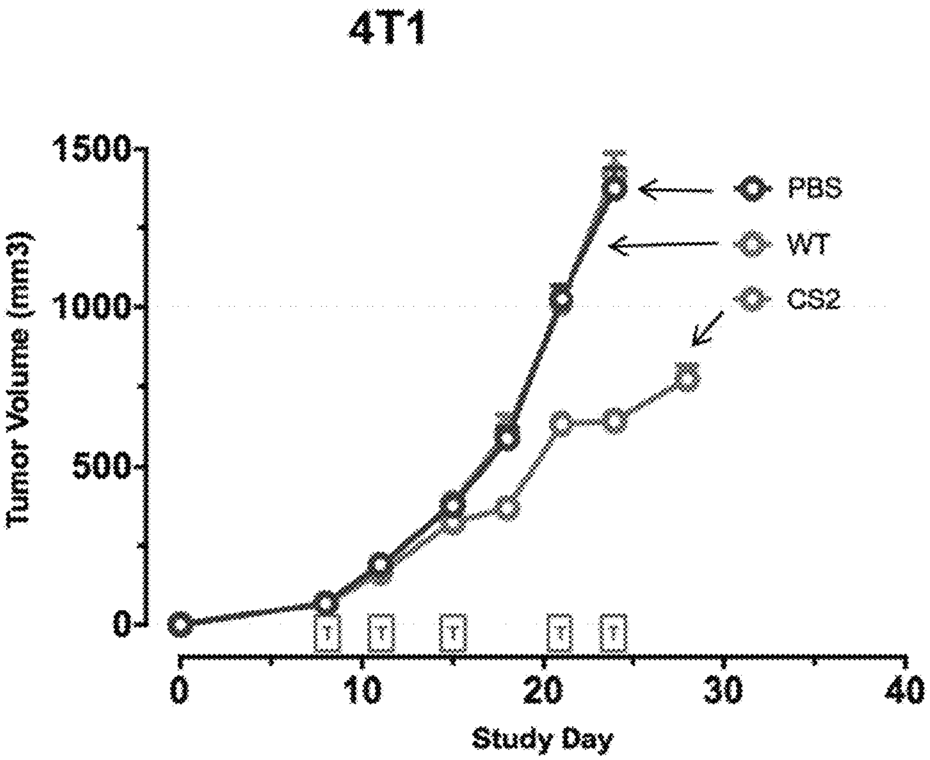
FIGS. 26A and 26B depict data demonstrating efficacy of DR-IL-18 in the 4T1 breast cancer model and B16-F10 melanoma model. (A) Tumor growth curves of 4T1 tumors engrafted into BALB/C mice after treatment with saline (PBS; black), WT IL-18 (blue), or the DR-IL-18 variant CS2 (pink). (B) Tumor growth curves of B16-F10 tumors engrafted into C57BL/6 mice after treatment with saline (PBS; black), WT IL-18 (blue), or the DR-IL-18 variant CS2 (pink). In both models, only DR-IL-18, but not WT IL-18 resulted in tumor growth inhibition. Treatments were administered after tumors exceeded an average volume 50 $mm^3$ as indicated by the boxes marked with "t".
Figure 26B:
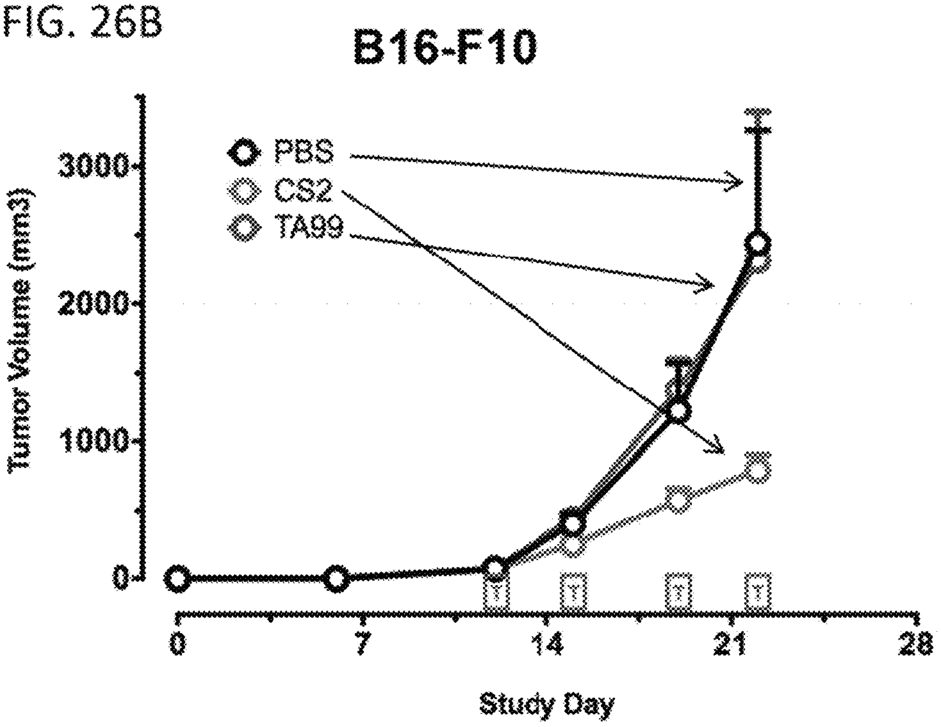

FIGS. 26A and 26B: data demonstrating efficacy of DR-IL-18 in the 4T1 breast cancer model and B16-F10 melanoma model. (A) Tumor growth curves of 4T1 tumors engrafted into BALB/C mice after treatment with saline (PBS; black), WT IL-18 (blue), or the DR-IL-18 variant CS2 (pink). (B) Tumor growth curves of B16-F10 tumors engrafted into C57BL/6 mice after treatment with saline (PBS; black), WT IL-18 (blue), or the DR-IL-18 variant CS2 (pink). In both models, only DR-IL-18, but not WT IL-18 resulted in tumor growth inhibition. Treatments were administered after tumors exceeded an average volume 50 $mm^3$ as indicated by the boxes marked with "t".

Figure 27A:
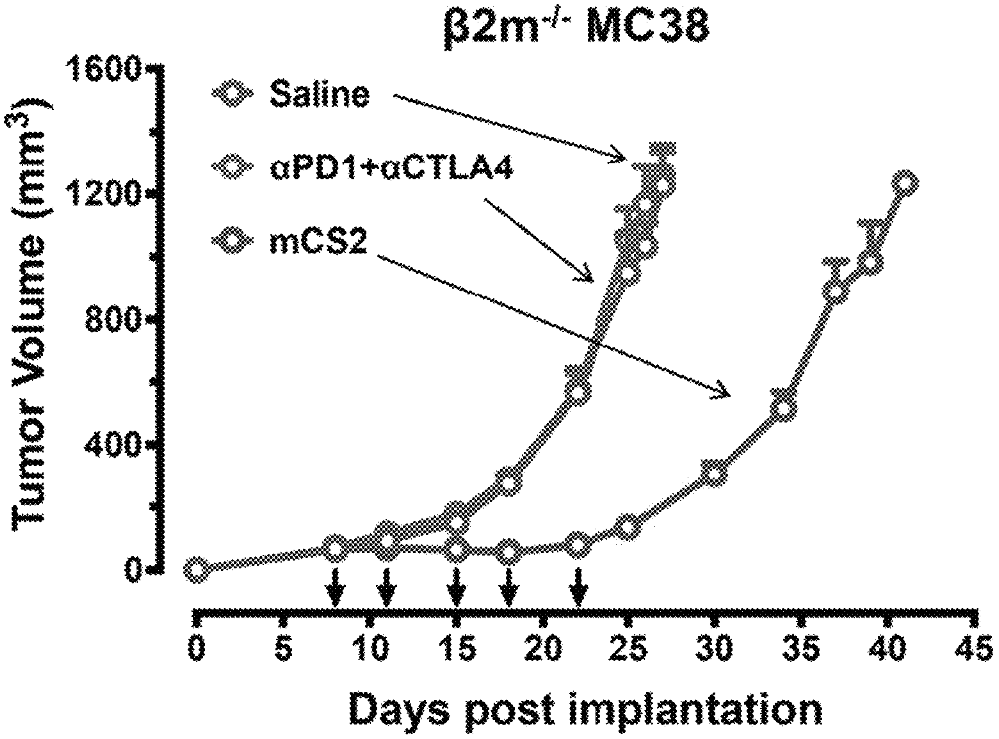
FIGS. 27A and 27B depict data that extend the data of FIG. 19A through 19C. Depicted is data demonstrating efficacy of DR-IL-18 in the treatment of additional MEC class I deficient tumor models that are resistant to immune checkpoint inhibitors. (A) B2m deficient MC38 cells were prepared using CRISPR/Cas9 mediated deletion as described for B2m deficient MUMMER cells. B2m−/− MC38 cells were implanted subcutaneously and treatment initiated at day 7 once tumors were ~65 mm3 on average. mCS2 was dosed at 0.32 mg/kg twice weekly for 5 doses. Anti-PD1 and anti-CTLA4 were given at 8 mg/kg at the same schedule. (B) RMA/S is a variant of the RMA lymphoma line that contains a spontaneous mutation in Tapasin. The result is a defect in antigen loading and therefore decreased MHC class I surface expression. It is congenic to C57BL/6 and refractory to immune checkpoint inhibitors. Mice were implanted with 1,000,000 RMA/S cells subcutaneously and treatment initiated at day 7. mCS2 was dosed at 0.32 mg/kg twice weekly. Anti-PD1 was given at 8 mg/kg at the same schedule. In both studies, only treatment with the DR-18 variant mnCS2 exhibited anti-tumor efficacy in the form of tumor growth inhibition ($B2m^{-/-}$ MC38) or tumor clearance (RMA/S).
Figure 27B:
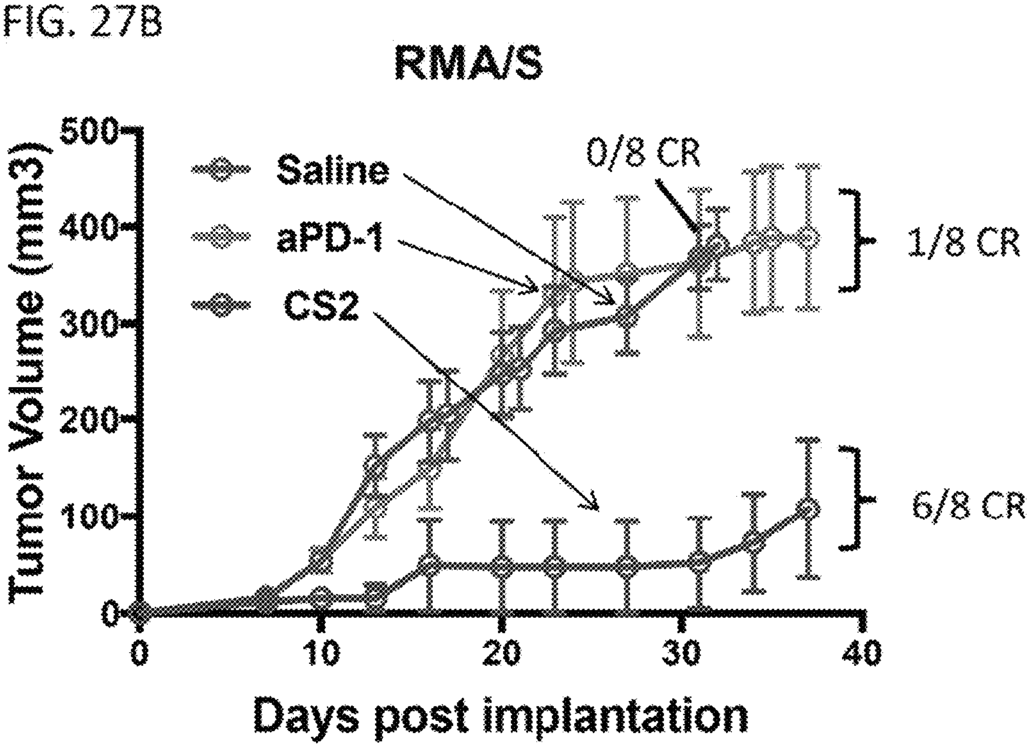

FIGS. 27A and 27B: These data extend those of FIG. 19A through 19C. Depicted is data demonstrating efficacy of DR-IL-18 in the treatment of additional MEC class I deficient tumor models that are resistant to immune checkpoint inhibitors: (A) B2m deficient MC38 cells were prepared using CRISPR/Cas9 mediated deletion as described for B2m deficient YUMMER cells. B2m−/−MC38 cells were implanted subcutaneously and treatment initiated at day 7 once tumors were ~65 mm3 on average. mCS2 was dosed at 0.32 mg/kg twice weekly for 5 doses. Anti-PD1 and anti-CTLA4 were given at 8 mg/kg at the same schedule. (B) RMA/S is a variant of the RMA lymphoma line that contains a spontaneous mutation in Tapasin. The result is a defect in antigen loading and therefore decreased MHC class I surface expression. It is congenic to C57BL/6 and refractory to immune checkpoint inhibitors. Mice were implanted with 1,000,000 RMA/S cells subcutaneously and treatment initiated at day 7. mCS2 was dosed at 0.32 mg/kg twice weekly. Anti-PD1 was given at 8 mg/kg at the same schedule.

EXAMPLE 4

Combination Therapy

Figure 28:
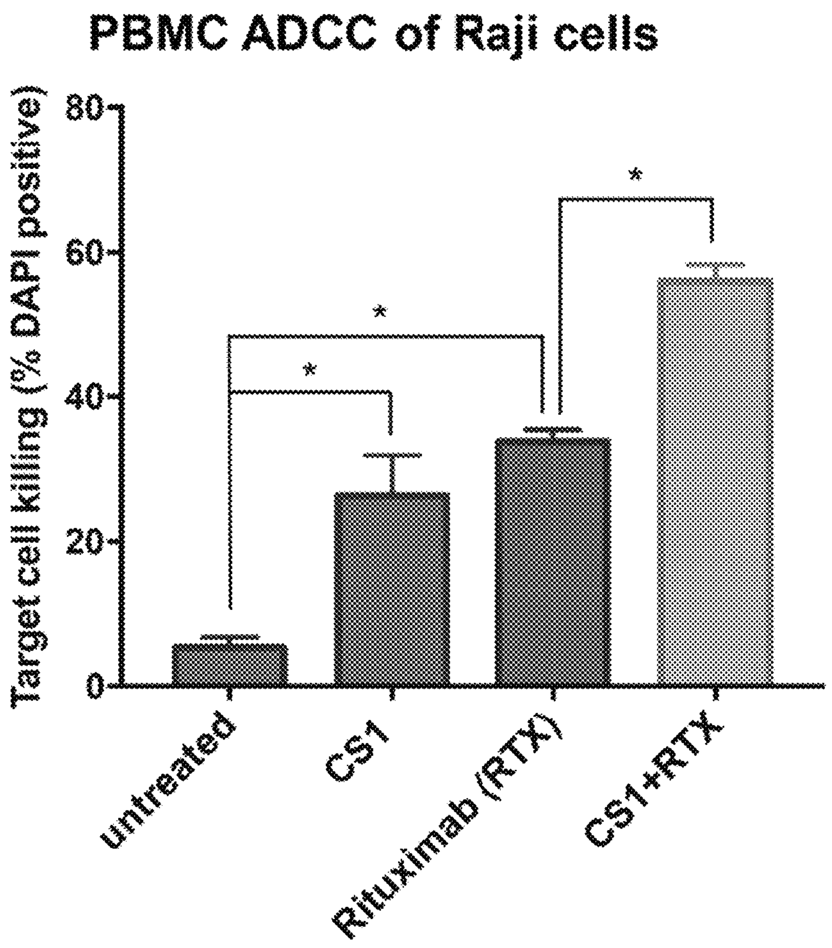
FIG. 28 depicts data demonstrating efficacy of DR-IL-18 to enhance anti-tumor antibody-dependent cell mediated cytotoxicity (ADCC). Ex viva cytotoxicity studies used CFSE labeled Raji (B cell lymphoma) cells and isolated human peripheral blood mononuclear cells (PBMCs). PBMCs and labeled Raji cells were incubated together at an effector:target (E:T) ratio of 1:10 for 25 hours. The human DR-IL-18 variant hCS-1 (1 uM), rituximab (10 ug/mL), or the combination of both agents were applied to the samples as indicated. Cytotoxicity was measured by flow cytometry and calculated as the fraction of CFSE cells that became DAPI positive. DR-18 stimulated significant tumor cell killing as a single agent and significantly enhanced the killing by the therapeutic antibody rituximab. * $p<0.05$ by two-way ANOVA with Tukey's correction for multiple comparisons.

FIG. 28: data demonstrating efficacy of DR-IL-18 variants to enhance anti-tumor antibody-dependent cell mediated cytotoxicity (ADCC) (supporting combination therapy with opsonizing agents such as tumor-targeting antibodies). Ex vivo cytotoxicity studies used CFSE labeled Raji (B cell lymphoma) cells and isolated human peripheral blood mononuclear cells (PBMCs). PBMCs and labeled Raji cells were incubated together at an effector:target (E:T) ratio of 1:10 for 25 hours. The human DR-IL-18 variant hCS-1 (1 uM), rituximab (10 ug/mL), or the combination of both agents were applied to the samples as indicated. Cytotoxicity was measured by flow cytometry and calculated as the fraction of CFSE cells that became DAPI positive. * $p<0.05$ by two-way ANOVA with Tukey's correction for multiple comparisons.

EXAMPLE 5

Efficacy Against Viral Infections

Figure 29A:
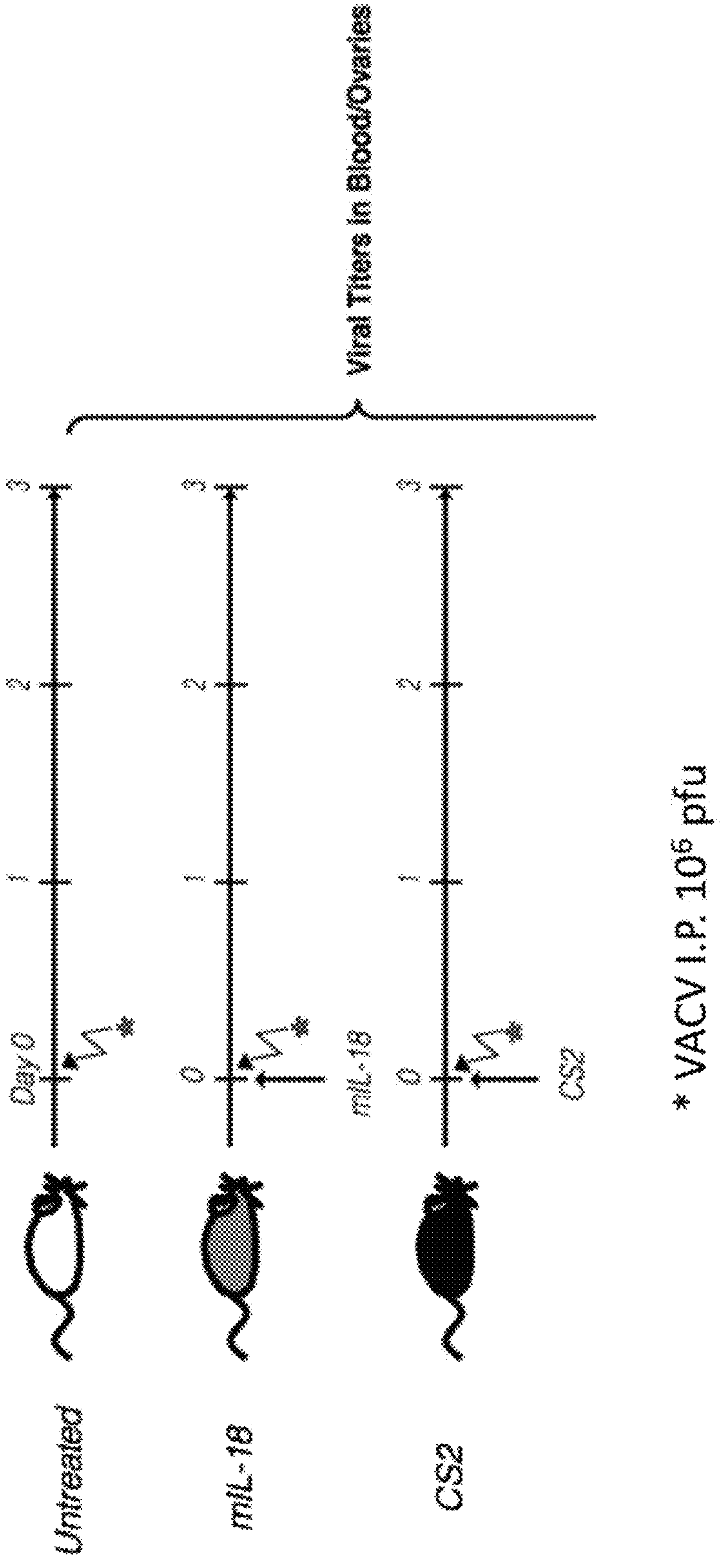
FIGS. 29A and 29B depict data demonstrating anti-viral efficacy of DR-18 variant mCS2 for the treatment viral infections (e.g., in this case in the treatment of systemic vaccinia virus infection). (A) Experimental design scheme.
Figure 29B:
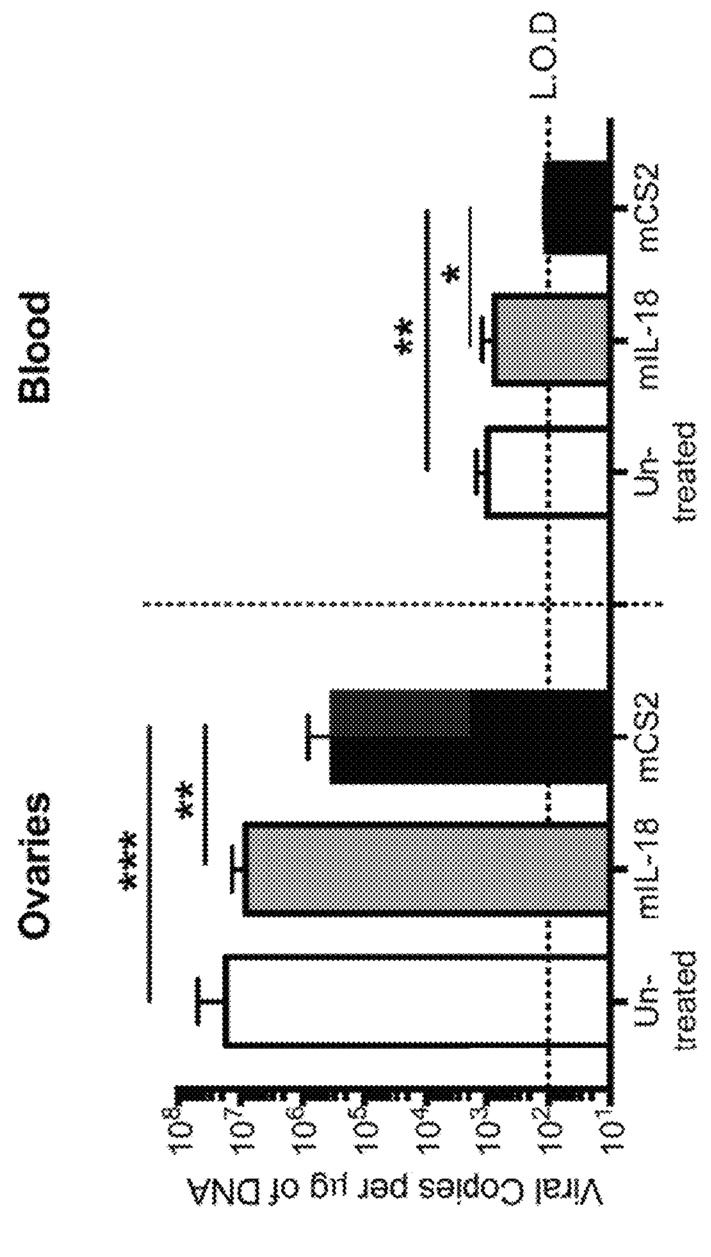

FIGS. 29A and 29B: data demonstrating anti-viral efficacy of DR-18 variants for the treatment of infection disease (e.g., for viral infections, e.g., in this illustrative example, mCS2 was used for treatment of systemic vaccinia virus infection). (A) Experimental design scheme. CS7BL/6 mice were infected with $10^6$ PFU of Vaccinia virus (VACV) intraperitoneally (IP) and administered 1 mg/kg WT mIL-18 or mCS2 IP. Mice were sacrificed and viral titers were measured in the blood and ovaries by RT-PCR on day 3 post-infection. (B) Quantification of VACV viral copies in ovaries and blood of treated mice at day 3 post infection. Treatment with CS2 showed a significant reduction of viral titers, whereas WT IL-18 was not effective. * $p<0.05$,  $p<0.01$, * $p<0.001$.

EXAMPLE 6

Second Generation Human DR-IL-18 Variants

FIG. 30A depicts data demonstrating that the second generation human DR-IL-18 variants are active. (FIG. 30A) WT IL-18 and h6-12, h6-27, h6-29, and h6-31 stimulate IL-18 HEK-Blue reporter cells. h6-12, h6-27, and h6-29 show enhanced potency compared to WT hIL-18, whereas 116-31 has equivalent potency as WT hIL-18. The data demonstrate, therefore, that all tested second generation human DR-IL-18 variants actively signal through IL-18R.

EXAMPLE 7

Making IL-18 Mimics

The primary amino acid sequence of a DR IL-18 variant polypeptide (SEQ ID NO: 90) is used for defining a structure that is fed into a memetic design protocol that (i) detects core secondary structure elements that compose the target template, and (ii) produces resulting de novo mimetic backbones. For example, each of the core secondary structure elements are idealized by reconstruction using loops from a clustered database of highly ideal fragments. Solutions for pairs of connected secondary structures are combinatorially recombined to produce fully connected backbones. Information on hotspots, compatible built-fragment amino acids, and layers is used to facilitate flexible backbone design and filtering. A de novo, synthetic amino acid sequence that can fold into a DR IL-18 mimic once produced is thereby generated. A protein having the generated amino acid sequence is produced via in vitro synthesis or via generation of a codon-optimized nucleic acid sequence (DNA or RNA) that encodes the IL-18 mimic (and the nucleic acid is transcribed and/or translated in vitro or is introduced into a cell for production of the IL-18 mimic).

The primary amino acid sequence of a D2D IL-18 variant polypeptide (SEQ ID NO: 124) is used for defining a structure that is fed into a memetic design protocol that (i) detects core secondary structure elements that compose the target template, and (ii) produces resulting de novo mimetic backbones. For example, each of the core secondary structure elements are idealized by reconstruction using loops from a clustered database of highly ideal fragments. Solutions for pairs of connected secondary structures are combinatorially recombined to produce fully connected backbones. Information on hotspots, compatible built-fragment amino acids, and layers is used to facilitate flexible backbone design and filtering. A de novo, synthetic amino acid sequence that can fold into a DR IL-18 mimic once produced is thereby generated. A protein having the generated amino acid sequence is produced via in vitro synthesis or via generation of a codon-optimized nucleic acid sequence (DNA or RNA) that encodes the IL-18 mimic (and the nucleic acid is transcribed and/or translated in vitro or is introduced into a cell for production of the IL-18 mimic).

Wild-type IL-18 amino acid sequences
HUMAN Interleukin-18 (mature form)
(SEQ ID NO: 30)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNED

MOUSE Interleukin-18 (mature form)
(SEQ ID NO: 31)
NFGRLHCTTAVIRNINDQVLFVDKRQPVFEDMTDIDQSASEPQTRLIIY

MYKDSEVRGLAVTLSVKDSKMSTLSCKNKIISFEEMDPPENIDDIQSDL

-continued

IFFQKRVPGHNKMEFESSLYEGHFLACQKEDDAFKLILKKKDENGDKSV

MFTLTNLHQS

Q14116|IL18_HUMAN Interleukin-18 (uncleaved precursor)
(SEQ ID NO: 32)
MAAEPVEDNCINFVAMKFIDNTLYFIAEDDENLESDYFGKLESKLSVIR

NLNDQVLFIDQGNRPLFEDMTDSDCRDNAPRTIFIISMYKDSQPRGMAV

TISVKCEKISTLSCENKIISFKEMNPPDNIKDTKSDIIFFQRSVPGHDN

KMQFESSSYEGYFLACEKERDLFKLILKKEDELGDRSIMFTVQNED

P70380|IL18_MOUSE Interleukin-18 (uncleaved precursor)
(SEQ ID NO: 33)
MAAMSEDSCVNFKEMMFIDNTLYFIPEENGDLESDNFGRLHCTTAVIRN

INDQVLFVDKRQPVFEDMTDIDQSASEPQTRLIIYMYKDSEVRGLAVTL

SVKDSKMSTLSCKNKIISFEEMDPPENIDDIQSDLIFFQKRVPGHNKME

FESSLYEGHFLACQKEDDAFKLILKKKDENGDKSVMFTLTNLHQS

| Generation 1 Human Interleukin-18 Decoy-Resistant variants amino acid sequences | |
|---|---|
| hCS1 | YFGKLESKLSVIRNLNDQVLFIDQGNRPLFEDMTDSDCRDNAPRTIFIIS TYKDSQPRGKAVTISVKCEKISTLSCENKIISFKEMNPPDNIKDTKSDIIF FQRDVPGHKHKMQFESSSYEGYFLACEKERDLFKLILKKEDELGDRSI MFTVQNED (SEQ ID NO: 34) |
| hCS2 | YFGKLESKLSVIRNLNDQVLFIDQGNRPLFEDMTDSDCRDNAPRTIFIIS TYKDKQPRAKAVTISVKCEKISTLSCENKIISFKEMNPPDNIKDTKSDIIF FQRDVPGHKHKMQFESSSYEGYFLACEKERDLFKLILKKEDELGDRSI MFTIQNED (SEQ ID NO: 35) |
| hCS3 | RFGKLESKLSVIRNLNDQVLFIDQGNRPLFEDMTDSDCRDNAPRTIFIIS TYKDSQPRGKAVTISVKCEKISTLSCENKIISFKEMNPPDNIKDTKSDIIF FQRDVPGHKHKMQFESSSYEGYFLACEKERDLFKLILKKEDELGDRSI MFTVQNED (SEQ ID NO: 36) |
| hCS4 | RFGKLESKLSVIRNLNDQVLFIDQGNRPLFEDMTDSDCRDNAPRTIFIIS TYRDSQPRGKAVTISVKCEKISTLSCENKIISFKEMNPPDNIKDTKSDIIF FQRNVPGHKYKMQFESSSYEGYFLACEKERDLFKLILKKEDELGDRSI MFTVQNED (SEQ ID NO: 37) |
| hC4 | YFGKLESQLSVIRNLNDQVLFIDQGNRPLFEDMTDSDCRDNAPRTIFIIS TYKDKQPRTKAVTISVKCEKISTLSCENKIISFKEMNPPDNIKDTKSDIIF FQRRVPGHHNKMQFESSSYEGYFLACEKERDLFKLILKKEDELGDRSI MFTVQKED (SEQ ID NO: 38) |
| hA8 | YFGKLESRLSVIRNLNDQVLFIDQGNRPLFEDMTDSDCRDNAPRTIFIIS KYKDKQPRAQAVTISVKCEKISTLSCENKIISFKEMNPPDNIKDTKSDIIF FQRDVPGHKHKMQFESSSYEGYFLACEKERDLFKLILKKEDELGDRSI MFTIQNED (SEQ ID NO: 39) |
| hD6 | YFGKLESRLSVIRNLNDQYLFIDQGNRPLFEDMTDSDCRDNAPRTIFIIS DYKDKQPRAXAVTISVKCEKISTLSCENKIISFKEMNPPDNIKDTKSDIIF FQRDVPGHKHKMQFESSSYEGYFLACEKERDLFKLILKKEDELGDRSI MFTIQNED (SEQ ID NO: 40) |
| hH12 | YFGKHESKLSVIRNLNDQVLFIDQGNRPLFEDMTDSDCRDNAPRTIFIIS TYRDSQPRGKAVTISVKCEKISTLSCENKIISFKEMNPPDNIKDTKSDIIF FQRDVPGHNNKMQFESSSYEGYFLACEKERDLFKLILKKEDELGDRSI MFTTQNED (SEQ ID NO: 41) |
| hB11 | YFGKIESKLSVIRNLNDQVLFIDQGNRPLFEDMTDSDCRDNAPRTIFIIS KYKDKQPRAQAVTISVKCEKISTLSCENKIISFKEMNPPDNIKDTKSDIIF FQRKVPGHQHKMQFESSSYEGYFLACEKERDLFKLILKKEDELGDRSI MFTVQKED (SEQ ID NO: 42) |
| hC3 | YFGKIESKLSVIRNLNDQVLFIDQGNRPLFEDMTDSDCRDNAPRTIFIIST YKDRQPRGKAVTISVKCEKISTLSCENKIISFKEMNPPDNIKDTKSDIIFF ERDVPGHHHKMQFESSSYEGYFLACEKERDLFKLILKKEDELGDRSIM FTIQNED (SEQ ID NO: 43) |

-continued

| Generation 1 Human Interleukin-18 Decoy-Resistant variants amino acid sequences | |
|---|---|
| hC2 | YFGKIESKLSVIRNLNDQVLFIDQGNRPLFEDMTDSDCRDNAPRTIFIIST YKDKQPRGKAVTISVKCEKISTLSCENKIISFKEMNPPDNIKDTKSDIIFF QRDVPGHKHKMQFESSSYEGYFLACEKERDLFKLILKKEDELGDRSIM FTTQHED (SEQ ID NO: 44) |
| hG10 | YFGKIESKLSVIRNLNDQVLFIDQGNRPLFEDMTDSDCRDNAPRTIFIIST YKDKQPRAKAVTISVKCEKISTLSCENKIISFKEMNPPDNIKDTKSDIIFF QRRVPGHHHKMQFESSSYEGYFLACEKERDLFKLILKKEDELGDRSIM FTIQKED (SEQ ID NO: 45) |
| hG1 | YFGKIESRLSVIRNLNDQVLFIDQGNRPLFEDMTDSDCRDNAPRTIFIIST YKDKQPRGKAVTISVKCEKISTLSCENKIISFKEMNPPDNIKDTKSDIIFF QRDVPGHDYKMQFESSSYEGYFLACEKERDLFKLILKKEDELGDRSIM FTIQKED (SEQ ID NO: 46) |
| hF1 | YFGKYESRLSVIRNLNDQVLFIDQGNRPLFEDMTDSDCRDNAPRTIFIIS TYRDSQPRGKAVTISVKCEKISTLSCENKIISFKEMNPPDNIKDTKSDIIF FQRDVPGHEHKMQFESSSYEGYFLACEKERDLFKLILKKEDELGDRSI MFTVQKED (SEQ ID NO: 47) |
| hD2 | HFGKYESKLSVIRNLNDQVLFIDQGNRPLFEDMTDSDCRDNAPRTIFIIS TYRDSQPRGKAVTISVKCEKISTLSCENKIISFKEMNPPDNIKDTKSDIIF FQRDVPGHHNKMQFESSSYEGYFLACEKERDLFKLILKKEDELGDRSI MFTVQKED (SEQ ID NO: 48) |
| hA1 | RFGKLESKLSVIRNLNDQVLFIDQGNRPLFEDMTDSDCRDNAPRTIFIIS TYRDSQPRAKAVTISVKCEKISTLSCENKIISFKEMNPPDNIKDTKSDIIF FQRDVPGHQHKMQFESSSYEGYFLACEKERDLFKLILKKEDELGDRSI MFTAQKED (SEQ ID NO: 49) |
| hB3 | RFGKLESRLSVIRNLNDQVLFIDQGNRPLFEDMTDSDCRDNAPRTIFIIS DYRDSQPRGRAVTISVKCEKISTLSCENKIISFKEMNPPDNIKDTKSDIIF FKRNVPGHKYKMQFESSSYEGYFLACEKERDLFKLILKKEDELGDRSI MFTVQHED (SEQ ID NO: 50) |
| hB4 | RFGKLESRLSVIRNLNDQVLFIDQGNRPLFEDMTDSDCRDNAPRTIFIIS NYRDSQPRGQAVTISVKCEKISTLSCENKIISFKEMNPPDNIKDTKSDIIF FKRRVPGHNHKMQFESSSYEGYFLACEKERDLFKLILKKEDELGDRSI MFTVQKED (SEQ ID NO: 51) |
| hH3 | RFGKLESRLSVIRNLNDQVLFIDQGNRPLFEDMTDSDCRDNAPRTIFIIS TYKDSQPRGKAVTISVKCEKISTLSCENKIISFKEMNPPDNIKDTKSDIIF FQRDVPGHKHKMQFESSSYEGYFLACEKERDLFKLILKKEDELGDRSI MFTVQNED (SEQ ID NO: 52) |
| hH5 | RFGKHESKLSVIRNLNDQVLFIDQGNRPLFEDMTDSDCRDNAPRTIFIIS TYRDSQPRGKAVTISVKCEKISTLSCENKIISFKEMNPPDNIKDTKSDIIF FERNVPGHKYKMQFESSSYEGYFLACEKERDLFKLILKKEDELGDRSI MFTVONED (SEQ ID NO: 53) |
| hH4 | RFGKLESRLSVIRNLNDQVLFIDQGNRPLFEDMTDSDCRDNAPRTIFIIS TYRDSQPRAKAVTISVKCEKISTLSCENKIISFKEMNPPDNIKDTKSDIIF FERDVPGHQHKMQFESSSYEGYFLACEKERDLFKLILKKEDELGDRSI MFTIQXED (SEO ID NO: 54) |
| hE1 | RFGKLESRLSVIRNLNDQVLFIDQGNRPLFEDMTDSDCRDNAPRTIFIIS TYRDSQPRTKAVTISVKCEKISTLSCENKIISFKEMNPPDNIKDTKSDIIF FQRNVPGHHDKMQFESSSYEGYFLACEKERDLFKLILKKEDELGDRSI MFTVQHED (SEQ ID NO: 55) |
| hG2 | RFGKLESRLSVIRNLNDQVLFIDQGNRPLFEDMTDSDCRDNAPRTIFIIS TYKDSQPRAKAVTISVKCEKISTLSCENKIISFKEMNPPDNIKDTKSDIIF FERDVPGHQHKMQFESSSYEGYFLACEKERDLFKLILKKEDELGDRSI MFTIQKED (SEQ ID NO: 56) |
| hB9 | RFGKHESKLSVIRNLNDQVLFIDQGNRPLFEDMTDSDCRDNAPRTIFIIS TYRDSQPRGKAVTISVKCEKISTLSCENKIISFKEMNPPDNIKDTKSDIIF FERNVPGHKYKMQFESSSYEGYFLACEKERDLFKLILKKEDELGDRSI MFTVQNED (SEQ ID NO: 57) |
| hE12 | RFGKYESKLSVIRNLNDQVLFIDQGNRPLFEDMTDSDCRDNAPRTIFIIS TYKDSQPRTKAVTISVKCEKISTLSCDNKIISFKEMNPPDNIKDTKSDIIF FQRDVPGHKHKMQFESSSYEGYFLACEKERDLFKLILKKEDELGDRSI MFTVQNED (SEQ ID NO: 58) |

-continued

| Generation 1 Human Interleukin-18 Decoy-Resistant variants amino acid sequences | |
|---|---|
| hC5 | RFGKLESRLSVIRNLNDQVLFIDQGNRPLFEDMTDSDCRDNAPRTIFIIS TYRDSQPRTKAVTISVKCEKISTLSCENKIISFKEMNPPDNIKDTKSDIIF FQRKVPGHNHKMQFESSSYEGYFLACEKERDLFKLILKKEDELGDRSI MFTVQKED (SEQ ID NO: 59) |

| Generation 2 Human Interleukin-18 Decoy-Resistant variants amino acid sequences | |
|---|---|
| 5-18 | YFGKLESKLSVIRNLNDQVLFIDQGNRPLFEDMTDSDCRDNAPRTIFIIS EYKDSELRGRAVTISVKCEKISTLSCENKIISFKEMNPPDNIKDTKSDIIF FPRAVPGHNRKVQFESSSYEGYFLACEKERDLFKLILKKEDELGDRSIM FTVQNED (SEQ ID NO: 73) |
| 5-29 | YFGKLESKLSVIRNLNDQVLFIDQGNRPLFEDMTDSDCRDNAPRTIFIIS KYKDSAGRGLAVTISVKCEKISTLSCENKIISFKEMNPPDNIKDTKSDIIF FERDVPGHSNKVQFESSSYEGYFLACEKERDLFKLILKKEDELGDRSIM FTVQNED (SEQ ID NO: 74) |
| 5-8 | YFGKLESKLSVIRNLNDQVLFIDQGNRPLFEDMTDSDCRDNAPRTIFIIS KYGDSAARGLAVTISVKCEKISTLSCENKIISFKEMNPPDNIKDTKSDIIF FQRSVPGHKRKMQFESSSYEGYFLACEKERDLFKLILKKEDELGDRSI MFTVQNED (SEQ ID NO: 75) |
| 5-6 | YFGKLESKLSVIRNLNDQVLFIDQGNRPLFEDMTDSDCRDNAPRTIFIIS KYGDSRGRGLAVTISVKCEKISTLSCENKIISFKEMNPPDNIKDTKSDIIF FERDVPGHNSKRQFESSSYEGYFLACEKERDLFKLILKKEDELGDRSIM FTVQNED (SEQ ID NO: 76) |
| 5-27 | YFGKLESKLSVIRNLNDQVLFIDQGNRPLFEDMTDSDCRDNAPRTIFIIS KYGDSVPRGLAVTISVKCEKISTLSCENKIISFKEMNPPDNIKDTKSDIIF FARAVPGHSRKTQFESSSYEGYFLACEKERDLFKLILKKEDELGDRSIM FTVQNED (SEQ ID NO: 77) |
| 5-20 | YFGKLESKLSVIRNLNDQVLFIDQGNRPLFEDMTDSDCRDNAPRTIFIIS KYSDSGARGLAVTISVKCEKISTLSCENKIISFKEMNPPDNIKDTKSDIIF FARAVPGHGRKTQFESSSYEGYFLACEKERDLFKLILKKEDELGDRSIM FTVQNED (SEQ ID NO: 78) |
| 5-2 | YFGKLESKLSVIRNLNDQVLFIDQGNRPLFEDMTDSDCRDNAPRTIFIIS KYSDSKARGMAVTISVKCEKISTLSCENKIISFKEMNPPDNIKDTKSDIIF FARDVPGHSSKRQFESSSYEGYFLACEKERDLFKLILKKEDELGDRSIM FTVQNED (SEQ ID NO: 79) |
| 5-9 | YFGKLESKLSVIRNLNDQVLFIDQGNRPLFEDMTDSDCRDNAPRTIFIIS KYSDSLARGLAVTISVKCEKISTLSCENKIISFKEMNPPDNIKDTKSDIIF FQRDVPGHSRKMQFESSSYEGYFLACEKERDLFKLILKKEDELGDRSI MFTVQNED (SEQ ID NO: 80) |
| 5-42 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF FQRNVPGHGRKMQFESSSYEGYFLACEKERDLFKLILKKEDELGDRSI MFTVQNED (SEQ ID NO: 81) |
| 5-13 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF FARSVPGHGRKTQFESSSYEGYFLACEKERDLFKLILKKEDELGDRSIM FTVQNED (SEQ ID NO: 82) |
| 5-12 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF FARDVPGHSGKRQFESSSYEGYFLACEKERDLFKLILKKEDELGDRSIM FTVQNED (SEQ ID NO: 83) |
| 5-1 | YFGKLESKLSVIRNLNDQVLFIDQGNRPLFEDMTDSDCRDNAPRTIFIIS KYTDSRPRGLAVTISVKCEKISTLSCENKIISFKEMNPPDNIKDTKSDIIF FERDVPGHSSKKQFESSSYEGYFLACEKERDLFKLILKKEDELGDRSIM FTVQNED (SEQ ID NO: 84) |
| 5-33 | YFGKLESKLSVIRNLNDQVLFIDQGNRPLFEDMTDSDCRDNAPRTIFIIS KYTDSRARGMAVTISVKCEKISTLSCENKIISFKEMNPPDNIKDTKSDIIF FERDVPGHNDKRQFESSSYEGYFLACEKERDLFKLILKKEDELGDRSIM FTVQNED (SEQ ID NO: 85) |

-continued

| Generation 2 Human Interleukin-18 Decoy-Resistant variants amino acid sequences | |
|---|---|
| 5-21 | YFGKLESKLSVIRNLNDQVLFIDQGNRPLFEDMTDSDCRDNAPRTIFIIS RYKDSGKRGLAVTISVKCEKISTLSCENKIISFKEMNPPDNIKDTKSDIIF FRRSVPGHSRKVQFESSSYEGYFLACEKERDLFKLILKKEDELGDRSIM FTVQNED (SEQ ID NO: 86) |
| 6-31 | YFGKLESKLSVIRNLNDQVLFIDQGNRPLFEDMTDSDCRDNAPRTIFIIS KYGDSGARGLAVTISVKCEKISTLSCENKIISFKEMNPPDNIKDTKSDIIF FERDVPGHSGKVQFESSSYEGYFLACEKERDLFKLILKKEDELGDRSIM FTVQNED (SEQ ID NO: 87) |
| 6-20 | YFGKLESKLSVIRNLNDQVLFIDQGNRPLFEDMTDSDCRDNAPRTIFIIS KYGDSRPRGMAVTISVKCEKISTLSCENKIISFKEMNPPDNIKDTKSDIIF FQRAVPGHNRKMQFESSSYEGYFLACEKERDLFKLILKKEDELGDRSI MFTVQNED (SEQ ID NO: 88) |
| 6-12 | YFGKLESKLSVIRNLNDQVLFIDQGNRPLFEDMTDSDCRDNAPRTIFIIS KYSDSLARGLAVTISVKCEKISTLSCENKIISFKEMNPPDNIKDTKSDIIF FQRDVPGHSRKMQFESSSYEGYFLACEKERDLFKLILKKEDELGDRSI MFTVQNED (SEQ ID NO: 89) |
| 6-27 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF FARSVPGHGRKTQFESSSYEGYFLACEKERDLFKLILKKEDELGDRSIM FTVQNED (SEQ ID NO: 90) |
| 6-29 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF FQRNVPGHGRKMQFESSSYEGYFLACEKERDLFKLILKKEDELGDRSI MFTVQNED (SEQ ID NO: 91) |
| 5-26 | YFGKLESKLSVIRNLNDQVLFIDQGNRPLFEDMTDSDCRDNAPRTIFIIS KYGDSVPRGLAVTISVKCEKISTLSCENKIISFKEMNPPDNIKDTKSDIIF FARAVPGHSRKTQFESSSYEGYFLACEKERDLFKLILKKEDELGDRSIM FTVQNED (SEQ ID NO: 191) |
| 5-17 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF FARSVPGHGRKTQFESSSYEGYFLACEKERDLFKLILKKEDELGDRSIM FTVQNED (SEQ ID NO: 192) |
| 5-41 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF FARDVPGHSGKRQFESSSYEGYFLACEKERDLFKLILKKEDELGDRSIM FTVQNED (SEQ ID NO: 193) |

| Mouse Interleukin-18 Decoy-Resistant variants amino acid sequences | |
|---|---|
| mCS1 | NFGRLHCTTAVIRNINDQVLFVDKRQPVFEDMTDIDQSASEPQTRLIIY GYADSRVRGKAVTLSVKDSKMSTLSCKNKIISFEEMDPPENIDDIQSDL IFFQKRVPGHNKMEFESSLYEGHFLACQKEDDAFKLILKKKDENGDKS VMFTLTNLHQS (SEQ ID NO: 60) |
| mCS2 | HFGRLHCTTAVIRNINDQVLFVDKRQPVFEDMTDIDQSASEPQTRLIIY AYGDSRARGKAVTLSVKDSKMSTLSCKNKIISFEEMDPPENIDDIQSDL IFFQKRVPGHNKMEFESSLYEGHFLACQKEDDAFKLILKKKDKNGDKS VMFTLTNLHQS (SEQ ID NO: 61) |
| mC1 | NFGRLHCTTAVIRNINDQVLFVDKRQPVFEDMTDIDQSASEPQTRLIIY AYVDRRLRGKAVTLSVKDSKMSTLSCKNKIISFEEMDPPENIDDIQSDL IFFQKKVPGHNKMEFESSLYEGHFLACQKEDDAFKLILKKKDENGDKS VMFTLTNLHQS (SEQ ID NO: 62) |
| mA12 | NFGRLHCTTAVIRNINDQVLFVDKRQPVFEDMTDIDQSASEPQTRLIIYS YSDKHMRGKAVTLSVKDSKMSTLSCKNKIISFEEMDPPENIDDIQSDLI FFQKLVPGHNKMEFESSLYEGHFLACQKEDDAFKLILKKKDENGDKS VMFTLTNLHQS (SEQ ID NO: 63) |
| mE8 | NFGRLHCTTAVIRNINDQVLFVDKRQPVFEDMTDIDQSASEPQTRLIIY VYTDGRRRGKAVTLSVKDSKMSTLSCKNKIISFEEMDPPENIDDIQSDL IFFQKKVPGHDKMEFESSLYEGHFLACQKEDDAFKLILKKKDENGDKS VMFTLTNLHQS (SEQ ID NO: 64) |

-continued

| Mouse Interleukin-18 Decoy-Resistant variants amino acid sequences | |
|---|---|
| mC10 | HFGRLHCTTAVIRNINDQVLFVDKRQPVFEDMTDIDQSASEPQTRLIIY AYGDSHMRGKAVTLSVKDSKMSTLSCKNKIISFEEMDPPENIDDIQSDL IFFQKQVPGHNKMEFESSLYEGHFLACQKEDDAFKLILKKKDENGDKS VMFTVTNLHQS (SEQ ID NO: 65) |
| mB7 | HFGRLHCTTAVIRNINDQVLFVDKRQPVFEDMTDIDQSASEPQTRLIIY AYGDSNAGGRAVTLSVKDSKMSTLSCKNKIISFEEMDPPENIDDIQSDL IFFQKKVPGHNKMEFESSLYEGHFLACQKEDDAFKLILKKKDENGDKS VMFTLTNLHQS (SEQ ID NO: 66) |
| mB1 | HFGRLHCTTAVIRNINDQVLFVDKRQPVFEDMTDIDQSASEPQTRLIIY GYADSDARAKAVTLSVKDSKMSTLSCKNKIISFEEMDPPENIDDIQSDL IFFQKSVPGHNKMEFESSLYEGHFLACQKEDDAFKLILKKKDENGDKS VMFTVTNLHQS (SEQ ID NO: 67) |
| mD1 | HFGRLHCTTAVIRNINDQVLFVDKRQPVFEDMTDIDQSASEPQTRLIIY GYSDRGSKGKAVTLSVKDSKMSTLSCKNKIISFEEMDPPENIDDIQSDLI FFQKQVPGHNKMEFESSLYEGHFLACQKEDDAFKLILKKKDENGDKS VMFFLTNLHQS (SEQ ID NO: 68) |
| mH7 | YFGRLHCTTAVIRNINDQVLFVDKRQPVFEDMTDIDQSASEPQTRLIIY MYADRRARGKAVTLSVKDSKMSTLSCKNKIISFEEMDPPENIDDIQSD LIFFQKKVPGHDKMEFESSLYEGHFLACQKEDDAFKLILKKKDENGDK SVMFTVTNLHQS (SEQ ID NO: 69) |
| mA7 | YFGRLHCTTAVIRNINDQVLFVDKRQPVFEDMTDIDQSASEPQTRLIIY AYGDNRVRGKAVTLSVKDSKMSTLSCKNKIISFEEMDPPENIDDIQSDL IFFQKRVPGHNKMEFESSLYEGHFLACQKEDDAFKLILKKKDENGDKS VMFTLTNLHQS (SEQ ID NO: 70) |
| mE1 | YFGRLHCTTAVIRNINDQVLFVDKRQPVFEDMTDIDQSASEPQTRLIIY GYGDSERGGRAVTLSVKDSKMSTLSCKNKIISFEEMDPPENIDDIQSDLI FFQKRVPGHDKMEFESSLYEGHFLACQKEDDAFKLILKKKDENGDKS VMFTLTNLHQS (SEQ ID NO: 71) |
| mH3 | YFGRLHCTTAVIRNINDQVLFVDKRQPVFEDMTDIDQSASEPQTRLIIY TRTDGGQKGVAVTLSVKDSKMSTLSCKNKIISFEEMDPPENIDDIQSDL IFFQKRVPGHDKMEFESSLYEGHFLACQKEDDAFKLILKKKDENGDKS VMFTLTNLHQS (SEQ ID NO: 72) |

| Human Decoy-to-the-Decoy (D2D) variants amino acid sequences | |
|---|---|
| hD2D-5F12 | HFGKLESKLSVIRNLNGQVLFIDQGNRPLFKDMTASDCRANAPR TIFIISFYKDSQPRGMAVTISVKCEKISTLSCENKIISFKEMNPPDNI KDTKSDIIFFIRSVPGADNKFQFESSSYEGYFLACEKERDLFKLIL KKEDELGDRSIMFTVQNED (SEQ ID NO: 92) |
| hD2D-5F11 | DFGKLESKLSVIRNLNDQVLFIDQGNRPLFADMTDNPCRSNAPR TIFIISFYKDSQPRGIAVTISVKCEKISTLSCENKIISFKEMNPPDNIK DTKSDIIFFLRSVPGPDNKMQFESSSYEGYFLACEKERDLFKLILK KEDELGDRSIMFTVQNED (SEQ ID NO: 93) |
| hD2D-5F10 | HFGKLESKLSVIRNLNGQVLFIDQGNRPEFADMEASPCRDNAPR TIFIISFYKDSQPRGLAVTISVKCEKISTLSCENKIISFKEMNPPDNI KDTKSDIIFFLRSVPGHDNKMQFESSSYEGYFLACEKERDLFKLIL KKEDELGDRSIMFTVQNED (SEQ ID NO: 94) |
| hD2D-5F08 | LFGKLESKLSVIRNLNGQVLFIDQGNRPLFADMTSSPCRSRAPRTI FIISFYKDSQPRGFAVTISVKCEKISTLSCENKIISFKEMNPPDNIKD TKSDIIFFIRSVPGHDNKIQFESSSYEGYFLACEKERDLFKLILKKE DELGDRSIMFTVQNED (SEQ ID NO: 95) |
| hD2D-5F06 | HFGKLESKLSVIRNLNDQVLFIDQGNRPLFTDMESKPCRDSAPRT IFIISMYKDSQPRGIAVTISVKCEKISTLSCENKIISFKEMNPPDNIK DTKSDIIFFIRSVPGHDNKFQFESSSYEGYFLACEKERDLFKLILK KEDELGDRSIMFTVQNED (SEQ ID NO: 96) |
| hD2D-5F04 | YFGKLESKLSVIRNLNRQVLFIDQGNRPLFrDMTYKDCRDNAPR TIFIISFYKDSQPRGFAVTISVKCEKISTLSCENKIISFKEMNPPDNI KDTKSDIIFFIRSVPGADNKIQFESSSYEGYFLACEKERDLFKLILK KEDELGDRSIMFTVQNED (SEQ ID NO: 97) |

-continued

| Human Decoy-to-the-Decoy (D2D) variants amino acid sequences | |
|---|---|
| hD2D-5F02 | HFGKLESKLSVIRNLNGQVLFIDQGNRPLFGDMEASPCRDNAPR TIFIISFYKDSQPRGMAVTISVKCEKISTLSCENKIISFKEMNPPDNI KDTKSDIIFFIRSVPGADNKLQFESSSYEGYFLACEKERDLFKLIL KKEDELGDRSIMFTVQNED (SEQ ID NO: 98) |
| hD2D-5F01 | HFGKLESKLSVIRNLNGQVLFIDQGNRPLFTDMTSSDCRDKAPRT IFIISFYKDSQPRGLAVTISVKCEKISTLSCENKIISFKEMNPPDNIK DTKSDIIFFLRSVPGPDNKFQFESSSYEGYFLACEKERDLFKLILK KEDELGDRSIMFTVQNED (SEQ ID NO: 99) |
| hD2D-5E10 | HFGKLESKLSVIRNLNGQVLFIDQGNRPLFADMESNRCRDSAPRT IFIISMYKDSQPRGFAVTISVKCEKISTLSCENKIISFKEMNPPDNIK DTKSDIIFFLRSVPGHDNKIQFESSSYEGYFLACEKERDLFKLILK KEDELGDRSIMFTVQNED (SEQ ID NO: 100) |
| hD2D-5E08 | YFGKLESKLSVIRNLNGQVLFIDQGNRPLFTDMTASPCRDNAPRT IFIISFYKDSQPRGLAVTISVKCEKISTLSCENKIISFKEMNPPDNIK DTKSDIIFFLRSVPGHDNKIQFESSSYEGYFLACEKERSLFKLILKK EDELGDRSIMFTVQNED (SEQ ID NO: 101) |
| hD2D-5E03 | DFGKLESKLSVIRNLNDQVLFIDQGNRPLFADMKSNVCRANAPR TIFIISMYKDSQPRGMAVTISVKCEKISTLSCENKIISFKEMNPPDN IKDTKSDIIFFIRSVPGPDNKLQFESSSYEGYFLACEKERDLFKLIL KKEDELGDRSIMFTVQNED (SEQ ID NO: 102) |
| hD2D-5E02 | HFGKLESKLSVIRNLNGQVLFIDQGNRPLFGDMEASPCRAKAPR TIFIISIYKDSQPRGFAVTISVKCEKISTLSCENKIISFKEMNPPDNIK DTKSDIIFFLRSVPGHDNKFQFESSSYEGYFLACEKERSLFKLILK KEDELGDRSIMFTVQNED (SEQ ID NO: 103) |
| hD2D-5D10 | HFGKLESKLSVIRNLNGQVLFIDQGNRPLFADMASNRCRANAPR TIFIISMYKDSQPRGFAVTISVKCEKISTLSCENKIISFKEMNPPDNI KDTKSDIIFFIRSVPGPDNKFQFESSSYEGYFLACEKERDLFKLILK KEDELGDRSIMFTVQNED (SEQ ID NO: 104) |
| hD2D-5D08 | YFGKLESKLSVIRNLNDQVLFIDQGNRPLFADMKAKACRSNAPR TIFIISFYKDSQPRGFAVTISVKCEKISTLSCENKIISFKEMNPPDNI KDTKSDIIFFLRSVPGADNKIQFESSSYEGYFLACEKERDLFKLIL KKEDELGDRSIMFTVQNED (SEQ ID NO: 105) |
| hD2D-5D06 | HFGKLESKLSVIRNLNHQVLFIDQGNRPLFTDMADNACRDNAPR TIFIISFYKDSQPRGLAVTISVKCEKISTLSCENKIISFKEMNPPDNI KDTKSDIIFFIRSVPGDDNKMQFESSSYEGYFLACEKERDLFKLIL KKEDELGDRSIMFTVQNED (SEQ ID NO: 106) |
| hD2D-5D05 | YFGKLESKLSVIRNLNGQVLFIDQGNRPLFTDMKSNLCRSNAPRT IFIISFYKDSQPRGIAVTISVKCEKISTLSCENKIISFKEMNPPDNIK DTKSDIIFFIRSVPGDDNKIQFESSSYEGYFLACEKERDLFKLILKK EDELGDRSIMFTVQNED (SEQ ID NO: 107) |
| hD2D-5D03 | HFGKLESKLSVIRNLNGQVLFIDQGNRPLFRDMAASHCRDSAPR TIFIISIYKDSQPRGFAVTISVKCEKISTLSCENKIISFKEMNPPDNIK DTKSDIIFFLRSVPGHDNKIQFESSSYEGYFLACEKERDLFKLILK KEDELGDRSIMFTVQNED (SEQ ID NO: 108) |
| hD2D-5D02 | YFGKLESKLSVIRNLNDQVLFIDQGNRPLFADMASNPCRYKAPR TIFIISMYKDSQPRGLAVTISVKCEKISTLSCENKIISFKEMNPPDNI KDTKSDIIFFLRSVPGADNKLQFESSSYEGYFLACEKERDLFKLIL KKEDELGDRSIMFTVQNED (SEQ ID NO: 109) |
| hD2D-5C10 | HFGKLESKLSVIRNLNGQVLFIDQGNRPLFTDMASNHCRYNAPR TIFIISMYKDSQPRGLAVTISVKCEKISTLSCENKIISFKEMNPPDNI KDTKSDIIFFLRSVPGADNKIQFESSSYEGYFLACEKERDLFKLIL KKEDELGDRSIMFTVQNED (SEQ ID NO: 110) |
| hD2D-5C09 | HFGKLESKLSVIRNLNGQVLFIDQGNRPLFADMTDNPCRSRAPRT IFIISFYKDSQPRGMAVTISVKCEKISTLSCENKIISFKEMNPPDNIK DTKSDIIFFIRSVPGHDNKFQFESSSYEGYFLACEKERDLFKLILK KEDELGDRSIMFTVQNED (SEQ ID NO: 111) |
| hD2D-5C08 | YFGKLESKLSVIRNLNGQVLFIDQGNRPLFTDMTASHCRSSAPRT IFIISLYKDSQPRGMAVTISVKCEKISTLSCENKIISFKEMNPPDNIK DTKSDIIFFLRSVPGHDNKFQFESSSYEGYFLACEKERDLFKLILK KEDELGDRSIMFTVQNED (SEQ ID NO: 112) |
| hD2D-5C05 | YFGKLESKLSVIRNLNGQVLFIDQGNRPLFTDMEYRLCRANAPR TIFIISFYKDSHPRGLAVTISVKCEKISTLSCENKIISFKEMNPPDNI |

-continued

| Human Decoy-to-the-Decoy (D2D) variants amino acid sequences | |
|---|---|
| | KDTKSDIIFFLRSVPGDDNKLQFESSSYEGYFLACEKERDLFKLIL KKEDELGDRSIMFTVQNED (SEQ ID NO: 113) |
| hD2D-5C04 | YFGKLESKLSVIRNLNGQVLFIDQGNRPLFTDMESSLCRDNAPRT IFIISLYKDSQPRGMAVTISVKCEKISTLSCENKIISFKEMNPPDNIK DTKSDIIFFLRSVPGADNKFQFESSSYEGYFLACEKERSLFKLILK KEDELGDRSIMFTVQNED (SEQ ID NO: 114) |
| hD2D-5C03 | YFGKLESKLSVIRNLNGQVLFIDQGNRPLFKDMEANDCRSSAPR TIFIISIYKDSQPRGLAVTISVKCEKISTLSCENKIISFKEMNPPDNIK DTKSDIIFFIRSVPGADNKMQFESSSYEGYFLACEKERDLFKLILK KEDELGDRSIMFTVQNED (SEQ ID NO: 115) |
| hD2D-5B11 | DFGKLESKLSVIRNLNDQVLFIDQGNRPLFADMKASACRANAPR TIFIISMYKDSQPRGLAVTISVKCEKISTLSCENKIISFKEMNPPDNI KDTKSDIIFFLRSVPGHDNKFQFESSSYEGYFLACEKERDLFKLIL KKEDELGDRSIMFTVQNED (SEQ ID NO: 116) |
| hD2D-5B10 | YFGKLESKLSVIRNLNGQVLFIDQGNRPLFGDMTAKHCRARAPR TIFIISFYKDSQPRGMAVTISVKCEKISTLSCENKIISFKEMNPPDNI KDTKSDIIFFIRSVPGADNKFQFESSSYEGYFLACEKERDLFKLIL KKEDELGDRSIMFTVQNED (SEQ ID NO: 117) |
| hD2D-5B06 | FFGKFESKLSVIRNLNGQVLFIDQGNRPLFTDMESKDCRDRAPRT IFIISFYKDSQPRGLAVTISVKCEKISTLSCENKIISFKEMNPPDNIK DTKSDIIFFLRSVPGHDNKLQFESSSYEGYFLACEKERDLFKLILK KEDELGDRSIMFTVQNED (SEQ ID NO: 118) |
| hD2D-5B05 | FFGKLESKLSVIRNLNGQVLFIDQGNRPLFADMASNHCRANAPR TIFIISLYKDSQPRGLAVTISVKCEKISTLSCENKIISFKEMNPPDNI KDTKSDIIFFIRSVPGHDNKMQFESSSYEGYFLACEKERDLFKLIL KKEDELGDRSIMFTVQNED (SEQ ID NO: 119) |
| hD2D-5B02 | YFGKLESKLSVIRNLNGQVLFIDQGNRPLFADMTSKRCRDNAPR TIFIISLYKDSQPRGFAVTISVKCEKISTLSCENKIISFKEMNPPDNI KDTKSDIIFFIRSVPGHDNKIQFESSSYEGYFLACEKERDLFKLILK KEDELGDRSIMFTVQNED (SEQ ID NO: 120) |
| hD2D-5A09 | LFGKHESKLSVIRNLNGQVLFIDQGNRPLFGDMESSPCRYNAPRT IFIISFYKDSQPRGLAVTISVKCEKISTLSCENKIISFKEMNPPDNIK DTKSDIIFFIRSVPGHDNKMQFESSSYEGYFLACEKERDLFKLILK KEDELGDRSIMFTVQNED (SEQ ID NO: 121) |
| hD2D-5A02 | YFGKLESKLSVIRNLNAQVLFIDQGNRPLFTDMTASPCRSSAPRTI FIISLYKDSQPRGLAVTISVKCEKISTLSCENKIISFKEMNPPDNIK DTKSDIIFFLRSVPGPDNKIQFESSSYEGYFLACEKERDLFKLILKK EDELGDRSIMFTVQNED (SEQ ID NO: 122) |
| hD2D-CS1 | YFGKLESKLSVIRNLNGQVLFIDQGNRPLFADMTDSDCRDNAPR TIFIISMYKDSQPRGMAVTISVKCEKISTLSCENKIISFKEMNPPDN IKDTKSDIIFFLRSVPGHDNKMQFESSSYEGYFLACEKERDLFKLI LKKEDELGDRSIMFTVQNED (SEQ ID NO: 123) |
| hD2D-CS2 | YFGKLESKLSVIRNLNGQVLFIDQGNRPLFADMTSSDCRDNAPR TIFIISFYKDSQPRGMAVTISVKCEKISTLSCENKIISFKEMNPPDNI KDTKSDIIFFLRSVPGHDNKMQFESSSYEGYFLACEKERDLFKLIL KKEDELGDRSIMFTVQNED (SEQ ID NO: 124) |
| hD2D-CS3 | YFGKLESKLSVIRNLNGQVLFIDQGNRPLFADMESSDCRDNAPR TIFIISFYKDSQPRGLAVTISVKCEKISTLSCENKIISFKEMNPPDNI KDTKSDIIFFLRSVPGHDNKMQFESSSYEGYFLACEKERDLFKLIL KKEDELGDRSIMFTVQNED (SEQ ID NO: 125) |

| Mouse Decoy-to-the-Decoy (D2D) variants amino acid sequences | |
|---|---|
| mD2D-A5 | YFGRYHCTTAVIRNINQQVLFVDKRQPVFADMGYTVQSASEPQT RLIIYMYKDSEVRGLAVTLSVKDSKMSTLSCKNKIISFEEMDPPE NIDDIQSDLIFFLKEVPGHRKLEFESSLYEGHFLACQKEDEAFKLI LKKKDENGDKSVMFTLTNLHQS (SEQ ID NO: 126) |
| mD2D-A6 | DFGRLHCTTAVIRNINDQVLFVDKRQPVFADMGSIAQSASEPQT RLIIYFYKDSEVRGLAVTLSVKDSKMYTLSCKNKIISFEEMDPPE NIDDIQSDLIFFLKAVPGDNKIEFESSLYEGHFLACQKEATAFKLI LKKKDENGDKSVMFTLTNLHQS (SEQ ID NO: 127) |

-continued

| Mouse Decoy-to-the-Decoy (D2D) variants amino acid sequences | |
|---|---|
| mD2D-A7 | YFGRLHCTTAVIRNINGQVLFVDKRQPVFRDMADTVQSASEPQT RLIIYFYKDSEVRGLAVTLSVKDSKMSTLSCKNKIISFEEMDPPEN IDDIQSDLIFFIKPVPGASKMEFESSLYEGHFLACQKEAGAFKLIL KKKDENGDKSVMFTLTNLHQS (SEQ ID NO: 128) |
| mD2D-A8 | HFGRLHCTTAVIRNINDQVLFVDKRQPVFKDMEYTVQSASEPQT RLIIYMYKDSEVRGLAVTLSVKDSKMSTLSCKNKIISFEEMDPPE NIDDIQSDLIFFIKAVPGDRKIEFESSLYEGHFLACQKEDNAFKLIL KKKDENGDKSVMFTLTNLHQS (SEQ ID NO: 129) |
| mD2D-A9 | YFGRLHCTTAVIRNINAQVLFVDKRQPVFADMADKGQSASEPQT RLIIYMYKDSEVRGLAVTLSVKDSKMSTLSCKNKIISFEEMDPPE NIDDIQSDLIFFLKPVPGDTKMEFESSLYEGHFLACQKEFGAFKLI LKKKDENGDKSVMFTLTNLHQS (SEQ ID NO: 130) |
| mD2D-A11 | YFGRLHCTTAVIRNINEQVLFVDKRQPVFADMGDRHQSASEPQT RLIIYMYKDSEVRGLAVTLSVKDSKMSTLSCKNKIISFEEMDPPE NIDDIQSDLIFFIKPVPGASKLEFESSLYEGHFLACQKEDDAFKLIL KKKDENGDKSVMFTLTNLHQS (SEQ ID NO: 131) |
| mD2D-A12 | HFGRLHCTTAVIRNINDQVLFVDKRQPVFRDMGAIGQSASEPQT RLIIYFYKDSEVRGLAVTLSVKDSKMSTLSCKNKIISFEEMDPPEN IDDIQSDLIFFIKPVPGDSKLEFESSLYEGHFLACQKEVDAFKLILK KKDENGDKSVMFTLTNLHQS (SEQ ID NO: 132) |
| mD2D-B4 | HFGRLHCTTAVIRNINSQVLFVDKRQPVFTDMGSIVQSASEPQTR LIIYMYKDSEVRGLAVTLSVKDSKMSTLSCKNKIISFEEMDPPENI DDIQSDLIFFIKGVPGDNKIEFESSLYEGHFLACQKEDRAFKLILK KKDENGDKSVMFTLTNLHQS (SEQ ID NO: 133) |
| mD2D-B7 | YFGRLHCTTAVIRNINSQVLFVDKRQPVFRDMEDTPQSASEPQTR LIIYFYKDSEVRGLAVTLSVKDSKMSTLSCKNKIISFEEMDPPENI DDIQSDLIFFIKRVPGDSKLEFESSLYEGHFLACQKEFEAFKLILK KKDENGDKSVMFTLTNLHQS (SEQ ID NO: 134) |
| mD2D-B11 | HFGRLHCTTAVIRNINAQVLFVDKRQPVFGDMTATVQSASEPQT RLIIYFYKDSEVRGLAVTLSVKDSKMSTLSCKNKIISFEEMDPPEN IDDIQSDLIFFIKPVPGDSKLEFESSLYEGHFLACQKEDNAFKLILK KKDENGDKSVMFTLTNLHQS (SEQ ID NO: 135) |
| mD2D-B12 | NFGRLHCTTAVIRNINNQVLFVDKRQPVFKDMEYTLQSASEPQT RLIIYFYKDSEVRGLAVTLSVKDSKMSTLSCKNKIISFEEMDPPEN IDDIQSDLIFFIKPVPGDNKLEFESSLYEGHFLACQKEYEAFKLILK KKDENGDKSVMFTLTNLHQS (SEQ ID NO: 136) |
| mD2D-C1 | YFGRLHCTTAVIRNINGQVLFVDKRQPVFADMEATRQSASEPQT RLIIYFYKDSEVRGLAVTLSVKDSKMSTLSCKNKIISFEEMDPPEN IDDIQSDLIFFIKGVPGANKMEFESSLYEGHFLACQKEDGAFKLIL KKKDENGDNSVMFTLTNLHQS (SEQ ID NO: 137) |
| mD2D-C3 | NFGRLHCTTAVIRNINGQVLFVDKRQPVFADMRAILQSASEPQT RLIIYFYKDSEVRGLAVTLSVKDSKMSTLSCKNKIISFEEMDPPEN IDDIQSDLIFFLKGVPGDNKLEFESSLYEGHFLACQKEDRAFKLIL KKKDENGDKSVMFTLTNLHQS (SEQ ID NO: 138) |
| mD2D-C5 | YFGRLHCTTAVIRNINAQVLFVDKRQPVFADMEATAQSASEPQT RLIIYFYKDSEVRGLAVTLSVKDSKMSTLSCKNKIISFEEMDPPEN IDDIQSDLIFFIKGVPGASKMEFESSLYEGHFLACQKEDGAFKLIL KKKDENGDKSVMFTLTNLHQS (SEQ ID NO: 139) |
| mD2D-C6 | LFGRLHCTTAVIRNINGQVLFVDKRQPVFADMGATLQSASEPQT RLIIYMYKDSEVRGLAVTLSVKDSKMSTLSCKNKIISFEEMDPPE NIDDIQSDLIFFLKPVPGDTKMEFESSLYEGHFLACQKEASAFKLI LKKKDLNGDKSVMFTLTNLIIQS (SEQ ID NO: 140) |
| mD2D-C9 | NFGRLHCTTAVIRNINGQVLFVDKRQPVFEDMAYTVQSASEPQT RLIIYFYKDSEVRGLAVTLSVKDSKMSTLSCKNKIISFEEMDPPEN IDDIQSDLIFFIKGVPGDSKMEFESSLYEGHFLACQKEYDAFKLIL KKKDENGDKSVMFTLTNLHQS (SEQ ID NO: 141) |
| mD2D-C10 | DFGRLHCTTAVIRNINDQVLFVDKRQPVFKDMFSKPQSASFPQT RLIIYFYKDSEVRGLAVTLSVKDSKMSTLSCKNKIISFEEMDPPEN IDDIQSDLIFFLKAVPGASKLEFESSLYEGHFLACQKEANAFKLIL KKKDENGDKSVMFTLTNLHQS (SEQ ID NO: 142) |

-continued

| Mouse Decoy-to-the-Decoy (D2D) variants amino acid sequences | |
|---|---|
| mD2D-C11 | LFGRLHCTTAVIRNINGQVLFVDKRQPVFADMGDKVQSASEPQT RLIIYMYKDSEVRGLAVTLSVKDSKMSTLSCKNKIISFEEMDPPE NIDDIQSDLIFFIKPVPGDNKLEFESSLYEGHFLACQKEDEAFKLIL KTKDENGDKSVMFTLTNLHQS (SEQ ID NO: 143) |
| mD2D-D1 | YFGRHHCTTAVIRNINQQVLFVDKRQPVFRDMAATRQSASEPQT RLIIYMYKDSEVRGLAVTLSVKDSKMSTLSCKNKIISFEEMDPPE NIDDIQSDLIFFLKGVPGDNKMEFESSLYEGHFLACQKEDDAFKL ILKKKDENGDKSVMFTLTNLHQS (SEQ ID NO: 144) |
| mD2D-D9 | NFGRLHCTTAVIRNINQQVLFVDKRQPVFTDMESIGQSASEPQTR LIIYFYKDSEVRGLAVTLSVKDSKMSTLSCKNKIISFEEMDPPENI DDIQSDLIFFLKAVPGANKLEFESSLYEGHFLACQKEDSAFKLILK KKDENGDKSVMFTLTNLHQS (SEQ ID NO: 145) |
| mD2D-D12 | FFGRHHCTTAVIRNINGQVLFVDKRQPVFGDMGDRVQSASEPQT RLIIYMYKDSEVRGLAVTLSVKDSKMSTLSCKNKIISFEEMDPPE NIDDIQSDLIFFIKAVPGDSKIEFESSLYEGHFLACQKEDGAFKLIL KKKDENGDKSVMFTLTNLHQS (SEQ ID NO: 146) |
| mD2D-E3 | VFGRHHCTTAVIRNINGQVLFVDKRQPVFKDMTYIDQSASEPQT RLIIYMYKDSEVRGLAVTLSVKDSKMSTLSCKNKIISFEEMDPPE NIDDIQSDLIFFLKAVPGDTKMEFESSLYEGHFLACQKEAQAFKLI LKKKDEIGDKSVMFTLTNLHQS (SEQ ID NO: 147) |
| mD2D-E4 | NFGRLHCTTAVIRNINGQVLFVDKRQPVFADMTATRQSASEPQT RLIIYMYKDSEVRGLAVTLSVKDSKMSTLSCKNKIISFEEMDPPE NIDDIQSDLIFFIKQVPGANKIEFESSLYEGHFLACQKEFRAFKLIL KKKDENGDKSVMFTLTNLHQS (SEQ ID NO: 148) |
| mD2D-E5 | DFGRLHCTTAVIRNINGQVLFVDKRQPVFGDMAYIGQSASEPQT RLIIYFYKDSEVRGLAVTLSVKDSKMSTLSCKNKIISFEEMDPPEN IDDIQSDLIFFIKAVPGHSKIEFESSLYEGHFLACQKESGAFKLILK KKDENGDKSVMFTLTNLHQS (SEQ ID NO: 149) |
| mD2D-E7 | YFGRLHCTTAVIRNINDQVLFVDKRQPVFRDMGSIAQSASEPQTR LIIYMYKDSEVRGLAVTLSVKDSKMSTLSCKNKIISFEEMDPPENI DDIQSDLIFFIKPVPGATKLEFESSLYEGHFLACQKEDGAFKLILK KKDENGDNSVMFTLTNLHQS (SEQ ID NO: 150) |
| mD2D-E8 | YFGRLHCTTAVIRNINEQVLFVDKRQPVFTDMEAIGQSASEPQTR LIIYFYKDSEVRGLAVTLSVKDSKMSTLSCKNKIISFEEMDPPENI DDIQSDLIFFIKGVPGDRKMEFESSLYEGHFLACQKEDGAFKLIL KKKDENGDKSVMFTLTNLHQS (SEQ ID NO: 151) |
| mD2D-E9 | FFGRLHCTTAVIRNINNQVLFVDKRQPVFEDMEYRLQSASEPQT RLIIYMYKDSEVRGLAVTLSVKDSKMSTLSCKNKIISFEEMDPPE NIDDIQSDLIFFLKPVPGASKLEFESSLYEGHFLACQKESDAFKLIL KKKDENGDKSVMFTLTNLHQS (SEQ ID NO: 152) |
| mD2D-E10 | NFGRLHCTTAVIRNINNQVLFVDKRQPVFADMEDRLQSASEPQT RLIIYMYKDSEVRGLAVTLSVKDSKMSTLSCKNKIISFEEMDPPE NIDDIQSDLIFFLKGVPGDNKMEFESSLYEGHFLACQKEDHAFKL ILKKKDENGDKSVMETLTNLHQS (SEQ ID NO: 153) |
| mD2D-E11 | YFGRLHCTTAVIRNINAQVLFVDKRQPVFRDMGYILQSASEPQT RLIIYLYKDSEVRGLAVTLSVKESKMSTLSCKNKIISFEEMDPPEN IDDIQSDLIFFLKPVPGDTKIEFESSLYEGHFLACQKEDNAFKLILK KKDENGDKSVMFTLTNLHQS (SEQ ID NO: 154) |
| mD2D-E12 | YFGRLHCTTAVIRNINDQVLFVDKRQPVFGDMADTAQSASEPQT RLIIYFYKDSEVRGLAVTLSVKDSKMSTLSCKNKIISFEEMDPPEN IDDIQSDLIFFIKPVPGDSKMEFESSLYEGHFLACQKEADAFKLIL KKKDENGDKSVMFTLTNLHQS (SEQ ID NO: 155) |
| mD2D-F3 | DFGRLHCTTAVIRNINGQVLFVDKRQPVFEDMAYIAQSASEPQT RLIIYFYKDSEVRGLAVTLSVKDSKMSTLSCKNKIISFEEMDPPEN IDDIQSDLIFFIKPVPGDSKIEFESSLYEGHFLACQKEADAFKLILK KKDENGDKSVMFTLTNLHQS (SEQ ID NO: 156) |
| mD2D-F4 | NFGRLHCTTAVIRNINEQVLSVDKRQPVFRDMKYILQSASEPQTR LIIYFYKDSEVRGLAVTLSVKDSKMSTLSCKNKIISFEEMDPPENI DDIQSDLIFFLKGVPGDNKMEFESSLYEGHFLACQKEYGAFKLIL KKKDENGDKSVMFTLTNLHQS (SEQ ID NO: 157) |
| mD2D-F5 | DFGRLHCTTAVIRNINEQVLFVDKRQPVFTDMAYILQSASEPQTR LIIYFYKDSEVRGLAVTLSVKESKMSTLSCKNKIISFEEMDPPENI |

-continued

| Mouse Decoy-to-the-Decoy (D2D) variants amino acid sequences | |
|---|---|
| | DDIQSDLIFFIKAVPGDSKLEFESSLYEGHFLACQKEDTAFKLILK KKDENGDKSVMFTLTNLHQS (SEQ ID NO: 158) |
| mD2D-F7 | DFGRLHCTTAVIRNINNQVLFVDKRQPVFKDMESTAQSASEPQT RLIIYMYKDSEVRGLAVTLSVKDSKMSTLSCKNKIISFEEMDPPE NIDDIQSDLIFFLKGVPGASKLEFESSLYEGHFLACQKEAGAFKLI LKKKDENGDKSVMFTLTNLHQS (SEQ ID NO: 159) |
| mD2D-F8 | HFGRLHCTTAVIRNINEQVLFVDKRQPVFADMEAIGQSASEPQTR LIIYFYKDSEVRGLAVTLSVKESKMSTLSCKNKIISFEEMDPPENI DDIQSDLIFFIKGVPGDTKLEFESSLYAGHFLACQKEDGAFKLILK KKDENGDKSVMFTLTNLHQS (SEQ ID NO: 160) |
| mD2D-F9 | IFGRLHCTTAVIRNINEQVLFVDKRQPVFKDMRYIVQSASEPQTR LIIYFYKDSEVRGLAVTLSVKDSKMSTLSCKNKIISFEEMDPPENI DDIQSDLIFFIKEVPGASKLEFESSLYEGHFLACQKEDEAFKLILK KKDENGDKSVMFTLTNLHQS (SEQ ID NO: 161) |
| mD2D-G1 | YFGRLHCTTAVIRNINAQVLFVDKRQPVFTDMGYTLQSASEPQT RLIIYLYKDSEVRGLAVTLSVKDSKMSTLSCKNKIISFEEMDPPEN IDDIQSDLIFFIKPVPGHNKIEFESSLYEGHFLACQKEDRAFKLILK KKDENGDKSVMFTLTNLHQS (SEQ ID NO: 162) |
| mD2D-G7 | NFGRLHCTTAVIRNINNQVLFVDKRQPVFRDMASTAQSASEPQT RLIIYMYKDSEVRGLAVTLSVKDSKMSTLSCKNKIISFEEMDPPE NIDDIQSDLIFFIKGVPGANKIEFESSLYEGHFLACQKEDDAFKLIL KKKDENGDKSVMFTLTNLHQS (SEQ ID NO: 163) |
| mD2D-G9 | DFGRLHCTTAVIRNINGQVLFVDKRQPVFEDMKDRAQSASEPQT RLIIYFYKDSEVRGLAVTLSVKDSKMSTLSCKNKIISFEEMDPPEN IDDIQSDLIFFLKAVPGHSKMEFESSLYEGHFLACQKEDEAFKLIL KKKDENGDKSVMFTLTNLHQS (SEQ ID NO: 164) |
| mD2D-H7 | NFGRLHCTTAVIRNINEQVLFVDKRQPVFADMTDIAQSASEPQTR LIIYMYKDSEVRGLAVTLSVKESKMSTLSCKNKIISFEEMDPPENI DDIQSDLIFFLKPVPGDIKMEFESSLYEGHFLACQKEYGAFKLILK KKDENGDNSVMFTLTNLHQS (SEQ ID NO: 165) |
| mD2D-E1 | YFGRLHCTTAVIRNINEQVLFVDKRQPVFADMTDTLQSASEPQT RLIIYFYKDSEVRGLAVTLSVKDSKMSTLSCKNKIISFEEMDPPEN IDDIQSDLIFFLKGVPGDNKMEFESSLYEGHFLACQKEDTAFKLIL KKKDENGDKSVMFTLTNLHQS (SEQ ID NO: 166) |
| mD2D-G8 | YFGRLHCTTAVIRNINEQVLFVDKRQPVFADMTDTLQSASEPQT RLIIYFYKDSEVRGLAVTLSVKDSKMSTLSCKNKIISFEEMDPPEN IDDIQSDLIFFLKGVPGDNKMEFESSLYEGHFLACQKEDTAFKLIL KKKDENGDKSVMFTLTNLHQS (SEQ ID NO: 167) |
| mD2D-H3 | YFGRLHCTTAVIRNINEQVLFVDKRQPVFADMTDTLQSASEPQT RLIIYFYKDSEVRGLAVTLSVKDSKMSTLSCKNKIISFEEMDPPEN IDDIQSDLIFFLKGVPGDNKMEFESSLYEGHFLACQKEDTAFKLIL KKKDENGDKSVMFTLTNLHQS (SEQ ID NO: 168) |
| mD2D-A10 | HFGRLHCTTAVIRNINGQVLFVDKRQPVFKDMKYIVQSASEPQT RLIIYMYKDSEVRGLAVTLSVKDSKMSTLSCKNKIISFEEMDPPE NIDDIQSDLIFFLKAVPGHSKIEFESSLYEGHFLACQKEDSAFKLIL KKKDENGDKSVMFTLTNLHQS (SEQ ID NO: 169) |
| mD2D-H1 | HFGRLHCTTAVIRNINGQVLFVDKRQPVFKDMKYIVQSASEPQT RLIIYMYKDSEVRGLAVTLSVKDSKMSTLSCKNKIISFEEMDPPE NIDDIQSDLIFFLKAVPGHSKIEFESSLYEGHFLACQKEDSAFKLIL KKKDENGDKSVMFTLTNLHQS (SEQ ID NO: 170) |
| mD2D-F12 | YFGRLHCTTAVIRNINGQVLFVDKRQPVFEDMKAKAQSASEPQT RLIIYFYKDSEVRGLAVTLSVKDSKMSTLSCKNKIISFEEMDPPEN IDDIQSDLIFFIKPVPGASKMEFESSLYEGHFLACQKEDGAFKLIL KKKDENGDKSVMFTLTNLHQS (SEQ ID NO: 171) |
| mD2D-G10 | YFGRLHCTTAVIRNINGQVLFVDKRQPVFEDMKAKAQSASEPQT RLIIYFYKDSEVRGLAVTLSVKDSKMSTLSCKNKIISFEEMDPPEN IDDIQSDLIFFIKPVPGASKMEFESSLYEGHFLACQKEDGAFKLIL KKKDENGDKSVMFTLTNLHQS (SEQ ID NO: 172) |
| mD2D-G12 | YFGRLHCTTAVIRNINGQVLFVDKRQPVFEDMKAKAQSASEPQT RLIIYFYKDSEVRGLAVTLSVKDSKMSTLSCKNKIISFEEMDPPEN IDDIQSDLIFFIKPVPGASKMEFESSLYEGHFLACQKEDGAFKLIL KKKDENGDKSVMFTLTNLHQS (SEQ ID NO: 173) |

-continued

| Mouse Decoy-to-the-Decoy (D2D) variants amino acid sequences | |
|---|---|
| mD2D-E2 | LFGRLHCTTAVIRNINGQVLFVDKRQPVFGDMGSIPQSASEPQTR LIIYFYKDSEVRGLAVTLSVKDSKMSTLSCKNKIISFEEMDPPENI DDIQSDLIFFIKHVPGATKMEFESSLYEGHFLACQKEDNAFKLILK KKDENGDKSVMFTLTNLHQS (SEQ ID NO: 174) |
| mD2D-G11 | LFGRLHCTTAVIRNINGQVLFVDKRQPVFGDMGSIPQSASEPQTR LIIYFYKDSEVRGLAVTLSVKDSKMSTLSCKNKIISFEEMDPPENI DDIQSDLIFFIKHVPGATKMEFESSLYEGHFLACQKEDNAFKLILK KKDENGDKSVMFTLTNLHQS (SEQ ID NO: 175) |
| mD2D-C4 | YFGRLHCTTAVIRNINSQVLFVDKRQPVFTDMAYTVQSASEPQT RLIIYFYKDSEVRGLAVTLSVKDSKMSTLSCKNKIISFEEMDPPEN IDDIQSDLIFFIKAVPGDSKLEFESSLYEGHFLACQKEDNAFKLILK KKDENGDKSVMFTLTNLHQS (SEQ ID NO: 176) |
| mD2D-F11 | YFGRLHCTTAVIRNINSQVLFVDKRQPVFTDMAYTVQSASEPQT RLIIYFYKDSEVRGLAVTLSVKDSKMSTLSCKNKIISFEEMDPPEN IDDIQSDLIFFIKAVPGDSKLEFESSLYEGHFLACQKEDNAFKLILK KKDENGDKSVMFTLTNLHQS (SEQ ID NO: 177) |
| mD2D-C2 | YFGRLHCTTAVIRNINGQVLFVDKRQPVFTDMGARVQSASEPQT RLIIYFYKDSEVRGLAVTLSVKDSKMYTLSCKNKIISFEEMDPPE NIDDIQSDLIFFLKPVPGDNKLEFESSLYEGHFLACQKESGAFKLI LKKKDENGDKSVMFTLTNLHQS (SEQ ID NO: 178) |
| mD2D-F10 | YFGRLHCTTAVIRNINGQVLFVDKRQPVFTDMGARVQSASEPQT RLIIYFYKDSEVRGLAVTLSVKDSKMYTLSCKNKIISFEEMDPPE NIDDIQSDLIFFLKPVPGDNKLEFESSLYEGHFLACQKESGAFKLI LKKKDENGDKSVMFTLTNLHQS (SEQ ID NO: 179) |
| mD2D-A2 | DFGRLHCTTAVIRNINGQVLFVDKRQPVFGDMKATGQSASEPQT RLIIYFYKDSEVRGLAVTLSVKDSKMSTLSCKNKIISFEEMDPPEN IDDIQSDLIFFIKAVPGANKLEFESSLYEGHFLACQKEAGAFKLIL KKKDENGDKSVMFTLTNLHQS (SEQ ID NO: 180) |
| mD2D-F6 | DFGRLHCTTAVIRNINGQVLFVDKRQPVFGDMKATGQSASEPQT RLIIYFYKDSEVRGLAVTLSVKDSKMSTLSCKNKIISFEEMDPPEN IDDIQSDLIFFIKAVPGANKLEFESSLYEGHFLACQKEAGAFKLIL KKKDENGDKSVMFTLTNLHQS (SEQ ID NO: 181) |
| mD2D-A1 | DFGRLHCTTAVIRNINSQVLFVDKRQPVFRDMGSIHQSASEPQTR LIIYFYKDSEVRGLAVTLSVKDSKMSTLSCKNKIISFEEMDPPENI DDIQSDLIFFLKAVPGANKLEFESSLYEGHFLACQKEDGAFKLIL KKKDENGDKSVMFTLTNLHQS (SEQ ID NO: 182) |
| mD2D-E6 | DFGRLHCTTAVIRNINSQVLFVDKRQPVFRDMGSIHQSASEPQTR LIIYFYKDSEVRGLAVTLSVKDSKMSTLSCKNKIISFEEMDPPENI DDIQSDLIFFLKAVPGANKLEFESSLYEGHFLACQKEDGAFKLIL KKKDENGDKSVMFTLTNLHQS (SEQ ID NO: 183) |
| mD2D-D4 | YFGRLHCTTAVIRNINEQVLFVDKRQPVFKDMKDKLQSASEPQT RLIIYFYKDSEVRGLAVTLSVKDSKMSTLSCKNKIISFEEMDPPEN IDDIQSDLIFFLKGVPGDNKLEFESSLYEGHFLACQKEFGAFKLIL KKKDENGDKSVMFTLTNLHQS (SEQ ID NO: 184) |
| mD2D-D6 | YFGRLHCTTAVIRNINEQVLFVDKRQPVFKDMKDKLQSASEPQT RLIIYFYKDSEVRGLAVTLSVKDSKMSTLSCKNKIISFEEMDPPEN IDDIQSDLIFFLKGVPGDNKLEFESSLYEGHFLACQKEFGAFKLIL KKKDENGDKSVMFTLTNLHQS (SEQ ID NO: 185) |
| mD2D-A3 | YFGRLHCTTAVIRNINGQVLFVDKRQPVFADMASTHQSASEPQT RLIIYFYKDSEVRGLAVTLSVKDSKMSTLSCKNKIISFEEMDPPEN IDDIQSDLIFFLKGVPGANKIEFESSLYEGHFLACQKEDDAFKLIL KKKDENGDKSVMFTLTNLHQS (SEQ ID NO: 186) |
| mD2D-A4 | YFGRLHCTTAVIRNINGQVLFVDKRQPVFADMASTHQSASEPQT RLIIYFYKDSEVRGLAVTLSVKDSKMSTLSCKNKIISFEEMDPPEN IDDIQSDLIFFLKGVPGANKIEFESSLYEGHFLACQKEDDAFKLIL KKKDENGDKSVMFTLTNLHQS (SEQ ID NO: 187) |
| mD2D-B10 | YFGRLHCTTAVIRNINGQVLFVDKRQPVFADMASTIIQSASEPQT RLIIYFYKDSEVRGLAVTLSVKDSKMSTLSCKNKIISFEEMDPPEN IDDIQSDLIFFLKGVPGANKIEFESSLYEGHFLACQKEDDAFKLIL KKKDENGDKSVMFTLTNLHQS (SEQ ID NO: 188) |

-continued

| Mouse Decoy-to-the-Decoy (D2D) variants amino acid sequences | |
|---|---|
| mD2D-B8 | YFGRLHCTTAVIRNINSQVLFVDKRQPVFGDMKYIVQSASEPQT RLIIYFYKDSEVRGLAVTLSVKDSKMSTLSCKNKIISFEEMDPPEN IDDIQSDLIFFLKGVPGDTKMEFESSLYEGHFLACQKESGAFKLIL KKKDENGDKSVMFTLTNLHQS (SEQ ID NO: 189) |
| mD2D-B9 | YFGRLHCTTAVIRNINSQVLFVDKRQPVFGDMKYIVQSASEPQT RLIIYFYKDSEVRGLAVTLSVKDSKMSTLSCKNKIISFEEMDPPEN IDDIQSDLIFFLKGVPGDTKMEFESSLYEGHFLACQKESGAFKLIL KKKDENGDKSVMFTLTNLHQS (SEQ ID NO: 190) |

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below. It will be apparent to one of ordinary skill in the art that various changes and modifications can be made without departing from the spirit or scope of the disclosure.

1. A method of making an IL-18 mimic of a parent IL-18 protein, the method comprising:
   (a) computationally designing a polypeptide that mimics the binding characteristics of a parent IL-18 protein, wherein the parent IL-18 protein: (i) is a decoy resistant (DR) IL-18 variant polypeptide that comprises at least one mutation relative to a wild type (WT) IL-18 and comprises an amino acid sequence that has 85% or more sequence identity with the WT IL-18, (ii) is capable of specifically binding to IL-18 receptor (IL-18R), and (iii) exhibits substantially reduced binding to IL-18 binding protein (IL-18BP); and
   (b) producing the polypeptide that was computationally designed in step (a), wherein the computationally designed polypeptide has 84% or less sequence identity with the wild type (WT) IL-18.
2. The method of 1, wherein the computationally designed polypeptide comprises a structural feature selected from the group consisting of: a beta trefoil fold, a four-helix bundle, an IL-1 family fold, an IL-17 family fold, a cysteine-knot, a knottin fold, an immunoglobulin domain, a fibronectin domain, an ankyrin repeat, a leucin rich repeat, a beta barrel, an inhibitor cystine knot, or any combination thereof.
3. The method of 1, wherein the computationally designed polypeptide comprises a topology selected from: HHH, EHEE, HEE, EEHE, and HEEH, wherein H indicates an $\alpha$-helix and E indicates $\beta$-strand.
4. The method of 1, wherein the computationally designed polypeptide comprises a Tumor Necrosis Factor Superfamily (TNESF) scaffold.
5. The method of any one of 1-4, wherein the WT IL-18 is human IL-18 comprising the amino acid sequence of SEQ ID NO: 30.
6. The method of any one of 1-4, wherein the WT IL-18 is murine IL-18 comprising the amino acid sequence of SEQ ID NO: 31.
7. The method of 5, wherein the parent IL-18 protein comprises at least one mutation selected from the group consisting of: Y1X, L5X, K8X, M51X, K53X, S55X, Q56X, P57X, G59X, M60X, E77X, Q103X, S105X, D110X, N111X, M113X, V153X, and N155X, relative to SEQ ID NO: 30.
8. The method of 5, wherein the parent IL-18 protein comprises at least one mutation selected from the group consisting of: Y1H, Y1R, L5H, L5I, L5Y, K8Q, K8R, M51T, M51K, M51D, M51N, M51E, M51R, K53R, K53G, K53S, K53T, S55K, S55R, Q56E, Q56A, Q56R, Q56V, Q56G, Q56K, Q56L, P57L, P57G, P57A, P57K, G59T, G59A, M60K, M60Q, M60R, M60L, E77D, Q103E, Q103K, Q103P, Q103A, Q103R, S105R, S105D, S105K, S105N, S105A, D110H, D110K, D110N, D110Q, D110E, D110S, D110G, N111H, N111Y, N111D, N111R, N111S, N111G, M113V, M113R, M113T, M113K, V153I, V153T, V153A, N155K, and N155H, relative to SEQ ID NO: 30.
9. The method of 5, wherein the parent IL-18 protein comprises the mutations M51X, K53X, Q56X, D110X, and N111X, relative to SEQ ID NO: 30.
10. The method of 5, wherein the parent IL-18 protein comprises the mutations M51X, K53X, Q56X, P57X, M60X, D110X, and N111X, relative to SEQ ID NO: 30.
11. The method of any one of 1-4, wherein the parent IL-18 protein comprises the amino acid sequence set forth in any one of SEQ ID NOs: 34-59, 73-91, 191-193, or a fragment thereof.
12. The method of any one of 1-11, wherein said computationally designing comprises using the parent IL-18 protein's primary amino acid sequence in defining a structure that is fed into a memetic design protocol that (i) detects core secondary structure elements that compose the target template, and (ii) produces resulting de novo mimetic backbones.
13. The method of 12, wherein each of the core secondary structure elements are idealized by reconstruction using loops from a clustered database of highly ideal fragments
14. The method of any one of 1-11, wherein said computationally designing comprises combinatorially recombining solutions for pairs of connected secondary structures to produce fully connected backbones.
15. The method of any one of 1-14, wherein said computationally designing comprises combining information on hotspots, compatible built-fragment amino acids and layers to facilitate flexible backbone design and filtering.
16. A method of treating or preventing a disease or disorder in a subject in need thereof, comprising administering to the subject the computationally designed polypeptide produced in any one of 1-15.

17. The method of 16, wherein the disease or disorder is selected from the group consisting of: a cancer, a cancer that is resistant to immune checkpoint inhibitors (ICIs), a cancer that is associated with a tumor that has lost expression of MEC class I, a metabolic disease or disorder, and an infectious disease.

18. The method of any one of 16-17, wherein the method comprises administering to the subject the computationally designed polypeptide and at least one other agent selected from the group consisting of: an immune checkpoint inhibitor, a cancer cell opsonizing agent, 19. The method of 18, wherein the immune checkpoint inhibitor is an agent that inhibits PD-L1, PD1, CTLA4, TIM3, TIGIT, LAG3, B7H3, B7H4, VISTA, ICOS, GITR, 41BB, OX40, or CD40, or any combination thereof.

20. The method of 18, wherein the cancer cell opsonizing agent targets one or more antigens selected from: CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGFR, PDGFRA, AXL, TWEAKR, PTHR2, FIAVCR2 (TIM3), G-D2 ganglioside, MUC1, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin $\alpha_v\beta_3$, TYRP1, GPNMB, CLDN18.2, FOLR1, CCR4, CXCR4, MICA, C242 antigen, DLL3, DLL4, EGFL7, vimentin, fibronectin extra domain-B, TROP-2, LRRC15, FAP, SLITRK6, NOTCH2, NOTCH3, Tenascin-3, STEAP1, and NRP1.

21. A method of making an IL-18 mimic of a parent IL-18 protein, the method comprising:

(a) computationally designing a polypeptide that mimics the binding characteristics of a parent IL-18 protein, wherein the parent IL-18 protein: (i) is a decoy-to-the-decoy (D2D) IL-18 variant polypeptide that comprises at least one mutation relative to a wild type (WT) IL-18 and comprises an amino acid sequence that has 85% or more sequence identity with the WI IL-18, (ii) is capable of specifically binding to IL-18 binding protein (IL-18BP), and (iii) exhibits substantially reduced binding to IL-18 receptor (IL-18R); and (b) producing the polypeptide that was computationally designed in step (a), wherein the computationally designed polypeptide has 84% or less sequence identity with the wild type (WT) IL-18.

22. The method of 21, wherein the computationally designed polypeptide comprises a structural feature selected from the group consisting of: a beta trefoil fold, a four-helix bundle, an IL-1 family fold, an IL-17 family fold, a cysteine-knot, a knottin fold, an immunoglobulin domain, a fibronectin domain, an ankyrin repeat, a leucin rich repeat, a beta barrel, an inhibitor cystine knot, or any combination thereof.

23. The method of 21, wherein the computationally designed polypeptide comprises a topology selected from: HHH, EHEE, HEE, EEHE, and HEEH, wherein H indicates an $\alpha$-helix and E indicates a $\beta$-strand.

24. The method of 21, wherein the computationally designed polypeptide comprises a Tumor Necrosis Factor Superfamily (TNFSF) scaffold.

25. The method of any one of 21-24, wherein the WI IL-18 is human IL-18 comprising the amino acid sequence of SEQ ID NO: 30.

26. The method of any one of 21-24, wherein the WI IL-18 is murine IL-18 comprising the amino acid sequence of SEQ ID NO: 31.

27. The method of 25, wherein the parent IL-18 protein comprises at least one mutation selected from the group consisting of Y1X, L5X, D17X, E31X, T34X, D35X, S36X, D37X, D40X, N41X, M51X, Q56X, M60X, Q103X, H109X, M113X, and R131X, relative to SEQ ID NO: 30.

28. The method of 25, wherein the parent IL-18 protein comprises at least one mutation selected from the group consisting of Y1D, Y1F, Y1H, Y1L, L5F, L5H, D17A, D17G, D17R, D17H, E31A, E31T, E31G, E31K, E31R, T34A, T34K T34E, D35S, D35A, D35Y, S36N, S36K, S36R, D37P, D37A, D37R, D37H, D371D37V, D40Y D40S, D40A, N41K, N41S, N41R, M51F, M51L, M51I, Q56H, M60L, M60F, M60I, Q103L, Q103I, H109A, H109P, H109D, M113L, M113I, M113F, and R131S, relative to SEQ ID NO: 30.

29. The method of any one of 21-24, wherein the parent IL-18 protein comprises the amino acid sequence set forth in any one of SEQ ID NOs.: 92-125, or a fragment thereof.

30. The method of 25, wherein the parent IL-18 protein comprises the mutations D17X, E30X, and Q103X, relative to SEQ ID NO: 30.

31. The method of 25, wherein the parent IL-18 protein comprises the mutations D17X, E30X, D35X, M51X, and Q103X, relative to SEQ ID NO: 30.

32. The method of any one of 21-31, wherein said computationally designing comprises using the parent IL-18 protein's primary amino acid sequence in defining a structure that is fed into a memetic design protocol that (i) detects core secondary structure elements that compose the target template, and (ii) produces resulting de novo mimetic backbones.

33. The method of 32, wherein each of the core secondary structure elements is idealized by reconstruction using loops from a clustered database of highly ideal fragments.

34. The method of any one of 21-31, wherein said computationally designing comprises combinatorially recombining solutions for pairs of connected secondary structures to produce fully connected backbones.

35. The method of any one of 21-34, wherein said computationally designing comprises combining information on hotspots, compatible built-fragment amino acids and layers to facilitate flexible backbone design and filtering.

36. A method of treating or preventing a disease or disorder in a subject in need thereof, comprising administering to the subject the computationally designed polypeptide produced in any one of 21-35.

37. The method of 36, wherein the disease or disorder is selected from the group consisting of: a cancer, a cancer that is resistant to immune checkpoint inhibitors (ICIs), a cancer that is associated with a tumor that has lost expression of WIC class I, a metabolic disease or disorder, and an infectious disease.

38. The method of any one of 36-37, wherein the method comprises administering to the subject the computationally designed polypeptide and at least one other agent selected from the group consisting of: an immune checkpoint inhibitor, a cancer cell opsonizing agent, 39. The method of 38, wherein the immune checkpoint inhibitor is an agent that inhibits PD-L1, PD1, CTLA4, TIM3, TIGIT, LAG3, B7H3, B7H4, VISTA, ICOS, GITR, 41BB, OX40, or CD40, or any combination thereof.

40. The method of 38, wherein the cancer cell opsonizing agent targets one or more antigens selected from: CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGFR, PDGFRA, AXL, TWEAKR, PTHR2, HAVCR2 (TIM3), GD2 ganglioside, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin $\alpha_v\beta_3$, TYRP1, GPNMB, CLDN18.2, FOLR1, CCR4, CXCR4, MICA, C242 antigen, DLL3, DLL4, EGFL7, vimentin, fibronectin extra domain-B, TROP-2, LRRC15, FAP, SLITRK6, NOTCH2, NOTCH3, Tenascin-3, STEAP1, and NRP1

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the disclosure. The appended claims are intended to be construed to include all such embodiments and equivalent variations.

What is claimed is:

1. A method of making a mimic of a parent IL-18 protein, the method comprising:

(a) computationally designing a polypeptide de novo from a parent IL-18 protein by:

(i) defining as a template a structure of the IL-18 parent protein in a complex with at least human IL-18Rα, wherein the parent IL-18 protein is a decoy resistant (DR) IL-18 variant polypeptide of wild-type (WT) human IL-18;

(ii) designating one or more hotspots in the template based on binding sites in the complex;

(iii) inputting the template comprising the one or more designated hotspots into a mimetic design protocol to generate a de novo polypeptide backbone; and (iv) outputting an amino acid sequence for the de novo designed polypeptide; and (b) producing the de novo designed polypeptide that was computationally designed in step (a), wherein the amino acid sequence of the produced de novo designed polypeptide has 84% or less sequence identity with the WT human IL-18 SEQ ID NO:30, has a beta trefoil fold, specifically binds to human IL-18 receptor (IL-18R), and exhibits substantially reduced binding to human IL-18 binding protein (IL-18BP) as compared with WT human IL-18 with a $K_D$ for IL-18BP measured by SPR that is 10 nM or greater.

2. The method of claim 1, wherein the DR IL-18 variant polypeptide comprises at least one mutation selected from the group consisting of: Y1X, L5X, K8X, M51X, K53X, S55X, Q56X, P57X, G59X, M60X, E77X, Q103X, S105X, D110X, N111X, M113X, V153X, and N155X, relative to SEQ ID NO: 30.

3. The method of claim 1, wherein the DR IL-18 variant polypeptide comprises at least one mutation selected from the group consisting of: Y1H, Y1R, L5H, L5I, L5Y, K8Q, K8R, M51T, M51K, M51D, M51N, M51E, M51R, K53R, K53G, K53S, K53T, S55K, S55R, Q56E, Q56A, Q56R, Q56V, Q56G, Q56K, Q56L, P57L, P57G, P57A, P57K, G59T, G59A, M60K, M60Q, M60R, M60L, E77D, Q103E, Q103K, Q103P, Q103A, Q103R, S105R, S105D, S105K, S105N, S105A, D110H, D110K, D110N, D110Q, D110E, D110S, D110G, N111H, N111Y, N111D, N111R, N111S, N111G, M113V, M113R, M113T, M113K, V153I, V153T, V153A, N155K, and N155H, relative to SEQ ID NO: 30.

4. The method of claim 1, wherein the DR IL-18 variant polypeptide comprises the mutations M51X, K53X, Q56X, D110X, and N111X, relative to SEQ ID NO: 30.

5. The method of claim 1, wherein the DR IL-18 variant polypeptide comprises the mutations M51X, K53X, Q56X, P57X, M60X, D110X, and N111X, relative to SEQ ID NO: 30.

6. The method of claim 1, wherein the DR IL-18 variant polypeptide comprises the amino acid sequence set forth in any one of SEQ ID NOs: 34-59, 73-91, 191-193, or a fragment thereof.

7. The method of claim 1, wherein the mimetic design protocol (i) detects core secondary structure elements that compose the template, iii) idealizes each of the core secondary structure elements, (iii) connects the idealized secondary structure elements using loops, and (iv) produces resulting fully connected de novo mimetic backbones.

8. The method of claim 7, wherein the loops are sourced from a clustered database of highly ideal fragments.

9. The method of claim 7, wherein said connecting comprises generating pairs of idealized secondary structure elements connected by loops to produce connected secondary structures and combinatorially recombining the connected secondary structures to produce the fully connected de novo mimetic backbones.

10. The method of claim 7, wherein producing said fully connected de novo mimetic backbones comprises combining information on hotspots, compatible built-fragment amino acids and layers to facilitate flexible backbone design and filtering.

11. The method of claim 1, wherein the amino acid sequence of the produced de novo designed polypeptide has 50% or less sequence identity with WT human IL-18 SEQ ID NO:30.

12. A method of treating or preventing a disease or disorder in a subject in need thereof, comprising administering to the subject the computationally designed polypeptide produced in any one of claims 1 and 2-10.

13. The method of claim 12, wherein the disease or disorder is selected from the group consisting of: a cancer, a cancer that is resistant to immune checkpoint inhibitors (ICIs), a cancer that is associated with a tumor that has lost expression of MHC class I, a metabolic disease or disorder, and an infectious disease.

14. The method of claim 12, wherein the method comprises administering to the subject the computationally designed polypeptide and at least one other agent selected from the group consisting of: an immune checkpoint inhibitor and a cancer cell opsonizing agent.

15. The method of claim 14, wherein the immune checkpoint inhibitor is an agent that inhibits PD-L1, PD1, CTLA4, TIM3, TIGIT, LAG3, B7H3, B7H4, VISTA, ICOS, GITR, 41BB, OX40, or CD40, or any combination thereof.

16. The method of claim 14, wherein the cancer cell opsonizing agent targets one or more antigens selected from: CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGFR, PDGFRA, AXL, TWEAKR, PTHR2, HAVCR2 (TIM3), GD2 ganglioside, MUC1, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin αvβ3, TYRP1, GPNMB, CLDN18.2, FOLR1, CCR4, CXCR4, MICA, C242 antigen, DLL3, DLL4, EGFL7, vimentin, fibronectin extra domain-B, TROP-2, LRRC15, FAP, SLITRK6, NOTCH2, NOTCH3, Tenascin-3, STEAP1, and NRP1.

17. A method of making a mimic of a parent IL-18 protein, the method comprising:

(a) computationally designing a polypeptide de novo from a parent IL-18 protein by:
  (i) defining as a template a structure of the IL-18 parent protein in a complex with at least human IL-18BP, wherein the parent IL-18 protein: (i) is a decoy-to-the-decoy (D2D) IL-18 variant polypeptide of wild-type (WT) human IL-18;
  (ii) designating one or more hotspots in the template based on binding sites in the complex;
  (iii) inputting the template comprising the one or more designated hotspots into a mimetic design protocol to generate a de novo polypeptide backbone; and
  (iv) outputting an amino acid sequence for the de novo designed polypeptide; and (b) producing the de novo designed polypeptide that was computationally designed in step (a), wherein the amino acid sequence of the produced de novo designed polypeptide has 84% or less sequence identity with WT human IL-18 SEQ ID NO:30, has a beta trefoil fold, specifically binds to human IL-18BP, and exhibits 10% or less of the binding affinity to human IL-18 receptor (IL-18R) as compared with WT human IL-18.

18. The method of claim 17, wherein the parent IL 18 protein D2D IL-18 variant polypeptide comprises at least one mutation selected from the group consisting of Y1X, L5X, D17X, E31X, T34X, D35X, S36X, D37X, D40X, N41X, M51X, Q56X, M60X, Q103X, H109X, M113X, and R131X, relative to SEQ ID NO: 30.

19. The method of claim 17, wherein the D2D IL-18 variant polypeptide comprises at least one mutation selected from the group consisting of Y1D, Y1F, Y1H, Y1L, L5F, L5H, D17A, D17G, D17R, D17H, E31A, E31T, E31G, E31K, E31R, T34A, T34K T34E, D35S, D35A, D35Y, S36N, S36K, S36R, D37P, D37A, D37R, D37H, D37L, D37V, D40Y D40S, D40A, N41K, N41S, N41R, M51F, M51L, M51I, Q56H, M60L, M60F, M60I, Q103L, Q103I, H109A, H109P, H109D, M113L, M113I, M113F, and R131S, relative to SEQ ID NO: 30.

20. The method of claim 17, wherein the D2D IL-18 variant polypeptide comprises the amino acid sequence set forth in any one of SEQ ID NOs.: 92-125, or a fragment thereof.

21. The method of claim 17, wherein the D2D IL-18 variant polypeptide comprises the mutations D17X, E30X, and Q103X, relative to SEQ ID NO: 30.

22. The method of claim 17, wherein the D2D IL-18 variant polypeptide comprises the mutations D17X, E30X, D35X, M51X, and Q103X, relative to SEQ ID NO: 30.

23. The method of claim 17, wherein the mimetic design protocol (i) detects core secondary structure elements that compose the template, iii) idealizes each of the core secondary structure elements, (iii) connects the idealized secondary structure elements using loops, and (iv) produces resulting fully connected de novo mimetic backbones.

24. The method of claim 23, wherein the loops are sourced from a clustered database of highly ideal fragments.

25. The method of claim 23, wherein said connecting comprises generating pairs of idealized secondary structure elements connected by loops to produce connected secondary structures and combinatorially recombining of the connected secondary structures to produce fully connected de novo mimetic backbones.

26. The method of claim 23, wherein producing said fully connected de novo mimetic backbones comprises combining information on hotspots, compatible built-fragment amino acids and layers to facilitate flexible backbone design and filtering.

27. A method of treating or preventing a disease or disorder in a subject in need thereof, comprising administering to the subject the computationally designed polypeptide produced in any one of claims 17 and 18-26.

28. The method of claim 27, wherein the disease or disorder is selected from the group consisting of: a cancer, a cancer that is resistant to immune checkpoint inhibitors (ICIs), a cancer that is associated with a tumor that has lost expression of MHC class I, a metabolic disease or disorder, and an infectious disease.

29. The method of claim 21, wherein the method comprises administering to the subject the computationally designed polypeptide and at least one other agent selected from the group consisting of: an immune checkpoint inhibitor and a cancer cell opsonizing agent.

30. The method of claim 29, wherein the immune checkpoint inhibitor is an agent that inhibits PD-L1, PD1, CTLA4, TIM3, TIGIT, LAG3, B7H3, B7H4, VISTA, ICOS, GITR, 41BB, OX40, or CD40, or any combination thereof.

31. The method of claim 29, wherein the cancer cell opsonizing agent targets one or more antigens selected from: CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGFR, PDGFRA, AXL, TWEAKR, PTHR2, HAVCR2 (TIM3), GD2 ganglioside, MUC1, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin αvβ3, TYRP1, GPNMB, CLDN18.2, FOLR1, CCR4, CXCR4, MICA, C242 antigen, DLL3, DLL4, EGFL7, vimentin, fibronectin extra domain-B, TROP-2, LRRC15, FAP, SLITRK6, NOTCH2, NOTCH3, Tenascin-3, STEAP1, and NRP1.

32. The method of claim 17, wherein the amino acid sequence of the produced de novo designed polypeptide has 50% or less sequence identity with WT human IL-18 SEQ ID NO:30.

* * * * *

UNITED STATES PATENT AND TRADEMARK OFFICE
CERTIFICATE OF CORRECTION

PATENT NO. : 12,029,778 B2
APPLICATION NO. : 16/871833
DATED : July 9, 2024
INVENTOR(S) : Aaron Ring Page 1 of 1

It is certified that error appears in the above-identified patent and that said Letters Patent is hereby corrected as shown below:

In the Claims

Column 296, Lines 30-34, cancel the text beginning with "29. The method of" to and ending with "a cancer cell opsonizing agent." and insert the following claim:
--29. The method of claim 27, wherein the method comprises administering to the subject the computationally designed polypeptide and at least one other agent selected from the group consisting of: an immune checkpoint inhibitor and a cancer cell opsonizing agent.--

Signed and Sealed this
Twenty-seventh Day of August, 2024

Katherine Kelly Vidal
*Director of the United States Patent and Trademark Office*